United States Patent
Malley et al.

(10) Patent No.: US 12,129,283 B2
(45) Date of Patent: Oct. 29, 2024

(54) PNEUMOCOCCAL FUSION PROTEIN VACCINES

(71) Applicant: THE CHILDREN'S MEDICAL CENTER CORPORATION, Boston, MA (US)

(72) Inventors: Richard Malley, Beverly, MA (US); Yingjie Lu, West Roxbury, MA (US); Fan Zhang, West Roxbury, MA (US)

(73) Assignee: THE CHILDREN'S MEDICAL CENTER CORPORATION

( * ) Notice: Subject to any disclaimer, the term of this patent is extended or adjusted under 35 U.S.C. 154(b) by 230 days.

(21) Appl. No.: 17/932,685

(22) Filed: Sep. 16, 2022

(65) Prior Publication Data

US 2023/0089151 A1    Mar. 23, 2023

Related U.S. Application Data

(62) Division of application No. 16/568,646, filed on Sep. 12, 2019, now abandoned.

(60) Provisional application No. 62/730,199, filed on Sep. 12, 2018.

(51) Int. Cl.
*C07K 14/47* (2006.01)
*C07K 14/315* (2006.01)

(52) U.S. Cl.
CPC .......... *C07K 14/47* (2013.01); *C07K 14/3156* (2013.01); *C07K 2319/00* (2013.01)

(58) Field of Classification Search
CPC ................................................. C07K 2319/00
See application file for complete search history.

(56) References Cited

U.S. PATENT DOCUMENTS

| | | | |
|---|---|---|---|
| 6,287,568 B1 | 9/2001 | Wang et al. | |
| 7,588,920 B2 | 9/2009 | Douchette-Stamm et al. | |
| 9,499,593 B2 | 11/2016 | Malley et al. | |
| 10,017,548 B2 | 7/2018 | Malley et al. | |
| 2002/0032323 A1 | 3/2002 | Kunsch et al. | |
| 2005/0002948 A1 | 1/2005 | Ryall | |
| 2006/0251675 A1 | 11/2006 | Hagen | |
| 2007/0128183 A1 | 6/2007 | Meinke et al. | |
| 2008/0032340 A1 | 2/2008 | Ghosh et al. | |
| 2008/0112964 A1 | 5/2008 | Kirkham et al. | |
| 2009/0054251 A1 | 2/2009 | O'Connor et al. | |
| 2009/0148894 A1 | 6/2009 | Broedel et al. | |
| 2009/0148897 A1 | 6/2009 | Dai | |
| 2009/0285846 A1 | 11/2009 | Tweten | |
| 2010/0003266 A1 | 1/2010 | Simon | |
| 2010/0020945 A1 | 1/2010 | Li et al. | |
| 2010/0022401 A1 | 1/2010 | Norlund et al. | |
| 2010/0166802 A1 | 7/2010 | Caplan et al. | |
| 2010/0209450 A1 | 8/2010 | Biemans et al. | |
| 2011/0027265 A1 | 2/2011 | Bubeck-Wardenburg | |
| 2011/0065660 A1 | 3/2011 | Baron et al. | |
| 2013/0115230 A1 | 5/2013 | Simon | |
| 2014/0154286 A1 | 6/2014 | Malley et al. | |
| 2014/0154287 A1 | 6/2014 | Malley et al. | |
| 2014/0178425 A1 | 6/2014 | Bagnoli et al. | |
| 2015/0374811 A1 | 12/2015 | Malley et al. | |
| 2016/0090404 A1 | 3/2016 | Malley et al. | |
| 2019/0119335 A1 | 4/2019 | Malley et al. | |

FOREIGN PATENT DOCUMENTS

| | | |
|---|---|---|
| CN | 101797381 A | 8/2010 |
| CN | 101951948 A | 1/2011 |
| EP | 1838345 A2 | 10/2007 |
| JP | 2002-504096 | 10/1998 |
| JP | H11-502820 A | 3/1999 |
| JP | 2008-509682 A | 2/2006 |
| JP | 2007-504237 A | 3/2007 |
| JP | 2010-517532 A | 8/2008 |
| JP | 2014-517835 A | 7/2014 |
| RU | 2164943 C2 | 4/2001 |
| RU | 2006117425 A | 12/2007 |
| RU | 2378008 C2 | 1/2010 |
| RU | 2407749 C2 | 12/2010 |
| WO | 1995021195 A2 | 8/1995 |
| WO | 1996/029094 A1 | 9/1996 |
| WO | 199818930 A2 | 5/1998 |
| WO | 1998/047530 A2 | 10/1998 |
| WO | 2002077021 A2 | 10/2002 |
| WO | 2003/094960 A2 | 11/2003 |
| WO | 2004/092209 A2 | 10/2004 |
| WO | 2005/037190 A2 | 4/2005 |
| WO | 2005/039501 A1 | 5/2005 |
| WO | 2006/017929 A1 | 2/2006 |
| WO | 2006/067632 A2 | 6/2006 |
| WO | 2006/084467 A1 | 8/2006 |
| WO | 2007/026249 A2 | 3/2007 |
| WO | 2007/067681 A2 | 6/2007 |
| WO | 2007/081583 A2 | 7/2007 |
| WO | 2007/150020 A1 | 12/2007 |

(Continued)

OTHER PUBLICATIONS

Anttila et al. "Avidity of IgG for *Streptococcus pneumoniae* type 6B and 23F polysaccharides in infants primed with pneumococcal conjugates and boosted with polysaccharide or conjugate vaccines." J Infect Dis., 177(6): 1614-1621 (1998).

Berry et al. "Effect of Defined Point Mutations in *Pneumolysin* Gene on the Virulence of *Streptococcus pneumoniae*" Infection and Immunity 63 (5): 1969-1974 (1995).

Centers for Disease Control and Prevention. "Preventing pneumococcal disease among infants and young children." Morbidity and Mortality Weekly Report. 49: 1-55 (2000).

Centers for Disease Control and Prevention. "Prevention of pneumococcal disease among infants and children—use of 13-valent pneumococcal conjugate vaccine and 23-valent pneumococcal polysaccharide vaccine." Morbidity and Mortality Weekly Report. 59: 1-24 (2010).

Daniels et al. "The Proline-Rich Region of Pneumococcal Surface Proteins A and C Contains Surface-Accessible Epitopes Common to All Pneumococci and Elicits Antibody-Mediated Protection against Sepsis" Infection and Immunity 78 (5):2163-2172 (2010).

(Continued)

*Primary Examiner* — Brian Gangle
*Assistant Examiner* — Lakia J Jackson-Tongue
(74) *Attorney, Agent, or Firm* — NIXON PEABODY LLP; David S. Resnick; Jeanne N. Jodoin

(57) ABSTRACT

Technologies for the prevention and/or treatment of pneumococcal infections.

21 Claims, 12 Drawing Sheets

Specification includes a Sequence Listing.

(56) References Cited

FOREIGN PATENT DOCUMENTS

| WO | 2008/094986 A2 | 8/2008 |
|---|---|---|
| WO | 2008/152448 A2 | 12/2008 |
| WO | 2009/016515 A2 | 2/2009 |
| WO | 2009/021548 A1 | 2/2009 |
| WO | 2009/029831 A1 | 3/2009 |
| WO | 2010/053559 A1 | 5/2010 |
| WO | 2010/071986 A1 | 7/2010 |
| WO | 2010/081875 A1 | 7/2010 |
| WO | 2011/008548 A1 | 1/2011 |
| WO | 2011/137354 A2 | 11/2011 |
| WO | 2012155007 A1 | 11/2012 |
| WO | 2012155053 A1 | 11/2012 |
| WO | 2014/018904 A1 | 1/2014 |
| WO | 2018183475 A1 | 10/2018 |

OTHER PUBLICATIONS

Douce et al. "Mutants of *Escherichia coli* heat-labile toxin lacking ADP-ribosyltransferase activity act as non-toxic, mucosal adjuvants." PNAS 92: 1644-1648 (1995).

Douce et al. "Genetically detoxified mutants of heat-labile toxin from *Escherichia coli* are able to act as oral adjuvants" Infect Immun. Sep. 67(9):4400-4406 (1999).

Ferreira et al. "DNA vaccines based on genetically detoxified derivatives of pneumolysin fail to protect mice against challenge with *Streptococcus pneumoniae*" FEMS Immunol Med Microbial 46: 291-297 (2006).

Giuliani et al. "Mucosal adjuvanticity and immunogenicity of LTR72, a novel mutant of *Escherichia coli* heat-labile enterotoxin with partial knockout of ADP-ribosyltransferase activity." J Exp Med. 187(7): 1123-1132 (1998).

Helppolainen et al. "Rhizavidin from Rhizobium etli: the first natural dimer in the avidin protein family." Biochem J. 405:397-405 (2007).

Holliger et al. "'Diabodies': small bivalent and bi specific antibody fragments." Proc Natl Acad Sci USA 15;90 (14):6444-6448 (1993).

Kim et al. "Efficiency of a pneumococcal opsonophagocytic killing assay improved by multiplexing and by coloring colonies." Clin Diagn Lab Immunol. 10( 4):616-621 (2003).

Kojima et al. "Quantitation of IgG subclass antibodies to pneumococcal capsular polysaccharides by ELISA, using Pneumovax-specific antibodies as a reference." Tohoku J Exp Med. 161(3):209-215 (1990).

Koskela et al. "Comparison of ELISA and RIA for measurement of pneumococcal antibodies before and after vaccination with 14-valent pneumococcal capsular polysaccharide vaccine." J Clin Pathol. 34(1):93-98 (1981).

Martinez et al. "A flow cytometric opsonophagocytic assay for measurement of functional antibodies elicited after vaccination with the 23-valent pneumococcal polysaccharide vaccine". Clin Diagn Lab Immunol. 6(4):581-586 (1999).

Moffitt et al. "Identification of Protective Pneumococcal Thl 7 Antigens from the Soluble Fraction of a Killed Whole Cell Vaccine." PLoS ONE 7(8):e43445 (2012).

Munro et al. "Assessment of biological activity of immunoglobulin preparations by using opsonized micro-organisms to stimulate neutrophil chemiluminescence." Clin Exp Immunol. 61(1): 183-188 (1985).

Ojo-Amaize et al. "A rapid and sensitive chemiluminescence assay for evaluation of functional opsonic activity of Haemophilus influenzae type b-specific antibodies." Clin Diagn Lab Immunol. 2(3):286-290 (1995).

Paton et al. "Purification and immunogenicity of genetically obtained pneumolysin toxoids and their conjugation to *Streptococcus pneumoniae* type 19F polysaccharide" Infect Immun 59(7):2297-2304 (1991).

PNEUMOVAX® 23(prescribing information). Whitehouse Station, NJ: Merck & Co. (2015).

PREVNAR 13® (prescribing information). New York, NY: Pfizer; Aug. 2017.

Richter et al. "Changes in pneumococcal serotypes and antimicrobial resistance after introduction of the 13 valent conjugate vaccine in the United States." Antimicrob Agents Chemother. 58:6484-6489 (2014).

Romero-Steiner et al. "Standardization of an opsonophagocytic assay for the measurement of functional antibody activity against *Streptococcus pneumoniae* using differentiated HL-60 cells." Clin Diagn Lab Immunol. 4(4):415-422 (1997).

Romero-Steiner et al. "Avidity determinations for Haemophilus influenzae Type b anti-polyribosylribitol phosphate antibodies." ClinDiagn Lab Immunol. 12(9):1029-1035 (2005).

Saunders et al. "Pneumolysin, the thiol- activated toxin of *Streptococcus pneumoniae*, does not require a thiol group for in vitro activity". Infect Immun 57(8):2547-2552 (1989).

Stack et al. "Minimum protective serum concentrations of pneumococcal anti-capsular antibodies in infant rats." J Infect Dis. 177(4):986-990 (1998).

Williams et al., "Innate imprinting by the modified heat-labile toxin of *Escherichia coli* (LTK63) provides generic protection against lung infectious disease." The Journal of Immunology, 173 :7435-7443 (2004).

Wu et al. "Thl 7-stimulating protein vaccines confer protection against Pseudomonas aeruginosa pneumonia." Am J Respir Crit Care Med. 186(5):420-427 (2012).

Zhang et al., "Multiple antigen-presenting system (MAPS) to induce comprehensive B- and T-cell immunity." Proc Natl Acad Sci USA. 110:13564-13569 (2013).

Poljak "Production and structure of diabodies." Structure. 2(12): 1121-1123 (1994).

Gruber et al. "Licensing of pneumococcal conjugate vaccines for children and adults: Regulatory perspective from the European Medicines Agency and the U.S. Food and Drug Administration." In: Siber GR, Klugman KP, Makela PH, eds. Pneumococcal Vaccines: The Impact of Conjugate Vaccine. Washington, DC ASM Press 183-96; (2008).

Ishizaka et al. "E6020: a synthetic Toll-like receptor 4 agonist as a vaccine adjuvant." Expert Rev. Vaccines. 6 (5):773-784 (2007).

Saeland et al. "Pneumococcal pneumonia and bacteremia model in mice for the analysis of protective antibodies." Microb Pathog. 29(2):81-91 (2000).

Evans et al. "Enhancement of antigen-specific immunity via the TLR4 ligands MPL adjuvant and Ribi.529." Expert Rev Vaccines, 2(2):219-229 (2003).

Singh et al. "Advances in vaccine adjuvants for infectious diseases." Current HIV Research 1(3):309-320 (2003).

Zhang et al. Design and evaluation of multiple antigen presenting system (MAPS)-based pneumococcal vaccine to prevent invasive disease and carriage, poster presented at the 10th International Symposium on Pneumococci and Pneumococcal Diseased (ISPPD-10), Glasgow, Scotland, Jun. 26-30, 2016.

Kehoe et al., "Cloning, expression, and mapping of the *Staphylococcus aureus* alpha-hemolysin determinant in *Escherichia coli* K-12." Infection and immunity 41.3 (1983): 1105-1111.

Meir et al. "Crystal structure of rhizavidin: insights into the enigmatic high-affinity interaction of an innate biotin-binding protein dimer." Journal of molecular biology 386.2 (2009): 379-390. (Abstract).

Menzies et al., "Site-directed mutagenesis of the alpha-toxin gene of *Staphylococcus aureus*: Role of histidines in toxin activity in vitro and in a murine model", Infection and Immunity, American Society for Microbiology, 62(5) 1843-1847 (May 1, 1994).

Moffitt et al. "Rationale and prospects for novel pneumococcal vaccines." Human vaccines & immunotherapeutics 12.2 (2016): 383-392.

O'Reilly et al., "Inactivation of the alpha-haemolysin gene of *Staphylococcus aureus* 8325-4 by site-directed mutagenesis and studies on the expression of its haemolysins." Microbial pathogenesis 1.2 (1986): 125-138.

Walker et al., "Key residues for membrane binding, oligomerization, and pore forming activity of staphylococcal alpha-hemolysin identified by cysteine scanning mutagenesis and targeted chemical modification", Journal of Biological Chemistry, American Society for Biochemistry and Molecular Biology, 270(39): 23065-23071 (Sep. 29, 1995).

(56) References Cited

OTHER PUBLICATIONS

International Search Report and Written Opinion for PCT/US2018/24810, 9 pages (mailed Aug. 31, 2018).
Zhang et al. "Protection against *Staphylococcus aureus* colonization and infection by B-and T-Cell-mediated mechanisms." MBio 9(5): 1-13 (2018).
Hytonen et al., "Efficient production of active chicken avidin using a bacterial signal peptide in *Escherichia coli*", Biochem 384(Pt 2) 385-390 (2004).
Insel et al., Response to oligosaccharide-protein conjugate vaccine against Hemophilus influenzae b in two patients with IgG2 deficiency unresponsive to capsular polysaccharide vaccine, N Engl J Med 315(8) 499-503 (1986).
International Search Report for PCT/US2012/037412 (Multiple Antigen Presenting Immunogenic Composition, and Methods and Uses Thereof, filed May 11, 2012), issued by ISA/FIPS, 3 pages (Aug. 23, 2012).
International Search Report for PCT/US2012/037541 (Modified Biotin-Binding Protein, Fusion Proteins Thereof and Applications, filed May 11, 2012), issued by ISA/FIPS, 4 pages (Aug. 30, 2012).
Izard et al., "Signal peptides: exquisitely designed transport promoters", Mol Microbiol 13(5) 765-773 (1994).
Jin et al., "Conjugates of group A and W135 capsular polysaccharides of neisseria meningitidis bound to recombinant *Staphylococcus aureus* enterotoxin C1: preparation, physicochemical characterization, and immunological properties in mice", Infect Immun 73(12) 7887-7893 (2005).
Lees et al., "Enhanced immunogenicity of protein-dextran conjugates: I. Rapid stimulation of enhanced antibody responses to poorly immunogenic molecules", Vaccine 12(13) 1160-1166 (1994).
Pollabauer et al., "The influence of carrier protein on the immunogenicity of simultaneously administered conjugate vaccines in infants", Vaccine 27(11) 1674-1679 (2009).
Rosenberg, Protein Analysis and Purification, Springer Science+Business Media, New York, pp. 153-182 (1996).
Sanabria-Valentin et al., "Lipopolysaccharide modification strategies of Helicobacter pylori during persistent colonization", Dissertation, Department of Basic Medical Science, New York University, 2008.
Sano et al., In Methods in Enzymology vol. 326, pp. 305-307 (2000).
Scott et al., Immunogenicity of biotinylated hapten-avidin complexes, Mol Immunol 21(11) 1055-1060 (1984).
Sen et al., "In vivo humoral immune responses to isolated pneumococcal polysaccharides are dependent on the presence of associated TLR ligands", J Immunol 175(5) 3084-3091 (2005).
Takakura et al., "Tamavidin, a versatile affinity tag for protein purification and immobilization", Abstract J Biotechnol 145(4) 317-322 (2010).
Thermo Scientific Avidin-Biotin Technical Handbook, 2009, p. 16-17. Found on the Internet on May 5, 2016 at:https://www.thermofisher.com/content/dam/LifeTech/Images/integration/1601675_AvBi_HB_INTL.pdf.
Wardenburg et al., "Vaccine protection against *Staphylococcus aureus* pneumonia", J Exp Med 205(2) 287-294 (2008).
Written Opinion for PCT/US2012/037412 (Multiple Antigen Presenting Immunogenic Composition, and Methods and Uses Thereof, filed May 11, 2012), issued by ISA/FIPS, 4 pages (Aug. 23, 2012).
Written Opinion for PCT/US2012/037541 (Modified Biotin-Binding Protein, Fusion Proteins Thereof and Applications, filed May 11, 2012), issued by ISA/FIPS, 3 pages (Aug. 30, 2012).
Zhang et al., "Multiple antigen-presenting system (MAPS) to induce comprehensive B- and T-cell immunity", Proc Natl Acad Sci USA 110(33) 13564-13569 (2013).
Avci et al., "A mechanism for glycoconguate vaccine activation of the adaptive immune system and its implications for vaccine design", Nature Medicine 17(12) 1602-1609 (Dec. 2001) doi:10.1038/nm.2535.
Colino et al., "Noncovalent Association of Protein and Capsular Polysaccharide on Bacteria-Sized Latex Beads as a Model for Polysaccharide-Specific Humoral Immunity to Intact Gram-Positive Extracellular Bacteria", J. of Immun. at: https://www.jimmunol.org/cji/doi/10.4049/jimmunol.1300722.
Colino, J. et al., Parameters Underlying Distinct T Cell-Dependent Polysaccharide-Specific IgG Responses to an Intact Gram-Positive Bacterium versus a Soluble Conjugate Vaccine, Journal of Immunology, 183: 1551-1559 (2009).
Cortajarena et al., "A receptor-binding region in *Escherichia coli* alpha-haemolysin", Abstract J Biol Chem 278(21) 19159-19163 (2003).
Dagan et al., "Glycoconjugate vaccines and immune interference: a review", Vaccine 28(34) 5513-5523 (2010).
Database, UniProt KB/TrEMBL, B3Q265_RHIE6, Sep. 2, 2008.
Database, UniProt KB/TrEMBL, F2AA21_RHIET, May 31, 2011.
Database, UniProt KB/TrEMBL, Q8KKW2_RHIEC, Oct. 1, 2002.
Elgert, "Immunology: understanding the immune system", John Wiley & Sons p. 111 (2009).
EP Communication issue Apr. 9, 2015 corresponding to EP Application No. 1278163631.
Fauvart et al., "Genome sequence of Rhizobium etli CNPAF512, a nitrogen-fixing symbiont isolated from bean root nodules in Brazil", J Bacteriol 193(12) 3158-3159 (2011).
Gaj et al., "The AviD-tag, a NeutrAvidin/avidin specific peptide affinity tag for the immobilization and purification of recombinant proteins", Protein Expr Purif 56(1) 54-61 (2007).
Gonzalez et al., "The mosaic structure of the symbiotic plasmid of Rhizobium etli CFN42 and its relation to other symbiotic genome compartments", Genome Biol 4(6) R36 (2003).
Grun et al., "One-step biotinylation procedure for carbohydrates to study carbohydrate-protein interactions", Anal Biochem 354(1) 64-63 (2006).
Helppolainen et al., "Bradavidin II from Bradyrhizobium japonicum: a new avidin-like biotin-binding protein", Biochem Biophys Acta 1784(7-8) 1002-1010 (2008).
Helppolainen et al., "Rhizavidin from Rhizobium etli: the first natural dimer in the avidin protein family", Biochem 405(3) 397-405 (2007).
Hermanson, Bioconjugate Tequniques, Elsevier Science, ProQuest Ebook Central, http://ebookcentral.proquest.com/lib.uspto-ebooks/details.action?docID=307203. Created from uspto-ebooks on Sep. 6, 2017, pp. 570-592 (1996).
Hsu et al., "Profiling carbohydrate-receptor interaction with recombinant innate immunity receptor-Fc fusion proteins", J Biol Chem 284(50) 34479-34489 (2009).
Huang et al., Robust stimulation of humoral and cellular immune responses following vaccination with antigen-loaded beta-glucan particles, Mbio 1(3) e00164-10 (2010).

PNEUMOCOCCAL FUSION PROTEIN VACCINES

CROSS-REFERENCE TO RELATED APPLICATIONS

This application is a Divisional application of U.S. application Ser. No. 16/568,646 filed Sep. 12, 2019, which claims the benefit of U.S. Provisional Application No. 62/730,199 filed Sep. 12, 2018, the contents of which are hereby incorporated herein in their entirety.

SEQUENCE LISTING

The instant application contains a Sequence Listing which has been submitted electronically in computer readable form and is hereby incorporated by reference in its entirety. Said ASCII copy, created on Sep. 12, 2022, is named 701039-093500USPT_SL.xml and is 252,415 bytes in size.

BACKGROUND

*Streptococcus pneumoniae* remains a leading cause of serious illness, including bacteremia, sepsis, meningitis and pneumonia, among children and adults worldwide. Morbidity and mortality among infants, young children, the elderly and subjects who have certain underlying medical conditions is high.

*S. pneumoniae* is a Gram-positive encapsulated coccus that colonizes the nasopharynx in about 5-10% of healthy adults and 20-40% of healthy children. Normal colonization becomes infectious when *S. pneumoniae* is carried into the Eustachian tubes, nasal sinuses, lungs, bloodstream, meninges, joint spaces, bones and peritoneal cavity. *S. pneumoniae* infection is the most frequent cause of bacteremia, pneumonia, meningitis, sinusitis and acute otitis media [CDC, 2010].

Pneumococcal disease can be invasive or noninvasive. The most common form of noninvasive disease, non-bacteremic pneumococcal pneumonia, remains one of the most frequent causes for pneumonia hospitalizations. Invasive pneumococcal disease (IPD) is defined as *S. pneumoniae* isolated from a normally sterile site (e.g., cerebrospinal fluid, blood, joint fluid, pleural fluid or peritoneal fluid). The highest incidence of IPD is found at the extremes of age—in elderly adults and in young children younger than 2 years of age. In the U.S., prior to advent of the first pneumococcal vaccine, *S. pneumoniae* caused approximately 17,000 cases of invasive disease each year among children younger than 5 years of age, including 700 cases of meningitis and 200 deaths [CDC, 2000]. The highest morbidity and mortality rates have been reported in developing countries, but the disease burden is also considerable in industrialized countries.

*S. pneumoniae* has several virulence factors that enable the organism to evade the immune system. Examples include a polysaccharide capsule that prevents phagocytosis by host immune cells, proteases that inhibit complement-mediated opsonization, and proteins that cause lysis of host cells. In the polysaccharide capsule, the presence of complex polysaccharides forms the basis for dividing pneumococci into different serotypes. To date, close to 100 serotypes of *S. pneumoniae* have been identified.

Two vaccines for *S. pneumoniae* are currently available in the U.S.: Pneumococcal Conjugate Vaccine (PCV13 or Prevnar 13®) and Pneumococcal Polysaccharide Vaccine (PPSV23 or Pneumovax®). PCV13 cannot confer protection against most of the known serotypes of *S. pneumoniae*. While PPSV23 includes polysaccharide components of more serotypes of *S. pneumoniae* than PCV13, it induces an immune response that is neither long-lasting nor anamnestic upon subsequent challenge. PPSV23 protects adults and the elderly against invasive pneumococcal disease; however, no consistent effect has been observed in the prevention of pneumonia [Gruber et al, 2008].

Thus, there is a medical need for a vaccine that provides T-cell dependent immunity against a broad range of serotypes of *S. pneumoniae*.

SUMMARY

The present disclosure addresses the lack of suitable technologies for the prevention and/or treatment of pneumococcal infection. Among other things, the present disclosure addresses challenges in providing vaccines with sufficient immunogenicity to protect against invasive pneumococcal disease and pneumonia. Technologies described herein can induce a T- and B-cell response and/or provide immunity against a broad range of *S. pneumoniae* serotypes, including one or more serotypes not included in commercially-available vaccines, e.g., PCV13 or PPSV23.

In some embodiments, a fusion protein described herein, when administered to a subject, can induce a higher Th17 response by at least 25% or more including, e.g., at least 30%, at least 40%, at least 50%, at least 60%, at least 70%, at least 80%, at least 90%, at least 95%, at least 98%, or more, as compared to that induced by individual antigenic components of the fusion protein. In some embodiments, a fusion protein described herein, when administered to a subject, can induce a higher Th17 response by at least 1.1-fold or more, including, e.g., at least 1.2-fold, at least 1.3-fold, at least 1.4-fold, at least 1.5-fold, at least 2-fold, at least 3-fold, at least 4-fold, at least 5-fold, at least 10-fold, or higher, as compared to that induced by individual antigenic components of the fusion protein.

In some embodiments, a fusion protein described herein, when administered to a subject, can induce an immune response to one or more representative non-vaccine pneumococcal serotype(s) that is/are not included in a commercially-available vaccine, e.g., PCV13 or PPSV23. In some embodiments, a fusion protein described herein, when administered to a subject, can induce an immune response to one or more non-vaccine pneumococcal serotypes selected from the group consisting of 6B, 16F, 15A, and 35B.

BRIEF DESCRIPTION OF THE DRAWINGS

The present teachings described herein will be more fully understood from the following description of various illustrative embodiments, when read together with the accompanying drawings. It should be understood that the drawings described below are for illustration purposes only and are not intended to limit the scope of the present teachings in any way.

CERTAIN DEFINITIONS

Figure 1:
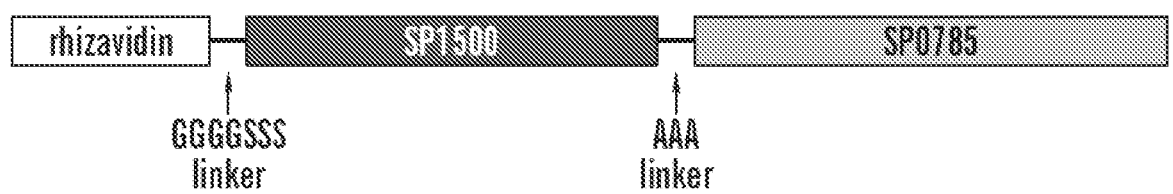
FIG. 1 is a schematic of an exemplary CP1 fusion protein. Such an exemplary CP1 fusion protein comprises a biotin-binding protein such as, e.g., a truncated rhizavidin protein (e.g., amino acids 45-179 of a wild-type rhizavidin protein (denoted Rhavi)), a first linker (e.g., a GGGGSSS linker (SEQ ID NO: 37)), a SP1500 polypeptide (e.g., amino acids 27-278 of *S. pneumoniae* protein SP1500), a second linker (e.g., the amino acid sequence or linker AAA (SEQ ID NO: 38)), and a SP0785 polypeptide (e.g., amino acids 33-399 of *S. pneumoniae* protein SP0785). In some embodiments, a CP1 fusion protein may further comprise a His tag. For a GGGGSSS linker (SEQ ID NO: 37), the SSS amino acid sequence can be from the Sac I site on a PET21/24b plasmid, with the GGGG amino acid sequence (SEQ ID NO: 61) added to create a flexible linker with minimal steric hindrance. Alternatively, the GGGGSSS linker (SEQ ID NO: 37) can be synthesized. The AAA amino acid sequence (SEQ ID NO: 38) can be from the Not I site on a PET21/24b plasmid, or synthesized.

In this application, unless otherwise clear from context, (i) the term "a" may be understood to mean "at least one"; (ii) the term "or" may be understood to mean "and/or"; (iii) the terms "comprising" and "including" may be understood to encompass itemized components or steps whether presented by themselves or together with one or more additional components or steps; and (iv) the terms "about" and "approximately" may be understood to permit standard variation as would be understood by those of ordinary skill in the art; and (v) where ranges are provided, endpoints are included.

About: The term "about", when used herein in reference to a value, refers to a value that is similar, in context to the referenced value. In general, those skilled in the art, familiar with the context, will appreciate the relevant degree of variance encompassed by "about" in that context. For example, in some embodiments, the term "about" may encompass a range of values that within 25%, 20%, 19%, 18%, 17%, 16%, 15%, 14%, 13%, 12%, 11%, 10%, 9%, 8%, 7%, 6%, 5%, 4%, 3%, 2%, 1%, or less of the referred value.

Administration: As used herein, the term "administration" typically refers to the administration of a composition to a subject or system to achieve delivery of an agent that is, or is included in, the composition. Those of ordinary skill in the art will be aware of a variety of routes that may, in appropriate circumstances, be utilized for administration to a subject, for example a human. For example, in some embodiments, administration may be ocular, oral, parenteral, topical, etc. In some particular embodiments, administration may be bronchial (e.g., by bronchial instillation), buccal, dermal (which may be or comprise, for example, one or more of topical to the dermis, intradermal, interdermal, transdermal, etc.), enteral, intra-arterial, intradermal, intragastrical, intramedullary, intramuscular, intranasal, intraperitoneal, intrathecal, intravenous, intraventricular, within a specific organ (e.g., intrahepatic), mucosal, nasal, oral, rectal, subcutaneous, sublingual, topical, tracheal (e.g., by intratracheal instillation), vaginal, vitreal, etc. In some embodiments, administration may involve only a single dose. In some embodiments, administration may involve application of a fixed number of doses. In some embodiments, administration may involve dosing that is intermittent (e.g., a plurality of doses separated in time) and/or periodic (e.g., individual doses separated by a common period of time) dosing. In some embodiments, administration may involve continuous dosing (e.g., perfusion) for at least a selected period of time.

Agent: In general, the term "agent", as used herein, may be used to refer to a compound or entity of any chemical class including, for example, a polypeptide, nucleic acid, saccharide, lipid, small molecule, metal, or combination or complex thereof. In appropriate circumstances, as will be clear from context to those skilled in the art, the term may be utilized to refer to an entity that is or comprises a cell or organism, or a fraction, extract, or component thereof. Alternatively or additionally, as context will make clear, the term may be used to refer to a natural product in that it is found in and/or is obtained from nature. In some instances, again as will be clear from context, the term may be used to refer to one or more entities that is man-made in that it is designed, engineered, and/or produced through action of the hand of man and/or is not found in nature. In some embodiments, an agent may be utilized in isolated or pure form; in some embodiments, an agent may be utilized in crude form. In some embodiments, potential agents may be provided as collections or libraries, for example that may be screened to identify or characterize active agents within them. In some cases, the term "agent" may refer to a compound or entity that is or comprises a polymer; in some cases, the term may refer to a compound or entity that comprises one or more polymeric moieties. In some embodiments, the term "agent" may refer to a compound or entity that is not a polymer and/or is substantially free of any polymer and/or of one or more particular polymeric moieties. In some embodiments, the term may refer to a compound or entity that lacks or is substantially free of any polymeric moiety.

Amino acid: In its broadest sense, the term "amino acid", as used herein, refers to any compound and/or substance that can be incorporated into a polypeptide chain, e.g., through formation of one or more peptide bonds. In some embodiments, an amino acid has the general structure $H_2N—C(H)(R)—COOH$. In some embodiments, an amino acid is a naturally-occurring amino acid. In some embodiments, an amino acid is a non-natural amino acid; in some embodiments, an amino acid is a D-amino acid; in some embodiments, an amino acid is an L-amino acid. "Standard amino acid" refers to any of the twenty standard L-amino acids commonly found in naturally occurring peptides. "Non-standard amino acid" refers to any amino acid, other than the standard amino acids, regardless of whether it is prepared synthetically or obtained from a natural source. In some embodiments, an amino acid, including a carboxy- and/or amino-terminal amino acid in a polypeptide, can contain a structural modification as compared with the general structure above. For example, in some embodiments, an amino acid may be modified by methylation, amidation, acetylation, pegylation, glycosylation, phosphorylation, and/or substitution (e.g., of the amino group, the carboxylic acid group, one or more protons, and/or the hydroxyl group) as compared with the general structure. In some embodiments, such modification may, for example, alter the circulating half-life of a polypeptide containing the modified amino acid as compared with one containing an otherwise identical unmodified amino acid. In some embodiments, such modification does not significantly alter a relevant activity of a polypeptide containing the modified amino acid, as compared with one containing an otherwise identical unmodified amino acid. As will be clear from context, in some embodiments, the term "amino acid" may be used to refer to a free amino acid; in some embodiments it may be used to refer to an amino acid residue of a polypeptide.

Antibody: As used herein, the term "antibody" refers to a polypeptide that includes canonical immunoglobulin sequence elements sufficient to confer specific binding to a particular target antigen. As is known in the art, intact antibodies as produced in nature are approximately 150 kDa tetrameric agents comprised of two identical heavy chain polypeptides (about 50 kDa each) and two identical light chain polypeptides (about 25 kDa each) that associate with each other into what is commonly referred to as a "Y-shaped" structure. Each heavy chain is comprised of at least four domains (each about 110 amino acids long)—an amino-terminal variable (VH) domain (located at the tips of the Y structure), followed by three constant domains: CH1, CH2, and the carboxy-terminal CH3 (located at the base of the Y's stem). A short region, known as the "switch", connects the heavy chain variable and constant regions. The "hinge" connects CH2 and CH3 domains to the rest of the antibody. Two disulfide bonds in this hinge region connect the two heavy chain polypeptides to one another in an intact antibody. Each light chain is comprised of two domains—an amino-terminal variable (VL) domain, followed by a carboxy-terminal constant (CL) domain, separated from one another by another "switch". Intact antibody tetramers are comprised of two heavy chain-light chain dimers in which the heavy and light chains are linked to one another by a single disulfide bond; two other disulfide bonds connect the heavy chain hinge regions to one another, so that the dimers are connected to one another and the tetramer is formed. Naturally-produced antibodies are also glycosylated, typically on the CH2 domain. Each domain in a natural antibody has a structure characterized by an "immunoglobulin fold" formed from two beta sheets (e.g., 3-, 4-, or 5-stranded sheets) packed against each other in a compressed antiparallel beta barrel. Each variable domain contains three hypervariable loops known as "complement determining regions" (CDR1, CDR2, and CDR3) and four somewhat invariant "framework" regions (FR1, FR2, FR3, and FR4). When natural antibodies fold, the FR regions form the beta sheets that provide the structural framework for the domains, and the CDR loop regions from both the heavy and light chains are brought together in three-dimensional space so that they create a single hypervariable antigen binding site located at the tip of the Y structure. The Fc region of naturally-occurring antibodies binds to elements of the complement system, and also to receptors on effector cells, including for example effector cells that mediate cytotoxicity. As is known in the art, affinity and/or other binding attributes of Fc regions for Fc receptors can be modulated through glycosylation or other modification. In some embodiments, antibodies produced and/or utilized in accordance with the present invention include glycosylated Fc domains, including Fc domains with modified or engineered such glycosylation. For purposes of the present invention, in some embodiments, any polypeptide or complex of polypeptides that includes sufficient immunoglobulin domain sequences as found in natural antibodies can be referred to and/or used as an "antibody", whether such polypeptide is naturally produced (e.g., generated by an organism reacting to an antigen), or produced by recombinant engineering, chemical synthesis, or other artificial system or methodology. In some embodiments, an antibody is polyclonal; in some embodiments, an antibody is monoclonal. In some embodiments, an antibody has constant region sequences that are characteristic of mouse, rabbit, primate, or human antibodies. In some embodiments, antibody sequence elements are humanized, primatized, chimeric, etc., as is known in the art. Moreover, the term "antibody" as used herein, can refer in appropriate embodiments (unless otherwise stated or clear from context) to any of the art-known or developed constructs or formats for utilizing antibody structural and functional features in alternative presentation. For example, in some embodiments, an antibody utilized in accordance with the present invention is in a format selected from, but not limited to, intact IgA, IgG, IgE or IgM antibodies; bi- or multi-specific antibodies (e.g., Zybodies®, etc.); antibody fragments such as Fab fragments, Fab' fragments, F(ab')2 fragments, Fd' fragments, Fd fragments, and isolated CDRs or sets thereof; single chain Fvs; polypeptide-Fc fusions; single domain antibodies (e.g., shark single domain antibodies such as IgNAR or fragments thereof); cameloid antibodies; masked antibodies (e.g., Probodies®); Small Modular ImmunoPharmaceuticals ("SMIPs™"); single chain or Tandem diabodies (TandAb®); VHHs; Anticalins®; Nanobodies® minibodies; BiTE®s; ankyrin repeat proteins or DARPINs®; Avimers®; DARTs; TCR-like antibodies; Adnectins®; Affilins®; Transbodies®; Affibodies®; TrimerX®; MicroProteins; Fynomers®, Centyrins®; and KALBITOR®s. In some embodiments, an antibody may lack a covalent modification (e.g., attachment of a glycan) that it would have if produced naturally. In some embodiments, an antibody may contain a covalent modification (e.g., attachment of a glycan, a payload [e.g., a detectable moiety, a therapeutic moiety, a catalytic moiety, etc.], or other pendant group [e.g., polyethylene glycol, etc.]).

Antigen: The term "antigen", as used herein, refers to (i) an agent that induces an immune response; and/or (ii) an agent that binds to a T cell receptor (e.g., when presented by an MHC molecule) or to an antibody. In some embodiments, an antigen induces a humoral response (e.g., including production of antigen-specific antibodies); in some embodiments, an antigen induces a cellular response (e.g., involving T cells whose receptors specifically interact with the antigen). In some embodiments, an antigen induces a humoral response and a cellular response. In some embodiments, an antigen binds to an antibody and may or may not induce a particular physiological response in an organism. In general, an antigen may be or include any chemical entity such as, for example, a small molecule, a nucleic acid, a polypeptide, a carbohydrate, a lipid, a polymer (in some embodiments other than a biologic polymer (e.g., other than a nucleic acid or amino acid polymer)), etc. In some embodiments, an antigen is or comprises a polypeptide. In some embodiments, an antigen is or comprises a polysaccharide. Those of ordinary skill in the art will appreciate that, in general, an antigen may be provided in isolated or pure form, or alternatively may be provided in crude form (e.g., together with other materials, for example in an extract such as a cellular extract or other relatively crude preparation of an antigen-containing source). In some embodiments, antigens utilized in accordance with the present invention are provided in a crude form. In some embodiments, an antigen is a recombinant antigen. In some embodiments, an antigen is a polypeptide or a polysaccharide that, upon administration to a subject, induces a specific and/or clinically relevant immune response to such polypeptide or polysaccharide. In some embodiments, an antigen is selected to induce a specific and/or clinically relevant immune response to such polypeptide or polysaccharide.

Associated with: Two entities are "associated" with one another, as that term is used herein, if the presence, level and/or form of one is correlated with that of the other. In some embodiments, two or more entities are physically "associated" with one another if they interact, directly or indirectly, so that they are and/or remain in physical proximity with one another. In some embodiments, two or more entities that are physically associated with one another are covalently linked to one another. In some embodiments, two or more entities that are physically associated with one another are not covalently linked to one another but are non-covalently associated, for example by means of affinity interactions, electrostatic interactions, hydrogen bonds, van der Waals interaction, hydrophobic interactions, magnetism, and combinations thereof.

Binding: It will be understood that the term "binding", as used herein, typically refers to a non-covalent association between or among two or more entities. "Direct" binding involves physical contact between entities or moieties; indirect binding involves physical interaction by way of physical contact with one or more intermediate entities. Binding between two or more entities can typically be assessed in any of a variety of contexts—including where interacting entities or moieties are studied in isolation or in the context of more complex systems (e.g., while covalently or otherwise associated with a carrier entity and/or in a biological system or cell).

Carrier protein: As used herein, the term "carrier protein" refers to a protein or peptide that is coupled, complexed, or otherwise associated with a hapten (e.g., a small peptide or lipid) or less immunogenic antigen (e.g., a polysaccharide) and that induces or improves an immune response to such a coupled, or complexed, or otherwise associated hapten (e.g., a small peptide or lipid) or less immunogenic antigen (e.g., a polysaccharide). In some embodiments, such an immune response is or comprises a response to a hapten or less immunogenic antigen that is coupled, complexed, or otherwise associated with such a carrier protein. In some embodiments, such an immune response is or comprises a response to both a carrier protein and a hapten or less immunogenic antigen that is coupled, complexed, or otherwise associated with such a carrier protein. In some embodiments, no significant immune response to a carrier protein itself occurs. In some embodiments, immune response to a carrier protein may be detected; in some such embodiments, immune response to such a carrier protein is strong. In some embodiments, a carrier protein is coupled, complexed, or otherwise associated with one or more other molecules.

Colonization: As used herein, the term "colonization" generally refers to the ability of a microbe to grow at a target site or surface. For example, the term "colonization" refers to the ability of a microbe (e.g., a bacterium) to grow at an anatomical site (e.g., a mucosal membrane, gastrointestinal tract, injury site, organ, etc.) of a host.

Combination therapy: As used herein, the term "combination therapy" refers to those situations in which a subject is exposed to two or more therapeutic regimens (e.g., two or more therapeutic agents). In some embodiments, the two or more regimens may be administered simultaneously; in some embodiments, such regimens may be administered sequentially (e.g., all "doses" of a first regimen are administered prior to administration of any doses of a second regimen); in some embodiments, such agents are administered in overlapping dosing regimens. In some embodiments, "administration" of combination therapy may involve administration of one or more agent(s) or modality(ies) to a subject receiving the other agent(s) or modality(ies) in the combination. For clarity, combination therapy does not require that individual agents be administered together in a single composition (or even necessarily at the same time), although in some embodiments, two or more agents, or active moieties thereof, may be administered together in a combination composition, or even in a combination compound (e.g., as part of a single chemical complex or covalent entity).

Derivative: As used herein, the term "derivative", or grammatical equivalents thereof, refers to a structural analogue of a reference substance. That is, a "derivative" is a substance that shows significant structural similarity with the reference substance, for example sharing a core or consensus structure, but also differs in certain discrete ways. Such a substance would be said to be "derived from" said reference substance. In some embodiments, a derivative is a substance that can be generated from the reference substance by chemical manipulation. In some embodiments, a derivative is a substance that can be generated through performance of a synthetic process substantially similar to (e.g., sharing a plurality of steps with) one that generates the reference substance.

Domain: The term "domain" as used herein refers to a section or portion of an entity. In some embodiments, a "domain" is associated with a particular structural and/or functional feature of the entity so that, when the domain is physically separated from the rest of its parent entity, it substantially or entirely retains the particular structural and/or functional feature. Alternatively or additionally, a domain may be or include a portion of an entity that, when separated from that (parent) entity and linked with a different (recipient) entity, substantially retains and/or imparts on the recipient entity one or more structural and/or functional features that characterized it in the parent entity. In some embodiments, a domain is a section or portion of a molecule (e.g., a small molecule, carbohydrate, lipid, nucleic acid, or polypeptide). In some embodiments, a domain is a section of a polypeptide; in some such embodiments, a domain is characterized by a particular structural element (e.g., a particular amino acid sequence or sequence motif, α-helix character, β-sheet character, coiled-coil character, random coil character, etc.), and/or by a particular functional feature (e.g., binding activity, enzymatic activity, folding activity, signaling activity, etc.).

Dosage form or unit dosage form: Those skilled in the art will appreciate that the term "dosage form" may be used to refer to a physically discrete unit of an active agent (e.g., a therapeutic or diagnostic agent) for administration to a subject. Typically, each such unit contains a predetermined quantity of active agent. In some embodiments, such quantity is a unit dosage amount (or a whole fraction thereof) appropriate for administration in accordance with a dosing regimen that has been determined to correlate with a desired or beneficial outcome when administered to a relevant population (i.e., with a therapeutic dosing regimen). Those of ordinary skill in the art appreciate that the total amount of a therapeutic composition or agent administered to a particular subject is determined by one or more attending physicians and may involve administration of multiple dosage forms.

Dosing regimen: Those skilled in the art will appreciate that the term "dosing regimen" may be used to refer to a set of unit doses (typically more than one) that are administered individually to a subject, typically separated by periods of time. In some embodiments, a given therapeutic agent has a recommended dosing regimen, which may involve one or more doses. In some embodiments, a dosing regimen comprises a plurality of doses each of which is separated in time from other doses. In some embodiments, individual doses are separated from one another by a time period of the same length; in some embodiments, a dosing regimen comprises a plurality of doses and at least two different time periods separating individual doses. In some embodiments, all doses within a dosing regimen are of the same unit dose amount. In some embodiments, different doses within a dosing regimen are of different amounts. In some embodiments, a dosing regimen comprises a first dose in a first dose amount, followed by one or more additional doses in a second dose amount different from the first dose amount. In some embodiments, a dosing regimen comprises a first dose in a first dose amount, followed by one or more additional doses in a second dose amount same as the first dose amount. In some embodiments, a dosing regimen is correlated with a desired or beneficial outcome when administered across a relevant population (i.e., is a therapeutic dosing regimen).

Fragment: A "fragment" of a material or entity as described herein has a structure that includes a discrete portion of the whole, but lacks one or more moieties found in the whole. In some embodiments, a fragment consists of such a discrete portion. In some embodiments, a fragment includes a discrete portion of the whole which discrete portion shares one or more functional characteristics found in the whole. In some embodiments, a fragment consists of such a discrete portion. In some embodiments, a fragment consists of or comprises a characteristic structural element or moiety found in the whole. In some embodiments, a fragment of a polymer, e.g., a polypeptide or polysaccharide, comprises or consists of at least 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 275, 300, 325, 350, 375, 400, 425, 450, 475, 500 or more monomeric units (e.g., residues) as found in the whole polymer. In some embodiments, a polymer fragment comprises or consists of at least about 5%, 10%, 15%, 20%, 25%, 30%, 25%, 40%, 45%, 50%, 55%, 60%, 65%, 70%, 75%, 80%, 85%, 90%, 95%, 96%, 97%, 98%, or 99% of the monomeric units (e.g., residues) found in the whole polymer. The whole material or entity may in some embodiments be referred to as the "parent" of the whole.

Homology: As used herein, the term "homology" refers to the overall relatedness between polymeric molecules, e.g., between nucleic acid molecules (e.g., DNA molecules and/or RNA molecules) and/or between polypeptide molecules. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, 96%, 97%, 98% or 99% identical. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, 96%, 97%, 98% or 99% similar (e.g., containing residues with related chemical properties at corresponding positions). For example, as is well known by those of ordinary skill in the art, certain amino acids are typically classified as similar to one another as "hydrophobic" or "hydrophilic" amino acids, and/or as having "polar" or "non-polar" side chains. Substitution of one amino acid for another of the same type may often be considered a "homologous" substitution.

Identity: As used herein, the term "identity" refers to the overall relatedness between polymeric molecules, e.g., between nucleic acid molecules (e.g., DNA molecules and/or RNA molecules) and/or between polypeptide molecules. In some embodiments, polymeric molecules are considered to be "substantially identical" to one another if their sequences are at least 25%, 30%, 35%, 40%, 45%, 50%, 55%, 60%, 65%, 70%, 75%, 80%, 85%, 90%, 95%, 96%, 97%, 98% or 99% identical. Calculation of the percent identity of two nucleic acid or polypeptide sequences, for example, can be performed by aligning the two sequences for optimal comparison purposes (e.g., gaps can be introduced in one or both of a first and a second sequence for optimal alignment and non-identical sequences can be disregarded for comparison purposes). In some embodiments, the length of a sequence aligned for comparison purposes is at least 30%, at least 40%, at least 50%, at least 60%, at least 70%, at least 75%, at least 80%, at least 85%, at least 90%, at least 95%, at least 96%, at least 97%, at least 98%, at least 99%, at least 99.5%, or substantially 100% of the length of a reference sequence. The nucleotides at corresponding positions are then compared. When a position in the first sequence is occupied by the same residue (e.g., nucleotide or amino acid) as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. For example, the percent identity between two nucleotide sequences can be determined using the algorithm of Meyers and Miller, 1989, which has been incorporated into the ALIGN program (version 2.0). In some exemplary embodiments, nucleic acid sequence comparisons made with the ALIGN program use a PAM120 weight residue table, a gap length penalty of 12 and a gap penalty of 4. The percent identity between two nucleotide sequences can, alternatively, be determined using the GAP program in the GCG software package using an NWSgapdna.CMP matrix.

Improve, increase, inhibit or reduce: As used herein, the terms "improve", "increase", "inhibit", "reduce", or grammatical equivalents thereof, indicate values that are relative to a baseline or other reference measurement. In some embodiments, an appropriate reference measurement may be or comprise a measurement in a particular system (e.g., in a single subject) under otherwise comparable conditions absent presence of (e.g., prior to and/or after) a particular agent or treatment, or in presence of an appropriate comparable reference agent. In some embodiments, an appropriate reference measurement may be or comprise a measurement in comparable system known or expected to respond in a particular way, in presence of the relevant agent or treatment.

Immunologically effective amount or immunologically effective dose: As used herein, "immunologically effective amount" or "immunologically effective dose" refers to an amount of an antigenic or immunogenic substance, e.g., an antigen, immunogen, immunogenic complex, immunogenic composition, vaccine, or pharmaceutical composition, which when administered to a subject, either in a single dose or as part of a series of doses, that is sufficient to enhance a subject's own immune response against a subsequent exposure to a pathogen. In some embodiments, the pathogen is *S. pneumoniae*. In some embodiments, the immune response is against one or more different serotypes of *S. pneumoniae*. In some embodiments, the immune response is against two or more different serotypes of *S. pneumoniae*. In some embodiments, the immune response is against nine or more different serotypes of *S. pneumoniae*. In some embodiments, the immune response is against thirteen or more different serotypes of *S. pneumoniae*. In some embodiments, the immune response is against fifteen or more different serotypes of *S. pneumoniae*. In some embodiments, the immune response is against twenty-three or more different serotypes of *S. pneumoniae*. In some embodiments, the immune response is against twenty-four or more different serotypes of *S. pneumoniae*. An immunologically effective amount may vary based on the subject to be treated, the species of the subject, the degree of immune response desired to induce, etc. In some embodiments, an immunologically effective amount is sufficient for treatment or protection of a subject having or at risk of having disease. In some embodiments, an immunologically effective amount refers to a non-toxic but sufficient amount that can be an amount to treat, attenuate, or prevent infection and/or disease (e.g., bacterial infection, pneumococcal infection, bacterial colonization, pneumococcal colonization, complications associated with bacterial infection, complications associated with pneumococcal infection, etc.) in any subject. In some embodiments, an immunologically effective amount is sufficient to induce an immunoprotective response upon administration to a subject.

Immunoprotective response or protective response: As used herein, "immunoprotective response" or "protective response" refers to an immune response that mediates antigen or immunogen-induced immunological memory. In some embodiments, an immunoprotective response is induced by the administration of a substance, e.g., an antigen, immunogen, immunogenic complex, immunogenic composition, vaccine, or pharmaceutical composition to a subject. In some embodiments, immunoprotection involves one or more active immune surveillance, a more rapid and effective response upon immune activation as compared to a response observed in a naïve subject, efficient clearance of the activating agent or pathogen, followed by rapid resolution of inflammation. In some embodiments, an immunoprotective response is an adaptive immune response. In some embodiments, an immunoprotective response is sufficient to protect an immunized subject from productive infection by a particular pathogen or pathogens to which a vaccine is directed (e.g., *S. pneumoniae* infection).

Immunization: As used herein, "immunization", or grammatical equivalents thereof, refers to a process of inducing an immune response to an infectious organism or agent in a subject ("active immunization"), or alternatively, providing immune system components against an infectious organism or agent to a subject ("passive immunization"). In some embodiments, immunization involves the administration of one or more antigens, immunogens, immunogenic complexes, vaccines, immune molecules such as antibodies, immune sera, immune cells such as T cells or B cells, or pharmaceutical compositions to a subject. In some embodiments, immunization is performed by administering an immunologically effective amount of a substance, e.g., an antigen, immunogen, immunogenic complex, immunogenic composition, vaccine, immune molecule such as an antibody, immune serum, immune cell such as a T cell or B cell, or pharmaceutical composition to a subject. In some embodiments, immunization results in an immunoprotective response in the subject. In some embodiments, active immunization is performed by administering to a subject an antigenic or immunogenic substance, e.g., an antigen, immunogen, immunogenic complex, vaccine, or pharmaceutical composition. In some embodiments, passive immunization is performed by administering to a subject an immune system component, e.g., an immune molecule such as an antibody, immune serum, or immune cell such as a T cell or B cell.

Isolated: As used herein, the term "isolated", or grammatical equivalents thereof, refers to a substance and/or entity that has been (1) separated from at least some of the components with which it was associated when initially produced (whether in nature and/or in an experimental setting), and/or (2) designed, produced, prepared, and/or manufactured by the hand of man. Isolated substances and/or entities may be separated from about 10%, about 20%, about 30%, about 40%, about 50%, about 60%, about 70%, about 80%, about 90%, about 91%, about 92%, about 93%, about 94%, about 95%, about 96%, about 97%, about 98%, about 99%, or more than about 99% of the other components with which they were initially associated. In some embodiments, isolated agents are about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. In some embodiments, as will be understood by those skilled in the art, a substance may still be considered "isolated" or even "pure", after having been combined with certain other components such as, for example, one or more carriers or excipients (e.g., buffer, solvent, water, etc.); in such embodiments, percent isolation or purity of the substance is calculated without including such carriers or excipients. To give but one example, in some embodiments, a biological polymer such as a polypeptide or polysaccharide that occurs in nature is considered to be "isolated" when, a) by virtue of its origin or source of derivation is not associated with some or all of the components that accompany it in its native state in nature; b) it is substantially free of other polypeptides or nucleic acids of the same species from the species that produces it in nature; c) is expressed by or is otherwise in association with components from a cell or other expression system that is not of the species that produces it in nature. Thus, for instance, in some embodiments, a polypeptide or polysaccharide that is chemically synthesized or is synthesized in a cellular system different from that which produces it in nature is considered to be an "isolated" polypeptide or polysaccharide. Alternatively or additionally, in some embodiments, a polypeptide or polysaccharide that has been subjected to one or more purification techniques may be considered to be an "isolated" polypeptide or polysaccharide to the extent that it has been separated from other components a) with which it is associated in nature; and/or b) with which it was associated when initially produced.

Linker: As used herein, the term "linker" is used to refer to an entity that connects two or more elements to form a multi-element agent. For example, those of ordinary skill in the art appreciate that a polypeptide whose structure includes two or more functional or organizational domains often includes a stretch of amino acids between such domains that links them to one another. In some embodiments, a polypeptide comprising a linker element has an overall structure of the general form S1-L-S2, wherein S1 and S2 may be the same or different and represent two domains associated with one another by the linker (L). In some embodiments, a polypeptide linker is at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100 or more amino acids in length. In some embodiments, a linker is characterized in that it tends not to adopt a rigid three-dimensional structure, but rather provides flexibility to the polypeptide. A variety of different linker elements that can appropriately be used when engineering polypeptides (e.g., fusion polypeptides) are known in the art (Holliger et al, 1993; Poljak, 1994).

Pharmaceutical composition: As used herein, the term "pharmaceutical composition" refers to a composition in which an active agent is formulated together with one or more pharmaceutically acceptable carriers. In some embodiments, the active agent is present in unit dose amount appropriate for administration in a therapeutic regimen that shows a statistically significant probability of achieving a predetermined therapeutic effect when administered to a relevant population. In some embodiments, a pharmaceutical composition may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream, or foam; sublingually; ocularly; transdermally; or nasally, pulmonary, and to other mucosal surfaces.

Pharmaceutically acceptable: As used herein, the term "pharmaceutically acceptable" applied to the carrier, diluent, or excipient used to formulate a composition as disclosed herein means that the carrier, diluent, or excipient must be compatible with the other ingredients of the composition and not deleterious to the recipient thereof.

Polysaccharide: The term "polysaccharide" as used herein refers to a polymeric carbohydrate molecule composed of long chains of monosaccharide units bound together by glycosidic, phosphodiester, or other linkages, and on hydrolysis give the constituent monosaccharides or oligosaccharides. Polysaccharides range in structure from linear to highly branched. Examples include storage polysaccharides such as starch and glycogen, structural polysaccharides such as cellulose and chitin and microbial polysaccharides, and antigenic polysaccharides found in microorganisms including, but not limited to, capsular polysaccharides (CPS), O polysaccharides (OPS), core O polysaccharides (COPS), and lipopolysaccharides (LPS).

Polypeptide: The term "polypeptide", as used herein, generally has its art-recognized meaning of a polymer of at least three amino acids, e.g., linked to each other by peptide bonds. Those of ordinary skill in the art will appreciate that the term "polypeptide" is intended to be sufficiently general as to encompass not only polypeptides having a complete sequence recited herein, but also to encompass polypeptides that represent functional fragments (i.e., fragments retaining at least one activity) of such complete polypeptides. Moreover, those of ordinary skill in the art understand that protein sequences generally tolerate some substitution without destroying activity. Thus, any polypeptide that retains activity and shares at least about 30-40% overall sequence identity, often greater than about 50%, 60%, 70%, or 80%, and further usually including at least one region of much higher identity, often greater than 90% or even 95%, 96%, 97%, 98%, or 99% in one or more highly conserved regions, usually encompassing at least 3-4 and often up to 20 or more amino acids, with another polypeptide of the same class, is encompassed within the relevant term "polypeptide" as used herein. Polypeptides may contain L-amino acids, D-amino acids, or both and may contain any of a variety of amino acid modifications or analogs known in the art. Useful modifications include, e.g., terminal acetylation, amidation, methylation, etc. In some embodiments, proteins may comprise natural amino acids, non-natural amino acids, synthetic amino acids, and combinations thereof.

Prevention: The term "prevent" or "prevention", as used herein in connection with a disease, disorder, and/or medical condition, refers to reducing the risk of developing the disease, disorder and/or condition, and/or a delay of onset, and/or reduction in frequency and/or severity of one or more characteristics or symptoms of a particular disease, disorder or condition. In some embodiments, prevention is assessed on a population basis such that an agent is considered to "prevent" a particular disease, disorder or condition if a statistically significant decrease in the development, frequency, and/or intensity of one or more symptoms of the disease, disorder or condition is observed in a population susceptible to the disease, disorder, or condition. In some embodiments, prevention may be considered complete when onset of a disease, disorder or condition has been delayed for a predefined period of time.

Protein: As used herein, the term "protein" encompasses a polypeptide. Proteins may include moieties other than amino acids (e.g., may be glycoproteins, proteoglycans, etc.) and/or may be otherwise processed or modified. Those of ordinary skill in the art will appreciate that a "protein" can be a complete polypeptide chain as produced by a cell (with or without a signal sequence), or can be a characteristic portion thereof. Those of ordinary skill will appreciate that a protein can sometimes include more than one polypeptide chain, for example linked by one or more disulfide bonds or associated by other means. Polypeptides may contain 1-amino acids, d-amino acids, or both and may contain any of a variety of amino acid modifications or analogs known in the art. Useful modifications include, e.g., terminal acetylation, amidation, methylation, etc. In some embodiments, proteins may comprise natural amino acids, non-natural amino acids, synthetic amino acids, and combinations thereof. The term "peptide" is generally used to refer to a polypeptide having a length of less than about 100 amino acids, less than about 50 amino acids, less than 20 amino acids, or less than 10 amino acids. In some embodiments, proteins are antibodies, antibody fragments, biologically active portions thereof, and/or characteristic portions thereof.

Recombinant: As used herein, the term "recombinant" is intended to refer to polypeptides that are designed, engineered, prepared, expressed, created, manufactured, and/or isolated by recombinant means, such as polypeptides expressed using a recombinant expression vector transfected into a host cell; polypeptides isolated from a recombinant, combinatorial human polypeptide library; polypeptides isolated from an animal (e.g., a mouse, rabbit, sheep, fish, etc.) that is transgenic for or otherwise has been manipulated to express a gene or genes, or gene components that encode and/or direct expression of the polypeptide or one or more component(s), portion(s), element(s), or domain(s) thereof, and/or polypeptides prepared, expressed, created or isolated by any other means that involves splicing or ligating selected nucleic acid sequence elements to one another, chemically synthesizing selected sequence elements, and/or otherwise generating a nucleic acid that encodes and/or directs expression of the polypeptide or one or more component(s), portion(s), element(s), or domain(s) thereof. In some embodiments, one or more of such selected sequence elements is found in nature. In some embodiments, one or more of such selected sequence elements is designed in silico. In some embodiments, one or more such selected sequence elements results from mutagenesis (e.g., in vivo or in vitro) of a known sequence element, e.g., from a natural or synthetic source such as, for example, in the germline of a source organism of interest (e.g., of a human, a mouse, etc.).

Reference: As used herein, the term "reference" describes a standard or control relative to which a comparison is performed. For example, in some embodiments, an agent, animal, subject, population, sample, sequence or value of interest is compared with a reference or control agent, animal, subject, population, sample, sequence or value. In some embodiments, a reference or control is tested and/or determined substantially simultaneously with the testing or determination of interest. In some embodiments, a reference or control is a historical reference or control, optionally embodied in a tangible medium. Typically, as would be understood by those skilled in the art, a reference or control is determined or characterized under comparable conditions or circumstances to those under assessment. Those skilled in the art will appreciate when sufficient similarities are present to justify reliance on and/or comparison to a particular possible reference or control.

Response: As used herein, a "response" to treatment may refer to any beneficial alteration in a subject's condition that occurs as a result of or correlates with treatment. Such alteration may include stabilization of the condition (e.g., prevention of deterioration that would have taken place in the absence of the treatment), amelioration of symptoms of the condition, and/or improvement in the prospects for cure of the condition, etc. It may refer to a subject's response or to a tumor's response. Subject or tumor response may be measured according to a wide variety of criteria, including clinical criteria and objective criteria. Techniques for assessing response include, but are not limited to, clinical examination, positron emission tomography, chest X-ray CT scan, MRI, ultrasound, endoscopy, laparoscopy, presence or level of biomarkers in a sample obtained from a subject, cytology, and/or histology. The exact response criteria can be selected in any appropriate manner, provided that when comparing groups of subjects and/or tumors, the groups to be compared are assessed based on the same or comparable criteria for determining response rate. One of ordinary skill in the art will be able to select appropriate criteria.

Risk: As will be understood from context, "risk" of a disease, disorder, and/or condition refers to a likelihood that a particular subject will develop the disease, disorder, and/or condition. In some embodiments, risk is expressed as a percentage. In some embodiments, risk is from 0, 1, 2, 3, 4, 5, 6, 7, 8, 9, 10, 20, 30, 40, 50, 60, 70, 80, 90 up to 100%. In some embodiments, risk is expressed as a risk relative to a risk associated with a reference sample or group of reference samples. In some embodiments, a reference sample or group of reference samples have a known risk of a disease, disorder, condition and/or event. In some embodiments a reference sample or group of reference samples are from subjects comparable to a particular subject. In some embodiments, relative risk is 0, 1, 2, 3, 4, 5, 6, 7, 8, 9, 10, or more.

Serotype: As used herein, the term "serotype", also referred to as a serovar, refers to a distinct variation within a species of bacteria or virus or among immune cells of different subjects. These microorganisms, viruses, or cells are classified together based on their cell surface antigens, allowing the epidemiologic classification of organisms to the sub-species level. A group of serovars with common antigens may be referred to as a serogroup or sometimes serocomplex.

Subject: As used herein, the term "subject" refers an organism, typically a mammal (e.g., a human, in some embodiments including prenatal human forms). In some embodiments, a subject is suffering from a relevant disease, disorder or condition. In some embodiments, a subject is susceptible to a disease, disorder, or condition. In some embodiments, a subject displays one or more symptoms or characteristics of a disease, disorder or condition. In some embodiments, a subject does not display any symptom or characteristic of a disease, disorder, or condition. In some embodiments, a subject is someone with one or more features characteristic of susceptibility to or risk of a disease, disorder, or condition. In some embodiments, a subject is a patient. In some embodiments, a subject is a subject to whom diagnosis and/or therapy is and/or has been administered.

Susceptible to: A subject who is "susceptible to" a disease, disorder, or condition is at risk for developing the disease, disorder, or condition. In some embodiments, a subject who is susceptible to a disease, disorder, or condition does not display any symptoms of the disease, disorder, or condition. In some embodiments, a subject who is susceptible to a disease, disorder, or condition has not been diagnosed with the disease, disorder, and/or condition. In some embodiments, a subject who is susceptible to a disease, disorder, or condition is a subject who has been exposed to conditions associated with development of the disease, disorder, or condition. In some embodiments, a risk of developing a disease, disorder, and/or condition is a population-based risk (e.g., family members of subjects suffering from the disease, disorder, or condition).

Symptoms are reduced: As used herein, "symptoms are reduced" when one or more symptoms of a particular disease, disorder or condition is reduced in magnitude (e.g., intensity, severity, etc.) and/or frequency, e.g., to a statistically and/or clinically significant or relevant level. For purposes of clarity, a delay in the onset of a particular symptom is considered one form of reducing the frequency of that symptom.

Treatment: As used herein, the term "treatment" (also "treat" or "treating") refers to any administration of a therapy that partially or completely alleviates, ameliorates, relieves, inhibits, delays onset of, reduces severity of, and/or reduces incidence of one or more symptoms, features, and/or causes of a particular disease, disorder, and/or condition. In some embodiments, such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition. In some embodiments, treatment may be of a subject who has been diagnosed as suffering from the relevant disease, disorder, and/or condition. In some embodiments, treatment may be of a subject known to have one or more susceptibility factors that are statistically correlated with increased risk of development of the relevant disease, disorder, and/or condition.

Vaccination: As used herein, the term "vaccination" refers to the administration of a composition intended to generate an immune response, for example to a disease-causing agent. For the purposes of the present invention, vaccination can be administered before, during, and/or after exposure to a disease-causing agent, and in some embodiments, before, during, and/or shortly after exposure to the agent. In some embodiments, vaccination includes multiple administrations, appropriately spaced in time, of a vaccinating composition. In some embodiments, vaccination initiates immunization.

DETAILED DESCRIPTION OF CERTAIN EMBODIMENTS

The present disclosure relates, generally, to novel immunogenic fusion proteins of *S. pneumoniae* that can be used, e.g., to induce and/or increase an immunoprotective response, or to reduce pneumococcal colonization in subjects at risk of or suffering from pneumococcal infection.

Two vaccines for *S. pneumoniae* are currently available in the U.S. PCV13, a 13-valent conjugate vaccine, has been approved for the prevention of invasive pneumococcal disease (IPD) caused by the 13 serotypes contained in the vaccine in children and for the prevention of pneumonia and IPD in adults. In this vaccine, covalent conjugation of saccharides of the 13 pneumococcal serotypes to the CRM197 protein creates saccharide-protein conjugates, which are capable of inducing a T cell-dependent immune response against one or more of the 13 pneumococcal serotypes represented by the saccharides. [PREVNAR 13 prescribing information, 2017]. While infections with *S. pneumoniae* of multidrug-resistant serotypes contained in PCV13 appeared to decrease after approval of this vaccine, an increase of infections with multidrug-resistant serotypes 35B, 23A, 23B and 15B, which are just a few of the over 84 known serotypes of *S. pneumoniae* not included in PCV13, was noted. Also, PCV13 was reported to have marginal activity against serotype 3, as its prevalence persists in the population [Richter et al, 2014].

The second vaccine, PPSV23, is a 23-valent polysaccharide vaccine and is indicated for the prevention of pneumococcal disease in adults greater than 50 years of age, or in persons greater than 2 years of age at increased risk of pneumococcal disease. It is composed of purified capsular polysaccharides from 23 pneumococcal serotypes. While this vaccine has the potential to protect against more serotypes when compared to PCV13, it does not provide protection against the emerging serotypes 35B, 23A and 23B. In addition, PPSV23 elicits a T cell-independent polysaccharide immune response that stimulates mature B-lymphocytes, but not T-lymphocytes. Thus, this vaccine only induces an immune response that is neither long-lasting nor anamnestic upon subsequent challenge. PPSV23 is not effective against colonization. In addition, polysaccharide-type vaccines are not used in infants and children less than 2 years of age, because these children respond poorly to T cell-independent antigens [PNEUMOVAX 23 prescribing information, 2017; CDC, 2010]. Data suggest that PPSV23 may protect adults and the elderly against IPD; however, no consistent effect has been observed in the prevention of pneumonia [Gruber et al, 2008].

The presently disclosed novel immunogenic proteins represent a substantial advance over the currently available options for immunizing patients against pneumococcal infection. Such immunogenic proteins can be used, e.g., to induce and/or increase an immunoprotective response or to reduce pneumococcal colonization in subjects, such as those at risk of or suffering from pneumococcal infection.

Fusion Proteins

The present disclosure describes novel immunogenic fusion proteins of *S. pneumoniae*. In WO2014/124228, the inventors demonstrated that the pneumococcal antigens SP0785 and SP1500 individually elicited a strong IL-17 recall response in re-stimulated human PBMCs and splenocytes of mice that have been exposed to pneumococcus. Immunization of mice with SP0785 plus cholera toxin adjuvant, or with SP1500 plus cholera toxin adjuvant, resulted in significant reduction of pneumococcal colonization (on the order of 100-fold). Immunization with a fusion of SP0785 to the pneumolysoid PdT, or a fusion of SP0785 to the pneumolysoid PdT further conjugated to a polysaccharide of *Salmonella typhi*, protected 80% of mice from sepsis in a lethal challenge with live *S. pneumoniae*. Immunization with a fusion of SP0785, SP1500 and the pneumolysoid PdT further conjugated to a polysaccharide of *Salmonella typhi*, also resulted in significant reduction of pneumococcal colonization (on the order of 10-fold).

Fusion proteins described and/or utilized herein provide improved immunogenicity and IL-17 response to protein stimulation, as well as further reduction of *S. pneumoniae* colonization and protection from invasive diseases.

A fusion protein includes one, two, or more polypeptides that elicit (e.g., primarily elicit) a T cell response, or that elicit both a T cell and a B cell response. In some embodiments, the fusion protein comprises one or more of the polypeptides listed in Table 1. In some embodiments, the fusion protein comprises two of the polypeptides listed in Table 1. In some embodiments, the fusion protein comprises three of the polypeptides listed in Table 1. In some embodiments, the fusion protein comprises one or more of polypeptides encoded by one or more of the genes listed in Table 1. In some embodiments, the fusion protein comprises two of polypeptides encoded by two or more of the genes listed in Table 1. In some embodiments, the fusion protein comprises three polypeptides encoded by three of the genes listed in Table 1.

TABLE 1

Exemplary Polypeptide Components of Fusion Proteins

| Locus tag name and description | Protein SEQ ID No. | DNA SEQ ID No. | NCBI Accession No. |
|---|---|---|---|
| rhizavidin, full-length | 1 | 9 | — |
| rhizavidin, truncated [aa 45-179] (denoted Rhavi) | 2 | 10 | n/a |
| SP0785, full-length (TIGR4 strain) | 3 | 11 | ABJ54007.1 |
| SP0785, truncated [aa 33-399] | 4 | 12 | n/a |
| SP0785, consensus full-length | 5 | n/a | n/a |
| SP1500, full-length (TIGR4 strain) | 6 | 13 | AAK75591.1 |
| SP1500, truncated [aa 27-278] | 7 | 14 | n/a |
| SP1500, consensus full-length | 8 | n/a | n/a |

In some embodiments, a fusion protein comprises one or more antigenic polypeptides of *S. pneumoniae* having an amino acid sequence comprising any of SEQ ID NOs: 3-8, or antigenic fragments thereof. In some embodiments, a fusion protein comprises two antigenic polypeptides having an amino acid sequence comprising any of SEQ ID NOs:3-8, or antigenic fragments thereof. In some embodiments, a fusion protein comprises (i) two antigenic polypeptides having an amino acid sequence comprising any of SEQ ID NOs:3-8, or antigenic fragments thereof, and (i) a biotin-binding moiety comprising SEQ ID NO:1 or 2, or biotin-binding fragments thereof. In some such embodiments, at least one antigenic polypeptide is or comprises an SP0785 polypeptide (e.g., SEQ ID NOs:3-5). In some such embodiments, at least one antigenic polypeptide is or comprises an SP1500 polypeptide (e.g., SEQ ID NOs:6-8).

In some embodiments, a fusion protein comprises one or more polypeptides homologous to the S. pneumoniae polypeptides listed in Table 1, e.g., an SP0785 polypeptide or an SP1500 polypeptide isolated from different serotypes of S. pneumoniae. Individual serotypes of S. pneumoniae contain numerous mutations relative to each other, and some of these result in different protein sequences between the different serotypes. One of skill in the art may readily substitute an amino acid sequence, or a portion thereof, with the homologous amino acid sequence from a different S. pneumoniae serotype. In some embodiments, antigenic polypeptides have at least 80%, 85%, 90%, 95%, 96%, 97%, 98%, 99%, or 99.5% identity to the polypeptides listed in Table 1, or antigenic fragments thereof. Serotypic variation may be used to design such variants of the polypeptides listed in Table 1.

In some embodiments, fusion proteins described herein comprise one or more fragments of polypeptides listed in Table 1, e.g., biotin-binding fragments of rhizavidin, antigenic fragments of a SP0785 polypeptide with or without a signal sequence, or antigenic fragments of a SP1500 polypeptide with or without a signal sequence. In some embodiments, fusion proteins described herein comprise truncation mutants that are close in size to the polypeptides listed in Table 1. For example, they may lack at most one, two, three, four, five, ten, or twenty amino acids from one or both termini (referring to component polypeptides in a fusion protein). In some embodiments, a fragment is a truncated fragment of any of SEQ ID NOs:1-8 lacking 1-5, 1-10, or 1-20 amino acid residues from the N-terminus, C-terminus, or both, of any one of SEQ ID NOs:1-8. In some embodiments, a fragment is a truncated fragment of any of SEQ ID NOs:1-8 lacking 1-10 amino acid residues from the N-terminus, C-terminus, or both, of any one of SEQ ID Nos:1-8. For instance, a fragment may lack 10 amino acid residues at both the N-terminus and C-terminus of any one of SEQ ID NOs:1-8, resulting in a protein lacking 20 amino acid residues. Internal deletions, e.g., of 1-10, 11-20, 21-30, or 31-40 amino acids, are also contemplated.

In some embodiments, a fusion protein comprises an N-terminal polypeptide and a C-terminal polypeptide. In some embodiments, one or both of the N-terminal polypeptide and the C-terminal polypeptide is an antigenic polypeptide, for example, a polypeptide having an amino acid sequence comprising one or more of SEQ ID NOs:3-8, or an antigenic fragment or variant thereof. In some embodiments, one or both of the N-terminal polypeptide and the C-terminal polypeptide is a biotin-binding moiety, for example a polypeptide having an amino acid sequence comprising SEQ ID NO:1 or 2, or a biotin-binding fragment thereof. In some embodiments, one of the N-terminal polypeptide or the C-terminal polypeptide is a biotin-binding moiety, for example a polypeptide having an amino acid sequence comprising SEQ ID NO:1 or 2, or a biotin-binding fragment thereof, and the other terminal polypeptide is an antigenic polypeptide, for example, a polypeptide having an amino acid sequence comprising one or more of SEQ ID NOs:3-8, or an antigenic fragment or variant thereof.

In some embodiments, the N-terminal polypeptide and the C-terminal polypeptide are directly bound to each other. In some embodiments, the N-terminal polypeptide and the C-terminal polypeptide are linked via a linker peptide. The length and/or amino acids of a linker, when present, can be adjusted to obtain a more flexible, semi-rigid, or rigid linker. Exemplary flexible peptide linkers are shown as SEQ ID NOs:37-40. A linker can generally be from 1-40, such as 3-10 or 10-30 and specifically 3, 4, 5, 6, 7, 8, 9, 10, 11, 12, 13, 14, 15, 16, 17, 18, 19 or 20 amino acids in length. In some embodiments, the fusion protein comprises one linker. In some embodiments, the fusion protein comprises two linkers. In some embodiments, the one or two linkers are selected from SEQ ID NO:37 (GGGGSSS) and SEQ ID NO:38 (AAA). In some embodiments, the fusion protein comprises SEQ ID NO:37 (GGGGSSS) and SEQ ID NO:38 (AAA). In some embodiments, the fusion protein comprises an amino acid sequence AAA (SEQ ID NO: 38) residual from a Not I restriction site. In some embodiments, the fusion protein comprises a linker of SEQ ID NO:37 (GGGGSSS) and an amino acid sequence AAA (SEQ ID NO: 38) residual from a Not I restriction site.

Exemplary fusion proteins are shown in Table 2.

TABLE 2

Exemplary Fusion Proteins

| Locus tag name and description | Protein SEQ ID No. | DNA SEQ ID No. |
| --- | --- | --- |
| SP1500-SP0785 | 17 | 27 |
| SP0785-SP1500 | 18 | 28 |
| Rhavi-SP1500-SP0785 | 19 | 29 |
| Rhavi-SP0785-SP1500 | 20 | 30 |
| SP1500-SP0785-Rhavi | 21 | 31 |
| SP0785-SP1500-Rhavi | 22 | 32 |
| Rhavi-linker (GGGGSSS)-SP1500-linker (AAA)-SP0785 (also denoted CP1) | 23 | 33 |
| Rhavi-linker (GGGGSSS)-SP0785-linker (AAA)-SP1500 | 24 | 34 |
| SP1500-linker (GGGGSSS)-SP0785-linker (AAA)-Rhavi | 25 | 35 |
| SP0785-linker (GGGGSSS)-SP1500-linker (AAA)-Rhavi | 26 | 36 |

In some embodiments, the present disclosure provides fusion proteins with at least 80%, 85%, 90%, 95%, 96%, 97%, 98%, 99%, 99.5%, or 100% sequence identity to a fusion protein listed in Table 2. In some embodiments, a fusion protein is or includes an amino acid sequence having at least 80%, 85%, 90%, 95%, 97%, 98%, 99%, 99.5%, or 100% identity to any one of SEQ ID NOs:17-26. In some embodiments, a fusion protein is or includes an amino acid sequence having at least 80%, 85%, 90%, 95%, 97%, 98%, 99%, 99.5%, or 100% identity to SEQ ID NO:23. In some embodiments, a fusion protein is or includes an amino acid sequence having at least 80%, 85%, 90%, 95%, 97%, 98%, 99%, 99.5%, or 100% identity to CP1.

In some embodiments, a fusion protein described herein comprises an antigenic fragment of a fusion protein shown in Table 2. In some embodiments, a fusion protein is or includes an antigenic fragment of any of SEQ ID NOs:17-26. For example, a fusion protein may lack at most one, two three, four, five, ten, or twenty amino acids from the N-terminus, C-terminus, or both, of any one of SEQ ID NOs:17-26. In some embodiments, the same number of residues is removed from the N-terminus and the C-terminus, while in other embodiments, a different number of residues is removed from the N-terminus compared to the C-terminus. In some embodiments, a fusion protein is or includes an antigenic fragment of SEQ ID NO:23. In some embodiments, a fusion protein is or includes an antigenic fragment of CP1.

In some embodiments, a fusion protein described herein comprises a biotin-binding moiety. In some embodiments, the fusion protein comprises a biotin-binding moiety, and one or more polypeptide antigens. In some embodiments, the fusion protein comprises a biotin-binding moiety and two or more polypeptide antigens. As used herein, a "biotin-binding moiety" refers to a biotin-binding polypeptide or protein, a biotin-binding fragment thereof, or a biotin-binding domain thereof. In some embodiments, the biotin-binding moiety of the fusion protein comprises rhizavidin or a biotin-binding fragment thereof, as further described in WO 2012/155053, the contents of which are herein incorporated by reference in their entirety.

In some embodiments, a fusion protein described herein comprises a biotin-binding moiety that is or comprises a polypeptide having at least 80%, 85%, 90%, 95%, 96%, 97%, 98%, 99%, or 100% identity to the sequence of SEQ ID NO:1 (rhizavidin), or biotin-binding fragment thereof. In some embodiments, the fusion protein comprises a biotin-binding moiety that is or comprises a polypeptide having at least 80%, 85%, 90%, 95%, 96%, 97%, 98%, 99%, or 100% identity to the sequence of SEQ ID NO:2 (amino acids 45-179 of rhizavidin, denoted Rhavi), or biotin-binding fragment thereof. In some embodiments, the fusion protein comprises a polypeptide comprising an amino acid sequence having at least 80%, 85%, 90%, 95%, 96%, 97%, 98%, 99%, or 100% identity to the sequence of SEQ ID NO:4 (amino acids 33-399 of S. pneumoniae SP0785 polypeptide), or an antigenic fragment thereof. In some embodiments, the fusion protein comprises a polypeptide comprising an amino acid sequence having at least 80%, 85%, 90%, 95%, 96%, 97%, 98%, 99%, or 100% identity to the sequence of SEQ ID NO:7 (amino acids 27-278 of S. pneumoniae SP1500 polypeptide), or an antigenic fragment thereof.

In some embodiments, a fusion protein described herein comprises each of: (a) a biotin-binding moiety that is or comprises a polypeptide having at least 80%, 85%, 90%, 95%, 96%, 97%, 98%, 99%, or 100% identity to the sequence of SEQ ID NO:1 (rhizavidin), or biotin-binding fragment thereof, (b) a polypeptide comprising an amino acid sequence having at least 80%, 85%, 90%, 95%, 96%, 97%, 98%, 99%, or 100% identity to the sequence of SEQ ID NO:4 (amino acids 33-399 of S. pneumoniae SP0785 polypeptide), or an antigenic fragment thereof; and (c) a polypeptide comprising an amino acid sequence having at least 80%, 85%, 90%, 95%, 96%, 97%, 98%, 99%, or 100% identity to the sequence of SEQ ID NO:7 (amino acids 27-278 of S. pneumoniae SP1500 polypeptide) or an antigenic fragment thereof. In some embodiments, the fusion protein further comprises one or more linkers. In some embodiments, the one or more linkers are selected from SEQ ID NO:37 (GGGGSSS) and SEQ ID NO:38 (AAA). In some embodiments, the fusion protein comprises an amino acid sequence AAA (SEQ ID NO: 38) residual from a Not I restriction site. In some embodiments, the fusion protein comprises a linker of SEQ ID NO:37 (GGGGSSS) and an amino acid sequence AAA (SEQ ID NO: 38) residual from a Not I restriction site.

In some embodiments, a fusion protein described herein comprises each of: (a) a biotin-binding moiety that is or comprises a polypeptide having at least 80%, 85%, 90%, 95%, 96%, 97%, 98%, 99%, or 100% identity to the sequence of SEQ ID NO:2 (amino acids 45-179 of rhizavidin, denoted Rhavi), or biotin-binding fragment thereof, (b) a polypeptide comprising an amino acid sequence having at least 80%, 85%, 90%, 95%, 96%, 97%, 98%, 99%, or 100% identity to the sequence of SEQ ID NO:4 (amino acids 33-399 of S. pneumoniae SP0785 polypeptide) or an antigenic fragment thereof, and (c) a polypeptide comprising an amino acid sequence having at least 80%, 85%, 90%, 95%, 96%, 97%, 98%, 99%, or 100% identity to the sequence of SEQ ID NO:5 (amino acids 27-278 of S. pneumoniae SP1500 polypeptide) or an antigenic fragment thereof. In some embodiments, the fusion protein further comprises one or more linkers. In some embodiments, the one or more linkers are selected from SEQ ID NO:37 (GGGGSSS) and SEQ ID NO:38 (AAA). In some embodiments, the fusion protein comprises an amino acid sequence AAA (SEQ ID NO: 38) residual from a Not I restriction site. In some embodiments, the fusion protein comprises a linker of SEQ ID NO:37 (GGGGSSS) and an amino acid sequence AAA (SEQ ID NO: 38) residual from a Not I restriction site. In some embodiments, a fusion protein described herein comprises an amino acid sequence having at least 80%, 85%, 90%, 91%, 92%, 93%, 94%, 95%, 96%, 97%, 98%, 99%, or 100% identity to the sequence SEQ ID NO:23. In some embodiments, the fusion protein comprises the amino acid sequence SEQ ID NO:23. In some embodiments, the fusion protein consists of the amino acid sequence SEQ ID NO:23 (CP1).

In some embodiments, a fusion protein described herein includes a variant or fragment of a polypeptide listed in Table 1. In some embodiments, a fusion protein described herein includes a polypeptide encoded by a variant or fragment of a gene listed in Table 1. In some embodiments, a fragment included in a fusion protein described herein is close in size to a full-length polypeptide or a polypeptide listed in Table 1. For example, they may lack at most one, two, three, four, five, ten, twenty, or thirty amino acids from one or both termini. In some embodiments, the fragment is 25-50 amino acids in length, or 50-100, or 100-150, or 150-200, or 200-250, or 250-300, or 300-350 amino acids in length. In some embodiments, the fragments result from processing, or partial processing, of signal sequences by an expression host, e.g. E. coli, an insect cell line (e.g., the baculovirus expression system), or a mammalian (e.g., human or Chinese Hamster Ovary) cell line. The fragments described above or sub-fragments thereof (e.g., fragments of 8-50, 8-30, or 8-20 amino acid residues) preferably have one of the biological activities described below, such as increasing the amount of IL-17 released by at least 1.5 fold or 2 fold or more (e.g., either as an absolute measure or relative to a control protein).

The DNA and protein sequence of each gene and polypeptide may be identified by searching for the Locus Tag in a publicly available database, e.g., Entrez Gene (on the NCBI NIH web site on the World Wide Web, at www.ncbi.nlm.nih.gov/sites/entrez?db=gene), in the *Streptococcus pneumoniae* TIGR4 genome, and the indicated sequences are also included within the scope of the present disclosure.

Certain polypeptides of Table 1, variants thereof, and additional exemplary polypeptides and linkers which constitute components of various embodiments of the fusion proteins are described in greater detail below.

SP0785 Polypeptides (e.g., SEQ ID NOs:3-5) and Variants Thereof

SP0785 is a conserved hypothetical *S. pneumoniae* protein described in WO 2014/124228. In some embodiments, a SP0785 polypeptide is an efflux transporter protein conserved across *S. pneumoniae* strains. In some embodiments, a SP0785 polypeptide is or comprises a full-length SP0785 polypeptide. For example, in some embodiments, a full-length SP0785 polypeptide has 399 amino acids (38 kDa) and is represented by the amino acid sequence as set forth in SEQ ID NO: 3. Amino acids 1-32 of SEQ ID NO:3 are predicted to be a signal sequence and transmembrane domain of a SP0785 polypeptide (amino acids 1-32 of the full-length protein). In some embodiments, a fusion protein comprises a SP0785 polypeptide of *S. pneumoniae*. In some embodiments, a fusion protein comprises at least 7, 8, 9, 10, 11, 12, 13, 14, 15, 16, 17, 18, 19, 20, 25, 30, 35, 45, 50, 60, 65, 70, 75, 80, 85, 90, 95, 100, 150, 200, 250, 300, 350, 367, or 399 consecutive amino acids of a SP0785 polypeptide.

In some embodiments, a SP0785 polypeptide of the fusion protein comprises at least 7, 8, 9, 10, 11, 12, 13, 14, 15, 16, 17, 18, 19, 20, 25, 30, 35, 45, 50, 60, 65, 70, 75, 80, 85, 90, 95, 100, 150, 200, 250, 300, 350, 367, or 399 consecutive amino acids of the sequence shown in SEQ ID NO:3 [full-length]. In some embodiments, a SP0785 polypeptide of the fusion protein comprises an amino acid sequence that is at least 60% or more (including, e.g., at least 65%, 70%, 75%, 80%, 85%, 90%, 95%, 96%, 97%, 98%, 99%, or 100%) identical to at least 7, 8, 9, 10, 11, 12, 13, 14, 15, 16, 17, 18, 19, 20, 25, 30, 35, 45, 50, 60, 65, 70, 75, 80, 85, 90, 95, 100, 150, 200, 250, 300, 350, 367, or 399 consecutive amino acids of the sequence shown in SEQ ID NO:3 [full-length].

In some embodiments, a SP0785 polypeptide of the fusion protein comprises at least 7, 8, 9, 10, 11, 12, 13, 14, 15, 16, 17, 18, 19, 20, 25, 30, 35, 45, 50, 60, 65, 70, 75, 80, 85, 90, 95, 100, 150, 200, 250, 300, 350, or 367 consecutive amino acids of the sequence shown in SEQ ID NO:4 [minus signal sequence and transmembrane domain]. In some embodiments, a SP0785 polypeptide of the fusion protein comprises an amino acid sequence that is at least 60% or more (including, e.g., at least 65%, 70%, 75%, 80%, 85%, 90%, 95%, 96%, 97%, 98%, 99%, or 100%) identical to at least 7, 8, 9, 10, 11, 12, 13, 14, 15, 16, 17, 18, 19, 20, 25, 30, 35, 45, 50, 60, 65, 70, 75, 80, 85, 90, 95, 100, 150, 200, 250, 300, 350, or 367 consecutive amino acids of the sequence shown in SEQ ID NO:4 [minus signal sequence and transmembrane domain].

Sequence variation occurs at the protein level between different *S. pneumoniae* serotypes, and a consensus sequence illustrating combinations of SP785 sequences from different *S. pneumoniae* serotypes is provided as SEQ ID NO:5. Accordingly, in some embodiments, the fusion protein includes a polypeptide having an amino acid sequence comprising, or consisting of, SEQ ID NO:5, or an antigenic fragment thereof (e.g., in place of a polypeptide having an amino acid sequence comprising one of SEQ ID NO:3 or 4). In some embodiments, a SP0785 polypeptide of the fusion protein comprises at least 7, 8, 9, 10, 11, 12, 13, 14, 15, 16, 17, 18, 19, 20, 25, 30, 35, 45, 50, 60, 65, 70, 75, 80, 85, 90, 95, 100, 150, 200, 250, 300, 350, or 367 consecutive amino acids of the sequence shown in SEQ ID NO:5 [consensus]. In some embodiments, a SP0785 polypeptide of the fusion protein comprises an amino acid sequence that is at least 60% or more (including, e.g., at least 65%, 70%, 75%, 80%, 85%, 90%, 95%, 96%, 97%, 98%, 99%, or 100%) identical to at least 7, 8, 9, 10, 11, 12, 13, 14, 15, 16, 17, 18, 19, 20, 25, 30, 35, 45, 50, 60, 65, 70, 75, 80, 85, 90, 95, 100, 150, 200, 250, 300, 350, or 367 consecutive amino acids of the sequence shown in SEQ ID NO:5 [consensus].

An exemplary nucleotide sequence encoding a SP0785 polypeptide is provided herein as SEQ ID NO:11.

SP1500 Polypeptides (e.g., SEQ ID NOs:6-8) and Variants Thereof

SP1500 is described in WO 2014/124228. In some embodiments, a SP1500 polypeptide is an Amino Acid ABC Transporter, amino acid-binding polypeptide conserved across *S. pneumoniae* strains. In some embodiments, a SP1500 polypeptide is or comprises a full-length SP1500 polypeptide. For example, in some embodiments, a full-length SP1500 polypeptide has 278 amino acids (28 kDa) and is represented by the amino acid sequence as set forth in SEQ ID NO: 6. Amino acids 1-26 of SEQ ID NO:6 are predicted to be a signal sequence of a SP1500 polypeptide (amino acids 1-26 of the full-length protein). In some embodiments, a fusion protein comprises a SP1500 polypeptide of *S. pneumoniae*. In some embodiments, a fusion protein comprises at least 7, 8, 9, 10, 11, 12, 13, 14, 15, 16, 17, 18, 19, 20, 25, 30, 35, 45, 50, 60, 65, 70, 75, 80, 85, 90, 95, 100, 150, 200, 252, or 278 consecutive amino acids of a SP1500 polypeptide.

In some embodiments, a SP1500 polypeptide of the fusion protein comprises at least 7, 8, 9, 10, 11, 12, 13, 14, 15, 16, 17, 18, 19, 20, 25, 30, 35, 45, 50, 60, 65, 70, 75, 80, 85, 90, 95, 100, 150, 200, 252, or 278 consecutive amino acids of the sequence shown in SEQ ID NO:6 [full-length]. In some embodiments, a SP1500 polypeptide of the fusion protein comprises an amino acid sequence that is at least 60% or more (including, e.g., at least 65%, 70%, 75%, 80%, 85%, 90%, 95%, 96%, 97%, 98%, 99%, or 100%) identical to at least 7, 8, 9, 10, 11, 12, 13, 14, 15, 16, 17, 18, 19, 20, 25, 30, 35, 45, 50, 60, 65, 70, 75, 80, 85, 90, 95, 100, 150, 200, 252, or 278 consecutive amino acids of the sequence shown in SEQ ID NO:6 [full-length].

In some embodiments, a SP1500 polypeptide of the fusion protein comprises at least 7, 8, 9, 10, 11, 12, 13, 14, 15, 16, 17, 18, 19, 20, 25, 30, 35, 45, 50, 60, 65, 70, 75, 80, 85, 90, 95, 100, 150, 200, or 252 consecutive amino acids of the sequence shown in SEQ ID NO:7 [minus signal sequence]. In some embodiments, a SP1500 polypeptide of the fusion protein comprises an amino acid sequence that is at least 60% or more (including, e.g., at least 65%, 70%, 75%, 80%, 85%, 90%, 95%, 96%, 97%, 98%, 99%, or 100%) identical to at least 7, 8, 9, 10, 11, 12, 13, 14, 15, 16, 17, 18, 19, 20, 25, 30, 35, 45, 50, 60, 65, 70, 75, 80, 85, 90, 95, 100, 150, 200, or 252 consecutive amino acids of the sequence shown in SEQ ID NO:7 [minus signal sequence].

Sequence variation occurs at the protein level between different *S. pneumoniae* serotypes, and a consensus sequence illustrating combinations of SP1500 sequences from different *S. pneumoniae* serotypes is provided as SEQ ID NO:8. In some embodiments, the fusion protein includes a polypeptide having an amino acid sequence comprising, or consisting of, SEQ ID NO:8, or an antigenic fragment thereof (e.g., in place of a polypeptide having an amino acid sequence comprising one of SEQ ID NO:6 or 7). In some embodiments, a SP1500 polypeptide of the fusion protein comprises at least 7, 8, 9, 10, 11, 12, 13, 14, 15, 16, 17, 18, 19, 20, 25, 30, 35, 45, 50, 60, 65, 70, 75, 80, 85, 90, 95, 100, 150, 200, or 252 consecutive amino acids of the sequence shown in SEQ ID NO:8 [consensus]. In some embodiments, a SP1500 polypeptide of the fusion protein comprises an amino acid sequence that is at least 60% or more (including, e.g., at least 65%, 70%, 75%, 80%, 85%, 90%, 95%, 96%, 97%, 98%, 99%, or 100%) identical to at least 7, 8, 9, 10, 11, 12, 13, 14, 15, 16, 17, 18, 19, 20, 25, 30, 35, 45, 50, 60, 65, 70, 75, 80, 85, 90, 95, 100, 150, 200, or 252 consecutive amino acids of the sequence shown in SEQ ID NO:8 [consensus].

An exemplary nucleotide sequence encoding a SP1500 polypeptide is provided herein as SEQ ID NO:14.

Rhizavidin

In some embodiments, a fusion protein described herein is a component of non-covalent Multiple Antigen Presenting System (MAPS) immunogenic complexes. In some embodiments, MAPS complexes utilize the high affinity (dissociation constant $[K_D] \approx 10^{-15}M$) noncovalent binding between biotin, or biotin derivatives, and rhizavidin, a biotin-binding protein that has no significant predicted homology with human proteins.

Rhizavidin is a naturally occurring dimeric protein in the avidin protein family, was first discovered in *Rhizobium etli*, a symbiotic bacterium of the common bean. Rhizavidin has only a 22% amino acid identity with chicken avidin, a protein commonly found in eggs, but with high conservation of amino acid residues involved in biotin binding [Helppolainen et al, 2007]. In some embodiments, the nucleotide sequence of rhizavidin is set forth in SEQ ID NO:9. In some embodiments, the amino acid sequence of rhizavidin is set forth in SEQ ID NO:1. Amino acids 1-44 of SEQ ID NO:1 are predicted to be a signal sequence(s) of rhizavidin (amino acids 1-44 of the full-length protein). In some embodiments, a fusion protein comprises rhizavidin. In some embodiments, a fusion protein comprises at least 7, 8, 9, 10, 11, 12, 13, 14, 15, 16, 17, 18, 19, 20, 25, 30, 35, 45, 50, 60, 65, 70, 75, 80, 85, 90, 95, 100, 150, or 179 consecutive amino acids of a rhizavidin polypeptide.

In some embodiments, a rhizavidin polypeptide of the fusion protein comprises at least 7, 8, 9, 10, 11, 12, 13, 14, 15, 16, 17, 18, 19, 20, 25, 30, 35, 45, 50, 60, 65, 70, 75, 80, 85, 90, 95, 100, 150, or 179 consecutive amino acids of the sequence shown in SEQ ID NO:1 [full-length]. In some embodiments, a rhizavidin polypeptide of the fusion protein comprises an amino acid sequence that is at least 60% or more (including, e.g., at least 65%, 70%, 75%, 80%, 85%, 90%, 95%, 96%, 97%, 98%, 99%, or 100%) identical to at least 7, 8, 9, 10, 11, 12, 13, 14, 15, 16, 17, 18, 19, 20, 25, 30, 35, 45, 50, 60, 65, 70, 75, 80, 85, 90, 95, 100, 150, or 179 consecutive amino acids of the sequence shown in SEQ ID NO:1 [full-length].

In some embodiments, a rhizavidin polypeptide of the fusion protein comprises at least 7, 8, 9, 10, 11, 12, 13, 14, 15, 16, 17, 18, 19, 20, 25, 30, 35, 45, 50, 60, 65, 70, 75, 80, 85, 90, 95, 100, or 135 consecutive amino acids of the sequence shown in SEQ ID NO:2 [minus signal sequence]. In some embodiments, a rhizavidin polypeptide of the fusion protein comprises an amino acid sequence that is at least 60% or more (including, e.g., at least 65%, 70%, 75%, 80%, 85%, 90%, 95%, 96%, 97%, 98%, 99%, or 100%) identical to at least 7, 8, 9, 10, 11, 12, 13, 14, 15, 16, 17, 18, 19, 20, 25, 30, 35, 45, 50, 60, 65, 70, 75, 80, 85, 90, 95, 100, or 135 consecutive amino acids of the sequence shown in SEQ ID NO:2 [minus signal sequence].

In some embodiments, a rhizavidin polypeptide of the fusion protein is or comprises amino acids 50-179 of SEQ ID NO:1. In some embodiments, a rhizavidin polypeptide of the fusion protein is or comprises amino acids 55-179 of SEQ ID NO:1. In some embodiments, a rhizavidin polypeptide of the fusion protein is or comprises amino acids 60-179 of SEQ ID NO:1. In some embodiments, a rhizavidin polypeptide of the fusion protein is or comprises amino acids 65-179 of SEQ ID NO:1.

In some embodiments, a rhizavidin polypeptide of the fusion protein is or comprises amino acids 45-175 of SEQ ID NO:1. In some embodiments, a rhizavidin polypeptide of the fusion protein is or comprises amino acids 45-171 of SEQ ID NO:1. In some embodiments, a rhizavidin polypeptide of the fusion protein is or comprises amino acids 45-167 of SEQ ID NO:1. In some embodiments, a rhizavidin polypeptide of the fusion protein is or comprises amino acids 45-163 of SEQ ID NO:1.

Linker or Spacer

In some embodiments, a fusion protein comprises one or more linkers. In some embodiments, a linker is or comprises one or more amino acids. In some embodiments, a fusion protein comprises an antigenic polypeptide joined to a biotin-binding moiety by a linker. In some embodiments, a fusion protein comprises a first antigenic polypeptide, a second antigenic polypeptide, a biotin-binding moiety, and at least one linker. In some embodiments, the first antigenic polypeptide and the second antigenic polypeptide are joined by a linker. In some embodiments, the first antigenic polypeptide or the second antigenic polypeptide are joined to the biotin-binding moiety by a linker. In some embodiments, the first antigenic polypeptide and the second antigenic polypeptide are joined by a first linker; and the first antigenic polypeptide or the second antigenic polypeptide are joined to the biotin-binding moiety by a second linker.

In some embodiments, a linker interposes a structure between two protein moieties. In some embodiments, the structure is or comprises an α-helix. In some embodiments the structure is or comprises a β-strand. In some embodiments, the structure is or comprises a coil/bend. In some embodiments, the structure is or comprises a turn. In some embodiments, a linker decreases steric hindrance between two protein moieties joined by the linker. In some embodiments, a linker decreases unfavorable interactions between two protein moieties joined by the linker. In some embodiments, a linker comprises a mixture of glycine and serine residues. In some embodiments, the linker may additionally comprise threonine, proline, and/or alanine residues. In some embodiment a linker is hydrophilic. In some embodiments a linker is hydrophobic. In some embodiments a linker increases the stability of the fusion protein containing the linker.

In some embodiments, a linker does not interfere with the folding of an antigenic polypeptide to which it is joined. In some embodiments, a linker does not interfere with the antigenicity of an antigenic polypeptide to which it is joined. In some embodiments, a linker does not reduce the antigenicity of an antigenic polypeptide to which it is joined. In some embodiments, a linker does not eliminate the antigenicity of an antigenic polypeptide to which it is joined. In some embodiments the effect of the linker is determined by comparing the polypeptide with the polypeptide joined to the linker.

In some embodiments, a linker does not interfere with the folding of a biotin-binding moiety to which it is joined. In some embodiments, a linker does not interfere with the biotin-binding ability of a biotin-binding moiety to which it is joined. In some embodiments, a linker does not reduce the biotin-binding ability of a biotin-binding moiety to which it is joined. In some embodiments, a linker does not eliminate the biotin-binding ability of a biotin-binding moiety to which it is joined. In some embodiments the effect of the linker is determined by comparing the biotin-binding moiety with the biotin-binding moiety joined to the linker.

In some embodiments, a linker is not antigenic. In some embodiments, a linker does not elicit a T cell response. In some embodiments, a linker does not elicit a B cell response. In some embodiments, a linker does not induce a T cell or a B cell response.

In some embodiments, a linker comprises two or more amino acids. In some embodiments, a linker may be 3-100, 5-100, 10-100, 20-100 30-100, 40-100, 50-100, 60-100, 70-100, 80-100, 90-100, 5-55, 10-50, 10-45, 10-40, 10-35, 10-30, 10-25, 10-20, 10-15, 3-10, 3-9, 3-8, 3-7, 3-6, 3-5, 3-4, or 2-3 amino acids in length. In some embodiments, a linker comprises between 10-100, 10-90, 10-80, 10-70, 10-60, 10-50, 10-40, 10-30, 10-20, 10-15 amino acids. In some embodiments, the linker comprises at least 10, 15, 20, 25, 30, 35, 40, 45, 50, 55, 60, 65, 70, 75, 80, 85, 90, or 95 amino acids. In some embodiments, a linker is or comprises 2, 3, 4, 5, 6, 7, 8, 9, 10, 15, 20, 25, 30, 35, 40, 45, 50, 55, 60, 65, 70, 75, 80, 85, 90, 95, or 100 amino acids.

In some embodiments, a linker is a flexible linker. Flexible linkers may be useful for joining domains that require a certain degree of movement or interaction and may include small, non-polar (e.g. Gly) or polar (e.g. Ser or Thr) amino acids. Incorporation of Ser or Thr can also maintain the stability of the linker in aqueous solutions by forming hydrogen bonds with the water molecules, and therefore reduce unfavorable interactions between the linker and the protein moieties. In some embodiments a linker comprises small non-polar (e.g. Gly) or polar (e.g. Ser or Thr) amino acids. In some embodiments, a linker is a Gly-Ser linker.

In some embodiments, a linker is or comprises an amino acid sequence of GGGGSSS (SEQ ID NO:37). In some embodiments, a linker is or comprises a sequence of (GGGGS)$_n$ (SEQ ID NO:39), where n represents the number of repeating GGGGS (SEQ ID NO: 62) units and is 1, 2, 3, 4, 5, 6, 7, 8, 9, 10, 11, 12, 13, 14, 15, 16, 17, 18, 19, 20, 25, 30 or more. In some embodiments, a polypeptide linker may have an amino acid sequence that is or comprises GGGGSGGGGSGGGGS (SEQ ID NO:41) (i.e., (GGGGS)$_3$ (SEQ ID NO: 41)) or GGGGSGGGGSGGGGSGGGGSGGGGSGGGGS (SEQ ID NO:42) (i.e., (GGGGS)$_6$ (SEQ ID NO: 42)). In some embodiments, a linker comprises one or more of Gly, Ser, Thr, Ala, Lys, and Glu. In some embodiments, a linker is or comprises KESGSVSSEQLAQFRSLD (SEQ ID NO:43). In some embodiments, a linker is or comprises EGKSSGSGS-ESKST (SEQ ID NO:44). In some embodiments, a linker is or comprises (Gly)$_n$ (SEQ ID NO:45) where n represents the number of repeating Gly residues and is 1, 2, 3, 4, 5, 6, 7, 8, 9, 10, 11, 12, 13, 14, 15, 16, 17, 18, 19, 20, 25, 30 or more. In some embodiments a linker is or comprises GGG. In some embodiments, a linker is or comprises (Gly)$_6$ (SEQ ID NO:40). In some embodiments, a linker is or comprises (Gly)$_8$ (SEQ ID NO:46). In some embodiments, a linker is or comprises GSAGSAAGSGEF (SEQ ID NO:47). In some embodiments, a linker is or comprises an amino acid sequence of AAA (SEQ ID NO:38).

In some embodiments, a linker is a rigid linker. Rigid linkers are useful to keep a fixed distance between domains and to maintain their independent functions. Rigid linkers may also be useful when a spatial separation of the domains is critical to preserve the stability or bioactivity of one or more components in the fusion. In some embodiments, a linker is or comprises (EAAAK)$_n$ (SEQ ID NO:48) where n represents the number of repeating EAAAK (SEQ ID NO: 63) units and is 1, 2, 3, 4, 5, 6, 7, 8, 9, 10, 11, 12, 13, 14, 15, 16, 17, 18, 19, 20, 25, 30 or more. In some embodiments, a linker is or comprises A(EAAAK)$_n$A, (SEQ ID NO:49) where n represents the number of repeating EAAAK (SEQ ID NO: 63) units and is 1, 2, 3, 4, 5, 6, 7, 8, 9, 10, 11, 12, 13, 14, 15, 16, 17, 18, 19, 20, 25, 30 or more. In some embodiments, a linker is or comprises A(EAAAK)$_n$A (SEQ ID NO: 108), where n represents the number of repeating EAAAK (SEQ ID NO: 63) units and is 2, 3, 4, or 5. In some embodiments, a linker is or comprises A(EAAAK)$_4$ALEA (EAAAK)$_4$A (SEQ ID NO:50). In some embodiments, a linker is or comprises [A(EAAAK)$_n$A]$_m$, (SEQ ID NO:51) wherein n is 2, 3, or 4 and m is 1 or 2. In some embodiments, a linker is or comprises AEAAAKEAAAKA (SEQ ID NO:52).

In some embodiments a linker is or comprises (X-Pro)$_n$ (SEQ ID NO:53), with X designating any amino acid, where n represents the number of repeating X-Pro units and is 1, 2, 3, 4, 5, 6, 7, 8, 9, 10, 11, 12, 13, 14, 15, 16, 17, 18, 19, 20, 25, 30 or more. In some embodiments a linker is or comprises (Ala-Pro)$_n$ (SEQ ID NO:54), where n represents the number of repeating Ala-Pro units and is 1, 2, 3, 4, 5, 6, 7, 8, 9, 10, 11, 12, 13, 14, 15, 16, 17, 18, 19, 20, 25, 30 or more. In some embodiments a linker is or comprises (Ala-Pro)$_n$ (SEQ ID NO: 109), where n represents the number of repeating Ala-Pro units and is 5, 6, 7, 8, 9, 10, 11, 12, 13, 14, 15, 16, or 17.

In some embodiments a linker is or comprises (Lys-Pro)$_n$ (SEQ ID NO:55), where n represents the number of repeating Lys-Pro units and is 1, 2, 3, 4, 5, 6, 7, 8, 9, 10, 11, 12, 13, 14, 15, 16, 17, 18, 19, 20, 25, 30 or more. In some embodiments a linker is or comprises (Gln-Pro)$_n$ (SEQ ID NO:56), where n represents the number of repeating Gln-Pro units and is 1, 2, 3, 4, 5, 6, 7, 8, 9, 10, 11, 12, 13, 14, 15, 16, 17, 18, 19, 20, 25, 30 or more. In some embodiments, a linker is or comprises (Ala-Pro)$_7$ (SEQ ID NO:57).

In some embodiments a linker is or comprises GAPGGGGGAAAAAGGGGGGAP (GAG linker, SEQ ID NO:58). In some embodiments a linker is or comprises GAPGGGGGAAAAAGGGGGAPGGGG-GAAAAAGGGGGAP (GAG2 linker, SEQ ID NO:59). In some embodiments a linker is or comprises GAPGGGG-GAAAAAGGGGGAPGGGGGAAAAAGGGGG-GAPGGGGGAAAAAGGGGG GAP (GAG3 linker, SEQ ID NO:60).

Suitable linkers or spacers also include those having an amino acid sequence at least 50%, 55%, 60%, 65%, 70%, 75%, 80%, 85%, 90%, 91%, 92%, 93%, 94%, 95%, 96%, 97%, 98%, 99% or more homologous or identical to the above exemplary linkers.

Additional linkers suitable for use with some embodiments may be found in U.S. Patent Publication No. 2012/0232021, filed on Mar. 2, 2012, and [Chen, 2013] the disclosures of which is hereby incorporated by reference in their entireties.

Tagged Fusion Proteins

In some embodiments, a fusion protein described herein may comprise a tag. A tag may be N-terminal or C-terminal. For instance, tags may be added to a polypeptide (via additions or modifications on the encoding DNA sequence) to facilitate purification, detection, solubility, or confer other desirable characteristics on the protein. In some embodiments a tag may be a peptide, oligopeptide, or polypeptide that may be used in affinity purification. In some embodiments, a tag is, comprises, or is derived from one or more of polyhistidine (His), Glutathione S-transferase (GST), tandem affinity purification (TAP), FLAG, myc, human influenza hemagglutinin (HA), maltose binding protein (MBP), vesicular Stomatitis viral glycoprotein (VSV-G), thioredoxin, V5, avidin, streptavidin, biotin carboxyl carrier protein (BCCP), Calmodulin, Nus, S tags, lipoprotein D, and galactosidase. In some embodiments, a His tag is or comprises an amino acid sequence of $H_n$, wherein n is an integer between 2 and 10 (SEQ ID NO: 64). Exemplary His tags include HHHHHH (SEQ ID NO:15) and MSYYHHHHHH (SEQ ID NO:16). In other embodiments, the fusion protein is free of tags such as protein purification tags, and is purified by a method not relying on affinity for a purification tag. In some embodiments, the fusion protein comprises no more than 1, 2, 3, 4, 5, 10, or 20 additional amino acids on one or both termini of a polypeptide of Table 1 or fusion protein of Table 2.

In some embodiments, a fusion protein described herein may contain a membrane translocating sequence (MTS), to facilitate introduction of the fusion protein into a mammalian cell and subsequent stimulation of the cell-mediated immune response. Exemplary membrane translocating sequences include the hydrophobic region in the signal sequence of Kaposi fibroblast growth factor, the MTS of a synuclein, the third helix of the Antennapedia homeodomain, SN50, integrin 3 h-region, HIV Tat, pAntp, PR-39, abaecin, apidaecin, Bac5, Bac7, *P. berghei* CS protein, and those MTSs described in U.S. Pat. Nos. 6,248,558, 6,432, 680 and 6,248,558.

Nucleic Acids

In some embodiments, the present disclosure provides nucleic acids, e.g., DNA, RNA, or analogs thereof, encoding one or more of the polypeptides and/or fusion proteins described herein. An underlying DNA sequence for the polypeptides described herein may be modified in ways that do not affect the sequence of the protein product, and such sequences are included in the invention. In some embodiments, a DNA sequence may be codon-optimized to improve expression in a host such as a bacterial cell line, e.g., *E. coli*, an insect cell line (e.g., using the baculovirus expression system), or a mammalian (e.g., human or Chinese Hamster Ovary) cell line.

In some embodiments, the present disclosure provides nucleic acids, e.g., DNA, RNA, or analogs thereof, that are at least 70%, 80%, 85%, 90%, 95%, 97%, 98%, 99%, 99.5%, or 100% identical to a nucleic acid sequence provide in Table 1, Table 2, or a variant or portion thereof. In some embodiments, the nucleic acid is 600-2000, 800-1800, 1000-1600, 1200-1400 nucleotides in length. In some embodiments, the nucleic acid is 600-1600, 800-1800, 1000-2000, 2000-3000, or 3000-4000 nucleotides in length. In some embodiments, a nucleic acid may be used for recombinant production of a polypeptide or fusion protein of Table 1 or Table 2, or antigenic fragments thereof. In some embodiments, a nucleic acid may be used as a vaccine.

Nucleic acid sequences encoding variants of SP0785 (SEQ ID NOs:3 and 4) are provided as SEQ ID NOs:11 and 12. Nucleic acid sequences encoding variants of SP1500 (SEQ ID NOs:6 and 7) are provided as SEQ ID NOs:13 and 14. Nucleic acid sequences encoding different fusion proteins (SEQ ID NOs:17-26) are provided as SEQ ID NOs: 27-36. In all cases, due to degeneracy in the genetic code, other DNA sequences (including multiple codon-optimized sequences) could be contemplated by those of ordinary skill to encode such polypeptides and fusion proteins.

Nucleic acids encoding polypeptides or fusion proteins of Table 1 or Table 2, or fragments thereof, can be cloned into any of a variety of expression vectors, under the control of a variety of regulatory elements, and fusions can be created with other sequences of interest. Methods of cloning nucleic acids are routine and conventional in the art. For general references describing methods of molecular biology which are mentioned in this application, e.g., isolating, cloning, modifying, labeling, manipulating, sequencing and otherwise treating or analyzing nucleic acids and/or proteins, see, e.g., Sambrook et al, 1989; Ausubel et al, 1995; Davis et al, 1986; Hames et al, 1985; Dracopoli et al, 2018; and Coligan et al, 2018.

Uses of Fusion Proteins

In some embodiments, a fusion protein described herein does not have, or has minimal, hemolytic activity. For example, in some embodiments, the hemolytic activity of a fusion protein described herein can be established by turbidimetry ($OD_{420}$) after incubation of the fusion protein at different dilutions with red blood cells (e.g., sheep erythrocytes), to determine the protein concentration at which 50% of the red blood cells are lysed. In some such embodiments, the hemolytic activity of a fusion protein described herein can be characterized by an $OD_{420}$ of less than 0.4 or lower, including, e.g., less than 0.3, less than 0.25, less than 0.2, or lower, for a given protein concentration.

In some embodiments, polypeptides of *S. pneumoniae* and fusion proteins described herein, and fragments and variants thereof, are immunogenic. These polypeptides and fusion proteins may be immunogenic in mammals, for example mice, rats, guinea pigs, or humans. An antigenic polypeptide or fusion protein is typically one capable of raising a significant immune response in an assay or in a subject. The immune response may be innate, humoral, cell-mediated, or mucosal (combining elements of innate, humoral and cell-mediated immunity). For instance, an antigenic polypeptide or fusion protein may increase the amount of IL-17 produced by T cells. Alternatively or additionally, an antigenic polypeptide or fusion protein may (i) induce production of antibodies, e.g., neutralizing antibodies, that bind to the polypeptide and/or the whole bacteria, (ii) induce Th17 immunity, (iii) activate the CD4+ T cell response, for example by increasing the number of CD4+ T cells and/or increasing localization of CD4+ T cells to the site of infection or reinfection, (iv) activate the CD8+ T cell response, for example by increasing the number of CD8+ T cells and/or increasing localization of CD8+ T cells to the site of infection or reinfection, (v) activate both the CD4+ and the CD8+ response, (vi) activate CD4−/CD8− immunity, (vii) induce Th1 immunity, (viii) induce antimicrobial peptides, (ix) activate innate immunity, or any combination of the foregoing. In some embodiments, an antigenic polypeptide or fusion protein elicits production of a detectable amount of antibody specific to that antigen.

In some embodiments, a fusion protein described herein is an antigen or has antigenic properties. In some embodiments, a fusion protein described herein is a carrier protein or has carrier properties. In some embodiments, a fusion protein described herein is both an antigen and a carrier protein. In some embodiments, a fusion protein described herein has both carrier properties and antigenic properties.

In some embodiments, a fusion protein described herein is an antigen of an immunogenic complex (e.g., a Multiple Antigen Presenting System (MAPS) complex as described in WO 2012/155007, the entire contents of which are incorporated herein by reference for the purposes indicated herein). In some embodiments, a fusion protein described herein is a carrier protein of an immunogenic complex. In some embodiments, a fusion protein described herein is both a carrier protein and an antigen of an immunogenic complex.

In some embodiments, polypeptides of the fusion proteins described herein have less than 20%, 30%, 40%, 50%, 60% or 70% identity to human auto-antigens and/or gut commensal bacteria (e.g., certain *Bacteroides, Clostridium,*

*Fusobacterium, Eubacterium, Ruminococcus, Peptococcus, Peptostreptococcus, Bifidobacterium, Escherichia*, and *Lactobacillus* species). Examples of human autoantigens include insulin, proliferating cell nuclear antigen, cytochrome P450, and myelin basic protein.

A polypeptide included in a fusion protein described herein may comprise one or more immunogenic portions and one or more non-immunogenic portions. The immunogenic portions may be identified by various methods, including protein microarrays, ELISPOT/ELISA techniques, and/or specific assays on different deletion mutants (e.g., fragments) of the polypeptide in question. Immunogenic portions may also be identified by computer algorithms. Some such algorithms, like EpiMatrix (produced by EpiVax), use a computational matrix approach. Other computational tools for identifying antigenic epitopes include PEPVAC (Promiscuous EPitope-based VACcine, hosted by Dana Farber Cancer Institute on the world wide web at immunax.dfci.harvard.edu/PEPVAC), MHCPred (which uses a partial least squares approach and is hosted by The Jenner Institute on the world wide web at www.jenner.ac.uk/MHCPred), and Immune Epitope Database algorithms on the World Wide Web at tools.immuneepitope.org. An antigenic fragment of a polypeptide described herein comprises at least one immunogenic portion, as measured experimentally or identified by algorithm (for example, the SYFPEITHI algorithm found at www.syfpeithi.de).

Representative predicted epitopes of SP0785 and SP1500 are presented in Table 3 and Table 4, respectively.

TABLE 3

Top 20 of 353 total predicted MHC II binding sites (HLA-DRB1*0101) of an exemplary SP0785 polypeptide

| Allele | # | Start | End | SEQ ID NO: | Sequence | Method Used | Percentile Rank |
|---|---|---|---|---|---|---|---|
| HLA-DRB1*01:01 | 1 | 253 | 267 | 68 | SPAAGNNTGSKYPYT | Consensus (CombLib., SMM, NN) | 93.69 |
| HLA-DRB1*01:01 | 1 | 302 | 316 | 69 | VMDDSKNYVWIVDEQ | Consensus (comblib., smm, nn) | 91.95 |
| HLA-DRB1*01:01 | 1 | 252 | 266 | 70 | ASPAAGNNTGSKYPY | Consensus (comblib., smm, nn) | 90.60 |
| HLA-DRB1*01:01 | 1 | 251 | 265 | 71 | AASPAAGNNTGSKYP | Consensus (comblib., smm, nn) | 90.11 |
| HLA-DRB1*01:01 | 1 | 325 | 339 | 72 | SLGNADAENQEITSG | Consensus (comblib., smm, nn) | 89.98 |
| HLA-DRB1*01:01 | 1 | 224 | 238 | 73 | FTSKVYPDKKWTGKL | Consensus (comblib., smm, nn) | 89.54 |
| HLA-DRB1*01:01 | 1 | 268 | 282 | 74 | IDVTGEVGDLKQGFS | Consensus (comblib., smm, nn) | 89.54 |
| HLA-DRB1*01:01 | 1 | 352 | 366 | 75 | SSLEEGKEVKADEAT | Consensus (comblib., smm, nn) | 89.54 |
| HLA-DRB1*01:01 | 1 | 353 | 367 | 76 | SLEEGKEVKADEATN | Consensus (comblib., smm, nn) | 89.54 |
| HLA-DRB1*01:01 | 1 | 267 | 281 | 77 | TIDVTGEVGDLKQGF | Consensus (comblib., smm, nn) | 89.24 |
| HLA-DRB1*01:01 | 1 | 255 | 269 | 78 | AAGNNTGSKYPYTID | Consensus (comblib., smm, nn) | 89.19 |
| HLA-DRB1*01:01 | 1 | 110 | 124 | 79 | PQLPAPVGGEDATVQ | Consensus (comblib., smm, nn) | 89.05 |
| HLA-DRB1*01:01 | 1 | 111 | 125 | 80 | QLPAPVGGEDATVQS | Consensus (comblib., smm, nn) | 89.05 |
| HLA-DRB1*01:01 | 1 | 112 | 126 | 81 | LPAPVGGEDATVQSP | Consensus (comblib., smm, nn) | 89.05 |
| HLA-DRB1*01:01 | 1 | 113 | 127 | 82 | PAPVGGEDATVQSPT | Consensus (comblib., smm, nn) | 89.05 |
| HLA-DRB1*01:01 | 1 | 114 | 128 | 83 | APVGGEDATVQSPTP | Consensus (comblib., smm, nn) | 89.05 |
| HLA-DRB1*01:01 | 1 | 254 | 268 | 84 | PAAGNNTGSKYPYTI | Consensus (comblib., smm, nn) | 88.73 |
| HLA-DRB1*01:01 | 1 | 256 | 270 | 85 | AGNNTGSKYPYTIDV | Consensus (comblib., smm, nn) | 88.21 |

TABLE 3-continued

Top 20 of 353 total predicted MHC II binding sites (HLA-DRB1*0101) of an exemplary SP0785 polypeptide

| Allele | # | Start | End | SEQ ID NO: | Sequence | Method Used | Percentile Rank |
|---|---|---|---|---|---|---|---|
| HLA-DRB1*01:01 | 1 | 225 | 239 | 86 | TSKVYPDKKWTGKLS | Consensus (comblib., smm, nn) | 87.42 |
| HLA-DRB1*01:01 | 1 | 223 | 237 | 87 | SFTSKVYPDKKWTGK | Consensus (comblib., smm, nn) | 86.32 |

TABLE 4

Top 20 of 239 total predicted MHC II binding sites (HLA-DRB1*0101) of an exemplary SP1500 polypeptide

| Allele | # | Start | End | SEQ ID NO: | Sequence | Method Used | Percentile Rank |
|---|---|---|---|---|---|---|---|
| HLA-DRB1*01:01 | 1 | 125 | 139 | 88 | AQAGSSGYADFEANP | Consensus (comb.lib./smm/nn) | 93.70 |
| HLA-DRB1*01:01 | 1 | 54 | 68 | 89 | TVNWQPIDWDLKEAE | Consensus (comb.lib./smm/nn) | 90.32 |
| HLA-DRB1*01:01 | 1 | 146 | 160 | 90 | VANKEANQYQTFNEA | Consensus (comb.lib./smm/nn) | 90.02 |
| HLA-DRB1*01:01 | 1 | 53 | 67 | 91 | ITVNWQPIDWDLKEA | Consensus (comb.lib./smm/nn) | 89.97 |
| HLA-DRB1*01:01 | 1 | 52 | 66 | 92 | GITVNWQPIDWDLKE | Consensus (comb.lib./smm/nn) | 89.54 |
| HLA-DRB1*01:01 | 1 | 55 | 69 | 93 | VNWQPIDWDLKEAEL | Consensus (comb.lib./smm/nn) | 89.54 |
| HLA-DRB1*01:01 | 1 | 228 | 242 | 94 | KDGKFQEISQKWFGE | Consensus (comb.lib./smm/nn) | 89.54 |
| HLA-DRB1*01:01 | 1 | 229 | 243 | 95 | DGKFQEISQKWFGED | Consensus (comb.lib./smm/nn) | 89.54 |
| HLA-DRB1*01:01 | 1 | 230 | 244 | 96 | GKFQEISQKWFGEDV | Consensus (comb.lib./smm/nn) | 89.54 |
| HLA-DRB1*01:01 | 1 | 231 | 245 | 97 | KFQEISQKWFGEDVA | Consensus (comb.lib./smm/nn) | 89.54 |
| HLA-DRB1*01:01 | 1 | 239 | 253 | 98 | WFGEDVATKEVKEGQ | Consensus (comb.lib./smm/nn) | 89.54 |
| HLA-DRB1*01:01 | 1 | 124 | 138 | 99 | GAQAGSSGYADFEAN | Consensus (comb.lib./smm/nn) | 89.06 |
| HLA-DRB1*01:01 | 1 | 227 | 241 | 100 | YKDGKFQEISQKWFG | Consensus (comb.lib./smm/nn) | 88.56 |
| HLA-DRB1*01:01 | 1 | 220 | 234 | 101 | NEAFSSLYKDGKFQE | Consensus (comb.lib./smm/nn) | 87.65 |
| HLA-DRB1*01:01 | 1 | 51 | 65 | 102 | YGITVNWQPIDWDLK | Consensus (comb.lib./smm/nn) | 85.94 |
| HLA-DRB1*01:01 | 1 | 78 | 92 | 103 | WNGYSATDERREKVA | Consensus (comb.lib./smm/nn) | 85.92 |
| HLA-DRB1*01:01 | 1 | 208 | 222 | 104 | ARKEDTNLVKKINEA | Consensus (comb.lib./smm/nn) | 85.34 |

TABLE 4-continued

Top 20 of 239 total predicted MHC II binding sites (HLA-DRB1*0101) of an exemplary SP1500 polypeptide

| Allele | # | Start | End | SEQ ID NO: | Sequence | Method Used | Percent-ile Rank |
|---|---|---|---|---|---|---|---|
| HLA-DRB1*01:01 | 1 | 82 | 96 | 105 | SATDERREKVAFSNS | Consensus (comb.lib./smm/nn) | 84.78 |
| HLA-DRB1*01:01 | 1 | 79 | 93 | 106 | NGYSATDERREKVAF | Consensus (comb.lib./smm/nn) | 84.52 |
| HLA-DRB1*01:01 | 1 | 80 | 94 | 107 | GYSATDERREKVAFS | Consensus (comb.lib./smm/nn) | 84.52 |

Immunogenic and Vaccine Compositions

The present disclosure also provides immunogenic compositions (e.g., vaccine compositions) of, or comprising, one or more fusion proteins described herein. In some embodiments, the immunogenic composition comprises one or more fusion proteins with at least 80%, 85%, 90%, 95%, 96%, 97%, 98%, 99%, 99.5%, or 100% sequence identity to a fusion protein listed in Table 2. In some embodiments, the immunogenic composition comprises a fusion protein that is or includes an amino acid sequence having at least 80%, 85%, 90%, 95%, 97%, 98%, 99%, 99.5%, or 100% identity to any one of SEQ ID NOs:17-26. In some embodiments, the immunogenic composition comprises a fusion protein that is or includes an amino acid sequence having at least 80%, 85%, 90%, 95%, 97%, 98%, 99%, 99.5%, or 100% identity to SEQ ID NO:23. In some embodiments, the immunogenic composition comprises a fusion protein that is or includes an amino acid sequence having at least 80%, 85%, 90%, 95%, 97%, 98%, 99%, 99.5%, or 100% identity to CP1 (e.g., as described in FIG. 1).

In some embodiments, an immunogenic composition may also comprise portions of fusion proteins described herein, for example internal deletion mutants, truncation mutants, and fragments. In some embodiments, the portions of said fusion proteins are immunogenic. The immunogenicity of a portion of a fusion protein is readily determined using the same assays that are used to determine immunogenicity of the full-length fusion protein. In some embodiments, the portion of the fusion protein has substantially the same immunogenicity as the full-length fusion protein. In some embodiments, the immunogenicity is no less than 10%, 20%, 30%, 40%, or 50% that of the fusion proteins of Table 2.

Multi-Component Immunogenic and Vaccine Compositions

In some embodiments, an immunogenic composition described herein (e.g., a vaccine composition) includes a fusion protein described herein and additionally one or more, or two or more, known S. pneumoniae antigens. In some instances, the known S. pneumoniae antigens are predominantly antibody targets. In some instances, the known S. pneumoniae antigens are polysaccharides. In some instances, the known S. pneumoniae antigens protect from S. pneumoniae colonization, or from S. pneumoniae-induced sepsis, pneumonia, meningitis, otitis media, sinusitis, or infection of other sites or organs by S. pneumoniae.

One appropriate art-recognized class of S. pneumoniae antigens is Pneumococcal surface protein A (PspA) and derivatives of PspA. Derivatives of PspA include proline-rich segments with the non-proline block (PR+NPB, also referred to as PRN and further described in Daniels et al, 2010), and related constructs comprising all or a fragment of the proline-rich region of PspA (e.g., regions containing one or more of the sequences PAPAP (SEQ ID NO: 65), PKP, PKEPEQ (SEQ ID NO: 66) and PEKP (SEQ ID NO: 67) and optionally including a non-proline block). In some embodiments, fragments or variants of PspA comprise proline-rich segments with the non-proline block and 10, 20 30, 40 or more additional amino acids of PspA sequence. Peptides containing the NPB are particularly immunogenic, suggesting that the NPB may be an important epitope.

Another appropriate art-recognized class of S. pneumoniae antigen is the pneumolysoids. Pneumolysoids have homology to the S. pneumoniae protein pneumolysin (PLY or Ply), but have reduced toxicity compared to pneumolysin. Pneumolysoids can be naturally occurring or engineered derivatives of pneumolysin. In some embodiments, a pneumolysoid has at least 70%, 80%, 85%, 90%, 95%, 96%, 97%, 98%, or 99% identity to pneumolysin. In some embodiments, the pneumolysoid demonstrates less than one half, 1/10th, 1/20th, 1/50th, 1/100th, 1/200th, 1/500th, or 1/1000th the toxicity of pneumolysin in an assay for one or both of hemolytic activity towards erythrocytes and inhibition of polymorphonuclear leukocytes. Both assays are described in Saunders et al, 1989. Exemplary pneumolysoids include PdT, a triple mutant further described in Berry et al, 1995; Pd-A and Pd-B, further described in Paton et al, 1991; rPd2 and rPd3, further described in Ferreira et al, 2006; Ply8, MPLY, and L460D, further described in, e.g., US 2009/0285846 and L. Mitchell, 2011; or variants thereof. In some embodiments, the pneumolysin has a mutation in the catalytic center, such as at amino acid 428 or 433 or its vicinity.

Other appropriate S. pneumoniae antigens include choline-binding protein A (CbpA) and derivatives thereof (Ogunniyi et al, 2001); pneumococcal surface adhesin A (PsaA); caseinolytic protease; sortase A (SrtA); pilus 1 RrgA adhesin; PpmA; PrtA; PavA; LytA; Stk-PR; PcsB; RrgB and derivatives thereof. CpbA derivatives include constructs described in WO 2012/134975. Such constructs may comprise one or more copies of the R2 domain, R21 and/or R22 subdomains of CpbA, or active variants and fragments thereof, or any combination thereof. Such constructs may further comprise a pneumolysoid.

In some embodiments, an immunogenic composition (e.g., a vaccine composition) contains one or more fusion proteins described herein in combination with one or more polypeptides from Table 1, or antigenic fragments or variants thereof, in a mixture. In some embodiments, the mixture contains both full-length polypeptides and fragments resulting from processing, or partial processing, of signal sequences by an expression host, e.g. E. coli, an insect cell line (e.g., the baculovirus expression system), or a mammalian cell line (e.g., human or Chinese Hamster Ovary).

In some embodiments, an immunogenic composition contains one or more fusion proteins of any of SEQ ID NOs: 17-26 in the absence of any other antigens. In some embodiments, an immunogenic composition contains a fusion protein of SEQ ID NO:23 in the absence of any other antigens. In some embodiments, an immunogenic composition contains one or more fusion proteins of any of SEQ ID NOs:17-26 in combination with one or more additional proteins of any of SEQ ID NOs:1-8, in the absence of other antigens. In some embodiments, an immunogenic composition contains a fusion protein of SEQ ID NO:23 in combination with one or more additional proteins of any of SEQ ID NOs:1-8, in the absence of any other antigens.

In some embodiments, fusion proteins described herein may be conjugated to *S. pneumoniae* polysaccharides. In some embodiments, fusion proteins described herein may be non-covalently complexed to *S. pneumoniae* polysaccharides. The *S. pneumoniae* polysaccharides may be, for example, as described in U.S. Pat. Nos. 5,623,057, 5,371,197, or PCT/US2011/023526. The non-covalent complexes may be, for example, those of the Multiple Antigen Presenting System (MAPS), as described in PCT/US2012/037412, PCT/US2012/037541, and Zhang et al, 2013.

In some embodiments, a fusion protein described herein is covalently bound to another molecule. This may, for example, increase the half-life, solubility, bioabailability, or immunogenicity of the fusion protein. Molecules that may be covalently bound to the fusion protein include a carbohydrate, biotin, poly(ethylene glycol) (PEG), polysialic acid, N-propionylated polysialic acid, nucleic acids, polysaccharides, and PLGA. There are many different types of PEG, ranging from molecular weights of below 300 g/mol to over 10,000,000 g/mol. PEG chains can be linear, branched, or with comb or star geometries. In some embodiments, the fusion protein is covalently bound to a moeity that stimulates the immune system. An example of such a moeity is a lipid moeity. In some instances, lipid moieties are recognized by a Toll-like receptor (TLR) such as TLR-2 or TLR-4, and activate the innate immune system.

In some embodiments, a fusion protein and one or more additional components described herein are mixed together using known methods to form a multi-component immunogenic composition. In some embodiments, a fusion protein and one or more additional components described herein are nano-encapsulated using known methods. In some embodiments, a fusion protein and one or more additional components described herein are molded into nano- or microparticles using known methods. In some embodiments, a fusion protein and one or more additional components described herein are conjugated through a covalent bond using known methods to form a multi-component immunogenic composition. In some embodiments, a fusion protein and one or more additional components described herein are joined non-covalently using known methods to form a multi-component immunogenic composition. Additional methods of combining a fusion protein and one or more additional components are described in, e.g., PCT/US2012/37412 and PCT/US2009/44956.

Nucleic Acid-Based Immunogenic Compositions and Vaccines

The present disclosure also provides immunogenic compositions (e.g., vaccine compositions) of, or comprising, one or more nucleic acids encoding fusion proteins described herein. In some embodiments, the immunogenic composition comprises one or more nucleic acids encoding fusion proteins with at least 80%, 85%, 90%, 95%, 96%, 97%, 98%, 99%, 99.5%, or 100% sequence identity to a fusion protein listed in Table 2. In some embodiments, the immunogenic composition comprises a nucleic acid encoding a fusion protein that is or includes an amino acid sequence having at least 80%, 85%, 90%, 95%, 96%, 97%, 98%, 99%, 99.5%, or 100% identity to any one of SEQ ID NOs:17-26. In some embodiments, the immunogenic composition comprises a nucleic acid encoding a fusion protein that is or includes an amino acid sequence having at least 80%, 85%, 90%, 95%, 96%, 97%, 98%, 99%, or 99.5% identity to SEQ ID NO:23. In some embodiments, the immunogenic composition comprises a nucleic acid encoding a fusion protein that is or includes an amino acid sequence having at least 80%, 85%, 90%, 95%, 96%, 97%, 98%, 99%, 99.5%, or 100% identity to CP1.

In some embodiments, the immunogenic composition comprises one or more nucleic acids having at least 80%, 85%, 90%, 95%, 96%, 97%, 98%, 99%, 99.5%, or 100% identity to any one of SEQ ID NOs:27-36. In some embodiments, the immunogenic composition comprises a nucleic acid having at least 80%, 85%, 90%, 95%, 96%, 97%, 98%, 99%, 99.5%, or 100% identity to SEQ ID NO:33. In all cases, due to degeneracy in the genetic code, other DNA sequences (including multiple codon-optimized sequences) could encode such fusion proteins. In some embodiments, these nucleic acids are expressed in the immunized individual, resulting in production of the encoded *S. pneumoniae* fusion proteins, and the *S. pneumoniae* fusion proteins so produced have an immunostimulatory or immunoprotective effect in the immunized individual.

Such a nucleic acid-containing immunostimulatory composition may comprise, for example, an origin of replication, and/or a promoter that drives expression of one or more nucleic acids encoding one or more fusion proteins of SEQ ID NOs:27-36. Such a composition may also comprise a bacterial plasmid vector into which is inserted a promoter (sometimes a strong viral promoter), one or more nucleic acids encoding one or more fusion proteins of SEQ ID NOs:17-26, and a polyadenylation/transcriptional termination sequence. In some instances, the nucleic acid is DNA. In some instances, the nucleic acid is RNA.

Uses of Immunogenic and Vaccine Compositions

In some embodiments, an immunogenic composition or vaccine that includes one or more fusion proteins described herein is characterized in that one or more of the opsonization potential or immune responses to one or more fusion proteins is increased relative to a pre-determined level, as measured by ELISA and/or by a functional antibody assay. In some embodiments, one or more of the opsonization potential or immune response to the one or more fusion proteins is increased by at least 30% or more, including, e.g., at least 40%, at least 50%, at least 60%, at least 70%, at least 80%, at least 90% or more, relative to a predetermined level, as measured by ELISA and/or by a functional antibody assay. In some embodiments, one or more of the opsonization potential or immune responses to the one or more fusion proteins is increased at least 1-fold, 2-fold, 3-fold, 4-fold, or 5-fold relative to a pre-determined level, as measured by ELISA and/or by a functional antibody assay. In some embodiments, the pre-determined level is a pre-immune level (e.g., a level observed when a subject is not immunized, or is immunized in the absence of one or more fusion proteins described herein).

In some embodiments, an immunogenic composition or vaccine that includes one or more fusion proteins described herein, upon administration to a subject, induces an immune response against *S. pneumoniae*. In some embodiments, the immunogenic composition or vaccine, upon administration to a subject, induces an immune response against one or more serotypes of *S. pneumoniae*. In some embodiments, the immunogenic composition or vaccine, upon administration to a subject, induces a protective immune response against one or more serotypes of *S. pneumoniae*. In some embodiments, the immune response is an antibody or B cell response. In some embodiments, the immune response is a T cell response. In some embodiments, the immune response is an innate immune response. In some embodiments, the immune response is a CD4+ T cell response, including Th1, Th2, or Th17 response, or a CD8+ T cell response, or a CD4+ and a CD8+ T cell response, or a CD4−/CD8− T cell response. In some embodiments, the immune response is an antibody or B cell response and a T cell response. In some embodiments, the immune response is an antibody or B cell response, a T cell response, and an innate immune response.

In some embodiments, an immunogenic composition or vaccine that includes one or more fusion proteins described herein may be used for prophylactic and/or therapeutic treatment of *S. pneumoniae*. Accordingly, the present disclosure provides a method for immunizing a subject suffering from or susceptible to *S. pneumoniae* infection, comprising administering an immunologically effective amount of any immunogenic composition or vaccine that includes one or more fusion proteins described herein. The subject receiving the immunization may be a male or a female, and may be an infant, child, adolescent, or adult. In some embodiments, the subject being treated is a human. In other embodiments, the subject is a non-human animal.

In some embodiments, upon administration to a subject, an immunogenic composition or vaccine comprising a fusion protein described herein treats or prevents infection by *S. pneumoniae*. In some embodiments, upon administration to a subject, the immunogenic composition or vaccine treats or prevents Invasive Pneumococcal Disease (IPD) due to infection by *S. pneumoniae*. In some embodiments, upon administration to a subject, the immunogenic composition or vaccine treats or prevents bacteremia due to infection by *S. pneumoniae*. In some embodiments, upon administration to a subject, the immunogenic composition or vaccine treats or prevents sepsis due to infection by *S. pneumoniae*. In some embodiments, upon administration to a subject, the immunogenic composition or vaccine treats or prevents organ damage due to infection by *S. pneumoniae*. In some embodiments, upon administration to a subject, the immunogenic composition or vaccine treats or prevents meningitis due to infection by *S. pneumoniae*. In some embodiments, upon administration to a subject, the immunogenic composition or vaccine treats or prevents pneumonia due to infection by *S. pneumoniae*. In some embodiments, upon administration to a subject, the immunogenic composition or vaccine treats or prevents otitis media due to infection by *S. pneumoniae*. In some embodiments, upon administration to a subject, the immunogenic composition or vaccine treats or prevents sinusitis due to infection by *S. pneumoniae*.

In some embodiments, upon administration to a subject, an immunogenic composition or vaccine comprising a fusion protein described herein inhibits or reduces the rate of occurrence of infection by *S. pneumoniae*. In some embodiments, upon administration to a subject, the immunogenic composition or vaccine inhibits or reduces the rate of occurrence of Invasive Pneumococcal Disease (IPD) due to infection by *S. pneumoniae*. In some embodiments, upon administration to a subject, the immunogenic composition or vaccine inhibits or reduces the rate of occurrence of bacteremia due to infection by *S. pneumoniae*. In some embodiments, upon administration to a subject, the immunogenic composition or vaccine inhibits or reduces the rate of occurrence of sepsis due to infection by *S. pneumoniae*. In some embodiments, upon administration to a subject, the immunogenic composition or vaccine inhibits or reduces the rate of occurrence of organ damage due to infection by *S. pneumoniae*. In some embodiments, upon administration to a subject, the immunogenic composition or vaccine inhibits or reduces the rate of occurrence of meningitis due to infection by *S. pneumoniae*. In some embodiments, upon administration to a subject, the immunogenic composition or vaccine inhibits or reduces the rate of occurrence of pneumonia due to infection by *S. pneumoniae*. In some embodiments, upon administration to a subject, the immunogenic composition or vaccine inhibits or reduces the rate of occurrence of otitis media due to infection by *S. pneumoniae*. In some embodiments, upon administration to a subject, the immunogenic composition or vaccine inhibits or reduces the rate of occurrence of sinusitis due to infection by *S. pneumoniae*.

In some embodiments, upon administration to a subject, an immunogenic composition or vaccine comprising a fusion protein described herein reduces the severity of infection by *S. pneumoniae*. In some embodiments, upon administration to a subject, the immunogenic composition or vaccine reduces the severity of Invasive Pneumococcal Disease (IPD) due to infection by *S. pneumoniae*. In some embodiments, upon administration to a subject, the immunogenic composition or vaccine reduces the severity of bacteremia due to infection by *S. pneumoniae*. In some embodiments, upon administration to a subject, the immunogenic composition or vaccine reduces the severity of sepsis due to infection by *S. pneumoniae*. In some embodiments, upon administration to a subject, the immunogenic composition or vaccine reduces the severity of organ damage due to infection by *S. pneumoniae*. In some embodiments, upon administration to a subject, the immunogenic composition or vaccine reduces the severity of meningitis due to infection by *S. pneumoniae*. In some embodiments, upon administration to a subject, the immunogenic composition or vaccine reduces the severity of pneumonia due to infection by *S. pneumoniae*. In some embodiments, upon administration to a subject, the immunogenic composition or vaccine reduces the severity of otitis media due to infection by *S. pneumoniae*. In some embodiments, upon administration to a subject, the immunogenic composition or vaccine reduces the severity of sinusitis due to infection by *S. pneumoniae*.

In some embodiments, upon administration to a subject, an immunogenic composition or vaccine comprising a fusion protein described herein inhibits transmission of *S. pneumoniae* from the subject to another subject. In some embodiments, upon administration to a subject, the immunogenic composition or vaccine inhibits colonization by *S. pneumoniae* in the subject. In some embodiments, upon administration to a subject, the immunogenic composition or vaccine inhibits colonization by *S. pneumoniae* in the nasopharynx of the subject.

In some embodiments, an immunogenic composition or vaccine comprising a fusion protein described herein, upon administration to a subject, induces an immune response against *S. pneumoniae* in the subject at a level greater than a control composition. In some embodiments, the immunogenic composition or vaccine, upon administration to a subject, induces an immune response against one or more serotypes of *S. pneumoniae* at a level greater than a control composition. In some embodiments, the level greater is about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 30%, about 35%, about 40%, about 45%, about 50%, about 55%, about 60%, about 65%, about 70%, about 75%, about 80%, about 85%, about 90%, or about 95% of the control composition.

In some embodiments, an immunogenic composition or vaccine comprising a fusion protein described herein, upon administration to a subject, induces an immune response that can help protect against the establishment of S. pneumoniae at a level greater than a control composition. In some embodiments, the immunogenic composition or vaccine protects against colonization at a level greater than a control composition. In some embodiments, the immunogenic composition or vaccine inhibits infection by S. pneumoniae in a non-colonized or uninfected subject at a level greater than a control composition. In some embodiments, the immunogenic composition or vaccine reduces the duration of colonization by S. pneumoniae in a subject who is already colonized at a level greater than a control composition. In some embodiments, the level greater is about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 30%, about 35%, about 40%, about 45%, about 50%, about 55%, about 60%, about 65%, about 70%, about 75%, about 80%, about 85%, about 90%, or about 95% of the control composition.

Antibody Compositions

Some embodiments provide for an antibody composition comprising antibodies raised in a mammal immunized with an immunogenic composition or vaccine comprising a fusion protein described herein. In some embodiments, an antibody comprises at least one antibody selected from the group consisting of monoclonal Abs (mAbs) and anti-idiotype antibodies. In some embodiments, an antibody composition comprises an isolated gamma globulin fraction. In some embodiments, an antibody composition comprises polyclonal antibodies. In some embodiments, the antibody composition is administered to a subject.

Vaccine Formulations

Optimal amounts of components for a particular vaccine comprising a fusion protein described herein can be ascertained by standard studies involving observation of appropriate immune responses in subjects. Following an initial immunization, subjects can receive one or several booster immunizations adequately spaced in time.

The immunogenic composition or vaccine comprising a fusion protein described herein, and/or preparations thereof, may be formulated in a unit dosage form for ease of administration and uniformity of dosage. The specific therapeutically effective dose level for any particular subject or organism may depend upon a variety of factors including the severity or degree of risk of infection; the activity of the specific vaccine or vaccine composition employed; other characteristics of the specific vaccine or vaccine composition employed; the age, body weight, general health, sex of the subject, diet of the subject, pharmacokinetic condition of the subject, the time of administration (e.g., with regard to other activities of the subject such as eating, sleeping, receiving other medicines including other vaccine doses, etc.), route of administration, rate of excretion of the specific vaccine or vaccine composition employed; vaccines used in combination or coincidental with the vaccine composition employed; and like factors well known in the medical arts.

An immunogenic composition or vaccine comprising a fusion protein described herein for use in accordance with the present disclosure may be formulated into compositions (e.g., pharmaceutical compositions) according to known techniques. Vaccine preparation is generally described in Vaccine Design (Powell and Newman, 1995). For example, an immunologically amount of a vaccine product can be formulated together with one or more organic or inorganic, liquid or solid, pharmaceutically suitable carrier materials.

In general, pharmaceutically acceptable carrier(s) include solvents, dispersion media, and the like, which are compatible with pharmaceutical administration. For example, materials that can serve as pharmaceutically acceptable carriers include, but are not limited to sugars such as lactose, glucose, dextrose, and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; polyols such as glycerol, propylene glycol, and liquid polyethylene glycol; esters such as ethyl oleate and ethyl laurate; agar; buffering agents such as magnesium hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as preservatives, and antioxidants can also be present in the composition, according to the judgment of the formulator (Martin, 1975).

Vaccines may be formulated by combining one or more fusion proteins described herein with carriers and/or other optional components by any available means including, for example, conventional mixing, granulating, dissolving, lyophilizing, or similar processes.

Vaccines comprising one or more fusion proteins described herein may be lyophilized up until they are about to be used, at which point they are extemporaneously reconstituted with diluent. In some embodiments, vaccine components or compositions are lyophilized in the presence of one or more other components (e.g., adjuvants), and are extemporaneously reconstituted with saline solution. Alternatively, individual components, or sets of components may be separately lyophilized and/or stored (e.g., in a vaccination kit), the components being reconstituted and either mixed prior to use or administered separately to the subject.

Lyophilization can produce a more stable composition (for instance by preventing or reducing breakdown of polysaccharide antigens). Lyophilizing of vaccines or vaccine components is well known in the art. Typically, a liquid vaccine or vaccine component is freeze dried, often in the presence of an anti-caking agent (such as, for example, sugars such as sucrose or lactose). In some embodiments, the anti-caking agent is present, for example, at an initial concentration of 10-200 mg/ml. Lyophilization typically occurs over a series of steps, for instance a cycle starting at −69° C., gradually adjusting to −24° C. over 3 h, then retaining this temperature for 18 h, then gradually adjusting to −16° C. over 1 h, then retaining this temperature for 6 h, then gradually adjusting to +34° C. over 3 h, and finally retaining this temperature over 9 h.

In some embodiments, a vaccine comprising a fusion protein described herein is a liquid. In some embodiments the liquid is a reconstituted lyophylate. In some embodiments a vaccine has a pH of about 5, about 6, about 7, or about 8. In some embodiments a vaccine has a pH between about 5 and about 7.5. In some embodiments a vaccine has a pH between 5 and 7.5. In some embodiments a vaccine has a pH between about 5.3 and about 6.3. In some embodiments a vaccine has a pH between 5.3 and 6.3. In some embodiments a vaccine has a pH of about 5.0, about 5.1, about 5.2, about 5.3, about 5.4, about 5.5, about 5.6, about 5.7, about 5.8, about 5.9, about 6.0, about 6.1, about 6.2, about 6.3, about 6.4, about 6.5, about 6.6, about 6.7, about 6.8, about 6.9, about 7.0, about 7.1, about 7.2, about 7.3, about 7.4, or about 7.5.

Vaccines or vaccine components for use in accordance with the present disclosure may be incorporated into liposomes, cochleates, biodegradable polymers such as polylactide, poly-glycolide and poly-lactide-co-glycolides, or immune-stimulating complexes (ISCOMS).

In certain situations, it may be desirable to prolong the effect or release of a vaccine for use in accordance with the present invention, for example, by slowing the absorption of one or more vaccine components. Such delay of absorption may be accomplished, for example, by the use of a liquid suspension of crystalline or amorphous material with poor water solubility. The rate of absorption of the product then depends upon its rate of dissolution, which in turn, may depend upon size and form. Alternatively, or additionally, delayed absorption may be accomplished by dissolving or suspending one or more vaccine components in an oil vehicle. Injectable depot forms can also be employed to delay absorption. Such depot forms can be prepared by forming microcapsule matrices of one or more vaccine components a biodegradable polymer network. Depending upon the ratio of polymer to vaccine component, and the nature of the particular polymer(s) employed, the rate of release can be controlled.

Examples of biodegradable polymers that can be employed in accordance with the present disclosure include, for example, poly(orthoesters) and poly(anhydrides). One particular exemplary polymer is polylactide-polyglycolide.

Depot injectable formulations may also be prepared by entrapping the product in liposomes or microemulsions, which are compatible with body tissues.

Polymeric delivery systems can also be employed in non-depot formulations including, for example, oral formulations. For example, biodegradable, biocompatible polymers such as ethylene vinyl acetate, polyanhydrides, polyglycolic acid, collagen, polyorthoesters, and polylactic acid, etc., can be used in oral formulations. Polysaccharide antigens or conjugates may be formulated with such polymers, for example to prepare particles, microparticles, extrudates, solid dispersions, admixtures, or other combinations in order to facilitate preparation of useful formulations (e.g., oral).

Vaccines comprising one or more fusion proteins described herein for use in accordance with the present disclosure include immunogenic compositions, and may additionally include one or more additional active agents (i.e., agents that exert a biological effect—not inert ingredients). For example, it is common in vaccine preparation to include one or more adjuvants. It will be appreciated that such additional agents may be formulated together with one or more other vaccine components, or may be maintained separately and combined at or near the time of administration. In some embodiments, such additional components may be administered separately from some or all of the other vaccine components, within an appropriate time window for the relevant effect to be achieved.

Adjuvants

The vaccine formulations and immunogenic compositions comprising a fusion protein described herein may include an adjuvant. Adjuvants, generally, are agents that enhance the immune response to an antigen. Adjuvants can be broadly separated into two classes, based on their principal mechanisms of action: vaccine delivery systems and immunostimulatory adjuvants (see, e.g., Singh et al, 2003). In most vaccine formulations, the adjuvant provides a signal to the immune system so that it generates a response to the antigen, and the antigen is required for driving the specificity of the response to the pathogen. Vaccine delivery systems are often particulate formulations, e.g., emulsions, microparticles, immune-stimulating complexes (ISCOMs), nanoparticles, which may be, for example, particles and/or matrices, and liposomes. In contrast, immunostimulatory adjuvants are sometimes from or derived from pathogens and can represent pathogen associated molecular patterns (PAMP), e.g., lipopolysaccharides (LPS), monophosphoryl lipid A (MPL), or CpG-containing DNA, which activate cells of the innate immune system.

Alternatively, adjuvants may be classified as organic and inorganic. Inorganic adjuvants include alum salts such as aluminum phosphate, amorphous aluminum hydroxyphosphate sulfate, and aluminum hydroxide, which are commonly used in human vaccines. Organic adjuvants comprise organic molecules including macromolecules. Non-limiting examples of organic adjuvants include cholera toxin/toxoids, other enterotoxins/toxoids or labile toxins/toxoids of Gram-negative bacteria, interleukins (e.g., IL-1, IL-2, IL-4, IL-5, IL-6, IL-7, IL-12, IL-15, IL-18, etc.), interferons (e.g., gamma interferon), granulocyte macrophage colony stimulating factor (GM-CSF), macrophage colony stimulating factor (M-CSF), and tumor necrosis factor (TNF).

Adjuvants may also be classified by the response they induce. In some embodiments, the adjuvant induces the generation, proliferation, or activation of Th1 cells or Th2 cells. In other embodiments, the adjuvant induces the generation, proliferation, or activation of B cells. In yet other embodiments, the adjuvant induces the activation of antigen-presenting cells. These categories are not mutually exclusive; in some cases, an adjuvant activates more than one type of cell.

In some embodiments, the adjuvant induces the generation, proliferation, or activation of Th17 cells. The adjuvant may promote the CD4+ or CD8+ T cells to secrete IL-17. In some embodiments, an adjuvant that induces the generation, proliferation, or activation of Th17 cells is one that produces at least a 2-fold, and in some cases a 10-fold, experimental sample to control ratio in the following assay. In the assay, an experimenter compares the IL-17 levels secreted by two populations of cells: (1) cells from animals immunized with the adjuvant and a polypeptide known to induce Th17 generation, proliferation, or activation, and (2) cells from animals treated with the adjuvant and an irrelevant (control) polypeptide. An adjuvant that induces the generation, proliferation, or activation of Th17 cells may cause the cells of population (1) to produce more than 2-fold, or more than 10-fold more IL-17 than the cells of population (2). IL-17 may be measured, for example, by ELISA or ELISPOT. Certain toxins, such as cholera toxin and labile toxin (produced by enterotoxigenic *E. coli*, or ETEC), activate a Th17 response. Thus, in some embodiments, the adjuvant is a toxin or toxoid. Cholera toxin was successfully used in a mouse model to induce protective immunity in conjunction with certain polypeptides from Table 1. One form of labile toxin is produced by Intercell. Mutant derivates of labile toxin (toxoids) that are active as adjuvants but significantly less toxic can be used as well. Exemplary detoxified mutant derivatives of labile toxin include mutants lacking ADP-ribosyltransferase activity. Particular detoxified mutant derivatives of labile toxin include LTK7 (Douce et al, 1995) and LTK63 (Williams et al, 2004), LT-G192 (Douce et al, 1999), and LTR72 (Giuliani et al, 1998).

In some embodiments, the adjuvant comprises a VLP (virus-like particle). One such adjuvant platform, Alphavirus replicons, induces the activation of Th17 cells using alphavirus and is produced by Alphavax. In some embodiments of the Alphavirus replicon system, alphavirus may be engineered to express an antigen of interest, a cytokine of interest (for example, IL-17 or a cytokine that stimulates IL-17 production), or both, and may be produced in a helper cell line. More detailed information may be found in U.S. Pat. Nos. 5,643,576 and 6,783,939. In some embodiments, a vaccine formulation is administered to a subject in combination with a nucleic acid encoding a cytokine.

Certain classes of adjuvants activate toll-like receptors (TLRs) in order to activate a Th17 response. TLRs are well known proteins that may be found on leukocyte membranes, and recognize foreign antigens (including microbial antigens). Administering a known TLR ligand together with an antigen of interest (for instance, as a fusion protein) can promote the development of an immune response specific to the antigen of interest. One exemplary adjuvant that activates TLRs comprises Monophosphoryl Lipid A (MPL). Traditionally, MPL has been produced as a detoxified lipopolysaccharide (LPS) endotoxin obtained from Gram-negative bacteria, such as *S. minnesota*. In particular, sequential acid and base hydrolysis of LPS produces an immunoactive lipid A fraction (which is MPL), and lacks the saccharide groups and all but one of the phosphates present in LPS. A number of synthetic TLR agonists (in particular, TLR-4 agonists) are disclosed in Evans et al, 2003. Like MPL adjuvants, these synthetic compounds activate the innate immune system via TLR. Another type of TLR agonist is a synthetic phospholipid dimer, for example E6020 (Ishizaka et al, 2007). Various TLR agonists (including TLR-4 agonists) have been produced and/or sold by, for example, the Infectious Disease Research Institute (IRDI), Corixa, Esai, Avanti Polar Lipids, Inc., and Sigma Aldrich. Another exemplary adjuvant that activates TLRs comprises a mixture of MPL, Trehalose Dicoynomycolate (TDM), and dioctadecyldimethylammonium bromide (DDA). Another TLR-activating adjuvant is R848 (resiquimod).

In some embodiments, the adjuvant is or comprises a saponin. Typically, the saponin is a triterpene glycoside, such as those isolated from the bark of the *Quillaja saponaria* tree. A saponin extract from a biological source can be further fractionated (e.g., by chromatography) to isolate the portions of the extract with the best adjuvant activity and with acceptable toxicity. Typical fractions of extract from *Quillaja saponaria* tree used as adjuvants are known as fractions A and C.

In some embodiments, combinations of adjuvants are used. Three exemplary combinations of adjuvants are MPL and alum, E6020 and alum, and MPL and an ISCOM.

Adjuvants may be covalently or non-covalently bound to antigens. In some embodiments, the adjuvant may comprise a protein which induces inflammatory responses through activation of antigen-presenting cells (APCs). In some embodiments, one or more of these proteins can be recombinantly fused with an antigen of choice, such that the resultant fusion molecule promotes dendritic cell maturation, activates dendritic cells to produce cytokines and chemokines, and ultimately, enhances presentation of the antigen to T cells and initiation of T cell responses (e.g., see Wu et al, 2005).

In some embodiments, an immunogenic composition or vaccine comprising a fusion protein described herein is formulated and/or administered in combination with an adjuvant. In some embodiments, the adjuvant is selected from the group consisting of aluminum phosphate, aluminum hydroxide, and phosphate aluminum hydroxide. In some embodiments, the adjuvant comprises aluminum phosphate. In some embodiments, the adjuvant is aluminum phosphate.

Typically, the same adjuvant or mixture of adjuvants is present in each dose of a vaccine. Optionally, however, an adjuvant may be administered with the first dose of vaccine and not with subsequent doses (i.e., booster shots). Alternatively, a strong adjuvant may be administered with the first dose of vaccine and a weaker adjuvant or lower dose of the strong adjuvant may be administered with subsequent doses. The adjuvant can be administered before the administration of the antigen, concurrent with the administration of the antigen or after the administration of the antigen to a subject (sometimes within 1, 2, 6, or 12 hours, and sometimes within 1, 2, or 5 days). Certain adjuvants are appropriate for human subjects, non-human animals, or both.

Vaccines for use in accordance with the present disclosure may include, or be administered concurrently with, antimicrobial therapy. For example, such vaccines may include or be administered with one or more agents that kills or retards growth of a pathogen. Such agents include, for example, penicillin, vancomycin, erythromycin, azithromycin, and clarithromycin, cefotaxime, ceftriaxone, levoflaxin, gatifloxacin.

Alternatively or additionally, vaccines for use in accordance with the present invention may include, or be administered with, one or more other vaccines or therapies. For example, one or more non-pneumococcal antigens may be included in or administered with the vaccines.

Additional Components and Excipients

In addition to the fusion proteins described herein and the adjuvants described above, a vaccine formulation or immunogenic composition may include one or more additional components.

In some embodiments, the vaccine formulation or immunogenic composition may include one or more stabilizers such as sugars (such as sucrose, glucose, or fructose), phosphate (such as sodium phosphate dibasic, potassium phosphate monobasic, dibasic potassium phosphate, or monosodium phosphate), glutamate (such as monosodium L-glutamate), gelatin (such as processed gelatin, hydrolyzed gelatin, or porcine gelatin), amino acids (such as arginine, asparagine, histidine, L-histidine, alanine, valine, leucine, isoleucine, serine, threonine, lysine, phenylalanine, tyrosine, and the alkyl esters thereof), inosine, or sodium borate.

In some embodiments, the vaccine formulation or immunogenic composition includes one or more buffers such as a mixture of sodium bicarbonate and ascorbic acid. In some embodiments, the vaccine formulation may be administered in saline, such as phosphate buffered saline (PBS), or distilled water.

In some embodiments, the vaccine formulation or immunogenic composition includes one or more surfactants, for example, but not limited to, polysorbate 80 (TWEEN 80), polysorbate 20 (TWEEN 20), Polyethylene glycol p-(1,1,3, 3-tetramethylbutyl)-phenyl ether (TRITON X-100), and 4-(1,1,3,3-Tetramethylbutyl)phenol polymer with formaldehyde and oxirane (TYLOXAPOL). A surfactant can be ionic or nonionic.

In some embodiments, the vaccine formulation or immunogenic composition includes one or more salts such as sodium chloride, ammonium chloride, calcium chloride, or potassium chloride.

In some embodiments, a preservative is included in the vaccine or immunogenic composition. In other embodiments, no preservative is used. A preservative is most often used in multi-dose vaccine vials, and is less often needed in single-dose vaccine vials. In some embodiments, the preservative is 2-phenoxyethanol, methyl and propyl parabens, benzyl alcohol, and/or sorbic acid.

Methods of Administration

In some embodiments, an immunogenic composition or vaccine comprising a fusion protein described herein is administered to a subject at risk of developing pneumococcal disease, e.g. an infant, a toddler, a juvenile, or an older adult. In some embodiments, the immunogenic composition or vaccine is administered to a subject at elevated risk of developing pneumococcal disease, e.g., immunocompromised subjects, subjects having sickle cell disease or other hemoglobinopathies, congenital or acquired asplenia, splenic dysfunction, chronic renal failure or nephrotic syndrome, diseases associated with treatment with immunosuppressive drugs or radiation therapy, including malignant neoplasm, leukemia, lymphomas, Hodgkin's disease, or solid organ transplantation, congenital or acquired immunodeficiency, HIV infection, cerebrospinal fluid leaks, cochlear implant(s), chronic heart disease, chronic lung disease, diabetes mellitus, alcoholism, chronic liver disease, cigarette smoking, asthma, generalized malignancy, multiple myeloma, or solid organ transplantation. It will be appreciated that a subject can be considered at risk for developing a disease without having been diagnosed with any symptoms of the disease. For example, if the subject is known to have been, or to be intended to be, in situations with relatively high risk of infection, that subject will be considered at risk for developing the disease.

Any effective route of administration may be utilized such as, for example, oral, nasal, enteral, parenteral, intramuscular or intravenous, subcutaneous, transdermal, intradermal, rectal, vaginal, topical, ocular, pulmonary, or by contact application. In some embodiments, the immunogenic composition or vaccine may be injected (e.g., via intramuscular, intraperitoneal, intradermal and/or subcutaneous routes); or delivered via the mucosa (e.g., to the oral/alimentary, respiratory, and/or genitourinary tracts). Intranasal administration may be particularly useful in some contexts, for example for treatment of pneumonia or otitis media (as nasopharyngeal carriage of pneumococci can be more effectively prevented, thus attenuating infection at its earliest stage). In some embodiments, it may be desirable to administer different doses of the immunogenic composition or vaccine by different routes; in some embodiments, it may be desirable to administer different components of one dose via different routes.

In some embodiments, pharmaceutical compositions (e.g., immunogenic compositions or vaccines) are administered intradermally. Conventional technique of intradermal injection, the "Mantoux procedure", comprises steps of cleaning the skin, and then stretching with one hand, and with the bevel of a narrow gauge needle (26-31 gauge) facing upwards the needle is inserted at an angle of between 10-15°. Once the bevel of the needle is inserted, the barrel of the needle is lowered and further advanced while providing a slight pressure to elevate it under the skin. The liquid is then injected very slowly thereby forming a bleb or bump on the skin surface, followed by slow withdrawal of the needle.

Devices that are specifically designed to administer liquid agents into or across the skin have been described, for example the devices described in WO 99/34850 and EP 1092444, also the jet injection devices described for example in WO 01/13977; U.S. Pat. Nos. 5,480,381, 5,599, 302, 5,334,144, 5,993,412, 5,649,912, 5,569,189, 5,704,911, 5,383,851, 5,893,397, 5,466,220, 5,339,163, 5,312,335, 5,503,627, 5,064,413, 5,520,639, 4,596,556, 4,790,824, 4,941,880, 4,940,460, WO 97/37705 and WO 97/13537. Other methods of intradermal administration of the immunogenic compositions or vaccines may include conventional syringes and needles, or devices designed for ballistic delivery of solid vaccines (WO 99/27961), or transdermal patches (WO 97/48440; WO 98/28037); or applied to the surface of the skin (transdermal or transcutaneous delivery WO 98/20734; WO 98/28037).

As described above, pharmaceutical compositions (e.g., immunogenic compositions or vaccines) may be administered as a single dose or as multiple doses. It will be appreciated that an administration is a single "dose" so long as all relevant components are administered to a subject within a window of time; it is not necessary that every component be present in a single composition. For example, administration of two different immunogenic compositions or vaccines, within a period of less than 24 h, is considered a single dose. To give but one example, immunogenic compositions or vaccines having different antigenic components may be administered in separate compositions, but as part of a single dose. As noted above, such separate compositions may be administered via different routes or via the same route. Alternatively or additionally, in embodiments wherein an immunogenic composition or vaccine is combined with additional types of active agents, the immunogenic composition or vaccine may be administered via one route, and a second active agent may be administered by the same route or by a different route.

Pharmaceutical compositions (e.g., immunogenic compositions or vaccines) are administered in such amounts and for such time as is necessary to achieve a desired result. In some embodiments of the present invention, the immunogenic composition or vaccine comprises an immunologically effective amount of at least immunogenic composition. The exact amount required to achieve an immunologically effective amount may vary, depending on the immunogenic composition, and from subject to subject, depending on the species, age, and general condition of the subject, the stage of the disease, the particular pharmaceutical mixture, its mode of administration, and the like.

The amount of fusion protein(s) described herein in each pharmaceutical composition (e.g., immunogenic composition or vaccine) dose is selected to allow the vaccine, when administered as described herein, to induce an appropriate immunoprotective response without significant adverse side effects.

In some embodiments, a pharmaceutical composition comprising a fusion protein described herein induces a Th1 and/or Th17 cell response upon administration to a subject. In some embodiments, the pharmaceutical composition induces an opsonic/bactericidal response against *S. pneumoniae* upon administration to a subject. In some embodiments, the pharmaceutical composition comprising a fusion protein disclosed herein reduces rate of transmission and/or colonization of the mucosal surfaces by *Streptococcus pneu-*

*moniae* upon administration to a subject. In some embodiments, the pharmaceutical composition reduces rate of transmission and/or colonization of the nasopharynx or the lungs by *S. pneumoniae* upon transmission.

Some embodiments provide for a method of immunizing a subject against *S. pneumoniae* infection comprising administering to the subject an immunologically effective amount of an immunogenic composition comprising a fusion protein described herein. Some embodiments provide for a method of immunizing a subject against *S. pneumoniae* infection comprising administering to the subject an immunologically effective amount of a vaccine composition comprising a fusion protein described herein. Some embodiments provide for a method of immunizing a subject against *S. pneumoniae* infection comprising administering to the subject an immunologically effective amount of a pharmaceutical composition comprising a fusion protein described herein.

Combination Prophylaxis or Combination Therapy

In some embodiments, an immunogenic composition or vaccine comprising a fusion protein described herein may be administered in combination with another agent. In some embodiments, the agent is or comprises PCV13. In some embodiments, the agent is or comprises PPSV23. In some embodiments, the agent is or comprises an antibiotic.

Dosing

In some embodiments, administration of an immunogenic composition or vaccine comprising a fusion protein described herein may involve the delivery of a single dose. In some embodiments, administration may involve an initial dose followed by one or several additional immunization doses, adequately spaced. An immunization schedule is a program for the administration of one or more specified doses of one or more specified pneumococcal vaccines, by one or more specified routes of administration, at one or more specified ages of a subject.

The present disclosure provides immunization methods that involve administering at least one dose of a vaccine to an infant subject. In some embodiments, the infant subject is 18 months old or younger. In some embodiments, the infant subject is 12 months old or younger. In some embodiments, the infant subject has previously received one or more doses of a conjugated pneumococcal polysaccharide vaccine; in other embodiments, the infant subject is naïve to pneumococcal vaccines. In some embodiments, the infant subject has previously been infected with, or exposed to infection by *S. pneumoniae*.

The present disclosure provides immunization methods that involve administering at least one dose of a vaccine to a toddler subject. In some embodiments, the toddler subject is 5 years old or younger. In some embodiments, the toddler subject is 4 years old or younger. In some embodiments, the toddler subject has previously received one or more doses of a conjugated pneumococcal polysaccharide vaccine; in other embodiments, the toddler subject is naïve to pneumococcal vaccines. In some embodiments, the toddler subject has previously been infected with, or exposed to infection by *S. pneumoniae*.

The present disclosure provides immunization methods that involve administering at least one dose of a vaccine to a juvenile subject. In some embodiments, the juvenile subject is 18 years old or younger. In some embodiments, the juvenile subject is 15 years old or younger. In some embodiments, the juvenile subject has previously received one or more doses of a conjugated pneumococcal polysaccharide vaccine; in other embodiments, the juvenile subject is naïve to pneumococcal vaccines. In some embodiments, the juvenile subject has previously been infected with, or exposed to infection by *S. pneumoniae*.

The present disclosure provides immunization methods that involve administering at least one dose of a vaccine to an adult subject. In some embodiments, the adult subject is older than about 50 years of age. In some embodiments, the adult subject is older than about 65 years of age. In some embodiments, the adult subject has previously received one or more doses of a conjugated pneumococcal polysaccharide vaccine; in other embodiments, the adult subject is naïve to pneumococcal vaccines. In some embodiments, the adult subject has previously been infected with, or exposed to infection by *S. pneumoniae*.

Immunization schedules of the present disclosure are provided to induce an immune response (e.g., an immunoprotective response) in a subject sufficient to reduce at least one measure selected from the group consisting of incidence, prevalence, frequency, and/or severity of at least one infection, disease, or disorder, and/or at least one surrogate marker of the infection, disease, or disorder, in a population and/or subpopulation of the subject(s). A supplemental immunization schedule is one which has this effect relative to the standard schedule which it supplements. A supplemental schedule may call for additional administrations and/or supra-immunogenic doses of the immunogenic compositions or vaccines disclosed herein, found in the standard schedule, or for the administration of immunogenic compositions or vaccines not part of the standard schedule. A full immunization schedule of the present invention may comprise both a standard schedule and a supplemental schedule. Exemplary sample immunization schedules are provided for illustrative purposes. Detailed descriptions of methods to assess immunogenic response discussed herein allow one to develop alterations to the sample immunization schedules without undue experimentation.

In one embodiment of the present disclosure, a first administration of a pneumococcal vaccine usually occurs when a subject is more than about 2 weeks old, more than about 5 weeks old, more than about 1 year old, more than about 2 years old, more than about 15 years old, or more than about 18 years old.

In one embodiment of the present disclosure, a first administration of a pneumococcal vaccine usually occurs when a subject is more than about 50 years old, more than about 55 years old, more than about 60 years old, more than about 65 years old, or more than about 70 years old.

In some embodiments of the disclosure, a single administration of vaccine is employed. It is possible that the purposes of the present invention can be served with a single administration, especially when one or more utilized vaccine polypeptides, polysaccharide(s) and/or conjugate(s) or combinations thereof is/are strong, and in such a situation a single dose schedule is sufficient to induce a lasting immune-protective response.

In some embodiments, it is desirable to administer two or more doses of vaccine, for greater immune-protective efficacy and coverage. Thus, in some embodiments, a number of doses is at least two, at least three or more doses. There is no set maximum number of doses, however it is good clinical practice not to immunize more often than necessary to achieve the desired effect.

Without being bound by theory, a first dose of vaccine administered according to the disclosure may be considered a "priming" dose. In some embodiments, more than one dose is included in an immunization schedule. In such a scenario, a subsequent dose may be considered a "boosting" dose.

A priming dose may be administered to a naïve subject (a subject who has never previously received a conjugated polysaccharide vaccine). In some embodiments, a priming dose may be administered to a subject who has previously received conjugated polysaccharide vaccine at least five or more years previous to administration of an initial vaccine dose according to the invention. In other embodiments, a priming dose may be administered to a subject who has previously received a conjugated polysaccharide vaccine at least twenty or more years previous to administration of a priming vaccine according to the invention.

When an immunization schedule calls for two or more separate doses, the interval between doses is considered. The interval between two successive doses may be the same throughout an immunization schedule, or it may change as the subject ages. In immunization schedules of the present invention, once a first vaccine dose has been administered, there is a first interval before administration of a subsequent dose. A first interval is generally at least about 2 weeks, 1 month, 6 weeks, 2 months, 3 months, 6 months, 9 months, 12 months, or longer. Where more than one subsequent dose(s) are administered, second (or higher) intervals may be provided between such subsequent doses. In some embodiments, all intervals between subsequent doses are of the same length; in other embodiments, second intervals may vary in length. In some embodiments, the interval between subsequent doses may be at least about 12 months, at least about 15 months, at least about 18 months, at least about 21 months or at least about 2 years. In some embodiments, the interval between doses may be up to 3 years, up to about 4 years, or up to about 5 years or 10 years or more. In some embodiments, intervals between subsequent doses may decrease as the subject ages.

It will be appreciated by those skilled in the art that a variety of possible combinations and sub-combinations of the various conditions of timing of the first administration, shortest interval, largest interval and total number of administrations (in absolute terms, or within a stated period) exist, and all of these combinations and sub-combinations should be considered to be within the inventor's contemplation though not explicitly enumerated here.

Assays for Determining Immune Response

In some embodiments, a method of assessing the immunogenicity of a pharmaceutical composition, immunogenic composition, or vaccine comprising a fusion protein described herein comprises evaluating, measuring, and/or comparing an immune response using one or more in vitro bioassays, including B cell and T cell responses such as antibody levels by ELISA, multiplex ELISA, MSD, Luminex, flow cytometry, Th1/Th17 cell response, cytokine level measurement and functional antibody levels as measured by OPK, serum bactericidal killing (SBA), agglutination, motility, cytotoxicity, or adherence; and in vivo assays in animal models of pneumococcal disease (e.g. pneumonia, bacteremia, meningitis, sepsis, otitis media, nasopharyngeal colonization). Parameters of in vivo assays include bacterial clearance from mucosal surfaces or bloodstream, reduction or prevention of bacteremia, meningitis, sepsis, or otitis media, reduction or prevention of colonization of the nasopharynx, reduction of mortality, and passive and active protection following challenge with the pneumococcal pathogens that are the targets of the immunogenic composition. In some embodiments, the immune response is compared to a control composition.

In some embodiments, a method of assessing the potency of a pharmaceutical composition, immunogenic composition, or vaccine comprising a fusion protein described herein comprises evaluating, measuring, and/or comparing an immune response using one or more in vitro bioassays, including B cell and T cell responses such as antibody levels by ELISA, multiplex ELISA, MSD, Luminex, flow cytometry, Th1/Th17 cell response, cytokine level measurement and functional antibody levels as measured by OPK, serum bactericidal killing (SBA), internalization, activity neutralization, agglutination, motility, cytotoxicity, or adherence; and in vivo assays in animal models of pneumococcal disease (e.g. pneumonia, bacteremia, meningitis, sepsis, otitis media, nasopharyngeal colonization). Parameters include bacterial clearance or reduction from mucosal surfaces or bloodstream, reduction or prevention of bacteremia, meningitis, sepsis, or otitis media, reduction or prevention of colonization of the nasopharynx, reduction of mortality, and passive and active protection following challenge with the pneumococcal pathogens that are the targets of the immunogenic composition. In some embodiments, the immune response is compared to a control composition.

Generally speaking, it may be desirable to assess humoral responses, cellular responses, and/or interactions between the two. Where humoral responses are being assessed, antibody titers and/or types (e.g., total IgG, IgG1, IgG2, IgM, IgA, etc.) to specific pathogen antigens (e.g., polypeptides or polysaccharides, either serotype-specific or conserved across two or more serotypes) may be determined, for example before and/or after administration of an initial or a boosting dose of vaccine (and/or as compared with antibody levels in the absence of antigenic stimulation). Cellular responses may be assessed by monitoring reactions such as delayed type hypersensitivity responses, etc. to the antigens. Cellular responses can also be measured directly by evaluating the response of peripheral blood mononuclear cells (PBMCs) monocytes to stimulation with the antigens of interest. Precursor and memory B cell populations may be assessed in enzyme-linked immunospot (ELISpot) assays directed against specific pathogen antigens.

The RIA method detects specific antibodies through incubation of sera with radio-labeled polysaccharides or polypeptides in suspension (e.g., Schiffman et al, 1980). The antigen-antibody complexes are then precipitated with ammonium sulfate and the radiolabeled pellets assayed for counts per minute (cpm).

In the ELISA detection method, specific antibodies from the sera of vaccinated subjects are quantitated by incubation with antigens (e.g., polypeptides or polysaccharides, either serotype-specific or conserved across two or more serotypes) which have been adsorbed to a solid support (e.g., Koskela and Leinonen (1981); Kojima et al, 1990; Concepcion and Frasch, 2001). The bound antibody is detected using enzyme-conjugated secondary detection antibodies. The ELISA also allows isotyping and subclassing of the immune response (i.e., IgM vs. IgG or IgG1 vs. IgG2) by using isotype- or subclass-specific secondary antibodies and can be adapted to evaluate the avidity of the antibodies (Anttila et al, 1998; Romero-Steiner et al, 2005). Multiplex assays (e.g., Luminex) facilitate simultaneous detection of antibodies to multiple antigens. Antigens are conjugated to spectrally distinct microspheres that are mixed and incubated with serum. The antibodies bound to the antigens on the coated microspheres are detected using a secondary antibody (e.g., R-Phycoerythrin-conjugated goat anti-human IgG).

An approach for assessing functional antibody in serum is the opsonophagocytic assay (OPA) which quantitates only the antibodies that can opsonize the bacteria, leading to ingestion and killing of the bacteria. The standard assay utilizes a human phagocytic effector cell, a source of complement, bacteria, and diluted sera. The assay readout is the serum endpoint titer at which there is >50% killing compared to bacteria incubated with complement and human cells alone (Romero-Steiner et al, 1997). This killing OPA can also be multiplexed by utilizing target strains of pathogen that carry different antibiotic resistance markers (Kim et al, 2003). Another type of multiplex opsonic assay is a nonkilling assay in which the uptake by phagocytic effector cells of fluorescent stained encapsulated pathogen or fluorescent microspheres conjugated with antigens from a target pathogen in the presence of diluted sera plus a complement source is evaluated by FC (Martinez et al, 1999). Opsonic activity of serum antibody plus complement can also be evaluated by measuring the oxidative response of phagocytic human effector cells to ingested pathogen (Munro et al. 1985; Ojo-Amaize et al. 1995).

Certain in vivo model systems can be used to evaluate the protection afforded by serum antibodies induced by immunogenic compositions or vaccines comprising a fusion protein described herein. In such passive protection systems, mice or rats are challenged with the pathogen plus diluted sera, and the endpoint titer of the sera which provides protection against pneumonia, bacteremia, colonization of organs or tissues, or mortality is determined (Stack et al. 1998; Saeland et al. 2000).

In some embodiments, efficacy of immunization may be determined by assaying one or more cytokine levels by stimulating T cells from a subject after immunization. The one or more cytokine levels may be compared to the one or more cytokine levels in the same subject before immunization. Increased levels of the one or more cytokine, such as a 1.5 fold, 2-fold, 5-fold, 10-fold, 20-fold, 50-fold or 100-fold or more increase over pre-immunization cytokine levels, would indicate an increased response to the immunogenic composition or vaccine. In some embodiments, the one or more cytokines are selected from GM-CSP; IL-1α; IL-1β; IL-2; IL-3; IL-4; IL-5; IL-6; IL-7; IL-8; IL-10; IL-12; IL-17A, IL-17F or other members of the IL-17 family; IL-22; IL-23; IFN-α; IFN-β; IFN-γ; MIP-1α; MIP-1β; TGF-β; TNFα, or TNF-β. In a non-limiting example, efficacy of immunization may be determined by assaying IL-17 levels (particularly IL-17A) by stimulating T cells from a subject after immunization. The IL-17 levels may be compared to IL-17 levels in the same subject before immunization. Increased IL-17 (e.g., IL-17A) levels, such as a 1.5 fold, 2-fold, 5-fold, 10-fold, 20-fold, 50-fold or 100-fold or more increase, would indicate an increased response to the immunogenic composition or vaccine.

In some embodiments, one may assay neutrophils in the presence of T cells or antibodies from the patient for pneumococcal killing. Increased pneumococcal killing, such as a 1.5 fold, 2-fold, 5-fold, 10-fold, 20-fold, 50-fold or 100-fold or more increase, would indicate an increased response to the immunogenic composition or vaccine. For example, one may measure Th17 cell activation, where increased Th17 cell activation, such as a 1.5 fold, 2-fold, 5-fold, 10-fold, 20-fold, 50-fold or 100-fold or more increase, correlates with an increased response to the immunogenic composition or vaccine. In another non-limiting example, one may measure Th1 cell activation, where increased Th1 cell activation, such as a 1.5 fold, 2-fold, 5-fold, 10-fold, 20-fold, 50-fold or 100-fold or more increase, correlates with an increased response to the immunogenic composition or vaccine. One may also measure levels of an antibody specific to the immunogenic composition or vaccine, where increased levels of the specific antibody, such as a 1.5 fold, 2-fold, 5-fold, 10-fold, 20-fold, 50-fold or 100-fold or more increase, are correlated with increased efficacy. In some embodiments, two or more of these assays are used. For example, one may measure IL-17 levels and the levels of immunogenic composition- or vaccine-specific antibody. Alternatively, one may follow epidemiological markers such as incidence of, severity of, or duration of pneumococcal infection in vaccinated individuals compared to unvaccinated individuals.

Immunogenic composition or vaccine efficacy may also be assayed in various model systems such as the mouse challenge model. For instance, BALB/c or C57BL/6 strains of mice may be used. After administering the test immunogenic composition or vaccine to a subject (as a single dose or multiple doses), the experimenter administers a challenge dose of S. pneumoniae. In some cases, a challenge dose administered intranasally is sufficient to cause S. pneumoniae colonization (especially nasal colonization) in an unvaccinated animal, and in some cases a challenge dose administered via aspiration is sufficient to cause sepsis and a high rate of lethality in unvaccinated animals. In some cases, a challenge dose administered via intraperitoneal injection is sufficient to cause sepsis and a high rate of lethality in unvaccinated animals. In some cases, a challenge dose administered via intravenous injection is sufficient to cause sepsis and a high rate of lethality in unvaccinated animals. One can then measure the reduction in colonization or the reduction in lethality in vaccinated animals.

Certain in vivo model systems can be used to evaluate the protection afforded by serum antibodies induced by vaccines of the present invention. In such passive protection systems, mice or rats are challenged with the pathogen plus diluted sera, and the endpoint titer of the sera which provides protection against bacteremia, colonization of organs or tissues, or mortality is determined (Stack et al. 1998; Saeland et al. 2000).

EXEMPLIFICATION

Example 1: Induction of Th17 Response and Protection from Pneumococcal Nasal Colonization in Mice Mediated by SP0785 and SP1500 Components of Fusion Protein CP1

Objective:

This Example compares the ability of individual *Streptococcus pneumoniae* proteins SP0785 and SP1500 with an exemplary fusion protein CP1 to stimulate a Th17 response and protect mice from nasal colonization with *S. pneumoniae* after nasal immunization with the adjuvant cholera toxin (CT). An exemplary fusion protein CP1 is a fusion protein comprising a truncated rhizavidin (amino acids [45-179], denoted Rhavi), a SP0785 polypeptide, and a SP1500 polypeptide. In some embodiments, a fusion protein CP1 is or comprises Rhavi-linker (GGGGSSS)-SP1500-linker (AAA)-SP0785.

Summary:
1. *S. pneumoniae* proteins SP0785 and SP1500, and fusion protein CP1 can each generate a robust Th17 response in mice as demonstrated by secretion of interleukin 17A (IL-17A) after intranasal immunization with the adjuvant cholera toxin (CT).

2. *S. pneumoniae* nasal colonization was significantly reduced by separate intranasal immunizations of mice with SP1500 or SP0785 and CT, or with CP1 and CT.

Materials and Methods:

Recombinant Protein Production

Histidine-tagged recombinant proteins were expressed in *Escherichia coli* and purified using Ni-nitrilotriacetic acid affinity chromatography. A second purification was executed with size-exclusion chromatography with a Superdex 200 column. Protein concentration was measured using a bicinchoninic acid (BCA) protein assay kit (Bio-Rad).

Formulation

Cholera toxin (CT) was used as adjuvant for intranasal immunization to facilitate induction of T-cell responses to proteins alone. Proteins or pneumococcal whole cell vaccine (amount indicated in Table 5) were mixed with 1 µg of CT in saline solution in a final volume of 20 µl per dose prior to administration.

Intranasal Mouse Immunization Protocol

For intranasal immunization with CT adjuvanted proteins and pneumococcal whole cell vaccine with chloroform inactivation (WCC), C57BL/6 mice (groups of n=10) received 2 immunizations 1 week apart. Peripheral blood samples were taken 3 weeks after the last immunization for ex vivo IL-17A stimulation in the presence of appropriate antigen(s) as stimulant.

TABLE 5

Mouse intranasal immunization study groups

| Group | Antigen | Dose (Protein) | Adjuvant | # of Mice | Immunization Schedule (days) | Blood Collection (days) |
|---|---|---|---|---|---|---|
| A | — | — | CT | 10 | 0, 7 | 28 |
| B | SP0785 | 10 µg | CT | 10 | 0, 7 | 28 |
| C | — | — | CT | 10 | 0, 7 | 28 |
| D | SP1500 | 10 µg | CT | 10 | 0, 7 | 28 |
| E | CP1 | 15 µg | CT | 10 | 0, 7 | 28 |
| F | Rhavi | 15 µg | CT | 10 | 0, 7 | 28 |
| G | WCC | 100 µg | CT | 10 | 0, 7 | 28 |

Abbreviations:
CP1: fusion protein 1 (Rhavi-linker (GGGGSSS)-SP1500-linker (AAA)-SP0785);
Rhavi: truncated rhizavidin, amino acids [45-179];
WCC: pneumococcal whole cell vaccine (chloroform inactivation);
CT: cholera toxin
Note:
all recombinant proteins were His-tagged.

IL-17A Induction and Measurement from Whole Blood

Ex vivo stimulation of peripheral blood samples taken 3 weeks after the last intranasal immunization was performed in 96-well round-bottom plates. All stimulants were diluted in stimulation medium (DMEM F-12; 10% FBS, 50 µM 2-mercaptoethanol, 10 µg/ml ciprofloxacin) at a final concentration of 10 µg/ml. In each well, 25 µl of heparinized blood was added to 225 µl of stimulation medium containing indicated stimulants, followed by incubation at 37° C. with 5% $CO_2$ for 6 days. Supernatants were collected after centrifugation, and IL-17A was analyzed with an ELISA kit (R&D systems).

Nasopharyngeal *S. pneumoniae* Infection and Measurement of Colonization

One to 2 weeks after blood collection, mice were intranasally challenged with $10^7$ CFU of type 6B pneumococci (603 strain). Nasopharyngeal wash on euthanized mice was conducted 7 days post infection. The *S. pneumoniae* CFU per nasal wash were calculated after growth on blood agar plates.

Statistical Analyses

Statistical analyses were performed using PRISM (GraphPad Software). All data on IL-17A concentration and nasopharyngeal colonization densities were analyzed using the Mann-Whitney U test. The geometric mean concentrations of IL-17A was calculated for each group, and the geometric mean density of colonization was calculated for each group.

Results and Discussion:

IL-17A Response and Reduction in Colonization after Intranasal Immunization with SP1500, SP0785, or CP1.

Figure 2:
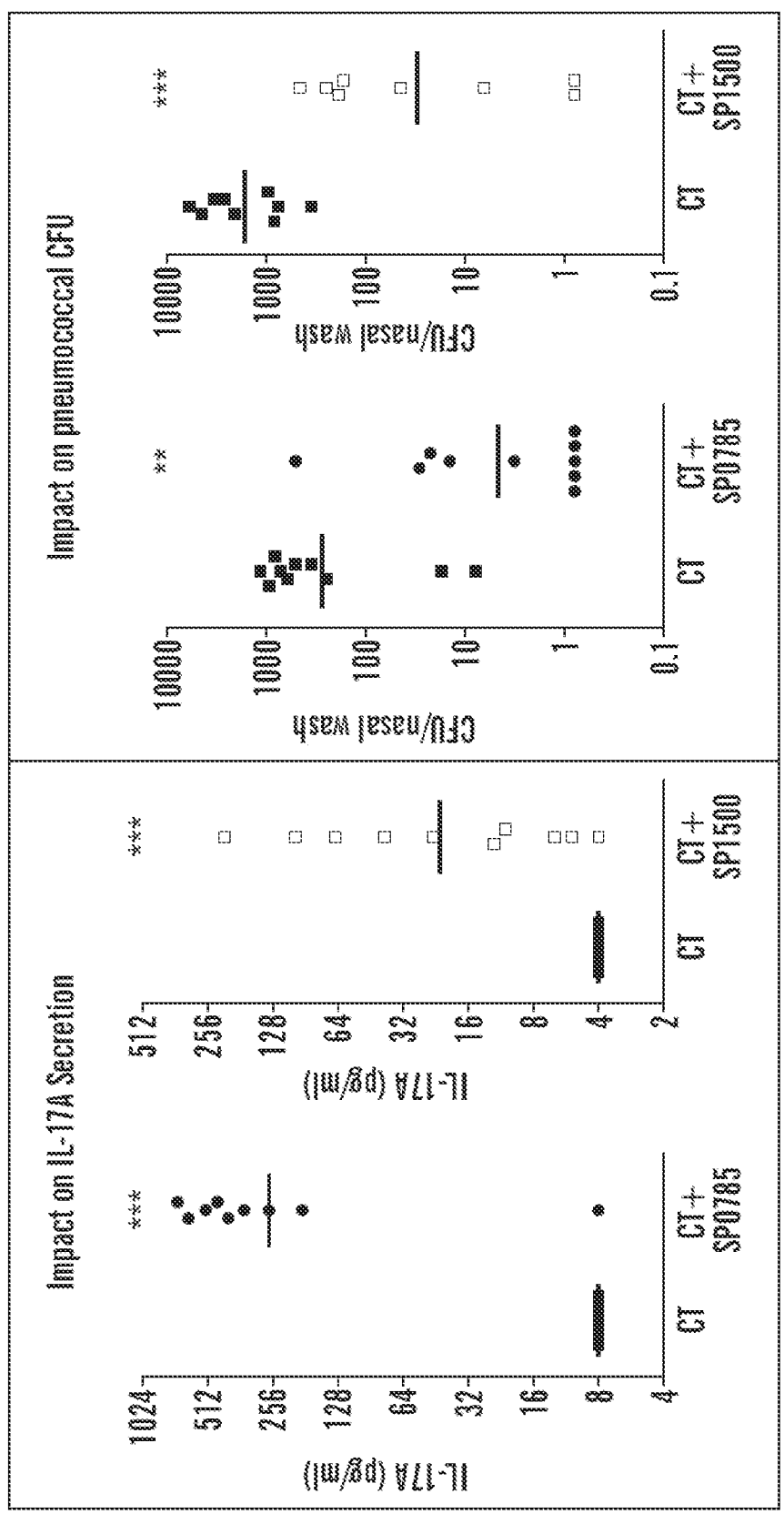
FIG. 2 illustrates immune responses to SP1500 and SP0785 polypeptide components of an exemplary fusion protein CP1. The left panel shows Th17 response to a SP1500 polypeptide and a SP0785 polypeptide of an exemplary fusion protein CP1. Th17 responses are shown as geometric mean concentration of IL-17A secreted in media after stimulation of peripheral blood samples of mice immunized with cholera toxin alone, or with a SP1500 or SP0785 polypeptide adjuvanted with cholera toxin. Each point on the graph represents secreted IL-17A for one mouse. The right panel shows protection from colonization by S. pneumoniae following immunization with cholera toxin alone, or with a SP1500 or SP0785 polypeptide adjuvanted with cholera toxin and intranasal challenge with S. pneumoniae. Each point on the graph represents S. pneumoniae CFU per nasal wash for one mouse. The horizontal bars in both panels represent the geometric mean of secreted IL-17A (left panel) and geometric mean of CFU per nasal wash for each group (right panel), respectively. The data were statistically analyzed by Mann-Whitney U test. CT: cholera toxin; CFU: colony forming unit; ELISA: enzyme-linked immunosorbent assay; IL-17A: interleukin 17A.  $p<0.01$; * $p<0.001$.

As seen in FIG. 2, left panel, intranasal immunization with either SP0785 or SP1500 adjuvanted with CT induced a strong antigen-specific Th17 response compared to immunization with CT alone, as indicated by increased IL-17A production after ex vivo stimulation of peripheral blood with purified SP0785 or SP1500. The increased IL-17A secretion correlated with a corresponding statistically significant reduction in *S. pneumoniae* CFU recovered from the nasopharyngeal wash 7 days after challenge of immunized mice (FIG. 2, right panel).

Figure 3:
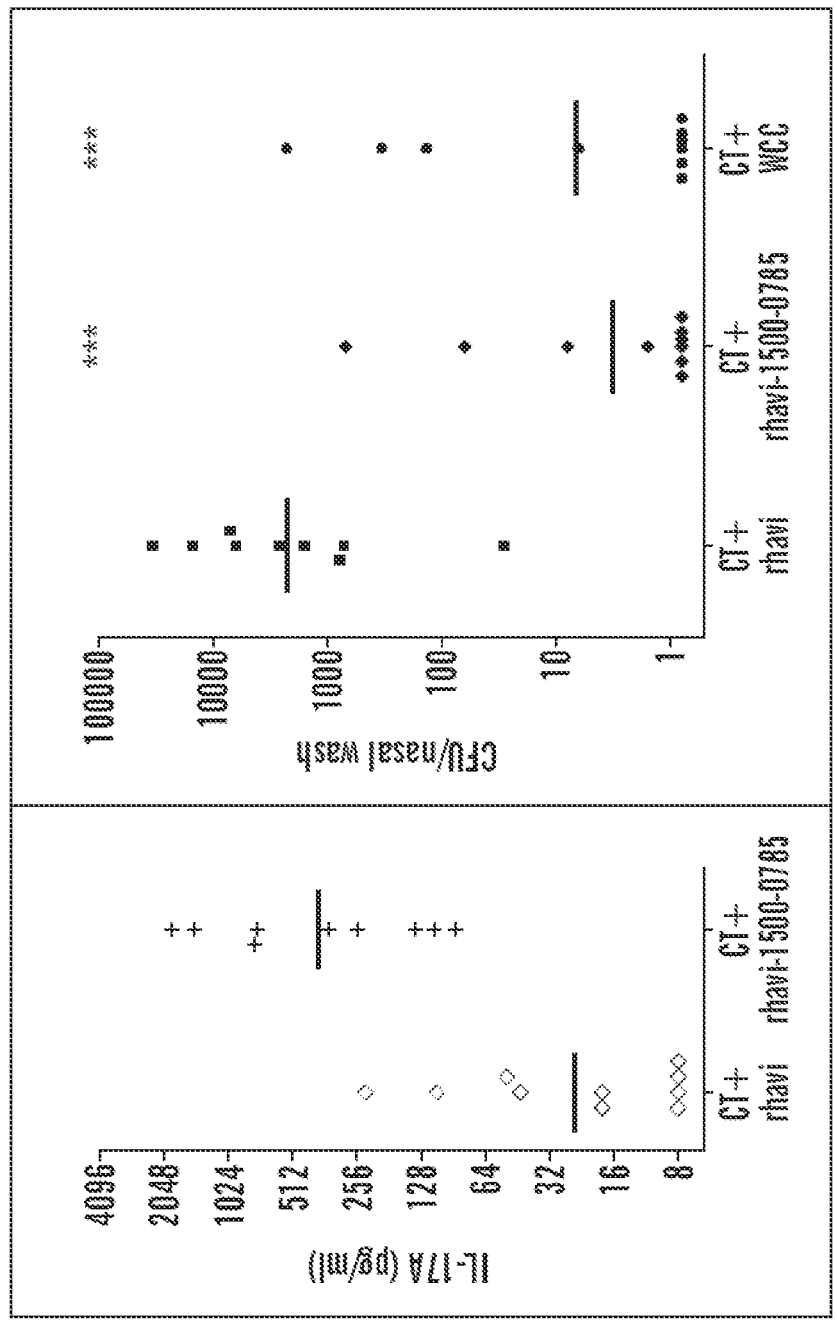
FIG. 3 illustrates immune responses to an exemplary fusion protein CP1. The left panel shows Th17 response to an exemplary fusion protein CP1. Th17 responses are shown as geometric mean concentration of IL-17 secreted in media after stimulation of peripheral blood samples of mice immunized with a truncated rhizavidin protein (Rhavi) or with CP1, both adjuvanted with cholera toxin. Each point on the graph represents secreted IL-17A for one mouse. The right panel shows protection from colonization by S. pneumoniae following immunization with a truncated rhizavidin protein (Rhavi), CP1, or killed (inactivated) pneumococcal whole cells (WCC), adjuvanted with cholera toxin, and intranasal challenge with S. pneumoniae. Each point on the graph represents S. pneumoniae CFU per nasal wash for one mouse. The horizontal bars in both panels represent the geometric mean of secreted IL-17A (left panel) and geometric mean of CFU per nasal wash for each group (right panel), respectively. The data were statistically analyzed by Mann-Whitney U test. CT: cholera toxin; CFU: colony forming unit; IL-17A: interleukin 17A; rhavi: truncated rhizavidin protein; (amino acids 45-179 of a full-length rhizavidin protein). *** $p<0.001$.

As seen in FIG. 3, left panel, when Rhavi protein was compared to the protein fusion of Rhavi-linker (GGGGSSS)-SP1500-linker (AAA)-SP0785 (CP1) after intranasal immunization with CT, CP1 retained the antigen specific induction of IL-17A. When these mice were challenged with *S. pneumoniae* and compared to pneumococcal whole cell vaccine intranasal immunization, Rhavi alone had no protective effect as measured by pneumococcal CFU, while CP1 had a protective effect that was comparable to killed (inactivated) pneumococcal whole cells (FIG. 3, right panel).

Example 2: Killing-Activity of Anti-Sera Against Fusion Protein CP1

Materials and Methods:

Growth of Bacteria

*S. pneumoniae* strains 6B, 15A, 16F, and 35B were inoculated into 10 mL cultures of Todd Hewitt Broth (THB) with yeast extract. Cultures were incubated at 37° C. in 5% $CO_2$ for 4-7 hours until the $OD_{600}$ reached 0.5-0.8 (mid-logarithmic phase). The bacteria were harvested by spinning for 7 minutes at 3,000 g at 4° C. and the bacterial pellet was resuspended in 10 mL of THB with 10% glycerol with storage at −80° C. Colony forming unit (CFU) estimations were determined by serially dilutions of frozen stocks on Trypticase soy agar with 5% sheep blood (Becton, Dickenson, and Company) with 37° C. in 5% $CO_2$ incubation for 18 to 24 hrs.

Concentrated Opsonophagocytic Assay (COPA)

Frozen stocks of *S. pneumoniae* were thawed and resuspended at $2 \times 10^5$ CFU/ml in assay buffer (Hank's buffered saline with 10% heat inactivated FBS). To a 96 well plate, 10 µl of bacteria suspension was added to each well followed by 20 µl of heat inactivated rabbit serum diluted in assay buffer to be tested in the assay. The bacteria and rabbit serum were incubated at room temperature for 30 min with shaking. To each well, 10 µl of baby rabbit complement (Pel-Freeze Biologicals) was added followed by incubation at room temperature for 30 min with shaking. HL60 cells (ATCC) were washed with assay buffer and resuspend to $1 \times 10^7$ cells/ml. To each well, 40 µl of HL60 suspension was added (200:1 HL60 to bacteria ratio) followed by incubation with shaking at 37° C. with 5% $CO_2$ for 1 hour. The plate was transferred to ice and incubated for 20 minutes. Each sample (undiluted, 1/5 and 1/25 dilutions in water) was then plated on 5% blood agar plates. After overnight incubation at 37° C. with 5% $CO_2$, the CFU were counted for each sample and dilution.

Rabbit Serum

New Zealand White rabbits (n=3) were immunized with 100 ug of Rhavi-linker (GGGGSSS)-SP1500-linker (AAA)-SP0785(CP1, His-tagged) and 0.625 mg of elemental aluminum from $AlPO_4$ per dose for a total of three doses with two weeks between each immunization (rabbits 87, 88, and 1762). Sera were collected prior to immunization (P0) and two weeks after the third immunization (P3) and stored at −80° C.

Results and Discussion:

S. pneumoniae Opsonophagocytic Activity of Antibodies Directed Against CP1

Figure 4:
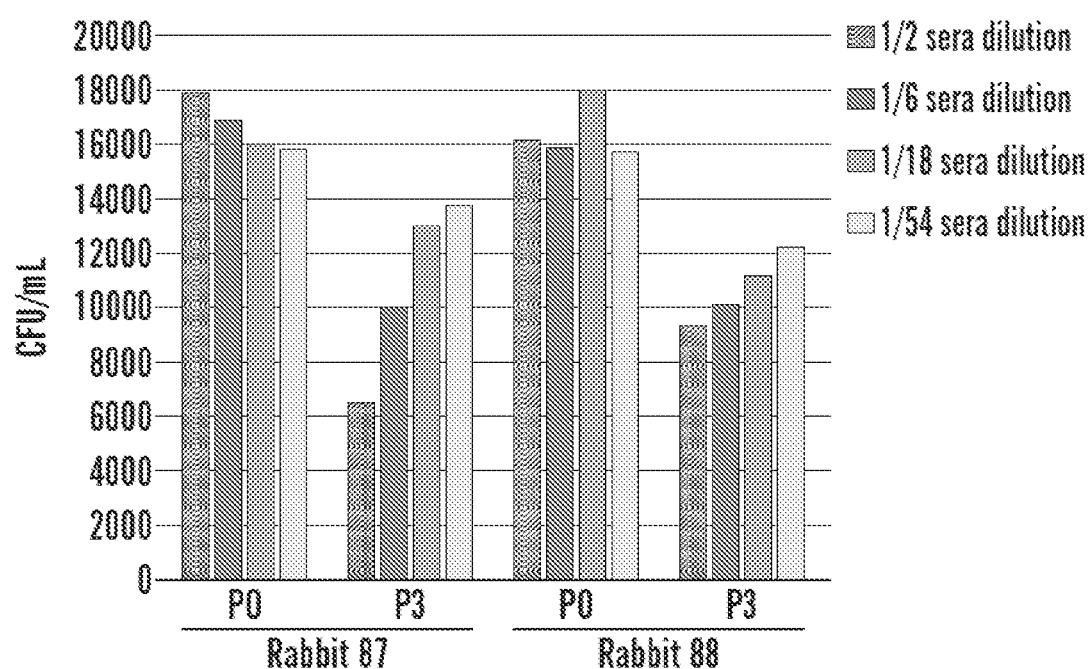
FIG. 4 illustrates the presence of functional antibodies against a representative S. pneumoniae serotype (e.g., serotype 6B) in CP1 immune sera. S. pneumoniae serotype 6B was incubated in a modified concentrated opsonophagocytic assay (COPA) with heat inactivated pre-immune (P0) and immune (P3) serum, at various dilutions, from each of two rabbits (87 and 88) immunized with CP1 adjuvanted with aluminum phosphate. The colony forming units (CFU) for each dilution and sera combination were enumerated on blood agar plates after overnight incubation. The presence of functional antibodies is shown by killing of S. pneumoniae, i.e., reduction of CFUs following incubation with immune sera. Each vertical bar on the graph represents CFU/ml for each sample of the indicated CP1 serum and dilution, at the indicated timepoint (bottom of graph).
Figure 5:
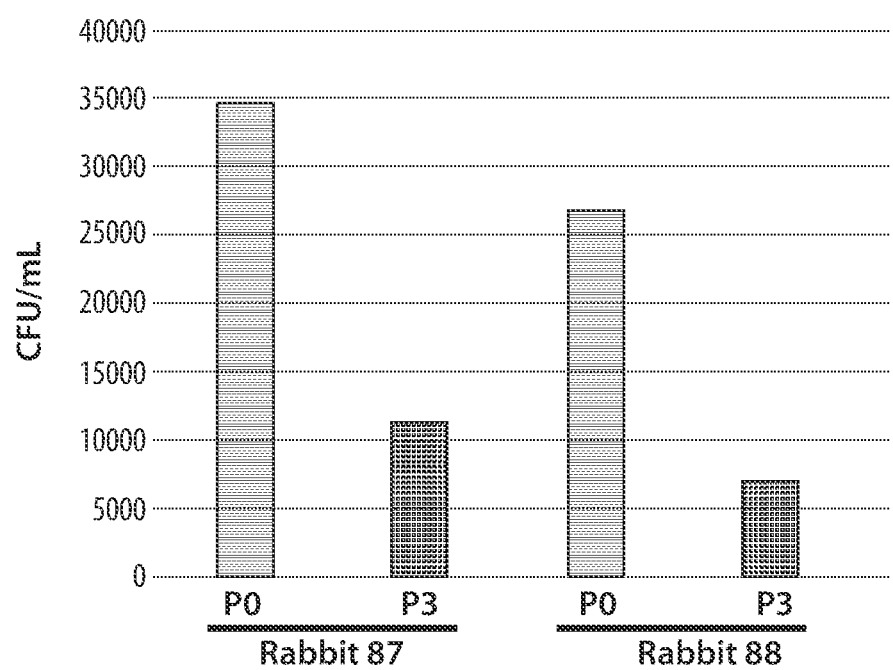
FIG. 5 illustrates the presence of functional antibodies against a representative S. pneumoniae serotype (e.g., serotype 15A) in CP1 immune sera. S. pneumoniae serotype 15A was incubated in a modified concentrated opsonophagocytic assay (COPA) with heat inactivated pre-immune (P0) and immune (P3) serum, at 1/2 dilution, from each of two rabbits (87 and 88) immunized with CP1 adjuvanted with aluminum phosphate. The colony forming units (CFU) for each serum were enumerated on blood agar plates after overnight incubation. The presence of functional antibodies is shown by killing of S. pneumoniae, i.e., reduction of CFUs following incubation with immune sera. Each vertical bar on the graph represents CFU/ml for each sample of the indicated CP1 serum at the indicated timepoint (bottom of graph).
Figure 6:
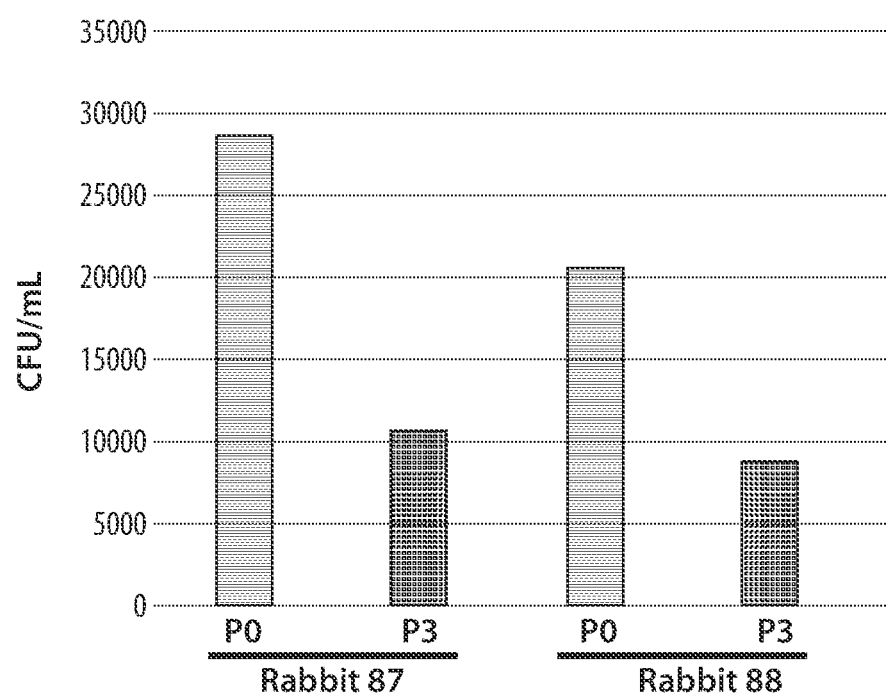
FIG. 6 illustrates the presence of functional antibodies against a representative S. pneumoniae serotype (e.g., serotype 35B) in CP1 immune sera. S. pneumoniae serotype 35B was incubated in a modified concentrated opsonophagocytic assay (COPA) with heat inactivated pre-immune (P0) and immune (P3) serum, at 1/2 dilution, from each of two rabbits (87 and 88) immunized with CP1 adjuvanted with aluminum phosphate. The colony forming units (CFU) for each serum were enumerated on blood agar plates after overnight incubation. The presence of functional antibodies is shown by killing of S. pneumoniae, i.e., reduction of CFUs following incubation with immune sera. Each vertical bar on the graph represents CFU/ml for each sample of the indicated CP1 serum at the indicated timepoint (bottom of graph).
Figure 7:
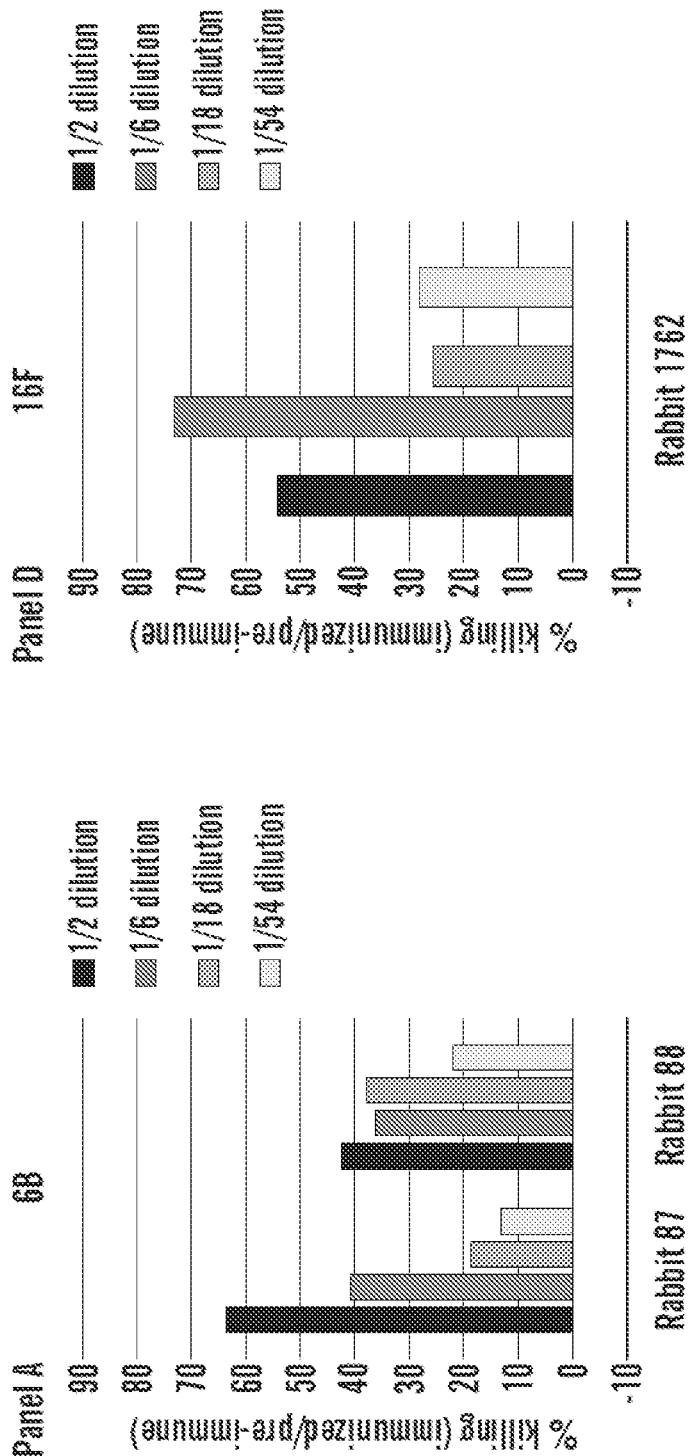
FIG. 7 illustrates the presence of functional antibodies against representative S. pneumoniae serotypes. S. pneumoniae serotypes 6B (Panel A), 16F (Panel D), 15A (Panel B), and 35B (Panel C) were separately incubated in a modified concentrated opsonophagocytic assay (COPA) with heat-inactivated pre-immune (P0) and immune (P3) sera, at various dilutions, from rabbits (87, 88, and 1762) immunized with CP1 adjuvanted with aluminum phosphate. The presence of functional antibodies is shown by killing of S. pneumoniae. Results are expressed as percent killing activity, i.e., the percent reduction in S. pneumoniae colony forming units (CFU), following incubation with immune (P3) sera, relative to incubation with matched pre-immune (P0) sera. Each vertical bar of Panels A-D represents the percent killing activity observed with the indicated dilution of the indicated CP1 serum (bottom of each graph), against the indicated S. pneumoniae serotype (top of each graph)
Figure 7:
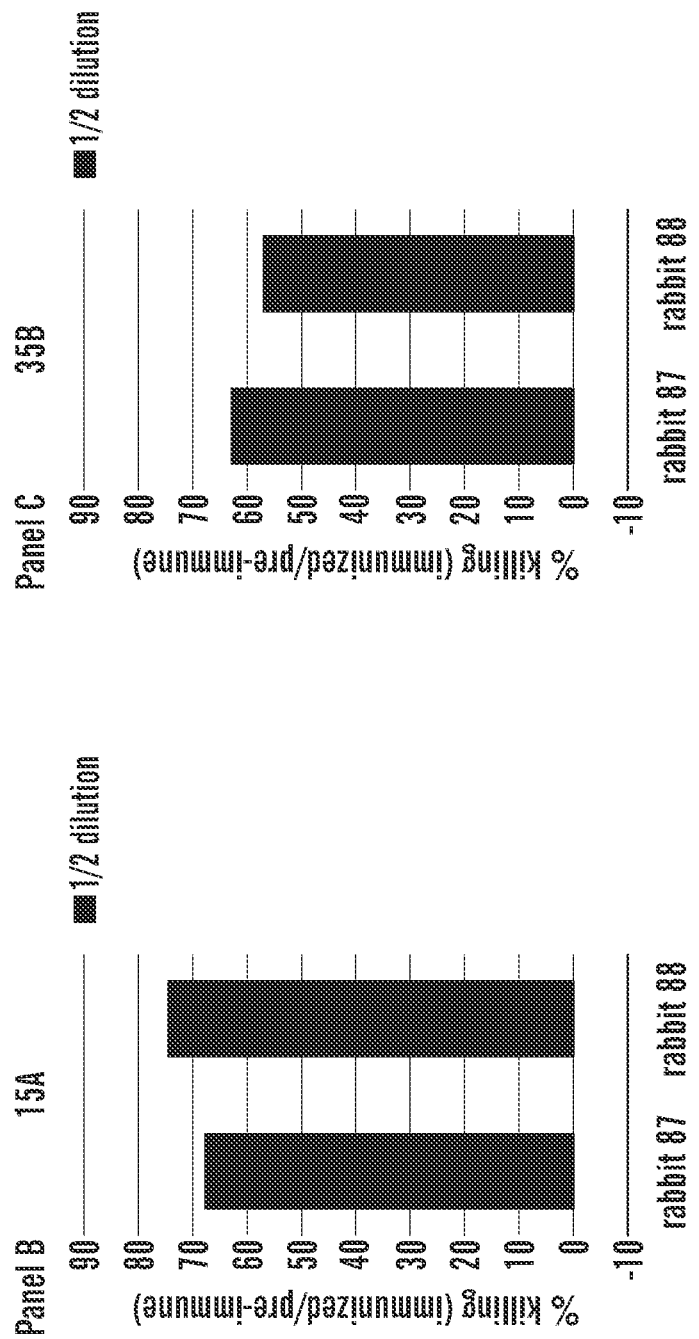

A modified concentrated opsonophagocytic assay (COPA) was established to investigate protein antibody-mediated killing of S. pneumoniae. Sera from two rabbits immunized with CP1 (P3 from rabbits 87 and 88) were assayed in comparison to the pre-immune sera (P0). At all dilutions tested for both rabbits, incubation with the P3 immune serum resulted in a reduction of the CFU (FIG. 4), or in alternative display of the same results, an increase in percent killing activity (FIG. 7, Panel A), compared to incubation with the pre-immune serum (P0) for S. pneumoniae serotype 6B, a type incorporated into the commercially available Prevnar 13 vaccine. The killing activity of the immune serum was dependent on both HL60 cells and active complement (data not shown). The same sera were assayed on two serotypes not incorporated into commercially available vaccines, S. pneumoniae serotype 15A (FIG. 5 and FIG. 7, Panel B: 1/2 dilution) and serotype 35B (FIG. 6 and FIG. 7, Panel C: 1/2 dilution). Serum from a third rabbit immunized with CP1 (P3 from rabbit 1762) was assayed in comparison to the pre-immune serum (P0) against S. pneumoniae serotype 16F, a further serotype not incorporated into commercially available vaccines (FIG. 7, Panel D: 1/2, 1/6, 1/18, 1/54 dilutions). For all rabbits and non-vaccine serotypes tested, incubation with the P3 immune sera resulted in a reduction of the CFU, or alternatively displayed, an increase in percent killing activity, compared to incubation with the pre-immune sera (P0). The killing activity of the immune sera was dependent on both HL60 cells and active complement (data not shown).

Example 3: Comparison of Induction of Th17 Response in Mice Following-Immunization with a Mixture (Unconjugated) of SP0785, SP1500, and a Truncated Rhizavidin Protein Rhavi, or with Fusion Proteins CP1 or SP0785-Linker (SSSGG)-SP1500-Linker (SSVDKL)-PdT Materials and Methods:

Recombinant Protein Production

Histidine-tagged recombinant proteins were expressed in Escherichia coli and purified using Ni-nitrilotriacetic acid affinity chromatography. A second purification was executed with size-exclusion chromatography with a Superdex 200 column. Protein concentration was measured using a bicinchoninic acid (BCA) protein assay kit (Bio-Rad).

Formulation

Cholera toxin (CT) was used as adjuvant for intranasal immunization to facilitate induction of T-cell responses to proteins alone. Proteins (amount indicated in Table 6) were mixed with 1 μg of CT in saline solution to a final volume of 20 μl per dose prior to administration.

Intranasal Mouse Immunization Protocol

For intranasal immunization with CT adjuvanted proteins, C57BL/6 mice (groups of n=15) received 2 immunizations 1 week apart. Peripheral blood samples were taken 3 weeks after the last immunization for ex vivo IL-17A stimulation in the presence of appropriate antigen(s) as stimulant.

TABLE 6

Mouse intranasal immunization study groups

| Group | Antigen | Dose (Protein) | Adjuvant | # of Mice | Immunization Schedule (days) | Blood Collection (days) |
|---|---|---|---|---|---|---|
| A | — | — | CT | 15 | 0, 7 | 28 |
| B | CP1 | 10 μg | CT | 15 | 0, 7 | 28 |
| C | Rhavi + SP0785 + SP1500 mixture | 10 μg | CT | 15 | 0, 7 | 28 |
| D | SP0785-linker (SSSGG)-SP1500-linker (SSVDKL)-PdT | 17 μg | CT | 15 | 0, 7 | 28 |
| E | SP0785 | 10 μg | CT | 15 | 0, 7 | 28 |
| F | SP1500 | 10 μg | CT | 15 | 0, 7 | 28 |

Abbreviations:
CP1: fusion protein 1 (Rhavi-linker (GGGGSSS)-SP1500-linker (AAA)-SP0785);
Rhavi: truncated rhizavidin, amino acids [45-179];
CT: cholera toxin
Note:
all recombinant proteins were His-tagged.

IL-17A Induction and Measurement from Whole Blood

Ex vivo stimulation of peripheral blood samples taken 3 weeks after the last intranasal immunization was performed in 96-well round-bottom plates. All stimulants (purified proteins or killed (inactivated) pneumococcal whole cells) were diluted in stimulation medium (DMEM F-12; 10% FBS, 50 μM 2-mercaptoethanol, 10 μg/ml ciprofloxacin) at a final concentration of 10 μg/ml. In each well, 25 μl of heparinized blood was added to 225 μl of stimulation medium containing indicated stimulants, followed by incubation at 37° C. with 5% $CO_2$ for 6 days. Supernatants were collected after centrifugation, and IL-17A was analyzed with an ELISA kit (R&D systems).

Statistical Analyses

Statistical analyses were performed using PRISM (GraphPad Software). All data on IL-17A concentration were analyzed using the Mann-Whitney U test. The geometric mean concentrations of IL-17A was calculated for each group.

Results and Discussion:

IL-17A Responses after Intranasal Immunization with a Mixture of SP1500, SP0785, and Rhavi Proteins, or with CP1 or SP0785-Linker (SSSGG)-SP1500-Linker (SSVDKL)-PdT.

Figure 8:
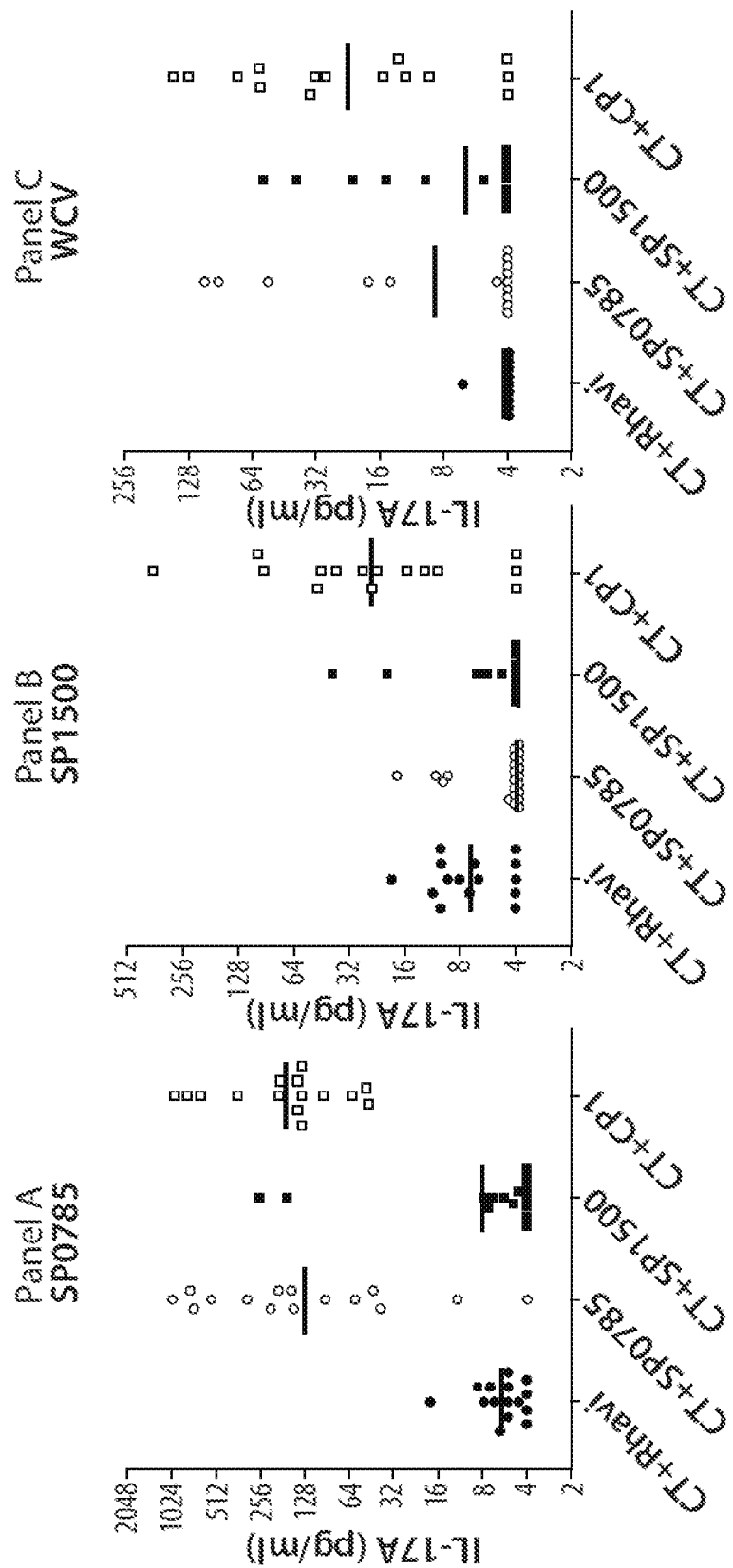
FIG. 8 illustrates immune responses (e.g., Th17 responses) to an exemplary fusion protein CP1 compared to a SP1500 or SP0785 polypeptide. Mice were immunized with CP1, SP1500, or SP0785 polypeptides, adjuvanted with cholera toxin, or were immunized with Rhavi protein adjuvanted with cholera toxin (control). Th17 responses are shown as geometric mean concentration of IL-17A secreted in media after stimulation of peripheral blood samples of immunized mice with purified SP0785 polypeptide (Panel A), purified SP1500 polypeptide (Panel B), or killed (inactivated) pneumococcal whole cells (WCV; Panel C). Each point on the graphs represents secreted IL-17A for one mouse. Horizontal bars represent the geometric mean of secreted IL-17A for each group. CT: cholera toxin.

As seen in FIG. 8, intranasal immunization with CP1 adjuvanted with CT induced a stronger antigen-specific Th17 response compared to immunization with SP0785 or SP1500 adjuvanted with CT, or with CT alone (control). The Th17 response is indicated by increased IL-17A production after ex vivo stimulation of peripheral blood of immunized mice with purified SP0785 (Panel A), purified SP1500 (Panel B), or killed (inactivated) pneumococcal whole cells (WCV; Panel C).

Figure 9:
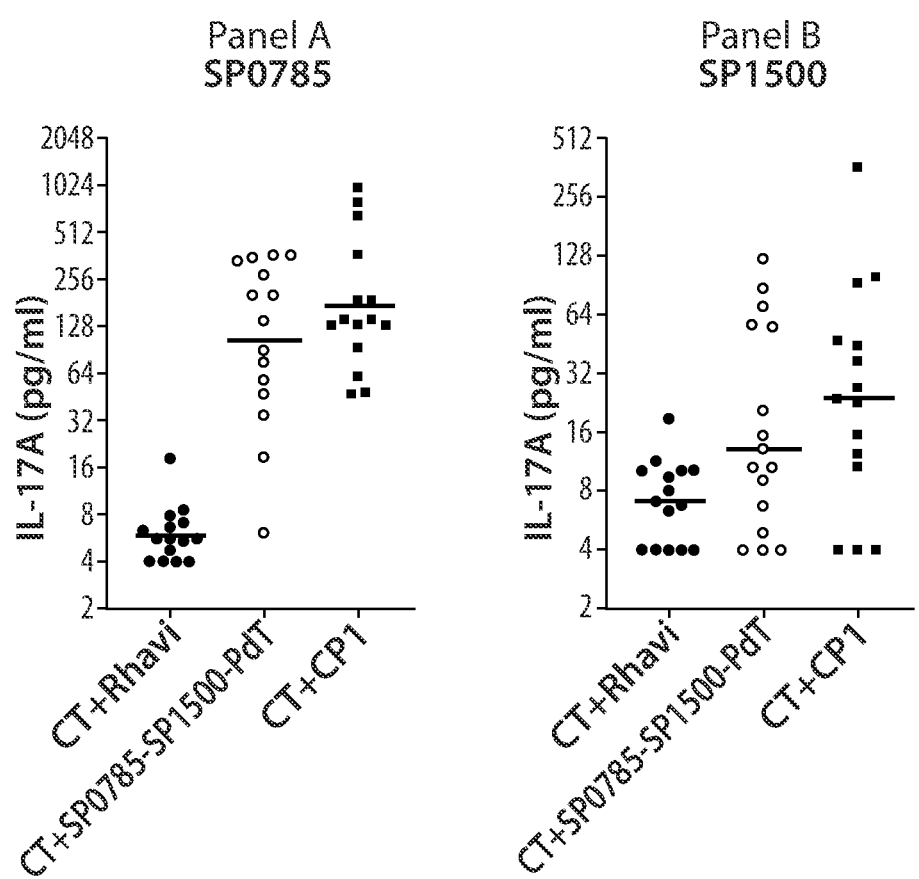
FIG. 9 illustrates immune responses (e.g., Th17 responses) to an exemplary fusion protein CP1 compared to a fusion protein SP0785-linker (SSSGG)-SP1500-linker (SSVDKL)-PdT. Mice were immunized with CP1 or SP0785-linker (SSSGG)-SP1500-linker (SSVDKL)-PdT, adjuvanted with cholera toxin, or were immunized with Rhavi protein adjuvanted with cholera toxin (control). Th17 responses are shown as geometric mean concentration of IL-17A secreted in media after stimulation of peripheral blood samples of immunized mice with purified SP0785 polypeptide (Panel A), or purified SP1500 polypeptide (Panel B). Each point on the graphs represents secreted IL-17A for one mouse. Horizontal bars represent the geometric mean of secreted IL-17A for each group. CT: cholera toxin.

As seen in FIG. 9, intranasal immunization with CP1 adjuvanted with CT also induced a stronger antigen-specific Th17 response compared to immunization with fusion protein SP0785-linker (SSSGG)-SP1500-linker (SSVDKL)-PdT adjuvanted with CT, or with CT alone (control). The Th17 response is indicated by increased IL-17A production after ex vivo stimulation of peripheral blood of immunized mice with purified SP0785 (Panel A), or purified SP1500 (Panel B).

Figure 10:
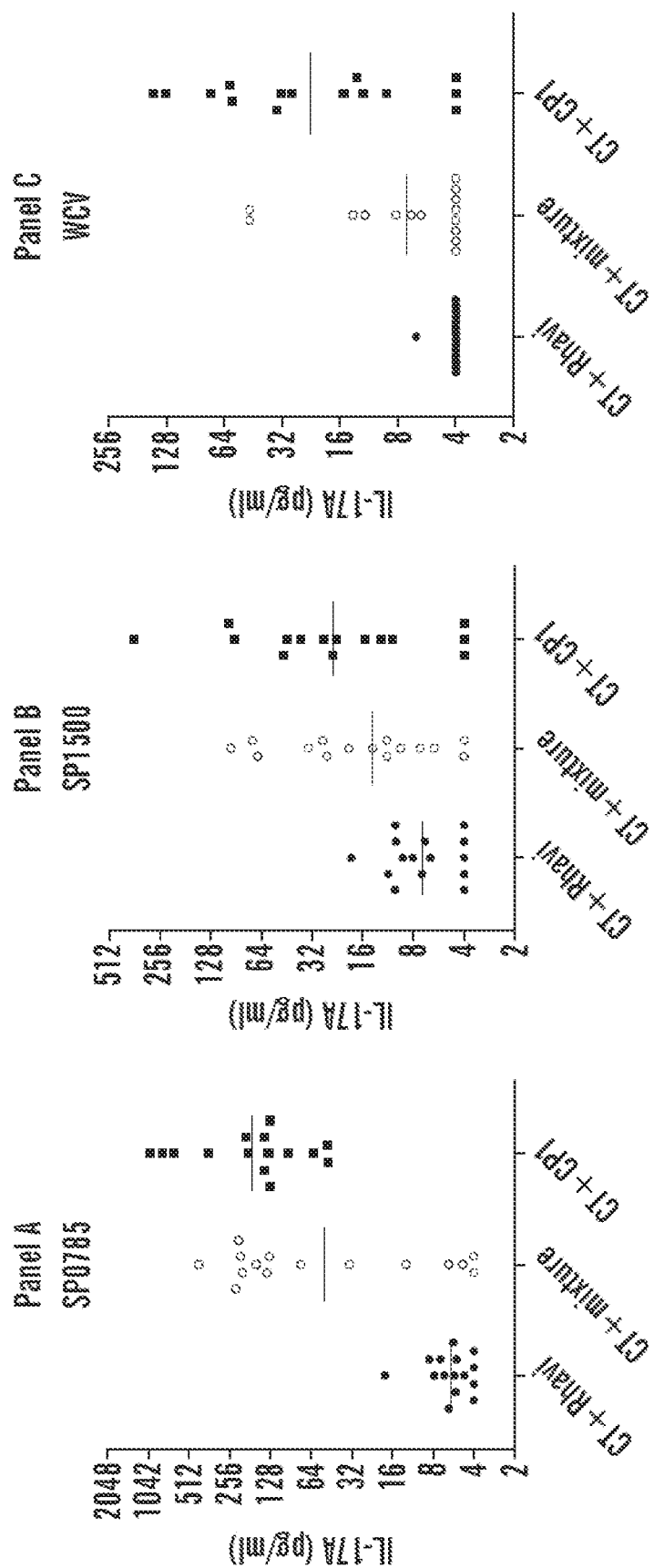
FIG. 10 illustrates immune responses (e.g., Th17 responses) to an exemplary fusion protein CP1 compared to a mixture (unconjugated) of SP0785, SP1500, and Rhavi polypeptides. Mice were immunized with CP1 or a mixture (unconjugated) of SP0785, SP1500, and Rhavi polypeptides, adjuvanted with cholera toxin, or were immunized with Rhavi protein adjuvanted with cholera toxin (control). Th17 responses are shown as geometric mean concentration of IL-17A secreted in media after stimulation of peripheral blood samples of immunized mice with purified SP0785 polypeptide (Panel A), purified SP1500 polypeptide (Panel B), or killed (inactivated) pneumococcal whole cells (WCV; Panel C). Each point on the graphs represents secreted IL-17A for one mouse. Horizontal bars represent the geometric mean of secreted IL-17A for each group. CT: cholera toxin; mixture: mixture (unconjugated) of SP0785, SP1500, and Rhavi polypeptides.

As seen in FIG. 10, intranasal immunization with CP1 adjuvanted with CT induced a stronger antigen-specific Th17 response compared to immunization with a combination (mixture) of SP0785, SP1500, and Rhavi adjuvanted with CT, or with CT alone (control). The Th17 response is indicated by increased IL-17A production after ex vivo stimulation of peripheral blood of immunized mice with purified SP0785 (Panel A), purified SP1500 (Panel B), or killed (inactivated) pneumococcal whole cells (WCV; Panel C).

Example 4: Comparison of Hemolytic Activity of CP1 and SP0785-Linker (SSSGG)-SP1500-Linker (SSVDKL)-PdT Materials and Methods:
Recombinant Protein Production Histidine-tagged recombinant fusion proteins CP1 and SP0785-linker (SSSGG)-SP1500-linker (SSVDKL)-PdT were expressed in *Escherichia coli* and purified using Ni-nitrilotriacetic acid affinity chromatography. A second purification was executed with size-exclusion chromatography with a Superdex 200 column. Protein concentration was measured using a bicinchoninic acid (BCA) protein assay kit (Bio-Rad).

Assay for Hemolytic Activity of Fusion Proteins

Assay was adapted from Benton et al, 1997. Assay buffer contained 10 mM Dithiothreitol, 0.1% Bovine Serum Albumin in PBS pH 7.4, and 2% sheep red blood cells. Sheep red blood cells were prepared as follows: add 200 μl sheep blood+1 ml PBS pH 7.4, mix well, pellet, and wash 3× at 8,000 rpm for 30 sec each; finally resuspend blood cells in 10 ml chilled PBS and keep on ice until used. Assay was performed by diluting a pneumolysin standard (Ply), pneumolysoid PdT, and fusion proteins to test (CP1 and SP0785-linker (SSSGG)-SP1500-linker (SSVDKL)-PdT) at the indicated concentrations across the plate with 100 μl/well, then adding 50 μl of 2% sheep red blood cells to all wells. Plate was incubated for 30 min at 37° C. After incubation, plate was centrifuged for 5 min at 2,000 rpm at room temperature and 100 μl of supernatant was transferred to an empty 96 well plate to measure absorbance at $OD_{420}$. [Benton, K. A., J. C. Paton, and D. E. Briles. 1997. Differences in virulence for mice among *Streptococcus pneumoniae* strains of capsular types 2, 3, 4, 5, and 6 are not attributable to differences in pneumolysin production. Infect Immun. 65:1237-44.]

Figure 11:
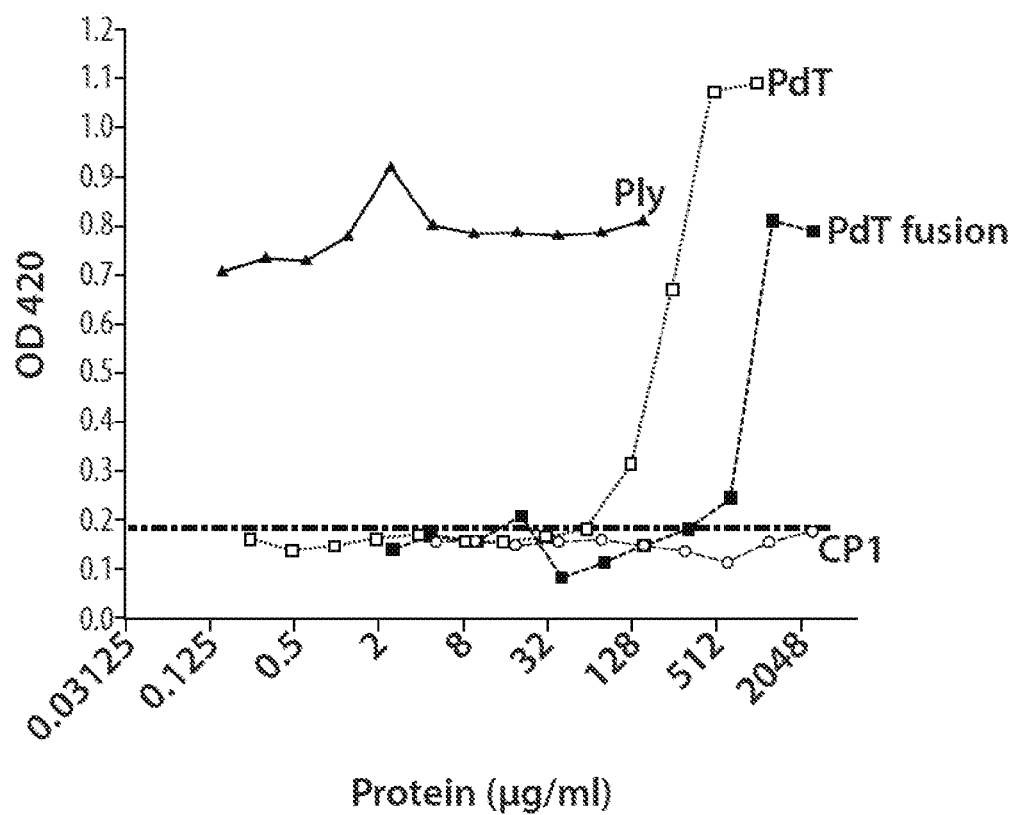
FIG. 11 illustrates hemolytic activity of an exemplary fusion protein CP1 and fusion protein SP0785-linker (SSSGG)-SP1500-linker (SSVDKL)-PdT (PdT fusion) against sheep red blood cells. Sheep red blood cells were incubated with positive control protein pneumolysin (Ply), pneumolysoid PdT, CP1, or fusion protein SP0785-linker (SSSGG)-SP1500-linker (SSVDKL)-PdT at the concentrations indicated on the x axis. Hemolytic activity as measured by $OD_{420}$ of the supernatants is plotted on the y axis.

Results and Discussion:

As seen in FIG. 11, incubation of sheep red blood cells with fusion protein CP1 did not result in hemolysis at any concentration tested. Incubation with fusion protein SP0785-linker (SSSGG)-SP1500-linker (SSVDKL)-PdT or pneumolysoid PdT alone, at concentrations above 1 mg/ml and 0.5 mg/ml respectively, resulted in nearly complete hemolysis of sheep red blood cells. These results show that SP0785 and SP1500 moieties of the two fusion proteins do not contribute to hemolytic activity. Hemolytic activity of fusion protein SP0785-linker (SSSGG)-SP1500-linker (SSVDKL)-PdT is attributable instead to the pneumolysoid PdT.

| Sequences |
|---|
| SEQ ID NO: 1, rhizavidin protein, full-length [amino acids 1-179]:<br>MIITSLYATFGTIADGRRTSGGKTMIRTNAVAALVFAVATSALAPDASNFKDFSSIASASSSWQ<br>NQSGSTMIQVDSFGNVSGQYVNRAQGTCCQNSPYPLTGRVNGTFIAFSVGWNNSTENCNSATG<br>WTGYAQVNGNNTEIVTSWNLAYEGGSGPAIEQGQDTFQYVPTTENKSLLKD |
| SEQ ID NO: 2, truncated rhizavidin protein, denoted Rhavi [amino acids 45-179]:<br>FDASNFKDFSSIASASSSWQNQSGSTMIQVDSFGNVSGQYVNRAQGTCCQNSPYPLTGRVNGT<br>FIAFSVGWNNSTENCNSATGWTGYAQVNGNNTEIVTSWNLAYEGGSGPAIEQGQDTFQYVPTTE<br>NKSLLKD |
| SEQ ID NO: 3, SP0785 protein, full-length [amino acids 1-399], TIGR4 strain:<br>MKKKNGKAKKWQLYAAIGAASVVLGAGGILLFRQPSQTALKDEPTHLVV<br>AKEGSVASSVLLSGTVTAKNEQYVYFDASKGDLDEILVSVGDKVSEGQAL<br>VKYSSSEAQAYDSASRAVARADRHINELNQARNEAASAPAPQLPAPVGG<br>EDATVQSPTPVAGNSVASIDAQLGDARDARADAAAQLSKAQSQLDATTVL<br>STLEGTVVEVNSKSPTGASQVMVHIVSNENLQVKGELSEYNLANLSV<br>GQEVSFTSKVYPDKKWTGKLSYISDYPKNNGEAASPAAGNNTGSKYPYTI<br>DVTGEVGDLKQGFSVNIEVKSKTKAILVPVSSLVMDDSKNYVWIVDEQQK<br>AKKVEVSLGNADAENQEITSGLTNGAKVISNPTSSLEEGKEVKADEATN |
| SEQ ID NO: 4, SP0785 protein lacking signal sequence [amino acids 33-399]:<br>Note: One T394A mismatch with SP0785 NCBI Sequences ABJ54007.1 and YP816180<br>FRQPSQTALKDEPTHLVVAKEGSVASSVLLSGTVTAKNEQYVYFDASKGDLDEILVSVGDKVSE<br>GQALVKYSSSEAQAYDSASRAVARADRHINELNQARNEAASAPAPQLPAPVGGEDATVQSPTP<br>VAGNSVASIDAQLGDARDARADAAAQLSKAQSQLDATTVLSTLEGTVVEVNSNVSKSPTGASQV<br>MVHIVSNENLQVKGELSEYNLANLSVGQEVSFTSKVYPDKKWTGKLSYISDYPKNNGEAASPAA<br>GNNTGSKYPYTIDVTGEVGDLKQGFSVNIEVKSKTKAILVPVSSLVMDDSKNYVWIVDEQQKAK<br>KVEVSLGNADAENQEITSGLTNGAKVISNPTSSLEEGKEVKADEATN |
| SEQ ID NO: 5, consensus SP0785 protein [amino acids 1-399]: (SEQ ID NOS 110-134, respectively, in order of appearance): |
| WP_081570978  1  MKKKNGKAKKWQLYAAIGAASVVLGAGGILLFRQPSQTALKDEPTHLIVAKEGSVASSVLLSGTVTAKNEQYVYFDASK  80 |
| WP_054387396  1  MKKKNGKAKKWQLYAAIGAASVVLGAGGILLFRQPSQTALKDEPTHLIVAKEGSVASSVLLSGTVTAKNEQYVYFDASK  80 |
| WP_097557828  1  MKKKNGKAKKWQLYAAIGAASVVLGAGGILLFRQPSQTALKDEPTHLVVAKEGSVASSVLLSGTVTAKNEQYVYFDASK  80 |
| WP_000728643  1  MKKKNGKAKKWQLYAAIGAASVVLGAGGILLFRQPSQTALKDEPTHLVVAKEGSVASSVLLSGTVTAKNEQYVYFDASK  80 |
| WP_061633543  1  MKKKNGKAKKWQLYAAIGAASVVLGAGGILLFRQPSQTALKDEPTHFVVAKEGSVASSVLLSGTVTAKNEQYVYFDASK  80 |
| WP_050965059  1  MKKKNGKAKKWQLYAAIGAASVVLGAGGILLFRQPSQTALKDEPTHLVVAKEGSVASSVLLSGTVTAKNEQYVYFDASK  80 |
| WP_055387306  1  MKKKNGKAKKWQLYAAIGAASVVLGAGGILLFRQPSQTALKDEPTHLVVAKEGSVASSVLLSGTVTAKNEQYVYFDASK  80 |
| WP_050203943  1  MKKKNGKAKKWQLYAAIGAASVVLGAGGILLFRQPSQTALKDEPIHLVVAKEGSVASSVLLSGTVTAKNEQYVYFDASK  80 |
| WP_000728633  1  MKKKNGKAKKWQLYAAIGAASVVLGAGGILLFRQPSQTALKDEPIHLVVAKEGSVASSVLLSGTVTAKNEQYVYFDASK  80 |
| WP_088799985  1  MKKKNGKAKKWQLYAAIGAASVVLGAGGILLFRQPSQTALKDEPTHLVVAKEGSVASSVLLSGTVTAKNEQYVYFDASK  80 |
| WP_061764363  1  MKKKNGKAKKWQLYAAIGAASVVLGAGGILLFRQPSQTALKDEPTHLVVAKEGSVASSVLLSGTVTAKNEQYVYFDASK  80 |
| WP_050259582  1  MKKKNGKAKKWQLYAAIGAASVVLGAGGILLFRQPSQTALKDEPTHLVVAKEGSVASSVLLSGTVTAKNEQYVYFDASK  80 |
| WP_023396621  1  MKKKNGKAKKWQLYAAIGAASVVLGAGGILLFRQPSQTALKDELTHLVVAKEGSVASSVLLSGTVTAKNEQYVYFDASK  80 |
| WP_000728632  1  MKKKNGKAKKWQLYAAIGAASVVLGAGGILLFRQPSQTALKDEPTHLVVAKEGSVASSVLLSGTVTAKNEQYVYFDASK  80 |
| WP_061366281  1  MKKKNGKAKKWQLYAAIGAASVVLGAGGILLFRQPSQTALKDEPIHLVVAKEGSVASSVLLSGTVTAKNEQYVYFDASK  80 |
| WP_061743315  1  MKKKNGKAKKWQLYAAIGAASVVLGAGGILLFRQPSQTALKDEPTHLVVAKEGSVASSVLLSGTVTAKNEQYVYFDASK  80 |
| WP_057525500  1  MKKKNGKAKKWQLYAAIGAASVVLGAGGILLFRQPSQTALKDEPIHLVVAKEGSVASSVLLSGTVTAKNEQYVYFDASK  80 |
| WP_000728639  1  MKKKNGKAKKWQLYAAIGAASVVLGAGGILLFRQPSQTALKDEPTHLVVAKEGSVASSVLLSGTVTAKNEQYVYFDASK  80 |
| WP_084572368  1  MKKKNGKAKKWQLYAAIGAASVVLGAGGILLFRQPSQTALKDEPTHLVVAKEGSVASSVLLSGTVTAKNEQYVYFDASK  80 |

| | | |
|---|---|---|
| WP_084354434 | MKKKNGKAKKWQLYAAIGAASVVVLGAGGILLFRQPYQTALKDEPTHLVVKEGSVASSVLLSGTVTAKNEQVYFPDASK | 80 |
| WP_050214972 | MKKKNGKAKKWQLYAAIGAASVVVLGAGGILLFRQPSQTAVKDEPTHLVVAKEGSVASSVLLSGTVTAKNEQVYFDASK | 80 |
| WP_050208881 | MKKKNGKAKKWQLYAAIGAASVVVLGAGGILLFRQPSQTALKDEPIHLVVAKEGSVASSVLLSGTVTAKNEQVYFDASK | 80 |
| WP_088793209 | MKKKNGKAKKWQLYAAIGAASVVVLGAGGILLFRQPSQTALKDEPTHLVVAKEGSVASSILLSGTVTAKNEQVYFDASK | 80 |
| WP_069123032 | MKKKNGKAKKWQLYAAIGAASVVVLGAGGILLFRQPSQTALKDEPTHLVVAKEGSVASSILLSGTVTAKNEQVYFDASK | 80 |
| WP_000728647 | MKKKNGKAKKWQLYAAIGAASVVVLGAGGILLFRQPSQTALKDEPTHLVVANEGSVASSVLLSGTVTAKNEQVYFDASK | 80 |
| WP_081570978 | GDLDEILVSVGDKVSEGQALVKYSSEAQAAYDSASRAVARADRHINELNQARNEAASAPAPQLPAPVGGEDATVQSPTP | 160 |
| WP_054387396 | GDLDEILVSVGDKVSEGQALVKYSSEAQAAYDSASRAVARADRHINELNQARNEAASAPAPQLPAPVGGEDATVQSPTP | 160 |
| WP_097557828 | GDLDEILVSVGDKVSEGQALVKYSSEAQAAYDSASRAVARADRHINELNQARNEAASAPAPQLPAPVGGEDATVONPTP | 160 |
| WP_000728643 | GDLDEILVSVGDKVSEGQALVKYSSEAQAAYDSASRAVARADRHINELNQARNEAASAPAPQLPAPVGGEDATVQSPTP | 160 |
| WP_061633543 | GDLDEILVSVGDKVSEGQALVKYSSEAQAAYDSASRAVARADRHINELNQARNEAASAPTPQLPAPQLPAPVGGEDATVQSPTP | 160 |
| WP_050965059 | GDLDEILVSVGDKVSEGQALVKYSSEAQAAYDSASRAVARADRHINELNQARNEAASAPAPQLPAPVGGEDATVQSPTP | 160 |
| WP_055387306 | GDLDEILVSVGDKVSEGQALVKYSSEAQAAYDSASRAVARADRHINELNQARNEAASAPAPQLPAPVGGEDATVQSPTP | 160 |
| WP_050203943 | GDLDEILVSVGDKVSEGQALVKYSSEAQAAYDSASRAVARADRHINELNQARNEAASAPAPQLPAPVGGEDATVQSPTP | 160 |
| WP_000728633 | GDLDEILVSVGDKVSEGQALVKYSSEAQAAYDSASRAVARADRHINELNQARNEAASAPAPQLPAPVGGEDATVQSPTP | 160 |
| WP_088799985 | GDLDEILVSVGDKVSEGQALVKYSSEAQAAYDSASRAVARADRHINELNQARNEAASALAPQLPAPVGGEDATVQSPTP | 160 |
| WP_061764363 | GDLDEILVSVGDKVSEGQALVKYSSEAQAAYDSASRAVARADRHINELNQARNEAASALAPQLPAPVGGEDATVQSPTP | 160 |
| WP_050259582 | GDLDEILVSVGDKVSEGQALVKYSSEAQAAYDSASRAVARADRHINELNQARNEAASAPAPQLPAPVGGEDATVPSPTP | 160 |
| WP_023396621 | GDLDEILVSVGDKVSEGQALVKYSSEAQAAYDSASRAVARADRHINELNQARNEAASAPAPQLPAPVGGEDATVQSPTP | 160 |
| WP_000728632 | GDLDEILVSVGDKVSEGQALVKYSSEAQAAYDSASRAVARADRHINELNQARNEAASAPAPQLPAPVGGEDATVQSPTP | 160 |
| WP_061366281 | GDLDEILVSVGDKVSEGQALVKYSSEAQAAYDSASRAVARADRHINELNQARNEAASAPAPQLPAPVGGEDATVQSPTP | 160 |
| WP_061743315 | GDLDEILVSVGDKVSEGQALVKYSSEAQAAYDSASRAVAKADRHINELNQARNEAASAPAPQLPAPVGGEDATVQSPTP | 160 |
| WP_057525500 | GDLDEILVSVGDKVSEGQALVKYSSEAQAAYDSASRAVAKADRHINELNQARNEAASAPAPQLPAPVGGEDATVQSPTP | 160 |
| WP_000728639 | GDLDEILVSVGDKVSEGQALVKYSSEAQAAYDSASRAVAKADRHINELNQARNEAASAPAPQLPAPVGGEDATVQSPTP | 160 |
| WP_084354434 | GDLDEILVSVGDKVSEGQALVKYSSEAQAAYDSASRAVARVDCHINELNQARNEAASAPAPQLPAPVGGEDATVQSPTP | 160 |
| WP_050214972 | GDLDEILVSVGDKVSEGQALVKYSSEAQAAYDSASRAVARADRHINELNQARNEAASAPAPQLPAPVGGEDATVQSPTP | 160 |
| WP_050208881 | GDLDEILVSVGDKVSEGQALVKYSSEAQAVYDSASRAVAKADRHINELNQARNEAASAPAPQLPAPVGGEDATVQSPTP | 160 |
| WP_088793209 | GDLDEILVSVGDKVSEGQALVKYSSEAQAAYDSASRAVAKADRHINELNQVRNEAASAPAPQLPAPVGGEDATVQSPTP | 160 |
| WP_069123032 | GDLDEILVSVGDKVSEGQALVKYSSEAQAAYDSASRAVAKADRHINELNQARNEAASAPAPQLPAPVGGEDATVQSPTP | 160 |
| WP_000728647 | GDLDEILVSVGDKVSEGQALVKYSSEAQAAYDSASRAVAKADRHINELNQARNEAASAQAPQLPAPVGGEDATVQSPTP | 160 |
| WP_081570978 | VAGNSVASIDAQLGDARDARADAAAQLSKAQSQLDATTVLSTLEGTVVEVNSNVSKSPTGASQVMVHIVSNENLQVKGEL | 240 |
| WP_054387396 | VAGNSVASIDAQLGDARDARADAAAQLSKAQSQLDATTVLSTLEGTVVEVNSNVSKSPTGASQVMVHIVSNENLQVKGEL | 240 |
| WP_097557828 | VAGNSVASIDAQLGDARDARADAAAQLSKAQSQLDATTVLSTLEGTVVEVNSNVSKSPTGASQVMVHIVSNENLQVKGEL | 240 |
| WP_000728643 | VAGNSVASIDAQLGDARDARADAAAQLSKAQSQLDATTVLSTLEGTVVEVNSNVSKSPTGASQVMVHIVSNENLQVKGEL | 240 |
| WP_061633543 | VAGNSVASIDAQLGDARDARADAAAQLSKAQSQLDATTVLSTLEGTVVEVNSNVSKSPTGASQVMVHIVSNENLQVKGEL | 240 |
| WP_050965059 | VAGNSVASIDAQLGDARDARADAAAQLSKAQSQLDATTVLSTLEGTVVEVNSNVSKSPTGASQVMVHIVSNENLQVKGEL | 240 |
| WP_055387306 | VAGNSVASIDAQLGDARDARADAAAQLSKAQSQLDATTVLSTLEGTVVEVNSNVSKSPTGASQVMVHIVSNENLQVKGEL | 240 |
| WP_050203943 | VAGNSVASIDAQLGDARDARADAAAQLSKAQSQLDATTVLSTLEGTVVEVNSNVSKSPTGASQVMVHIVSNENLQVKGEL | 240 |
| WP_000728633 | VAGNSVASIDAQLGDARDARADAAAQLSKAQSQLDATTVLSTLEGTVVEVNSNVSKSPTGASQVMVHIVSNENLQVKGEL | 240 |
| WP_088799985 | VAGNSVASIDAQLGDARDARADAAAQLSKAQSQLDATTVLSTLEGTVVEVNSNVSKSPTGASQVMVHIVSNENLQVKGEL | 240 |
| WP_061764363 | VAGNSVASIDAQLGDARDARADAAAQLSKAQSQLDATTVLSTLEGTVVEVNSNVSKSPTGASQVMVHIVSNENLQVKGEL | 240 |
| WP_050259582 | VAGNSVASIDAQLGDARDARADAAAQLSKAQSQLDATTVLSTLEGTVVEVNSNVSKSPTGASQVMVHIVSNENLQVKGEL | 240 |
| WP_023396621 | VAGNSVASIDAQLGDARDARADAAAQLSKAQSQLDATTVLSTLEGTVVEVNSNVSKSPTGASQVMVHIVSNENLQVKGEL | 240 |
| WP_000728632 | VAGNSVASIDAQLGDARDARADAAAQLSKAQSQLDATTVLSTLEGTVVEVNSNVSKSPTGASQVMVHIVSNENLQVKGEL | 240 |
| WP_061366281 | VAGNSVASIDAQLGDARDARADAAAQLSKAQSQLDATTVLSTLEGTVVEVNSNVSKSPTGASQVMVHIVSNENLQVKGEL | 240 |
| WP_061743315 | VAGNSVASIDAQLGDARDARADAAAQLSKAQSQLDATTVLSTLEGTVVEVNSNVSKSPTGASQVMVHIVSNENLQVKGEL | 240 |
| WP_057525500 | VAGNSVASIDAQLGDARDARADAAAQLSKAQSQLDATTVLSTLEGTVVEVNSNVSKSPTGASQVMVHIVSNENLQVKGEL | 240 |
| WP_000728639 | VAGNSVASIDAQLGDARDARADAAAQLSKAQSQLDATTVLSTLEGTVVEVNSNVSKSPTGASQVMVHIVSNENLQVKGEL | 240 |

-continued

| | | Sequences | |
|---|---|---|---|
| WP_084354434 | 161 | VAGNSVASIDAQLGDARDARADAAAQLSKAQSQLDATTVLSTLEGTVVEVNSVSKSPTGASQVMVHIVSNENLQVKGEL | 240 |
| WP_084572368 | 161 | VAGNSVASIDAQLGDARDARADAAAQLSKAQSQLDATTVLSTLEGTVVEVNSVSKSPTGASQVMVHIVSNENLQVKGEL | 240 |
| WP_050214972 | 161 | VAGNSVASIDAQLGDARDARADAAAQLSKAQSQLDATTVLSTLEGTVVEVNSVSKSPTGASQVMVHIVSNENLQVKGEL | 240 |
| WP_050208881 | 161 | VAGNSVASIDAQLGDARDARADAAAQLSKAQSQLDATTVLSTLEGTVVEVNSVSKSPTGASQVMVHIVSNENLQVKGEL | 240 |
| WP_088793209 | 161 | VAGNSVASIDAQLGDARDARADAAAQLSKAQSQLDATTVLSTLEGTVVEVNSVSKSPTGASQVMVHIVSNENLQVKGEL | 240 |
| WP_069123032 | 161 | VAGNSVASIDAQLGDARDARADAAAQLSKAQSQLDATTVLSTLEGTVVEVNSVSKSPTGASQVMVHIVSNENLQVKGEL | 240 |
| WP_000728647 | 161 | VAGNSVASIDAQLGDARDARADAAAQLSKAQSQLDATTVLSTLEGTVVEVNSVSKSPTGASQVMVHIVSNENLQVKGEL | 240 |
| WP_081570978 | 241 | SEYNLANLSVGQEVSFTSKVYPDKKWTGKLSYISDYPKNNGEAASPAAGNNTGSKYPYTIDVTGEVGDLKQGFSVNIEVK | 320 |
| WP_054387396 | 241 | SEYNLANLSVGQEVSFTSKVYPDKKWTGKLSYISDYPKNNGEAASPAAGNNTGSKYPYTIDVTGEVGDLKQGFSVNIEVK | 320 |
| WP_097557828 | 241 | SEYNLANLSVGQEVSFTSKVYPDKKWTGKLSYISDYPKNNGEAASPAAGNNTGSKYPYTIDVTGEVGDLKQGFSVNIEVK | 320 |
| WP_000728643 | 241 | SEYNLANLSVGQEVSFTSKVYPDKKWTGKLSYISDYPKNNGEAASPAAGNNTGSKYPYTIDVTGEVGDLKQGFSVNIEVK | 320 |
| WP_061633543 | 241 | SEYNLANLSVGQEVSFTSKVYPDKKWTGKLSYISDYPKNNGEAASPAAGNNTGSKYPYTIDVTGEVGDLKQGFSVNIEVK | 320 |
| WP_050965059 | 241 | SEYNLANLSVGQEVSFTSKVYPDKKWTGKLSYISDYPKNNGEAASPAAGNNTGSKYPYTIDVTGEVGDLKQGFSVNIEVK | 320 |
| WP_055387306 | 241 | SEYNLANLSVGQEVSFTSKVYPDKKWTGKLSYISDYPKNNGEAASPAAGNNTGSKYPYTIDVTGEGGDLKQGFSVNIEVK | 320 |
| WP_050203943 | 241 | SEYNLANLSVGQEVSFTSKVYPDKKWTGKLSYISDYPKNNGEAASPAAGNNTGSKYPYTIDVTGEVGDLKQGFSVNIEVK | 320 |
| WP_000728633 | 241 | SEYNLANLSVGQEVSFTSKVYPDKKWTGKLSYISDYPKNNGEAASPAAGNNTGSKYPYTIDVTGEVGDLKQGFSVNIEVK | 320 |
| WP_087999985 | 241 | SEYNLANLSVGQEVSFTSKVYPDKKWTGKLSYISDYPKNNGEAASPAAGNNTGSKYPYTIDVTGEGGDLKQGFSVNIEVK | 320 |
| WP_061743363 | 241 | SEYNLANLSVGQEVSFTSKVYPDKKWTGKLSYISDYPKNNGEAASPAAGNNTGSKYPYTIDVTGEVGDLKQGFSVNIEVK | 320 |
| WP_050259582 | 241 | SEYNLANLSVGQEVSFTSKVYPDKKWTGKLSYISDYPKNNGEAASPASGNNTGSKYPYTIDVTGEIGDLKQGFSVNIEVK | 320 |
| WP_023396621 | 241 | SEYNLANLSVGQEVSFTSKVYPDKKWTGKLSYISDYPKNNGEAASPASGNNTGSKYPYTIDVTGEIGDLKQGFSVNIEVK | 320 |
| WP_061366281 | 241 | SEYNLANLSVGQEVSFTSKVYPDKKWTGKLSYISDYPKNNGEAASPAAGNNTGSKYPYTIDVTGEVGDLKQGFSVNIEVK | 320 |
| WP_061743315 | 241 | SEYNLANLSVGQEVSFTGRLSYISDYPKNNGEAASPAAGNNTGSKYPYTIDVTGEVGDLKQGFSVNIEVK | 320 |
| WP_057525500 | 241 | SEYNLANLSVGQEVSFTSKVYPDKKWTGKLSYISDYPKNNGEAASPAAGNNTGSKYPYTIDVTGEVGDLKQGFSVNIEVK | 320 |
| WP_084354434 | 241 | SEYNLANLSVGQEVSFTSKVYPDKKWTGKLSYISDYPKNNGEAASPAAGNNTGSKYPYTIDVTGEVGNLKQGFSVNIEVK | 320 |
| WP_084572368 | 241 | SEYNLANLSVGQEVSFTSKVYPDKKWTGKLSYISDYPKNNGEAASPAAGNNTGSKYPYTIDVTGEVGDLKQGFSVNIEVK | 320 |
| WP_050214972 | 241 | SEYNLANLSVGQEVSFTSKVYPDKKWTGKLSYISDYPKNNGEAASPAAGNNTGSKYPYTIDVTGEVGDLKQGFSVNIEVK | 320 |
| WP_050208881 | 241 | SEYNLANLSVGQEVSFTSKVYPDKKWTGKLSYISDYPKNNGEAASPAAGNNTGSKYPYTIDVTGEVGDLKQGFSVNIEVK | 320 |
| WP_088793209 | 241 | SEYNLANLSVGQEVSFTSKVYPDKKWTGKLSYISDYPKNNGEAASPAAGNNTGSKYPYTIDVTGEVGDLKQGFSVNIEVK | 320 |
| WP_069123032 | 241 | SEYNLANLSVGQEVSFTSKVYPDKKWTGKLSYISDYPKNNGEAASPAAGNNTGSKYPYTIDVTGEVGDLKQGFSVNIEVK | 320 |
| WP_000728647 | 241 | SEYNLANLSVGQEVSFTSKVYPDKKWTGKLSYISDYPKNNGEAASPAAGNNTGSKYPYTIDVTGEVGDLKQGFSVNIEVK | 320 |
| WP_081570978 | 321 | SKTKAILVPVSSLVMDNSKNYVWIVDEQQKAKKVEVSLGNADAENQEITSGLTNGAKVISNPTSSLEEGKEVKADEATN | 399 |
| WP_054387396 | 321 | SKTKAILVPVSSLVMDDSKNYVWIVDEQQKAKKVEVSLGNADAENQEITSGLTNGAKVISNPTSSLEEGKEVKADEATN | 399 |
| WP_097557828 | 321 | SKTKAILVPVSSLVMDDSKNYVWIVDEQQKAKKVEVSLGNADAENQEITSGLTNGAKVISNPTSSLEEGKEVKADEATN | 399 |
| WP_000728643 | 321 | SKTKAILVPVSSLVMDDSKNYVWIVDEQQKAKKVEVSLGNADAENQEITSGLTNGAKVISNPTSSLEEGKEVKADEATN | 399 |
| WP_061633543 | 321 | SKTKAILVPVSSLVMDDSKNYVWIVDEQQKAKKVEVSLGNADAENQEITSGLTNGAKVISNPTSSLEEGKEVKADEATN | 399 |
| WP_050965059 | 321 | SKTKAILVPVSSLVMDDSKNYVWIVDEQQKAKKVEVSLGNADAENQEITSGLTNGAKVISNPTSSLEEGKEVKADEATN | 399 |
| WP_055387306 | 321 | SKTKAILVPVSSLVMDDSKNYVWIVDEQQKAKKVEVSLGNADAENQEITSGLTNGAKVISNPTFSLEEGKEVKADEATN | 399 |
| WP_050203943 | 321 | SKTKAILVPVSSLVMDDSKNYVWIVDEQQKAKKVEVSLGNADAENQEITSGLTNGAKVISNPTSSLEEGKEVKADEATN | 399 |
| WP_000728633 | 321 | SKTKAILVPVSSLVMDDSKNYVWIVDEQQKAKKVEVSLGNADAENQEITSGLTNGAKVISNPTSSLEEGKEVKADEATN | 399 |
| WP_087999985 | 321 | SKTKAILVPVSSLVMDDSKNYVWIVDEQQKAKKVEVSLGNADAENQEITSGLTNGAKVISNPTSSLEEGKEVKADEATN | 399 |
| WP_061764363 | 321 | SKTKAILVPVSSLVMDDSKNYVWIVDEQQKAKKVEVSLGNADAENQEITSGLTNGAKVISNPTSSLEEGKEVKADEATN | 399 |
| WP_050259582 | 321 | SKTKAILVPVSSLVMDDSKNYVWIVDEQQKAKKVEVSLGNADAENQEITSGLTNGAKVISNPTSSLEEGKEVKADEATN | 399 |
| WP_023396621 | 321 | SKTKAILVPVSSLVMDDSKNYVWIVDEQQKAKKVEVSLGNADAENQEITSGLTNGAKVISNPTSSLEEGKEVKADEATN | 399 |
| WP_000728632 | 321 | SKTKAILVPVSSLVMDDSKNYVWIVDEQQKAKKVEVSLGNADAENQEITSGLTNGAKVISNPTSSLEEGKEVKADEATN | 399 |
| WP_061366281 | 321 | SKTKAILVPVSSLVMDDSKNYVWIVDEQQKAKKVEVSLGNADAENQEITSGLTNGAKVISNPTSSLEEGKEVKADEATN | 399 |
| WP_061743315 | 321 | SKTKAILVPVSSLVMDDSKNYVWIVDEQQKAKKVEVSLGNADAENQEITSGLTNGAKVISNPTSSLEEGKEVKADEATN | 399 |
| WP_057525500 | 321 | SKTKAILVPVSSLVMDDSKNYVWIVDEQQKAKKVEVSLGNADAENQEITSGLTNGAKVISNPTSSLEEGKEVKADEATN | 399 |

| | Sequences | |
|---|---|---|
| WP_000728639 | SKTKAILVPVSSLVMDDSKNYWNIVDEQQKAKKVEVSLGNADAENQEITSGLTNGAKVISNPTSSLEEGKEVKADEATN | 399 |
| WP_084572368 | SKTKAILVPVSSLVMDDSKNYWNIVDEQQKAKKVEVSLGNADAENQEITSGLTNGAKVISNPTSSLEEGKEVKADEATN | 399 |
| WP_084354434 | SKTKAILVPVSSLVMDDSKNYWNIVDEQQKAKKVEVSLGNADAENQEITSGLTNGAKVISNPTSSLEEGKEVKADEATN | 399 |
| WP_050214972 | SKTKAILVPVSSLVMDDSKNYWNIVDEQQKAKKVEVSLGNADAENQEITSGLTNGAKVISNPTSSLEEGKEVKADEATN | 399 |
| WP_050208881 | SKTKAILVPVSSLVMDDSKNYWNIVDEQQKAKKVEVSLGNADAENQEITSGLTNGAKVISNPTSSLEEGKEVKADEATN | 399 |
| WP_088793209 | SKTKAILVPVSSLVMDDSKNYWNIVDEQQKAKKVEVSLGNADAENQEITSGLTNGAKVISNPTSSLEEGKEVTDEATN | 399 |
| WP_069123032 | SKTKAILVPVSSLVMDDSKNYWNIVDEQQKAKKVEVSLGNADAENQEITSGLTNGAKVISNPTSSLEEGKEVKADEATN | 399 |
| WP_000728647 | SKTKAILVPVSSLVMDDSKNYWNIVDEQQKAKKVEVSLGNADAENQEITSGLTNGAKVISNPTSSLEEGKEVKADEATN | 399 |

SEQ ID NO: 6, SP1500 protein, full-length [amino acids 1-278], TIGR4 strain:
MKKWMLVLVSLMTALFLVACGKNSETSGDNWSKYQSNKSITIGFDSTFVPMGFAQKDGSYAGF
DIDLATAVFEKYGITVNWQPIDWDLKEAELTKGTIDLIWNGYSATDERREKVAFSNSYMKNEQV
LVTKKSSGITTAKDMTGKTLGAQAGSSGYADFEANPEILKNIVANKEANQYQTFNEALIDLKND
RIDGLLIDRVYANYLEAEGVLNDYNVFTVGLETEAFAVGARKEDTNLVKKINEAFSSLYKDGK
FQEISQKWFGEDVATKEVKEGQ SEQ ID NO: 7, SP1500 protein lacking signal sequence [amino acids 27-278]:
TSGDNWSKYQSNKSITIGFDSTFVPMGFAQKDGSYAGFPIDLATAVFEKYGITVNWQPIDWDLK
EAELTKGTIDLIWNGYSATDERREKVAFSNSYMKNEQVLVTKKSSGITTAKDMTGKTLGAQAGS
SGYADFEANPEILKNIVANKEANQYQTFNEALIDLKNDRIDGLLIDRVYANYLEAEGVLNDYN
VFTVGLETEAFAVGARKEDTNLVKKINEAFSSLYKDGKFQEISQKWFGEDVATKEVKEGQ SEQ ID NO: 8, consensus SP1500 protein [amino acids 1-278] (SEQ ID NOS 6 and 135-157, respectively, in order of appearance):

| | | |
|---|---|---|
| WP_000759187 | 1  ------MKKWMLVLVSLMTALFLVACGKNSETSGDNWSKYQSNKSITIGFDSTFVPHGFAQKDGSYAGFPIDLATAV | 72 |
| WP_050213573 | 1  ------MKKWKLVLVSLKTALFLVACGKNSSETSGDNWSKYQSNKSITIGFDSTFVPKGFAQKDGSYAGFPIDLATAV | 72 |
| WP_061814735 | 1  ------MKKWMLVLVSLMTALFLVACGKNSETSGDNWSKYQSNKSITIGFDSTFVPMGFAQKDGSYAGFPIDLATAV | 72 |
| WP_084843602 | 1  ------MKKWMKCHVLVSLMTALFLVACGKNSETSGDNWSKYQSNKSITIGFDSTFVPKGFAQKDGSYAGFPIDLATAV | 72 |
| WP_000759185 | 1  ------MKKWMLVLVSLMTALFLVACGKNSSETSGDNWSKYQSNKSITIGFDSTFVPMGFAQKDGSYAGFPIDLATAV | 72 |
| WP_050261378 | 1  ------MKKWMLVLVSLMTALFLVACGKNTSETSGDNWSKYESNKSITIGFDSTFVPMGFAQKDGSYAGFPIDLATAV | 72 |
| WP_050220771 | 1  ------MKKWMLVLVSLMTALFLVACGKNSETSGDNWSKYESNKSITIGFDSTFVPMGFAQKDGSYAGFPIDLATAV | 72 |
| CKA82396     | 1  ------mkkwMKKWMLVLVSLMTALFLVACGKNSETSGDNWSKYESNKSITIGFDSTFVPMGFAQKDGSYAGFPIDLATAV | 72 |
| WP_088802838 | 1  ------MKKWMLVLVSLMTALFLVACGKNSETSGDNWSKYQSNKSITIGFDSTFVPMGFAQKDGSYAGFPIDLATAV | 72 |
| WP_049512265 | 1  ------MKKWMLVLVSLMTALFLVACGKNSETSGDNWSKYESNKSITIGFDSTFVPMGFAQKDGSYAGFPIDLATAV | 72 |
| CKL85404     | 1  ------mkkwMKKWMLVLVSLKTALFLVACGKNSETSGDNWSKYESNKSITIGFDSTFVPKGFAQKDGSYAGFPIDLATAV | 72 |
| EHZ28755     | 1  ------MLVLVLVSLMTALFLVACGKNSETSGDNWSKYESNKSITIGFDSTFVPKGFAQKDGSYAGFPIDLATAV | 72 |
| WP_100128002 | 1  ------MKKWILVLVSLMTALFLVACGKNSETSGDNWSKYESNKSITIGFDSTFVPKGFAQKDGSYAGFPIDLATAV | 72 |
| WP_053039665 | 1  ------MKKWHHLVLVSLMTALFLVACGKNASEISGDNWSKYESNKSITIGFDSTFVPMGFAQKDGSYAGFPIDLATAV | 72 |
| WP_101514844 | 1  ------MKKWMLVLVSLMTALFLVACGKNASEISGDNWSKYESNKSITIGFDSTFVPMGFAQKDGSYAGFPIDLATAV | 72 |
| WP_050242061 | 1  ------MKKWMFVLVSLMTALFLVACGKNASETSGDNWSKYESNKSITIGFDSTFVPMGFAQKDGSYAGFPIDLATAV | 72 |
| WP_023941000 | 1  ------MLVLVLVSLMTALFLVACGKNASETSGDNWSKYESNKSITIGFDSTFVPMGFAQKDGSYAGFPIDLATAV | 72 |
| EHE15463     | 1  ------MLVLVLVSLKTALFLVACGKNASETSGDNWSKYQSNKSITIGFDSTFVPMGFAQKDGSYAGFPIDLATAV | 72 |
| EHE34295     | 1  ------MLVLVLVSLMTALFLVACGKNASETSGDNWSKYESNKSITIGFDSTFVPMGFAQKDGSYAGFPIDLATAV | 72 |
| CCM08008     | 1  ------mkkwMKKWMLVLVSLMTALFLVACGKNASETSGDNWSKYESNKSITIGFDSTFVPKGFAQKDGSYAGFPIDLATAV | 72 |
| KGI27253     | 1  ------MKKWMLVLVSLMTALFLVACGKNASETSGDNWSKYQSNKSITIGFDSTFVPKGFAQKDGSYAGFPIDLATAV | 72 |
| WP_088777969 | 1  ------MKKWMLVLVSLMIALFLVACGKNTSETSGDNWSKYESNKSITIGFDSTFVPKGFAQKDGSYAGFPIDLATAV | 72 |
| WP_050223531 | 1  ------MKKHLVLVSLMTALFLVACGKNTSETSGDNWSKYESNKSITIGFDSTFVPKGFAQKDGSYAGFPIDLATAV | 72 |
| CKJ33697     | 1  mkkwmkkWMKKWKLVLVSLMTALFLVACGKNTSETSGDNWSKYESNKSITIGFDSTFVPKGFAQKDGSYAGFPIDLATAV | 72 |
| WP_000759187 | 73 FEKYGITVNWQPIDMDLKEAELTKGTIDLIWNGYSATDERREKVAFSNSYATDERREKVAFSNSYMKNEQVLVTKKSSGITTAKDMTGKTLGAQA | 152 |
| WP_050213573 | 73 FEKYGITVNWQPIDWDLKEAELTKGTIDLIWNGYSATDERREKVAFSNSYATDERREKVAFSNSYMKNEQVLVTKKSSGITTAKDMTGKTLGAQA | 152 |

| | | Sequences | |
|---|---|---|---|
| WP_061814735 | 73 | FEKYGITVNWQPIDWDLKEAELTKGTIDLIWNGYSATDERREKVAFSNSYMKNEQVLVTKKSSGITTAKDMTGKTLGAQA | 152 |
| WP_084843602 | 73 | FEKYGITVNWQPIDWDLKEAELTKGTIDLIWNGYSATDERREKVAFSNSYMKNEQVLVTKKLSGITTAKDMTGKTLGAQA | 152 |
| WP_000759185 | 73 | FEKYGITVNWQPIDWDLKEAELTKGTIDLIWNGYSATDERREKVAFSNSYMKNEQVLVTKKLSGITTAKDMTGKTLGAQA | 152 |
| WP_050261378 | 73 | FEKYGITVNWQPIDWDLKEAELTKGTIDLIWNGYSATDERREKVAFSNSYMKNEQVLVTKKLSGITTAKDMAGKTLGAQA | 152 |
| WP_050220771 | 77 | FEKYGITVNWQPIDWDLKEAELTKGTIDLIWNGYSATDERREKVAFSNSYMKNEQVLVTKKSSGITTAKDMAGKTLGAQA | 156 |
| CKA82396 | 73 | FEKYGITVNWQPIDWDLKEAELTKGTIDLIWNGYSATDERREKVAFSNSYMKNEQVLVTKKSSGITTAKDMAGKTLGAQA | 152 |
| WP_088802838 | 73 | FEKYGITVNWQPIDWDLKEAELTKGTIDLIWNGYSATDERREKVAFSNSYMKNEQVLVTKKSSGITTAKDMAGKTLGAQA | 152 |
| WP_049512265 | 77 | FEKYGITVNWQPIDWDLKEAELTKGTIDLIWNGYSATDERREKVAFSNSYMKNEQVLVTKKLSGITTAKDMTGKTLGAQA | 156 |
| CKL85404 | 69 | FEKYGITVNWQPIDWDLKEAELTKGTIDLIWNGYSATDERREKVAFSNSYMKNEQVLVTKKLSGITTAKDMNGKTLGAQA | 148 |
| EHZ28755 | 73 | FEKYGITVNWQPIDWDLKEAELTKGTIDLIWNGYSATYERREKVAFSNSYMKNEQVLVTKKLSGITTAKDMTGKTLGAQA | 152 |
| WP_100128002 | 73 | FEKYGITVNWQPIDWDLKEAELTKGTIDLIWNGYSATDERREKVAFSHSYMKNEQVLVTKKSSGITTAKDMAGKTLGAQA | 152 |
| WP_053039665 | 73 | FEKYGITVNWQPIDWDLKEAELTKGTIDLIWNGYSATDERREKVAFSNSYMKNEQVLVTKKSSGITTAKDMAGKTLGAQA | 152 |
| WP_101514844 | 73 | FEKYGITVNWQPIDWDLKEAELTKGTIDLIWNGYSATDERREKVAFSNSYMKNEQVLVTKKSSGITTAKDMAGKTLGAQA | 152 |
| WP_050242061 | 73 | FEKYGITVNWQPIDWDLKEAELTKGTIDLIWNGYSATDERREKVAFSNSYMKNEQVLVTKKSSGITTAKDMAGKTLGAQA | 152 |
| WP_023941000 | 69 | FEKYGITVNWQPIDWDLKEAELTKGTIDLIWNGYSATDERREKVAFSNSYMKNEQVLVTKKSSGITTAKDMTGKTLGAQA | 148 |
| EHE15463 | 69 | FEKYGITVNWQPIDWDLKEAELTKGTIDLIWNGYSATDERREKVAFSNSYMKNEQVLVTKKSSGITTAKDMTGKTLGAQA | 148 |
| EHE34295 | 73 | FEKYGITVNWQPIDWDLKEAELTKGTIDLIWNGYSATYERREKVAFSNSYMKNEQVLVTKKLSGITTAKDMTGKTLGAQA | 152 |
| CCM08008 | 77 | FEKYGITVNWQPIDWDLKEAELTKGTIDLIWNGYSATDERREKVAFSNSYMKNEQVLVTKKLSGITTAKDMTGKTLGAQA | 156 |
| KG127253 | 73 | FEKYGITINWQPIDWDLKEAELTKGTIDLIWNGYSATDERREKVAFSNSYMKNEQVLVTKKLSGITTAKDMAGKTLGAQA | 152 |
| WP_088777969 | 73 | FEKYGITVNWQPIDWDLKEAELTKGTIDLIWNGYSATDERREKVAFSHSYMKNEQVLVTKKSSGITTAKDMAGKTLGAQA | 152 |
| WP_050223531 | 73 | FEKYGITVNWQPIDWDLKEAELTKGTIDLIWNGYSATDERREKVAFSNSYMKNEQVLVTKKLSGITTAKDMTGKTLGAQA | 152 |
| CKJ33697 | 81 | FEKYGITVNWQPIDWDLKEAELTKGTIDLIWNGYSATDERREKVAFSNSYMKNEQVLVTKKLSGITTAKDMTGKILGAQA | 160 |
| WP_000759187 | 153 | GSSGYADFEANPEILKNIVANKEANQYQTFNEALIDLKNDRIDGLLIDRVYANYYLEAEGVLNDYNVFTVGLETEAFAVG | 232 |
| WP_050213573 | 153 | GSSGYADFEANPEILKNIVANKEANQYQTFNEALIDLKNDRIDGLLIDRVYANYYLEAEGVLNDYNVFTVGLETEAFAVG | 232 |
| WP_084843602 | 153 | GSSGYADFEANPAILKDIVANKEANQYQTFNEALIDLKNDRIDGLLIDRVYANYYLEAEGVLNDYNVFTVGLETEAFAVG | 232 |
| WP_000759185 | 153 | GSSGYADFEANPEILKNIVANKEANQYQTFNEALIDLKNDRIDGLLIDRVYANYYLEAEGVLNDYNVFTVGLETEAFAVG | 232 |
| WP_050261378 | 153 | GSSGYADFEANPEILKNIVANKEANQYQTFNEALIDLKNDRIDGLLIDRVYANYYLEAEGVLNDYNVFTVGLETEAFAVG | 232 |
| WP_050220771 | 157 | GSSGYADFEANPEILKNIVANKEANQYQTFNEALIDLKNDRIDGLLIDRVYANYYLEAEGVLNDYNVFTVGLETEAFAVG | 236 |
| CKA82396 | 153 | GSSGYADFEANPEILKNIVANKEANQYQTFNEALIDLKNDRIDGLLIDRVYANYYLEAEGVLNDYNVFTVGLETEAFAVG | 232 |
| WP_088802838 | 153 | GSSGYADFEANPAILKDIVANKEANQYQTFNEALIDLKNDRIDGLLIDRVYANYYLEAEGVLNDYNVFTVGLETEAFAVG | 232 |
| WP_049512265 | 157 | GSSGYADFEANPAILKDIVANKEANQYQTFNEALIDLKNDRIDGLLIDRVYANYYLEAEGVLNDYNVFTVGLETEAFAVG | 236 |
| CKL85404 | 149 | GSSGYADFEANPAILKDIVANKEANQYQTFNEALIDLKNDRIEGLLIDRVYANYYLEAEGVLNDYNVFTVGLETEAFAVG | 228 |
| EHZ28755 | 153 | GSSGYADFEANPEILKNIVANKEANQYQTFNEALIDLKNDRIDGLLIDRVYANYYLEAEGVLNDYNVFTVGLETEAFAVG | 232 |
| WP_100128002 | 153 | GSSGYADFEANPEILKNIVANKEANQYQTFNEALIDLKNDRIDGLLIDRVYANYYLEAEGVLNDYNVFTVGLETEAFAVG | 232 |
| WP_053039665 | 153 | GSSGYADFEANPEILKNIVANKEANQYQTFNEALIDLKNDRIDGLLIDRVYANYYLEAEGVLNDYNVFTVGLETEAFAVG | 232 |
| WP_101514844 | 153 | GSSGYADFEANPEILKNIVANKEANQYQTFNEALIDLKNDRIDGLLIDRVYANYYLEAEGVLNDYNVFTVGLETEAFAVG | 232 |
| WP_050242061 | 153 | GSSGYADFEANPEILKNIVANKEANQYQTFNEALIDLKNDRIDGLLIDRVYANYYLEAEGVLNDYNVFTVGLETEAFAVG | 232 |
| WP_023941000 | 149 | GSSGYADFEANPEILKNIVANKEANQYQTFNEALIDLKNDRIDGLLIDRVYANYYLEAEGVLNDYNVFTVGLETEAFAVG | 228 |
| EHE15463 | 149 | GSSGYADFEANPEILKNIVANKEANQYQTFNEALIDLKNDRIDGLLIDRVYANYYLEAEGVLNDYNVFTVGLETEAFAVG | 228 |
| EHE34295 | 153 | GSSGYADFEANPAILKDIVANKEANQYQTFNEALIDLKNDRIDGLLIDRVYANYYLEAEGVLNDYNVFTVGLETEAFAVG | 232 |
| CCM08008 | 157 | GSSGYADFEANPAILKDIVANKEANQYQTFNEALIDLKNDRIDGLLIDRVYANYYLEAEGVLNDYNVFTVGLETEAFAVG | 236 |
| KG127253 | 153 | GSSGYADFEANPEILKNIVANKEANQYQTFNEALIDLKNDRIDGLLIDRVYANYYLEAEGVLNDYNVFTVGLEIEAFAVG | 232 |
| WP_088777969 | 153 | GSSGYADFEANPEILKNIVANKEANQYQTFNEALIDLKNDRIDGLLIDRVYANYYLEAEGVLNDYNVFTVGLETEAFAVG | 232 |
| WP_050223531 | 153 | GSSGYADFEANPAILKDIVANKEANQYQTFNEALIDLKNDRIDGLLIDRVYANYYLEAEGVLNDYNVFTVGLETEAFAVG | 232 |
| CKJ33697 | 161 | GSSGYADFEANPAILKDIVANKEANQYQTFNEALIDLKNDRIDGLLIDRVYANYYLEAEGVLNDYNVFTVGLETEAFAVG | 240 |
| WP_000759187 | 233 | ARKEDTNLVKKINEAFSSLYKDGKFQEISQKWFGEDVATKEVKEGQ | 278 |
| WP_050213573 | 233 | ARKEDTTLVKKINEAFSSLYKDGKFQEISQKWFGEDVATKEVKEGQ | 278 |

-continued

| | Sequences | |
|---|---|---|
| WP_061814735 | ARKEDTTLVKKINEDFSSLYKNGKFQEISQKWFGEDVATKEVKEGQ | 278 |
| WP_084843602 | ARKEDTNLVKKINEAFSSLYKDGKFQEISQKWFGEDVATKEVKEGQ | 278 |
| WP_000759185 | ARKEDTTLVKKINEAFSSLYKDGKFQEISQKWFGEDVATKEVKEGQ | 278 |
| WP_050261378 | ARKEDTTLVKKINEAFSSLYKDGKFQEISQKWFGEDVATKEVKEGQ | 278 |
| WP_050220771 | ARKEDTTLVKKINEAFSSLYKDGKFQEISQKWFGEDVATKEVKEGQ | 278 |
| CKA82396 | ARKEDTTLVKKINEAFSSLYKDGKFQEISQKWFGEDVATKEVKEGQ | 282 |
| WP_088802838 | ARKEDTTLVKKINEAFSSLYKDGKFQEISQKWFGEGVATKEVKEGQ | 278 |
| WP_049512265 | ARKEDTTLVKKINEAFSSLYKDGKFQEISQKWFGEDVATKEVKEGQ | 278 |
| CKL85404 | ARKEDTTLVKKINEAFSSLYKDGKFQEISQKWFGEDVATKEVKEGQ | 282 |
| EHZ28755 | ARKEDTTLVKKINEAFSSLYKDGKFQEISQKWFGEDVATKEVKEGQ | 274 |
| WP_100128002 | ARKEDTTLVKKINEAFSSLYKDGKFQEISQKWFGEDVATKEVKEGQ | 278 |
| WP_053039665 | ARKEDTTLVKKINEAFSSLYKDGKFQEISQKWFGEDVATKEVKEGQ | 278 |
| WP_101514844 | ARKEDTTLVKKINEAFSSLYKDGKFQEISQKWFGEDVATKEVKEGQ | 278 |
| WP_050242061 | TRKEDTTLVKKINEAFSSLYKDGKFQEISQKWFGEDVATKEVKEGQ | 278 |
| WP_023941000 | ARKEDTTLVKKINEAFSSLYKDGKFQEISQKWFGEDVATKEVKEGQ | 278 |
| EHE15463 | SRKEDTTLVKKINEAFSSLYKDGKFQEISQKWFGEDVATKEVKEGQ | 274 |
| EHE34295 | ARKEDTTLVKKINEAFSSLYKDGKFQEISQKWFGEDVATKEVKEG- | 274 |
| CCM08008 | ARKEDTTLVKKINEAFSSLYKDGKFQEISQKWFGEDVATKEVKEGQ | 277 |
| KG127253 | ARKEDITLVKKINEAFSSLYKDGKFQEISQKWFGEDVATKEVKEGQ | 282 |
| WP_088779969 | ARKEDTTLVKKINEAFSSLYKDGKFQEISQKWFGEDVATKEVKEGQ | 278 |
| WP_050223531 | ARKEDTTLVKKINEAFSSLYKDGKFQEISQKWFGEDVATKEVKEGQ | 278 |
| CKJ33697 | ARKEDTTLVKKINEAFSSLYKDGKFQEISQKWFGEDVATKEVKEGQ | 286 |

SEQ ID NO: 9, rhizavidin gene encoding full-length vhizavidin protein:
TTGATTATTACGAGTTTATATGCAACTTCGGTACGATCCGACGGTCGGCGACGTCAGGAG
GAAAAACCATGATCCGTACTAATGCAGTGCAGTTCTTCAAGATTTTCAAGCATCGCATCAGCTCT
TGCTTTCGATGCAAGCAACTTCAAGATTTTCAAGACATCGACTCGTCGTTGCTGTAGCAACCTCAGCTCT
AACCAGTCCGGCTCGACGATGATCATTCAAGTCGACTCGTTCGGAAATGTCTCCGGCAATATG
TCGTGCGCAGGCACGGTTCCAGACTCTCCGTACCCGCGGCCGTGAATGCACG
TTTATCGCCTTCAGCGTTGGCTGAACAATTCTACCGAAATGTACCGGCTGAATCTGGCTGA
CGGGTTATGCGCAGTGACGGTAACAATACGAATTGTTACGACCTGAATCTGGCTATGA
AGCCGGTTCTGGCCCGGCCAATGAACAGGGTCAGATACCTTTCAGTACGTTCCGACCACGGA
AACAAAAGCCTGCTGAAAGAT SEQ ID NO: 10, rhizavidin gene encoding truncated rhizavidin protein, denoted Rhavi [amino acids 45-179]:
TTTGATGCGAGTAACTTAAAGATTTCAGCTCTTATTGCGAGCGCCAGTAGCTCTTGGCAGAATC
AGAGTGCCAGCACCATGATCGATTATCCAGGTGGATTCTTCGGCAACCTAGTGCCAGTATGTTAA
TCGTGCGCAGGCACGGTTCCAGACTCTCCGTACCCGCCGCGTGAATGCACG
TTTATCGCCTTCAGCGTTGGCTGAACAATTCTACCGAAAACTGTAATAGTGCAACCGGCTGA
CGGGTTATGCGCAGTGACGGTAACAATACGAATTGTTACGACCTGAATCTGGCTATGA
AGCCGGTTCTGGCCCGGCCAATGAACAGGGTCAGATACCTTTCAGTACGTTCCGACCACGGA
AACAAAAGCCTGCTGAAAGAT SEQ ID NO: 11, SP0785 gene encoding full-length SP0785 protein [amino acids 1-399], TIGR4 strain:
ATGAAGAAAAAGAATGGTAAAGCTAAAAGTGCAACTGTATGCAGCAAT
CGGTGCTGCCAGTGTAGTTGTATTGGGTGCTGGGGGGATTTTACTCTTTA
GACAACCTTCTCAGACTGCTCTAAAAGATGAGCCTACTCATCTTGTTGTT
GCCAAGGAAGCAAGCGTGGCCTCCTCTGTTTATTGTCAGGACAGTAAC
AGCAAAAATGAACAATATGTTTATTTGATGCTAGTAAGGGTGATTTAG

| Sequences |
|---|
| ATGAAATCCTTGTTTCTGTGGGCGATAAGGTCAGCGAAGGGCAGGCTTTA<br>GTCAAGTACAGTAGTTCAGAAGCGATCGCAGGCCGGCCCTATGAACTCAG<br>AGCAGTAGTAGGCAGATCGTCATATCAGAACTCAATCAAGCACGAA<br>ATGAACGCCGCTTCAGCTCCCGCTCCACAGTTACCAGCGCCAGTAGGAGGA<br>GAAGATGCAACGGTGCAAAGCCCAACTCCAGTGGCTGGAAATTCTGTTGC<br>TTCTATTGACCTCAATTGGTGATGCCCCTGATGCGCGTGCAGATGCTG<br>CGGCCCAATTAAGCAAGGCTCAAAGTCAATTGATGCAACAACTGTTCTC<br>AGTACCCTAGAGGGAGCTGTGGTCGAAGTCAATGCAATGTCTCTAAATC<br>TCCAACAGGGCGAGTCAAGTATGCTTCATATTGTCAGCAATGAAAATT<br>TACAAGTCAAGGGAGAATTCTGTAGTACAATCTAGCCAACCTTTCTGTA<br>GGTCAAGAAGTAAGCTATATTCTGACTATCCTAAAGTGTATCCTAAAAATGGAC<br>TGGGAAATTAAGCTATATTCTGACTATCCTAAAACAATGGTGAAGCAG<br>CTAGTGCCAGCAGCCCGGGAATAATACAGGTTCTAAATACCTTATACTATT<br>GATGTGACGAGGTTGTGATTGAACAAGTTTTCTGTCAACAT<br>TGAGGTTAAAAGCAAAACTAAGGCTATTCTTGTTCCTGTTAGCAGTCTAG<br>TAATGATGATAGTAAAAATTATGTCTGATTGTGGATGAACAACAAAAG<br>GCTAAAAAGTTGAGGTTTCATTGGGAAATGCTGACGCGAAAATCAAGA<br>AATCACTTCTGGTTTAACGAACGGTCAAGGTCATCAGTAATCCAACAT<br>CTTCCTTGGAAGAAGAAAAGAGGTGAAGGCTGATGAAGCAACTAAT |

SEQ ID NO: 12, SP0785 gene encoding SP0785 protein lacking signal sequence
[amino acids 33-399]:

| |
|---|
| TTTAGACAACCTTCTCAGACTGCTCTAAAAGATGAGCCTACTCATCTTGTTGCCAAGGAAGGAAGCCTGGCCTC<br>CTCTGTTTTATTGTCAGGACAGTAACAGCAAAAATGAACAATATGTTTATTTGATGCTAGTAAGGGTGATTTAG<br>ATGAAATCCTTTGTTTCTGTGGGCGATAAGGTCAGCGAAGGCAGGCTTTAGTCAAGTACAGTAGTTCAGAAGCGCAG<br>GCCGGCTATGAACTCAGTAGCAGTAGGCAGATCGTCATATCAGAACTCAATCAAGCACGAAATGAACGCCGCAG<br>AGCGCCTATGAATTCAGCTCCCGCTCCACAGTTACCAGCGCCAGTAGGAGGAGAAGATGCAACGGTGCAAAGCCCCAACTCCAGTGGCTGGAAATGA<br>AGCCCGCTTCAGCTCCCGCTCCACAGTTACCAGCGCCAGTAGGAGGAGAAGATGCAACGGTGCAAAGCCCCAACTCCAGTGGCTGGAAATGA<br>TGGCTCGGAAATTCTGTTGCTTCTATTGACGCTCAATTGGATGCAACAACTGTTCTCAGTACCCTAGAGGGAGCTGTGGTCGAAGTCAATAG<br>CAATGTCTCTAAATCTCCAACAGGGCGAGTCAAGTATGCTTCATATTGTCAGCAATGAAAATTTACAAGTCAAGG<br>GAGAATTGTCTGAGTACAATCTAGCAACCTTTCTGTAGGTCAATACTTTCTATATTGTCTAAAGTGTATCCTGAT<br>AAAAAATGGACTGGGAAATTAAGCTATATTTCTGACTATCCTAAAAACAATGGTGAAGCAGCTAGTCCAGCAGCCGG<br>GAATAATACAGGTTCTAAATGCAAAACTAAGGCTATTCTTGTTCCTGTTAGCAGTCGAGGTTGGTGATTTGAAGCAGTTTCTG<br>TCAACATTGAGGTTAAAAGCAAAACTAAGGCTATTCTTGTTCCTGTTAGCAGTCATCAAGCACGAAATGA<br>TATGTCTGATTGGTGATTGAACAACAACAAAAGGTCAAAAAAGTTGAGTTTCATTGGGAAATGCTGACGCAGAAAATCA<br>AGAAATCACTTCTGGTTTAACGAACGGTCAAGGTCATCAGTAATCCAACATCTCCAAGATCTTCCTTGGAAGAAGAAAAGAGG<br>TGAAGGCTGATGAAGCAACTAAT |

SEQ ID NO: 13, SP1500 gene encoding full-length SP1500 protein [amino acids
1-278], TIGR4 strain:

| |
|---|
| ATGAAAAAATGGATGCTTGTATTAGTCAGTCTGATGACTGCTTTGTTCTT<br>AGTAGCTGTGTGGAAAAATTCTAGCGAAACTAGTGGAGATAATTGGTCAA<br>AGTAGGAGTCTAACAAGTCTATTACTATGGATTTGATAGTACTTTTGTT<br>CCAATGGGATTTGCTCAGAAAGATGGTTCTTATGCAGGATTTGATATTGA<br>TTTAGCTACACAGTCTGTTTTTGAAAATAACGGAATCACGGTAAATTGCAAC<br>CGATTGATTGGGAGATTTGAAACAGACGAAGCTGAATTGACAAAAGGAACGATTGAT<br>CTGATTTGAATGGCTATTCCGCTACAGACGAACGCCGTGAAAAGGTGGC<br>TTTGAGTAACTCATATATGAAGAATGAGCAGGTATTGGTTACGACGAAAT<br>CATCTGGTATCACGACTGCAAAGACTACTGAAAAGACATTAGGAGCT<br>CAAGGTGTCTTGTTCATCTGGTTATGCGACTTTGAAGCAAATCCAGAATTT<br>GAAGAATATTGTCGCTAATAAGGAAGCGAATCAATACCAAACCTTTAATG |

| | Sequences |
|---|---|
| | AAGCCTTGATTGATTGAAAAACGATCGATTGATGGTCTATTGATTGAC<br>CGTGTCTATGCAAACTATTATTAGAAGACAGAAGAGTGTTTTAAACGATTA<br>TAATGTCTTTACAGTTGGACTAGAAACAGAAGCTTTTGCGTTGGAGCCC<br>GTAAGGAAGATACAAACTTGGTTAAGAACATAAATGAAGCTTTTCTAGT<br>CTTTACAAGGACGGCAAGTTCCAAGAAATCAGCCAAAATGGTTTGAGA<br>AGATGTAGCAACCAAAGAAGTAAAAGAAGGAGAG |

SEQ ID NO: 14, SP1500 gene encoding SP1500 protein lacking signal sequence [amino acids 27-278]:
ACTAGTGGAGATAATTGGTCAAAGTACCAGTCTAACAAGTCTATTACTATTGGATTTGATAGTACTTTGTTCCAAT
GGGATTTGCTCAGAAAGATGGTCTTCAGAGATTTGATATTGATTAGCTACAGCTGTTTTGAAAAATACGAA
TCACCGTAAATTGGCAACCGATTGATTGGGATTCGAAAGAAGCTGAATTGACAAAGGAACGATTGATCTGATTGG
AATGCTATTCCGTACAGACGAACGCCGTACAGAAAGGTGCTTTCAGTAACTCATATATGAAGAATGAGCAGTATT
GGTTACGAAGAAATCATCTGTATCATCAAAGATGCAAAGATTAGAGCATTAGAGCTGAAGCTGGTTCAT
CTGGTTATGCGGACTTTGAAGCAAATCCAGAAATTTGAAGAATATTGTCGCTAATAAGGAAGCGAATCAATACCAA
ACCTTAATGAAGCCTTGATTGATTTGAAAACGATGACATTAATGCTTACAGTCTTTACAGTTGAAAACAGAAGCTTTTGCGTTG
TTATTTAGAAGCAGAAGGTGTTTTAAGAGATACAAGCTTTAAGAATGAAATGAAGCTTTTCTAGTCTTTACAAGGACCGCAAGTTC
GAGCCCGTAAGAGAATACAAACTTGGTTAAGAAGATAATGAAGCTTTTCTAGTCTTTACAAGGACCGCAAGTTC
CAAGAAATCAGCCAAAATGGTTTGAGAAGATGTAGCAACCAAAGAAGTAAAAGAAGGACAG SEQ ID NO: 15, His tag 1:
HHHHHH SEQ ID NO: 16, His tag 2:
MSYYHHHHHH SEQ ID NO: 17, fusion protein SP1500-SP0785:
MTSGDNWSKYQSNKSITIGFDSTFVPMGFAQKDGSYAGFDIDLATAVFEKYGITVNWQPIDWDL
KEAELTKGTIDLIWNGYSATDERREKVAFSNSYMKNEQVLVTKKSSGITTAKDMTGKTLGAQAG
SSGYADFEANPEILKNIVANKEANQYQTFNEALIDLKNDRIDGLLIDRVYANYYLEAEGVLNDY
NVFTVGLETEARFAVGARKEDTNLVKKINEAFSSLYKDGKFQEISQKWFGEDVATKEVKEGQFRQ
PSQTALKDEPTHLVVAKEGSVASSVLLSGTVTAKNEQYVYFDASKGDLDEILVSVGDKVSEGQA
LVKYSSSEAQAAYDSASRAVARADRHINELNQARNEAASAPAPQLPAPVGGEDATVQSPTPVAG
NSVASIDAQLGDARDARADAAAQLSKAQSQLDATTVLSTLEGTvEVNSNVSKSPTGASQVMVH
IVSNENLQVKGELSEYNLANLSVGQEVSFTSKVYPDKKWTGKLSYISDYPKNNGEAASPAAGNN
TGSKYPYTIDVTGEVGDLKQGFSVNIEVKSKTKAILVPVSSLVMDDSKNYVWIVDEQQKAKKVE
VSLGNADAENQEITSGLTNGAKVISNPTSSLEEGKEVKADEATN SEQ ID NO: 18, fusion protein SP0785-SP1500:
MFRQPSQTALKDEPTHLVVAKEGSVASSVLLSGTVTAKNEQYVYFDASKGDLDEILVSVGDKVS
EGQALVKYSSSEAQAAYDSASRAVARADRHINELNQARNEAASAPAPQLPAPVGGEDATVQSPT
PVAGNSVASIDAQLGDARDARADAAAQLSKAQSQLDATTVLSTLEGTVVEVNSNVSKSPTGASQ
VMVHIVSNENLQVKGELSEYNLANLSVGQEVSFTSKVYPDKKWTGKLSYISDYPKNNGEAASPA
AGNNTGSKYPYTIDVTGEVGDLKQGFSVNIEVKSKTKAILVPVSSLVMDDSKNYVWIVDEQQKA
KKVEVSLGNADAENQEITSGLTNGAKVISNPTSSLEEGKEVKADEATNTSGDNWSKYQSNKSIT
IGFDSTFVPMGFAQKDGSYAGFDIDLATAVFEKYGITVNWQPIDWDLKEAELTKGTIDLIWNGY
SATDERREKVAFSNSYMKNEQVLVTKKSSGITTAKDMTGKTLGAQAGSSGYADFEANPEILKNI
VANKEANQYQTFNEALIDLKNDRIDGLLIDRVYANYYLEAEGVLNDYNVFTVGLETEARFAVGAR
KEDTNLVKKINEAFSSLYKDGKFQEISQKWFGEDVATKEVKEGQ -continued Sequences SEQ ID NO: 19, fusion protein Rhav1-SP1500-SP0785:
MFDASNFKDFSSIASASSSWQNQSGSTMIIQVDSFGNVSGQYVNRAQGTGCQNSPYPLTGRVNG
TFIAFSVGWNNSTENCNSATGWTGYAQVNGNNTEIVTSWNLAYEGGSGP
AIEQGQDTFQYVPTTENKSLLKDTSGDNWSKYQSNKSITIGFDSTFVPMGFAQKDGSYAGFDID
LATAVFEKYGITVNWQPIDWDLKEAELTKGTIDLIWNGYSATDERREKVAFSNSYMKNEQVLVT
KKSSGITTAKDMTGKTLGAQAGSSGYADFEANPEILKNIVANKEANQYQTFNEALIDLKNDRID
GLLIDRVYANYYLEAEGVLNDYNVFTVGLETEAFAVGARKEDTNLVKKINEAFSSLYKDGKFQE
ISQKWFGEDVATKEVKEGQFRQPSQTALKDEPTHLVVAKEGSVASSVLLSGTVTAKNEQYVYFD
ASKGDLDEILVSVGDKVSEGQALVKYSSSEAQAAYDSASRAVARADRHINELNQARNEAASAPA
PQLPAPVGGEDATVQSPTPVAGNSVASIDAQLGDARDARADAAAQLSKAQSQLDATTVLSTLEG
TVVEVNSNVSKSPTGASQVMHIVSNENLQVKGELSEYNLANLSVGQEVSFTSKVYPDKKWTGK
LSYISDYPKNNGEAASPAAGNNTGSKYPYTIDVTGEVGDLKQGFSVNIEVKSKTKAILVPSSL
VMDDSKNYVWIVDEQQKAKKVEVSLGNADAENQEITSGLT
NGAKVISNPTSSLEEGKEVKADEATN SEQ ID NO: 20, fusion protein Rhav1-SP0785-SP1500:
MFDASNFKDFSSIASASSSWQNQSGSTMIIQVDSFGNVSGQYVNRAQGTGCQNSPYP
LTGRVNGTFIAFSVGWNNSTENCNSATGWTGYAQVNGNNTEIVTSWNLAYEGGSGP
AIEQGQDTFQYVPTTENKSLLKDFRQPSQTALKDEPTHLVVAKEGSVASSVLLSGTVTAKNEQY
VYFDASKGDLDEILVSVGDKVSEGQALVKYSSSEAQAAYDSASRAVARADRHINELNQARNEAA
SAPAPQLPAPVGGEDATVQSPTPVAGNSVASIDAQLGDARDARADAAAQLSKAQSQLDATTVLS
TLEGTVVEVNSNVSKSPTGASQVMHIVSNENLQVKGELSEYNLANLSVGQEVSETSKYPDKK
WTGKLSYISDYPKNNGEAASPAAGNNTGSKYPYTIDVTGEVGDLKQGFSVNIEVKSKTKAILVP
VSSLVMDDSKNYVWIVDEQQKAKKVEVSLGNADAENQEITSGLTNGAKVISNPTSSLEEGKEVK
ADEATNTSGDNWSKYQSNKSITIGFDSTFVPMGFAQKDGSYAGFDIDLATAVFEKYGITVNWQP
IDWDLKEAELTKGTIDLIWNGYSATDERREKVAFSNSYMKNEQVLVTKKSSGITTAKDMTGKTL
GAQAGSSGYADFEANPEILKNIVANKEANQYQTFNEALIDLKNDRIDGLLIDRVYANYYLEAEG
VLNDYNVFTVGLE
TEAFAVGARKEDTNLVKKINEAFSSLYKDGKFQEISQKWFGEDVATKEVKEGQ SEQ ID NO: 21, fusion protein SP1500-SP0785-Rhav1:
MTSGDNWSKYQSNKSITIGFDSTFVPMGFAQKDGSYAGFDIDLATAVFEKYGITVNWQPIDWDL
KEAELTKGTIDLIWNGYSATDERREKVAFSNSYMKNEQVLVTKKSSGITTAKDMTGKTLGAQAG
SSGYADFEANPEILKNIVANKEANQYQTFNEALIDLKNDRIDGLLIDRVYANYYLEAEGVLNDY
NVFTVGLETEAFAVGARKEDTNLVKKINEAFSSLYKDGKFQEISQKWFGEDVATKEVKEGQFRQ
PSQTALKDEPTHLVVAKEGSVASSVLLSGTVTAKNEQYVYFDASKGDLDEILVSVGDKVSEGQA
LVKYSSSEAQAAYDSASRAVARADRHINELNQARNEAASAPAPQLPAPVGGEDATVQSPTPVAG
NSVASIDAQLGDARDARADAAAQLSKAQSQLDATTVLSTLEGTVVEVNSNVSKSPTGASQVMH
IVSNENLQVKGELSEYNLANLSVGQEVSFTSKVYPDKKWTGKLSYISDYPKNNGEAASPAAGNN
TGSKYPYTIDVTGEVGDLKQGFSVNIEVKSKTKAILVPSSLVMDDSKNYVWIVDEQQKAKKVE
VSLGNADAENQEITSGLTNGAKVISNPTSSLEEGKEVKADEATNFDASNFKDFSSIASASSSWQ
NQSGSTMIIQVDSFGNVSGQYVNRAQGTGCQNSPYPLTGRVNGTFIAFSVGWNNSTENCNSATG
WTGYAQVNGNNTEIVTSWNLAYEGGSGPAIEQGQDTFQVPTTENKSLLKD SEQ ID NO: 22, fusion protein SP0785-SP1500-Rhav1:
MFRQPSQTALKDEPTHLVVAKEGSVASSVLLSGTVTAKNEQYVYFDASKGDLDEILVSV
GDKVSEGQALVKYSSSEAQAAYDSASRAVARADRHINELNQARNEAASAPAPQLPAP
VGGEDATVQSPTPVAGNSVASIDAQLGDARDARADAAAQLSKAQSQLDATTVLSTLE
GTVVEVNSNVSKSPTGASQVMHIVSNENLQVKGELSEYNLANLSVGQEVSFTSKV
YPDKKWTGKLSYISDYPKNNGEAASPAAGNNTGSKYPYTIDVTGEVGDLKQGFSVN
IEVKSKTKAILVPSSLVMDDSKNYVWIVDEQQKAKKVEVSLGNADAENQEITSGLT

| | Sequences |
|---|---|
| | NGAKVISNPTSSLEEGKVKADEATNTSGDNWSKYQSNKSITIGFDSTFVPMGFAQKDGSYAGF DIDLATAVFEKYGITVNWQPIDWDLKEAELTKGTIDLIWNGYSATDERREKVAFSNSYMKNEQV LVTKKSSGITTAKDMTGKTLGAQAGSGYADFEANPEILKNIVANKEANQYQTFNEALIDLKND RIDGLLIDRVYANYLEAEGVLNDYNVFTVGLETEAFAVGARKEDTNLVKKINEAFSSLYKDGK FQEISQKWFGEDVATKEVKEGQFDASNFKDFSSIASASSSWNQSGSTMIIQVDSFGNVSGQYV NRAQGTGCQNSPYPLTGRVNGTFIAFSVGWNNSTENCNSATGWTGYAQVNGNNTEIVTSWNLAY EGGSGPAIEQGQDTFQYVPTTENKSLLKD |

SEQ ID NO: 23, fusion protein CP1, Rhavi-linker (

-continued

Sequences

SIASASSSWQNQSGSTMIIQVDSFGNVSGQYVNRAQGTGCQNSPYPLTGRVNGTFIAFSVGWNN
STENCNSATGWTGYAQVNGNNTEIVTSWNLAYEGGSGPAIEQGQDTFQYVPTTENKSLLKD

SEQ ID NO: 26, fusion protein SP0785-linker (GGGGSSS)-SP1500-linker
(AAA)-Rhavi:
MFRQPSQTALKDEPTHLVVAKEGSVASSVLLSGTVTAKNEQYVYPDASKGDLDEILVSV
GDKVSEGQALVKYSSEAQAAYDSASRAVARADRHINELNQARNEAASAPAPQLPAP
VGGEDATVQSPTPVAGNSVASIDAQLGDARDARDAAAQLSKAQSQLDATTVLSTLE
GTVVEVNSNVSKSPTGASQVMVHIVSNENLQVKGELSEYNLANLSVGQEVSFTSKVYPDKKWTG
KLSYIISDYPKNNGEAASPRAAGNNTGSKYPYTIDVTGEVGDLKQGFSVNIEVKSKTKAIIVPSS
LVMDDSKNYVWIVDBEQOKAKKVEVSLGNADAENQEITSGLTNGAKVISNPTSSLEEGKEVKADE
ATNGGGGSSSTSGDNWSKYQSNKSITIGFDSTFVPMGFAQKDGSYAGFPIDLATAVFEKYGITV
NWQPIDWDLKEAELTKGTIDLIWNGYSATDERREKVAFSNSYMNEQVLVTKKSSGITTAKDMTG
KTLGAQAGSSGYADFEANPEILKNIVANKEANQYQTFNEALIDLKNDRIDGLLIDRVYANYLE
AEGVLNDYNVFTVGLETEAPAVGARKEDTNLVKKINEAFSSLYKDGKFQEISQKWFGEDVATKE
VKEGQAAAPDASNFKDFSSIASASSSWQNQSGSTMIIQVDSFGNVSGQYVNRAQGTGCQNSPYP
LTGRVNGTFIAFSVGWNNSTENCNSATGWTGYAQVNGNNTEIVTSWNLAYEGGSGPAIEQGQDT
FQYVPTTENKSLLKD SEQ ID NO: 27, codon-optimized nucleic acid sequence encoding fusion protein
SP1500-SP0785
ATGACCAGCCGGCGACAATTGGTCCAAATACCAGAGACAACAAGAGACTCACGATCGGCTTCGACA
GCACTTTTGTGCCGATGGGTTTCGCGCAAAAAGACGGTAGCTACCGGGTTTCGATATTGACCT
GGCGACCGCTGTCTTTGAGAAATACGGCATTACGGTTAATTGGCAGCCATTGATTGGGACCTG
AAAGAGGCCGAACTCACCAAAGGCACCATCGACCTTGATCTGGAATGGTTACTCCCCAACCGATG
AGCGCTCCGAAAAGTTGCCTTCAGCAACACGCTATATGAAGAATGAACAAGTGTTGGTAACCAA
GAAATCTAGCGGCATTACGACCCGGAAAGACATGACCCGAGATTTCGAAAAACATCGTTGCGAATAAAG
AGTCCTGGGCTATGCGACTTCGAGGCGAATCCTGAAGGCGAATCAGTCGACCGAAAAACATCGTTGCGAATAAAG
TCTGCTGATCGTCCCGGTACGCCAACCTTTTACGAACCTGAACTAACATTATCTCGAAGCCGAGGCGCTTTCTGAACGATTAT
AATGTTTTACCGTGGGTCTCTGGAGACTGAGGCATTTCGCGTTGGTGCGCCAAGGAAGATACCA
ACCTGGTTAAAAAGATTAATGAGCATTAGCTGCTGCGACCGAAGAGGTTAAAGAGGGCCAATTTCGCCAA
CCGAGCCAGACTGCCTTGAAAGATGAGCCGACCATCTGGTTGTTGCGAAAGAGGGCAGCGTGG
CATCGAGCGTCGTCTGCCAACAGTCAGGTTACTGCCAAAACGACAATACGTGTACTTCCGATGC
TAGCAAGGGTGATCTGGATGAAATTCTGTGAGCCTGGGTGACAAGTTAGCGAAGGCCAGGCA
CTGGTGAAGTTCCACTTCCGAGCGAATTGAACAAGCGAATTCAAGCAGCGAAGCGCGCCAGCGC
GTGGTCAGCTGCCGCTCCCGGATTCGGAAGATGCGGTGCAGAGCGCCCCACCCCGGTTGCGGGT
AATTCGGTCCGCCAGCATCGATCGCCAGCTGGGTGACGCGCGATGCCCTGCCGATGCCGCTG
CTCAACTGACGCGAAGCTCAGAGCCAATGTGAGCGACGCTGAGCAGCGGTGCTCAGCACCTTGAGGGGAC
CGTTGTCGAAGCAAGCAAGAACTTCAGGTCAGGTGAGCGAGTATAACCTGCGAATCTGA
ATTGTGAGCAATGAAAATTCCAAGTGAAGTCGAGCAGCGTAGGCCCGGAGCCAATGAAATCTGACCGGCAAGTT
GCGTTTGGTCGAAGAGGTCAGCTTTACCAGCAAGAACATGCGAGGCAGCCTCCCCGGCAGCCGGCAACAAT
GAGTACATCAGCGACTATCCGTACACCATCGACGTAACCGGTGAAGGTGCCGACCTGAAACAGGGTT
TTAGCGTGAATATCGAAGTGAAGTCAAAGACGAAGCAATTTTGTTCCGGTTAGCTCCTGT
GATGGACCGATATCGAAGAATTATTGTGGATTGTGAGACCGAAGAACCAAGAAATACGCTGTGCGACAAGCCGT
GAGCCCGGCAATGCTGATGCCGAGAACCAAGAAATCACGCTGGTCTGACAACGGTGCGA
AAGTTATTAGCAACCCGACCAGCAGCCTGGAAGAGGGTAAAGAGGTCAAAGCTGACGAAGCTAC
GAAC -continued Sequences SEQ ID NO: 28, codon-optimized nucleic acid sequence encoding fusion protein SP0785-SP1500
ATGTTTCGCCAACCGAGCCAGCCTTGAAAGATGAGCCACCATCTGGTTGTTGCGAAAG
AGGGCAGCCGTGCAGCATCGAGCGTGCTGCTGAGCGGTACGCGGTTACTGCCAAAAACGAACAATACGT
GTACTTCGATGCTAGCAAGGGTGATCTGGATGAAATTCTGGTGAGCGTGGGTGACAAAGTTAGC
GAAGGCCAGGCACTGGTGAAGTATCATCCTCCGAGGCACAGGCAGCGTAACGAGGCCGCAAGC
GCGCAGTGGGCGTGCCGACCGTGCCAGCCGGTGGGTACGCGTAACGAGGCCGCAAG
CGCCGCACCCGACGTCCGCCGCAGCCATCGATGCGCGAAGATGCAGCTGGGTACGCGCGTGAGCCGACC
CGGTTGCGGTAATTCGTTGCCGACATCGAGAGCTCAACTGACGACCTGAAGAGCAAGGTGCTGAGCAC
CTTGGAGGGGTACCGTTGTCGAAGTCAACAGCAATGTGAGCAAGAGCCCAACGGGTGAGCGAGCCAG
GTTATGGTCCACATTGAGCGTGAGCTCAGCTTTACCGTCAAGGTGAGCTGAGCTGCGATAAGAAATG
TGGGAATCTGACCGGTTGATGAGAGGTCAACTCGCCGAAGAACAATGGCGAGCAGCCTCCCCGGCA
GCCGGCAAGTTGAGCTACATCGGCTCTAAGTATCCGTACACCATCGACGTAACCGTGAGGCTGCGACC
TGAAACAGGGTTTAGCGTGAATATCGAAGTGAAGTCAAGACCACAAGGCAATTTTGGTTCCGGT
TAGCTCCCTGTGATGAGACAAGAGAATTATGTGTGAATTGTCGACAGACAACAGAAGCG
AAAAAGTTGAAGGCAAGTTATTAGCAACCGACCAGCCTGGACAATGGGTCCGAGAGGGTAAAGAGTCAAAGC
CCAACGGTGCGAAAGTTACGAACAATTGTGCCAAGCGCTGCGACAATTGGCGCAAATTGTCATCACG
ATCGGCTTCGACAGCACTTTGTGCCGATGGGTTTCGCGCAGCAATACGGCTAGCTACGCGGTT
CGATATTGGACCTGGCGAAAGAGCCGAACTCCACCAAAGGCACCATCGACAGCTTGATCTGAATGGTTAC
TGATTTGGCAACCGATGAGCGTCCGAAAAAGTTGCCTTCAGCAACAGTTACTCGGCCTGTGATGAACAAG
TGTTGGTAACCAAGAAATCTAGCGCATTACGACCGCAAAGACAATGACCCGGTAAGACCGTGGG
TGCGCAGGCCGGTTCGCTGCTATGCGGAATCAGACCTTTAACGGATGCAGACTGATCGAGCTGAAAACG
GTTGCCGAATAAGAGGGCGAACGAGTAGCGAATCGGCTGTGTGATGCTGACGGACTATTATCGGAAGCC
ATCGCATTGACGGTCTGCTGATCGATGTGTGAGAGACTGAGGCATTCGCCGGTTGGTGCCGC
TCTGAACGATTATATGTTTTTACGGTCGGTCTGAAAAAGATTAAATGACGATTAGTCACTGTACAAGGACGGCA
AAGGAAGATACCAACCTGGTTAAAAGATATAGCAGAATTAAGGAAGAAGATAAGTCATAGTGAACATAAG
AGTTCCAAGAAATTAGCCAGAATGGTTCGGTGAAGATGTTGCGACGAAGAGGTTAAAGAGGG
CCAA SEQ ID NO: 29, codon-optimized nucleic acid sequence encoding fusion protein Rhavi-SP1500-SP0785:
ATGTTCGACGATCCAATCCAACTTTAAAGACTTTAGCAGCATGCGTCCGCAAGCTCTAGCTGCAGA
ATCAATCTGGTAGCACCATGATTATCCAAGTGACAGCTTGGTAACGTCAGCCGGTCAATATGT
TAATCGTGCACAGGGTTGTCAGATTCTCCGTACCCGCTGACCGGTCGTGTGTTAACGGC
ACGTTCATCCTTTCAGCGTCCGGTTGGAACAATTCTACTGAAAATTGCAACAGCCGACCGGTT
GGACGGGCTATGCACCAAGTGAATGCCAGCCATATGAACGCCAGGATCGTCACGTCTGAATCGTCCTACGACC
TGAGGGTGCAGCGTCCGCTATTGAACAACAGCGGGCGACAATTGGTCCAAATACCCAGAGCAACAAGA
GCAATAAGTCCCTTCTGAAAGACCAGATGACCTTCCAAATACCAGATCGTCCTACGACCT
GCAATCACGACTCCGATATTGAGGCCTCGAGCCCTGTCTTTGCGAGGCCCATCGACCTGATCTGA
CGCGGTTTCGATTGATTGGACCCGAAAGAGCCCGGAACCACCATCACCCAAGCGCACCAAGGCGGTAATTGG
ATGGTTACTCCGACCGATGAGCCTTCGCGAAAAAGTGCCTCCAGCAACAGCTATATGAAGAA
TGAACAAGTGTTGGTCGCAGGCCGGGCGAACGATTCTAGCGCATTACGCGCATTAGGCAGACCTAGCAGCTGA
CCGCTGGGGTGCCAGGCTCTGATTGACCGTCTGATCAATCGATGTGCCGAAAGCCGATGAGAGTGATCTGA
AAAACATCGTTGCGAATAAAAGAGGCGAACGAGTAGCCGAAACGAGTAGCGGCCTTTAACGACGAGAGCT
GAAAACGATTGCAGTCATGACGGCTCTGTGTCGCTGCAGCTATCCCCTGAGATAATCTCGGAAGCC GAGGGCGTTCTGAACGATTATAATGTTTTTACCGTGGGTCTGGAGAACTGAGGCATTCGCGGTTG
GTGCCGCGCAAGGAAGATACCAACCTGGTTAAAAAGATTAATGAGGCATTAGCTCACTGTACAA
GGACGGCAAGTTCCAAGAAATTAGCCAGAAGTGGTTCGGTGAAGATGTTGCGACGAAAGAGGTT
AAAGAGGGCCAATTTCGCCACCGAGTCGACTGCGTTGCGTCCTGCAGCCGACCATCTGGTTG
TTGCGAAAGAGGGCAGCCGTGGCATCGAACGTGCTGCTCAGCGTGTACGGTTACTGCCAAAACGA
ACAATACGTGACTTCGATGCTAGCAAGGGTGAATCTGGATGAAATTCTGTGAGCGTGGGTGAC
AAAGTTAGCCAAGGCCCGCAGTGGCCGTGCCACTGTGAAGTATTCATCCTCGAGGCACAGGCGTAACGA
GCGCAAGCCCGCAGCCGCCAGCCCGACCGTTGGCTGCGTGGGTGCCGAAGATGCGACGTGCAG
AGCCCCACCCCG -continued Sequences GACCTGATCTGGAATGGTTACTCCGCAACCGATGAGCTGCGGAAAAAGTTGCCTTCAGCAACA
GCTATATGAAGAATGAACAAGTGTTGGTACCAGCCGGTGTAACGCGCATTACGACCGAAAGA
CATGACCGGTAAGACGCTGGGTGCGCAGCCCGGTAGCTCTGGCTATGCGGATTTCGAGGCGAAT
CCTGAGATTCTGAAAACATCGTTCGGAATAAAGAGGGCGAACGAGTAGCAGACCTTTAACGAAG
CACTGATCGACCTGAAAAACGATGCCATTGACGGTCTGCTGATCGATCGTGTGTACGGAACTA
TTATCTGGAAGCCGAGGGCGTTCTGAACGATTATATGTTTTTACCGTGGGTCTGGAGACTGAG
GCAATTCGCCGTTGTGCGCCAAGGACGGCAAGTTCCAAGAAATTAGCCAGAAGTGGTTCGGTGAAGATGTTGC
GCTCACTGTACAAGGACGGTTAAAGAGGGCCAA SEQ ID NO: 31, codon-optimized nucleic acid sequence encoding fusion protein SP1500-SP0785-Rhavi:
ATGACCAGCGGCGACAATTGGTCCAAATACCAGAGCAACAAGAGCATCACGATCGGCTTCGACA
GCACTTTTGTCGATGGGTTCGCGAAGAACGTAGCTACGCGGGTTGATTGCTGATTATTGACCTT
GGCGACCGCTGTCTTTGAGAAATACGGCATTACGGTTAATTGGCAGCCGATTGATTGGACCTG
AAAGAGGCCGAACTCACCAAGGCACCATCGACTGACTCAGCTATATCGAATGGTTACTCCCAACCGATG
AGCGTCGCGAAAAAGTTGCCTTCAGCAACGATCGGTAAGACGGCTGGGTGCGCAGCGCGT
GAAATCTAGCCGCATTACGACCGAAAGACATGACCGGTAAGACGGCTGGGTGCGCAGGCCGGT
AGCTCTGGCTATGCGGATTTCGAGGCGAATCCTGAGGATTCTGAAAACATCGTTCGCGAATAAAG
AGGGCGAACCAGTACCAGATGTTTACGGAACTTTACGAAGACTGATCGACCTGAAAACGATCGG
TCTGCTGATCGATCGTGTGTACGGGGTCTGGAGACTGAGGCGATTGCGCCGGTGCGCAAGGACGGCAAGTTCAA
AATGTTTTACCGTGGGTCTGGAGACTGAGGCGATTCGCCGGTTGGTGCGCCAAGGAAGATACCA
ACCTGGTTAAAAGAGAATTAATGAGGCATTGAGCATGCTAGCCATCACCTGTACAAGGACGGCAAGTTCCAAGAAT
TAGCAGAAGTGGTTCGGTGAAGATGCTGCTGCTGAAAGATGAGCGAGCGTACGGTTAAAGAGGGCAGCGTGG
CATCGACGGTGCTGCTGGATCGCGTTACTCGCCAAAAACGAACAATACGTGTACTTCGATGC
TAGCAGCCGTCATTACGAATTCTGTGGTGAGCGTGGGTGACAACAAGTTAGCGAAGGCCAGGCA
CTGGTGAAGTATTCATCCTCCGAGGCACAGGCAGCGCGGCTAACGAACCAAGCCCAGCGCC
GCACCTGCCGACCGCTCACATTAACGAATTGAACCAAGGCGTCGAGCGCCAGGCCCGGTTCCGCGGT
AATTCGTCGCAGCAAGCTCGATGGGCAGCCAACTGACGGCGACGCACGGTGCTGCACGCGGGGATAC
CTCAACTGAGCGAAGTCAACAGCAATGTGAGCAAGAGCCCCAACGGGTGAGCAGCCAGGTTGGTCCAC
CGTTGTGCTGAAGTCAACAGCAATGTGAGCAAGAGCCCCAACGGGTGCAGCAGCCGGAATCTGA
ATTGGTCAATGAAATTAACGCACGTCAAGGTCAGCAGGTCTAGACAGCAACAATGCGAAATGAACCGGCGAAGTT
GCGTTGGCTAGCTTGGTCAGCTTTCAGGAGTCAGCTTAAGGCGAGAAAATGCGAATTCCCGAGCAAT
GAGCTACATCAGCGACTACCCGAAGAACATGCGAGGCGTAACCGGTCGAGGTGCAGCAAGGTT
ACCGGCTCTAAGTATCCGTAAGATCCCAAGACGACCAAGGCAATTTTTGGTTCCGGTTTAGCTCCCTGT
TTAGCCGTGAATATCGAAGTCAAGCAGCAACCAAGGCATGATCGTCCGCAGCGCTTAGCTGGCA
GATGACGATAGCAAGGATATGTGTGATTGCCACGCGAGCAAAGCGAAAAAAGTTGAA
GTGAGCCCTGGGCAATGCTGATGCCCCGAAGAACCAAGAAATCACGTCTGTCTGACCAAGCGTGCGA
AAGTTATTAGCAACCGACCAGCAGCCTGAAGAGGGTAAAGAGGTCAAAGCCGACGAAGCTAC
GAACTTCGACCACGCCATCCAACTTTAAAGACTTTAGCAGCAGCATCGTCCGCAAGCTCTAGCTGGCA
AATCAATCTGGTAGCACCATGATTATCCAAGTGACAGCTTTGTTAACGTCAGGGTCATATATG
TTAATCGTGCACAGGGTACGGTGTCAGAATTCTCGAGAATTCTCGATCAAGCCTGTAACCGG
CAGTTCATCGCTTTCAGCGGCGTTGAACAGTGGAATGCAATAACACCGAAATCGTCCTGAATCGTGCCGT
TGGACGGGCTATGCACAAGTGAAATGGCACAGCAGGCCAGGATAACCTTCCAATACGTCCCTACGAC
CGAGAATAAGTCCCTTCTGAAAGAC -continued

| Sequences |
|---|
| SEQ ID NO: 32, codon-optimized nucleic acid sequence encoding fusion protein SP0785-Rhavi: |
| ATGTTTCGCCAACCGAGCCAGACTGCGTTGCTGCAGCAGATGAGCCGACCCATCTGGTTGTTGCGAAAG<br>AGGGCAGGCGTGGCATCGAGCGTGCTGCTGAGCGGTACGGTTACTGCCAAAAACGAACAATACGT<br>GTACTTCGATGCTAGCAAGGGTATCTGGATGAAATTCTGTGAGCGTGGGTGCAAAGTTAGC<br>GAAGGCCAGGCACTGGTGAAGTATTCATCCTCGACCGTCAGAGGCAGCGTACGACAGCGCCAAGCC<br>GCGCAGTGGCGCCAGCTGCCAGCTGCCGACCGTCACATTAAACGAATTGAACCAAGCGCGTAACGAGGCCCAAG<br>CCCGGTTGCGGGTAATTCGTCGCCAGCCATCGATGCGCAGATCGTGATGCCCTG<br>CGGATGCGGCTGCTCAACTGACGAAGGCTGCAACAGCAATGAGCAAGAGCCCACGCGGTGCGAGCAC<br>CTTGAGGGGTACCGTTGTCGAAGTCAAACAGAAACTTACAGGTCAAGGGTGAGCTGCAGCAGTATAACC<br>GTTATGGTCCACATTGTGAGCGTTGGTCAAGAGGTCAGCTTTACCCAGCCAAGGTCTACCCGGATAAGAAATG<br>GACCGCAAGTGACTACATCAGCGACTACCGGAAGAACAATGGCAGGCAGCCTCCCCGGCA<br>GCCGGCAACAATACGGCTCTAAGTATCCGTACACCATCGACGTAACCGTGAGGTCGGCGACC<br>TGAAACAGGGTTTAGCGTGAATATCGAAGTAAGCACCAAGCCAATTTGGTTCCGT<br>TAGCTCCCTGGATGAGCGATAGGCAAGAATATGTGAGATTGTCGACAGCAACAGAAAGCG<br>AAAAAGTTGAAGTAGCCTGAATGCTGAGAACCAAGAAATCACGTCTGGTCTGA<br>CCACCGTGCGAAAGTTATTAGCAACCCGACAGCCAGCCTGGAACGAGGGTAAAGAGGTCAAAGC<br>CGACGAAGTACGACACCAGCGGCGACACTTTTGTGCGACACCAATTGTTCCGCGACAAGATCACG<br>ATCGGCTTCGACAGCACACCCTGCTCTTGTGCGAACTCACAGCCATTACGGTTAATTGGCAGCCGAT<br>TCGATATTGACCTGGCAGACCTGCAAAGAGGCGTGCGAACTCACCAAAGCCACATTCTGAATGGTTAC<br>TGATTGGGGACCTGAAAGAGCGTCGCGAAAAAGTTGCCTTCAGCAACAGCATCGACTCTGAATGAACAAG<br>TCCCAACCGATGAGCGTCTCGGTACATTAGCGCATTAGCGATTGCGAAGCAGCACGATGAACGCTGGG<br>TGTTGGTAACCAAGAAATTAGCGCGCATTACGAACAGGATAGCAGAGACAGAATTCTGAAAAACATC<br>GTTGCCAATGAGAATTAGCGGAACGAGTGATCATGTGTCTGATCGACCTTTAACGAAGGAGTGATCGACTGAAAACG<br>ATCCATTGACGATTATATGTTTTACCGTGGGTTCGGTGAAGATGTTCGGTCACAGTTAAAAGATTAAGCAGGACGGA<br>TCTGAACGATTATATGTTTTACCGTGGGTTCGGTGAAGATGTTGCGACGAAAGAGGTTAAAGAGGG<br>AAGGAAGATAACCAACCTGGTTAAAAGATTAAGCGCATTAGCTCACTGTACAAGGACGGA<br>AGTTCAAGAAATACCAACCTGGTTAAAAGATTAAGCAGATTGAGCATTAGCTCACTGTACAAGGACGGA<br>CCAATTCGACGACATCCAACTTAAAGACTTTAGCAGCATCGCGTCCGCAAGCTCTAGCTGGCAG<br>AATCAATCTGGTAGCACCAGGGTACGGGTTGTCAGATTATCCAAGTGGACAGCTTTCGTAACGCTCAGCCGGTCAATATG<br>TTAATCGTGCACAGGGTACGGGTTGTCAGATTCTCCGTACCCGCTGCAAATTCTACTGAACAATTCTACT<br>CACGTTCATCGCTTTCAGCCGGTTGGACCAATTCTACTGAAATTGCAACAGCGACCGGT<br>TGGACCGGCTATGCAAGTGAATGCAATAACACCGAAATCGTCACGTCTGAATCTGGCGT<br>ATGAGGGTGGCACCGTCCGCTATTGAACAGGCCAAGGATAACCTTCCAATACGTCCTACGAC<br>CGAGAATAAGTCCCTTCTGAAAGAC |

SEQ ID NO: 33, codon-optimized nucleic acid sequence encoding fusion protein CP1 Rhavi-linker (GGGGSSS)-SP1500-linker (AAA)-SP0785:
ATGTTTCGACCGTATCCAACTTTAAAGACTTTAGCAGCATCGCGTCCGCAAGCTC

| Sequences |
|---|
| GAAAGACATGACCGGTAAGACGCTGGTGCGCAGGCCGGTAGCTCTGGCTATGCGGATTTCGAGGCGAATCCTGAGA
TTCTGAAAAACATCGTTGCCAATAAGAGGCGACCAGTAGCACCTTTAACTGAAGCACTGACCTGAAAAAC
GATCGCATTGACGGTCTGCTGATCGATCGTGTATCGCGAACTATTATCTGGAAGCCGAGGCGTTCTGAACGATTA
TAATGTTTTTACCGTGGGTCTGGAGACTTGCGCGTCGACCTTTGGTGCGGCCAAGGAAGATACCAACCTGGTTAAAA
AGATTAATGAGGCATTAGCTACGACAAGGACGACCAAGTTCCAAGAAATTAGCCAGAAGTGGTTCGGTGAAGAT
GTTGCCACGAAAGAGGTTAAAGAGGGCAGGCAGCCGTGCAGCGTGGATCGCAGCCGTGCCATCTCGAGCCGCTGCTGAGCCGTACGGTTGACTACTGCCAAAGTGAGGCC
GACCCATCTGGTTGTTGCGAAAGAGGACAGCAGCAGCACTGGTGACGCCTGCAATCTGGACACGGTGGTGACCAAAGTTAGCGCA
GGCCAGGCACTGGAAGTATTCATCCTCCGAGGCACAGCGCAGCCAAGCCGCAGCCAGCCAGTGCCGCTGC
CGACCCTCACATTAACGAATTGAACCAAGCGCGTAACCAAGCCCGGTTGCCGGTAATTCGTCGCCAGCATCGATGCCGCAGCTG
TGGGTGGCGAAGATGCGACGGTGCAGAGCGCCGGATGCCGCCTGCTCAACTGAGCAAGGCCAGCAAGGCCAACTGACCGCGACGACGGT
GCTGAGCGCTGGAGGGTACCGGCCGGCTGCGAAGTCAACAGCAATCAAGCCTGAGCCAAGGTGAGCCGCAGCCAGTTA
TGGTCCACATTGTTGAGCAATGAAAACTTACAGGTCAAGGTGAGCTGAGCTGGAGGTATAACCTGGGGGAATCTGAGCGTT
GGTCAAGAGGTCAGCTTTACCAGGAGTCGGAGGATCCTCCGGACAGGTTTTAGCGTAGCAGTCAGGGGCCGGATATATCGAAGCTTAAGGACCCAACCATCGACG
CCCGAAGAACAATACAGGACGTCAGGAGGCGAACAATACCGGCTCTTAAGTGAAGCATTGGGTCAACCGGCAATTTTG
TAACCGGTTAGCTCCTCCGGGTGATGACGATGCGACAAGAATATGTGGATTGTCAGCAGGCAACAGAAGCGAAAAA
GTTCGGGTTGAGCCCCGACGATGAGCGAAGATGCGACAGCGCAGCCGCAAGGCCAGCAGCGTCAGCGCAGCCGTGAGCA
AGTTGAAGTGAGCCTGGGCAATGCTGGAAGAGGTGAAGAGGTAAAGCTCAAGCCGACGAAGCTACGAAAC
TTAGCAACCCGACCAGCAGCCTGAAGAGGTAAAGAGGCGAAGCGACTACGAAAC |

SEQ ID NO: 34, codon-optimized nucleic acid sequence encoding fusion protein
Rhavi-linker (GGGGSSS)-SPO785-linker (AAA)-SP1500:
ATGTTCGACGATCCAACTTAAGACTTTAGCAGCATCGCGTCCGCAAGCTCTAGCTGCAGA
ATCAATCTGGTAGCACCATGATTATCCAAGTGGACAGCAGCTTTGGTAACGTCAGCGATCAATATGT
TAATCTGCACAGGGTACGGGTTGCAGAATTCTCCGTACCCGTCGACCGCGTCGTGTTAACGGC
ACGTTCATCCGTTTCAGCGGTCGGTTGGAACAATTGCACTGAAAATTCGACGCAGCGACCGGTT
GGACCGGCTATGCACAAGTGAATGCCAGCGGTCCGGCTATTGAACGGCCAGGATACCTTCCAATATCGTCCCTACGACC
GAGAATAAGCGTCCCTTTGAAAGACCAGGTCCGGCGTTGGCCCGGTTGTTGTGCGAAAGAGGCAGCGCATCGAGCGT
GCTGCTGAGCGGTACCGGTTACTGCGAGCTGCCAAAAACGAACAATACGTTGTACTTGGATGCTAGCAAGGGT
GATCGGATGAATTCTGGTGAGCCTGGGTGACAAAGTTAGCGAAGGCCAGGCACTGGGGGGTCCGGACCG
TCACATTAACGAATTGAACCAAGCGCGTAACCAAGCCCGGTCCAGCAGCCCGCAAGCGCGCCAGCCTGCCG
GCTCCCGGTGGGTGGCGAAGATGCGACGCGTCGAAGAGCGTCCAGAGCGCCGACCCTGCGGATGCTGTCAACTGAG
CCAGCATCGATGCCAGCGGTGGATGGCAACTGGCCAACGGGTCTGCACCCCGGAGATCGCGCTGCTGGCGTTGTCAACCGTTGTGAA
CAAGCTGAGACAATGTGACAAGGCCCAAGTGCCGAGCCAGGTTATGGTCCACATTGTGAGCA
ATGAAAACTTACAGGTCAAGGGTGAGCTGAGCGAGCTGGAGCTATAACCTGGCGAATCTGAGCGTTGGTCA
AGAGGTCAGCTTTACCAGCAAGGTCTACCCGGACAGGTCTCCCGGACGCAGCCTCCCCCGGCAACAATACCGGCTCTA
AGTATCCGTACACCATCGACGTAACCGGTGAGGTGCGACCTGAACAGGGTTTAGCGTGAA
TATCGAAGTGAAGTCAAGACCAAAGCCAATTTGGTCCCGGTTAGCTCCTCCGGTTGATGACGAT
AGCAAGAATTATGTGGATTGTCGAGAGGCAACAAGACTGGTGACCAACGTGCGAAGAAAGAAAGGCGAAAGTTATTAG
GCAATGCTGATGCGAGCCCAAGAAATACGTGTGGTCGAACAGCGAAGCTACCGGACGACAAGCCGCG
CAACCAGCGGCACACATTGGTCCAAATACCAGAGCAACAAGAGCATCACGATCGCTTCGACAG
CACTTTTGTGCCGATGGGTTTCGCGAAAGACGTAGCTACGGGATTAATTGGGTTAATGGGACCTG
GCGAAACCGCGTGTCTTTGAGAAATACGGTTAATTACGGTTAATTGGCAGCGATTGATTGGACCTGA
AAGAGGCGAACTCACCAAGGCACCATCGACCTGATCTGAATGGTTACTCCGACCGATGA -continued

| Sequences |
|---|
| GCGTCGCGAAAAGTTGCCTTCAGCAACACAGCTATATGAAGAATGAACAAGTGTTGGTAACCAAG<br>AAATCTAGCCGCGAAAGACATGACCGGTTAAGACCGGTGGGTGCCCAGGCCGGTA<br>GCTCTGGCTATGCGGATTTCGAGGCGAATCCTGAGATTCTGAAAAACATCGTTGCGAATAAGA<br>GGCGAACCAGTACGCTTTAACGAACACTGACCTGAAAAACGATCGCATTGACGGT<br>CTGCTGATCGATCGTGTGTATACGCGAACTATTATCTGGAAGCCGAGGCGTTCTGAACGATTATA<br>ATGTTTTTACCTGTGGGTCTGGAGACTGAGGCATTAGCTCACTGACTGACGACGCAAGTTCCAAGATAAAA<br>CCTGGTTAAAAGATTAATGAGGCATTGTGCGACGAAGAGGTTAAAGAGGCCAA<br>AGCCAGAAGTGGTTCGGTGAAGATGTTGCGACGAAGAGGTTAAAGAGGGCCAA |

SEQ ID NO: 35, codon-optimized nucleic acid sequence encoding fusion protein
SP1500-linker (GGGGSSS)-SP0785-linker (AAA) -Rhavi:

ATGACCAGCG

| | Sequences |
|---|---|
| SEQ ID NO: 36, codon-optimized nucleic acid sequence encoding fusion protein SP0785-linker (GGGGSSS)-SP1500-linker (AAA)-Rhavi: | ATGTTTCGCCAACCGAGCCAGACTCGTTGCTGCAGGCAATGAGCGACCCATCTGGTTGTTGCGAAAG AGGGCAGGCAGCCGTGGCATTCGAGCGGTGCTGCTGAGTGAGATGTACGGTTACTGCCAAAAACGAACAATACGT GTACTTCGATGCTAGCAAGGGTGATCTGGATGAAATTCTGTGAGCGTGGGTGACAAAGTTAGC GAAGGCCAGGCACTGGTGAAGTATTCATCCTCCGAGGCACAGGCAGCGTACGACAGCGCAAGCC GCGCAGTGGCCGGTGCCGCAGCTGCCGGCTCCGGTGGGTGGCGAAGATGGCAGAGCCGTAACGAGGCCGCAAG CCGCGCCAGCAGCTGCCAGCCATCGAGCCAGTGGGTGACGCGGTGACGAGCCCGTGA CCGGTTGCGGGTAATTCGGTGCCACTGAGCAAGGCTGAGAGCCAACTGAGCCAAGGCTGATGCCGTG CGGATGCGGCTGCTCAACTGAGCGAAGTCAACAGCAATGTGAGCAAGAGCCCAACGGTGCGAGCCAG CTTGGAGGGTACCGTTGTGGAGCAATGGTTCAAGAACTTACAGGTCAAGGTGAGCTGAGCAGTATAACC GTTATGGTCCACATTGTGAGCCGTTGGTCAAGAGGTCAGCTTTTACCAGCAACAATGGCAGCTCCCCCGGCA GACCGCAAGTTGAGCTACATCAGCCAGTACCCGAAGAACAATGCAGGCAGCCTCCCCGGCA GCCGGCAACAATACCGGCTCTAAGTATCCGTACACCATCGACGTTAACCGTGAGGTCGCGACC TGAAACAGGGTTTTAGCGTGAATATCGACATAGCAAGAATTATGTGAAATTGTCGACAGCAACAGAAGCG TAGCTCCCTGGTGATGAGCAGATGAGCCAAGATGGTTGCTGGTCCTGATGCGAGAACCAAGAAATCACGTCTGGTCTGA AAAAAGTTGAAGTGAGCCTGTGATGCGAGAACCAAGAAATCACGTCTGGTCTGA CCAACCGTGCGAAAGTTATTAGCAACCGACAGCCTGGACAGCGGTAAAGAGGTCAAAGC CGACGAAGCTACGAACGGGCGGTGCGGTTCGAGTTGACCAGCCGGCGCAATTGGTCCGATGGGGTTTGTCCGCAAA CAGACGGTAGCCGCTTCGATATTGACCTGGCGACCGCTGTCTTTGAGAAATACGGCAT TACGGTTAATTGCAGCGCGATTGATTCCGCAACCAGGCTTGGAGACCTGAAAAGAGCGCGAACTTCACCAAGGCCACCATC GACCTGATCGGAATGGTTACTCCGCAACCAGTGTTGGTAACCAAGAATCTAGCGCATTACGACCGGAAAGA CATGACGGGCTAAGACGCTGGGTGCCGCAGGCCGGTAGCTCTGCTATGCGGATTTCGAGGCGAAT CCTGAGATTCTGAAAACATCGTTGCGAAAAACATGATCGCCATTGACGGTCTGCTGATCGATCGTGTGTTACGCGAACTA CACTGATCGACTCGAAAAACAACGATCCAGCGTTCTGAAACGATTATAATGTTTTACCGTGGTCTGGAGACTGAG GCATTCGGAGCGGCCGTTGGTGCCGCCAAGGAGAGAATACCAACCTGTTAAAAGATTAATGAGGCATTTA GCTCACTGTACAAGAGGTTAAAGAGCGGCAAGTTCAAGAACGCGCCATTCGACGCATCTGTTGAAGTGGTTCGGTGAAGATGTTGC GACGAAAGAGGTTAAAGAGCGGCAAGTTCAAGAACGCCATTCGACGCATCCAACTTTAAAGACTTTAGCA GCATCGCTCCGCAAGCTTAGCTGCAGAATCAATCTGTTAGCACCATGATTATCCAAGTGGA CAGCTTTGGTAACGTCAGCCGTCAATATGTTAATCGTCACAGGGTTGTCAGAATTCT CCGTACCCGCTGACGCGTTAACGACGACGTTCATCGCTTTCAGCGCTGGTTGGAACAATT CTACTGAAAATTGCAACAGCGCACCGGTTGAACCGGTTGATGAGGGTGCAGCGCGTCCGGCTATTGAACAGGGC CAGGAAATCGTCACGTCCAATACGTCCCTACGACCGAGAATAAGTCCCTTCTGAAAGAC |
| SEQ ID NO: 37, linker sequence [7 amino acids]: | GGGGSSS |
| SEQ ID NO: 38, linker sequence [3 amino acids]: | AAA |
| SEQ ID NO: 39, linker sequence [5 amino acid repeats]: | (GGGGS)$_n$ |
| SEQ ID NO: 40, linker sequence [6 amino acids]: | GGGGGG |

-continued

Sequences

SEQ ID NO: 41, linker sequence [15 amino acids]:
GGGGSGGGGSGGGGS

SEQ ID NO: 42, linker sequence [30 amino acids]:
GGGGSGGGGSGGGGSGGGGSGGGGSGGGGS

SEQ ID NO: 43, linker sequence [18 amino acids]:
KESGSVSSEQLAQFRSLD

SEQ ID NO: 44, linker sequence [14 amino acids]:
EGKSSGSGSESKST

SEQ ID NO: 45, linker sequence:
(Gly)$_n$

SEQ ID NO: 46, linker sequence [8 amino acids]:
GGGGGGGG

SEQ ID NO: 47, linker sequence [12 amino acids]:
GSAGSAAGSGEF

SEQ ID NO: 48, linker sequence [5 amino acid repeats]:
(EAAAK)$_n$

SEQ ID NO: 49, linker sequence:
A(EAAAK)$_n$A

SEQ ID NO: 50, linker sequence:
A(EAAAK)$_4$ALEA(EAAAK)$_4$A

SEQ ID NO: 51, linker sequence:
[A(EAAAK)$_n$A]$_m$

SEQ ID NO: 52, linker sequence [12 amino acids]:
AEAAAKEAAAKA

SEQ ID NO: 53, linker sequence [2 amino acid repeats]:
(XP)$_n$

SEQ ID NO: 54, linker sequence:
(AP)$_n$

SEQ ID NO: 55, linker sequence:
(KP)$_n$

SEQ ID NO: 56, linker sequence:
(QP)$_n$

SEQ ID NO: 57, linker sequence [14 amino acids]:
APAPAPAPAPAPAP

-continued

| Sequences |
|---|
| SEQ ID NO: 58, GAG linker sequence [21 amino acids]:<br>GAPGGGGAAAAGGGGGAP |
| SEQ ID NO: 59, GAG2 linker sequence [39 amino acids]:<br>GAPGGGGAAAAGGGGGAPGGGGAAAAGGGGGAP |
| SEQ ID NO: 60, GAG3 linker sequence [57 amino acids]:<br>GAPGGGGAAAAGGGGGAPGGGGAAAAGGGGGAPGGGGAAAAGGGGGAP |

REFERENCES

Anttila M, Eskola J, Ahman H, Käyhty H. Avidity of IgG for *Streptococcus pneumoniae* type 6B and 23F polysaccharides in infants primed with pneumococcal conjugates and boosted with polysaccharide or conjugate vaccines. J Infect Dis. 1998 June; 177(6):1614-21.

Ausubel F M et al. 1995. Current Protocols in Molecular Biology, N.Y., John Wiley & Sons.

Berry, A. M. et al. (1995) Infection and Immunity 63: 1969-74)

Centers for Disease Control and Prevention. Preventing pneumococcal disease among infants and young children. Morbidity and Mortality Weekly Report. 2000; 49:1-55.

Centers for Disease Control and Prevention. Prevention of pneumococcal disease among infants and children—use of 13-valent pneumococcal conjugate vaccine and 23-valent pneumococcal polysaccharide vaccine. Morbidity and Mortality Weekly Report. 2010; 59:1-24.

Coligan J E et al. 2018. Current Protocols in Protein Science, John Wiley & Sons, Inc.

Daniels, C. C. et al. (2010) Infection and Immunity 7S:2163-72

Davis et al. 1986. Basic Methods in Molecular Biology, Elsevir Sciences Publishing, Inc., New York.

Douce et al. Mutants of *Escherichia coli* heat-labile toxin lacking ADP-ribosyltransferase activity act as non-toxic, mucosal adjuvants. PNAS Vol. 92, pp. 1644-1648, February 1995.

Douce et al. Genetically detoxified mutants of heat-labile toxin from *Escherichia coli* are able to act as oral adjuvants" Infect Immun. 1999 September; 67(9):4400-6)

Dracopoli, N et al. 2018. Current Protocols in Human Genetics, John Wiley & Sons, Inc.;

Evans J T et al. Enhancement of antigen-specific immunity via the TLR-4 ligands MPL adjuvant and Ribi.529. Expert Rev Vaccines 2003 April; 2(2):219-29.

Ferreira et al. "DNA vaccines based on genetically detoxified derivatives of pneumolysin fail to protect mice against challenge with *Streptococcus pneumoniae*" FEMS Immunol Med Microbial (2006) 46: 291-297)

Giuliani M M et al. Mucosal adjuvanticity and immunogenicity of LTR72, a novel mutant of *Escherichia coli* heat-labile enterotoxin with partial knockout of ADP-ribosyltransferase activity. J Exp Med. 1998 Apr. 6; 187(7):1123-32.

Gruber M F, Pratt D, Haase M. Licensing of pneumococcal conjugate vaccines for children and adults: Regulatory perspective from the European Medicines Agency and the U.S. Food and Drug Administration. In: Siber G R, Klugman K P, Mäkelä P H, eds. Pneumococcal Vaccines: The Impact of Conjugate Vaccine. Washington, DC: ASM Press; 2008; 183-96.

Hames et al. 1985. Nucleic Acid Hybridization, IL Press.

Helppolainen S H, Nurminen K P, Määttä J A, Halling K K, Slotte J P, Huhtala T, et al. Rhizavidin from *Rhizobium etli*: the first natural dimer in the avidin protein family. Biochem J. 2007; 405:397-405.

Holliger P, Prospero T, Winter G. "Diabodies": small bivalent and bispecific antibody fragments. Proc Natl Acad Sci USA. 1993 Jul. 15; 90(14):6444-8.

Ishizaka S T et al. "E6020: a synthetic Toll-like receptor 4 agonist as a vaccine adjuvant." Expert Rev. Vaccines. 2007 October; 6(5):773-84.

Kim K H, Yu J, Nahm M H. Efficiency of a pneumococcal opsonophagocytic killing assay improved by multiplexing and by coloring colonies. Clin Diagn Lab Immunol. 2003 July; 10(4):616-21.

Kojima K, Ishizaka A, Oshika E, Taguchi Y, Tomizawa K, et al. Quantitation of IgG subclass antibodies to pneumococcal capsular polysaccharides by ELISA, using Pneumovax-specific antibodies as a reference. Tohoku J Exp Med. 1990 July; 161(3):209-15.

Koskela M, Leinonen M. Comparison of ELISA and RIA for measurement of pneumococcal antibodies before and after vaccination with 14-valent pneumococcal capsular polysaccharide vaccine. J Clin Pathol. 1981 January; 34(1):93-8.

Martin, E W, Ed. Remington's Pharmaceutical Sciences. 15th ed. Easton, PA: Mack Publishing Company, 1975.

Martinez J E, Romero-Steiner S, Pilishvili T, Barnard S, Schinsky J, et al. A flow cytometric opsonophagocytic assay for measurement of functional antibodies elicited after vaccination with the 23-valent pneumococcal polysaccharide vaccine. Clin Diagn Lab Immunol. 1999 July; 6(4):581-6.

Meyers and Miller. CABIOS, 1989, 4:11-17.

Mitchell L. Protective Immune Responses to *Streptococcus pneumoniae* Pneumolysoids, ASM2011 conference abstract, 2011.

Moffitt K L, Malley R, Lu, Y-J. Identification of Protective Pneumococcal Th17 Antigens from the Soluble Fraction of a Killed Whole Cell Vaccine. 2012 PLoS ONE 7(8): e43445.

Munro C S, Stanley P J, Cole P J. Assessment of biological activity of immunoglobulin preparations by using opsonized micro-organisms to stimulate neutrophil chemiluminescence. Clin Exp Immunol. 1985 July; 61(1): 183-8.

Ojo-Amaize E A, Church J A, Barka N E, Agopian M S, Peter J B. A rapid and sensitive chemiluminescence assay for evaluation of functional opsonic activity of *Haemophilus influenzae* type b-specific antibodies. Clin Diagn Lab Immunol. 1995 May; 2(3):286-90.

Paton J. C. et al. "Purification and immunogenicity of genetically obtained pneumolysin toxoids and their conjugation to *Streptococcus pneumoniae* type 19F polysaccharide" Infect Immun 1991 July; 59(7):2297-304

PNEUMOVAX® 23 (prescribing information). Whitehouse Station, NJ: Merck & Co.; May 2015.

PREVNAR 13@ (prescribing information). New York, NY: Pfizer; August 2017.

Poljak R J. Production and structure of diabodies. Structure. 1994 Dec. 15; 2(12):1121-3.

Powell M F and Newman M J, Eds. 1995. Vaccine Design: The Subunit and Adjuvant Approach. New York, NY: Plenum Press.

Richter S S, Diekema D J, Heilmann K P, Dohrn C L, Riahi F, Doern G V. Changes in pneumococcal serotypes and antimicrobial resistance after introduction of the 13 valent conjugate vaccine in the United States. Antimicrob Agents Chemother. 2014; 58:6484-9.

Romero-Steiner S, Libutti D, Pais L B, Dykes J, Anderson P, et al. Standardization of an opsonophagocytic assay for the measurement of functional antibody activity against *Streptococcus pneumoniae* using differentiated HL-60 cells. Clin Diagn Lab Immunol. 1997 July; 4(4):415-22.

Romero-Steiner S, Holder P F, Gomez de Leon P, Spear W, Hennessy T W, et al. Avidity determinations for *Haemo-* philus influenzae Type b anti-polyribosylribitol phosphate antibodies. Clin Diagn Lab Immunol. 2005 September; 12(9):1029-35.

Saeland E, Vidarsson G, Jonsdottir I. Pneumococcal pneumonia and bacteremia model in mice for the analysis of protective antibodies. Microb Pathog. 2000 August; 29(2):81-91.

Sambrook J et al. 1989. Molecular Cloning, a Laboratory Manual. Cold Harbor Laboratory Press, Cold Spring Harbor, N.Y.

Saunders F. K. et al. Pneumolysin, the thiol-activated toxin of Streptococcus pneumoniae, does not require a thiol group for in vitro activity. Infect Immun 1989 August; 57(8):2547-52). Singh et al. Curr. HIV Res. 2003 1:309-20.

Stack A M, Malley R, Thompson C M, Kobzik L, Siber G R, et al. Minimum protective serum concentrations of pneumococcal anti-capsular antibodies in infant rats. J Infect Dis. 1998 April; 177(4):986-90.

Williams et al, Innate imprinting by the modified heat-labile toxin of Escherichia coli (LTK63) provides generic protection against lung infectious disease. The Journal of Immunology 2004 173:7435-7443.

Wu W, Huang J, Duan B, Traficante D C, Hong H, et al. Th17-stimulating protein vaccines confer protection against Pseudomonas aeruginosa pneumonia. Am J Respir Crit Care Med. 2012 Sep. 1; 186(5):420-7.

Zhang F, Lu Y J, Malley R. Multiple antigen-presenting system (MAPS) to induce comprehensive B- and T-cell immunity. Proc Natl Acad Sci USA. 2013; 110:13564-9.

WO2012/155007
WO 2012/155053
US 2009/0285846

EQUIVALENTS

Those skilled in the art will recognize, or be able to ascertain using no more than routine experimentation, many equivalents to the specific embodiments of the invention described herein. The scope of the present invention is not intended to be limited to the above Description, but rather is as set forth in the following claims:

The invention claimed is:

1. A nucleic acid sequence comprising a promoter, operatively linked to a heterologous nucleic acid sequence comprising, in any order, a nucleic acid sequence of SEQ ID NO: 10 or a nucleic acid sequence at least 85% sequence identity to SEQ ID NO: 10; a nucleic acid sequence of SEQ ID NO: 14 or a nucleic acid sequence at least 85% sequence identity to SEQ ID NO: 14; and a nucleic acid sequence of SEQ ID NO: 12 or a nucleic acid sequence at least 85% sequence identity to SEQ ID NO: 12.

2. The nucleic acid sequence of claim 1, wherein the heterologous nucleic acid sequence comprises SEQ ID NO: 33 or SEQ ID NO: 34, or a nucleic acid sequence having at least 85% sequence identity to SEQ ID NO: 33 or SEQ ID NO: 34.

3. The nucleic acid sequence of claim 1, wherein the heterologous nucleic acid further comprises a nucleic acid that encodes at least one linker, or a nucleic acid that encodes an expression tag, or both.

4. The nucleic acid sequence of claim 3, wherein the nucleic acid sequence encoding at least one linker is located between SEQ ID NO: 10 and SEQ ID NO: 14, or SEQ ID NO: 14 and SEQ ID NO: 12, or SEQ ID NO: 10 and SEQ ID NO: 12.

5. The nucleic acid sequence of claim 3, wherein the nucleic acid sequence encoding at least one linker encodes a linker having an amino acid sequence selected from any of: GGGGSSS (SEQ ID NO: 37) or AAA (SEQ ID NO: 38) and any of: SEQ ID NOS: 39-60 and SEQ ID NO: 62, 63, 108, 109.

6. The nucleic acid sequence of claim 1, wherein the heterologous nucleic acid comprises in the following order:

a. a nucleic acid sequence of SEQ ID NO: 10 or a nucleic acid sequence at least 85% sequence identity to SEQ ID NO: 10; a nucleic acid sequence of SEQ ID NO: 14 or a nucleic acid sequence at least 85% sequence identity to SEQ ID NO: 14; and a nucleic acid sequence of SEQ ID NO: 12 or a nucleic acid sequence at least 85% sequence identity to SEQ ID NO: 12;

b. a nucleic acid sequence of SEQ ID NO: 10 or a nucleic acid sequence at least 85% sequence identity to SEQ ID NO: 10; a nucleic acid sequence of SEQ ID NO: 12 or a nucleic acid sequence at least 85% sequence identity to SEQ ID NO: 12; and a nucleic acid sequence of SEQ ID NO: 14 or a nucleic acid sequence at least 85% sequence identity to SEQ ID NO: 14;

c. a nucleic acid sequence of SEQ ID NO: 14 or a nucleic acid sequence at least 85% sequence identity to SEQ ID NO: 14; and a nucleic acid sequence of SEQ ID NO: 12 or a nucleic acid sequence at least 85% sequence identity to SEQ ID NO: 12, and a nucleic acid sequence of SEQ ID NO: 10 or a nucleic acid sequence at least 85% sequence identity to SEQ ID NO: 10; or d. a nucleic acid sequence of SEQ ID NO: 12 or a nucleic acid sequence at least 85% sequence identity to SEQ ID NO: 12; and a nucleic acid sequence of SEQ ID NO: 14 or a nucleic acid sequence at least 85% sequence identity to SEQ ID NO: 14; a nucleic acid sequence of SEQ ID NO: 10 or a nucleic acid sequence at least 85% sequence identity to SEQ ID NO: 10.

7. A cell transfected with the nucleic acid sequence of claim 1.

8. The cell of claim 7, wherein the cell is transfected with the nucleic acid sequence of claim 2.

9. The cell of claim 7, wherein the cell is transfected with the nucleic acid sequence of claim 6.

10. The cell of claim 7, wherein the cell is an expression host cell.

11. The cell of claim 10, wherein the expression host cell is selected from the group consisting of: *E. coli*, an insect cell line or a mammalian cell line.

12. The cell of claim 11, wherein the insect cell line is baculovirus expression system.

13. The cell of claim 11, wherein the mammalian cell line is a human cell line or Chinese Hamster ovary (CHO) cell line.

14. The cell of claim 1, wherein the heterologous nucleic acid sequence is codon-optimized to improve expression in the host cell.

15. The cell of claim 1, wherein the nucleic acid sequence further comprises a nucleic acid sequence encoding one or more of: polyadenylation sequence or termination sequence, a signal sequence.

16. An expression vector comprising the nucleic acid sequence of claim 1.

17. The expression vector of claim 16, comprising the nucleic acid sequence of claim 2.

18. The expression vector of claim 16, comprising the nucleic acid sequence of claim 6.

19. The cell of claim 7, comprising the expression vector of claim 16.

20. The cell of claim 7, comprising the expression vector of claim 17.

21. The cell of claim 7, comprising the expression vector of claim 18.

* * * * *

```
SEQUENCE LISTING

Sequence total quantity: 157
SEQ ID NO: 1            moltype = AA  length = 179
FEATURE                 Location/Qualifiers
REGION                  1..179
                        note = Description of Unknown:Rhizavidin sequence
source                  1..179
                        mol_type = protein
                        organism = unidentified
SEQUENCE: 1
MIITSLYATF GTIADGRRTS GGKTMIRTNA VAALPAVAT  SALAFDASNF KDFSSIASAS   60
SSWQNQSGST MIIQVDSFGN VSGQYVNRAQ GTGCQNSPYP LTGRVNGTFI AFSVGWNNST  120
ENCNSATGWT GYAQVNGNNT EIVTSWNLAY EGGSGPAIEQ GQDTFQYVPT TENKSLLKD   179

SEQ ID NO: 2            moltype = AA  length = 135
FEATURE                 Location/Qualifiers
REGION                  1..135
                        note = Description of Unknown: Truncated Rhizavidin sequence
source                  1..135
                        mol_type = protein
                        organism = unidentified
SEQUENCE: 2
FDASNFKDFS SIASASSSWQ NQSGSTMIIQ VDSFGNVSGQ YVNRAQGTGC QNSPYPLTGR   60
VNGTFIAFSV GWNNSTENCN SATGWTGYAQ VNGNNTEIVT SWNLAYEGGS GPAIEQGQDT  120
FQYVPTTENK SLLKD                                                   135

SEQ ID NO: 3            moltype = AA  length = 399
FEATURE                 Location/Qualifiers
source                  1..399
                        mol_type = protein
                        organism = Streptococcus pneumoniae
SEQUENCE: 3
MKKKNGKAKK WQLYAAIGAA SVVVLGAGGI LLFRQPSQTA LKDEPTHLVV AKEGSVASSV   60
LLSGTVTAKN EQYVYFDASK GDLDEILVSV GDKVSEGQAL VKYSSSEAQA AYDSASRAVA  120
RADRHINELN QARNEAASAP APQLPAPVGG EDATVQSPTP VAGNSVASID AQLGDARDAR  180
ADAAAQLSKA QSQLDATTVL STLEGTVVEV NSNVSKSPTG ASQVMVHIVS NENLQVKGEL  240
SEYNLANLSV GQEVSFTSKV YPDKKWTGKL SYISDYPKNN GEAASPAAGN NTGSKYPYTI  300
DVTGEVGDLK QGFSVNIEVK SKTKAILPV  SSLVMDDSKN YVWIVDEQQK AKKVEVSLGN  360
ADAENQEITS GLTNGAKVIS NPTSSLEEGK EVKADEATN                         399

SEQ ID NO: 4            moltype = AA  length = 367
FEATURE                 Location/Qualifiers
source                  1..367
                        mol_type = protein
                        organism = Streptococcus pneumoniae
SEQUENCE: 4
FRQPSQTALK DEPTHLVVAK EGSVASSVLL SGTVTAKNEQ YVYFDASKGD LDEILVSVGD   60
KVSEGQALVK YSSSEAQAAY DSASRAVARA DRHINELNQA RNEAASAPAP QLPAPVGGED  120
ATVQSPTPVA GNSVASIDAQ LGDARDARAD AAAQLSKAQS QLDATTVLST LEGTVVEVNS  180
NVSKSPTGAS QVMHIVSNE NLQVKGELSE YNLANLSVGQ EVSFTSKVYP DKKWTGKLSY   240
ISDYPKNNGE AASPAAGNNT GSKYPYTIDV TGEVGDLKQG FSVNIEVKSK TKAILPVSS   300
LVMDDSKNYV WIVDEQQKAK KVEVSLGNAD AENQEITSGL TNGAKVISNP TSSLEEGKEV  360
```

```
SEQ ID NO: 5           moltype = AA  length = 399
FEATURE                Location/Qualifiers
source                 1..399
                       mol_type = protein
                       organism = synthetic construct
REGION                 1..399
                       note = Description of Artificial Sequence: Synthetic
                        Polypeptide
VARIANT                308
                       note = X is any amino acid
VARIANT                121..122
                       note = X is any amino acid
VARIANT                394
                       note = X is any amino acid
VARIANT                140..141
                       note = X is any amino acid
VARIANT                37
                       note = X is any amino acid
VARIANT                48..49
                       note = X is any amino acid
VARIANT                306
                       note = X is any amino acid
VARIANT                384
                       note = X is any amino acid
VARIANT                60
                       note = X is any amino acid
VARIANT                124
                       note = X is any amino acid
VARIANT                288
                       note = X is any amino acid
VARIANT                337
                       note = X is any amino acid
VARIANT                45..46
                       note = X is any amino acid
VARIANT                51..52
                       note = X is any amino acid
VARIANT                282
                       note = X is any amino acid
VARIANT                156..157
                       note = X is any amino acid
VARIANT                351
                       note = X is any amino acid
VARIANT                41
                       note = X is any amino acid
VARIANT                132
                       note = X is any amino acid
VARIANT                269
                       note = X is any amino acid
VARIANT                111
                       note = X is any amino acid
SEQUENCE: 5
MKKKNGKAKK WQLYAAIGAA SVVVLGAGGI LLFRQPXQTA XKDEXXHXXV XXEGSVASSX   60
LLSGTVTAKN EQYVYFDASK GDLDEILVSV GDKVSEGQAL VKYSSSEAQA XYDSASRAVA  120
XXDXHINELN QXRNEAASAX XPQLPAPVGG EDATVXXPTP VAGNSVASID AQLGDARDAR  180
ADAAAQLSKA QSQLDATTVL STLEGTVVEV NSNVSKSPTG ASQVMVHIVS NENLQVKGEL  240
SEYNLANLSV GQEVSFTSKV YPDKKWTGXL SYISDYPKNN GXAASPAXGN NTGSKYPYTI  300
DVTGEXGXLK QGFSVNIEVK SKTKAILVPV SSLVMDXSKN YVWIVDEQQK XKKVEVSLGN  360
ADAENQEITS GLTNGAKVIS NPTXSLEEGK EVKXDEATN                         399

SEQ ID NO: 6           moltype = AA  length = 278
FEATURE                Location/Qualifiers
source                 1..278
                       mol_type = protein
                       organism = Streptococcus pneumoniae
SEQUENCE: 6
MKKWMLVLVS LMTALFLVAC GKNSSETSGD NWSKYQSNKS ITIGFDSTFV PMGFAQKDGS   60
YAGFDIDLAT AVFEKYGITV NWQPIDWDLK EAELTKGTID LIWNGYSATD ERREKVAFSN  120
SYMKNEQVLV TKKSSGITTA KDMTGKTLGA QAGSSGYADF EANPEILKNI VANKEANQYQ  180
TFNEALIDLK NDRIDGLLID RVYANYYLEA EGVLNDYNVF TVGLETEAFA VGARKEDTNL  240
VKKINEAFSS LYKDGKFQEI SQKWFGEDVA TKEVKEGQ                          278

SEQ ID NO: 7           moltype = AA  length = 252
FEATURE                Location/Qualifiers
source                 1..252
                       mol_type = protein
                       organism = Streptococcus pneumoniae
SEQUENCE: 7
```

(KADEATN                                                          367 appears before SEQ ID NO: 5 as continuation)

```
TSGDNWSKYQ  SNKSITIGFD  STFVPMGFAQ  KDGSYAGFDI  DLATAVFEKY  GITVNWQPID   60
WDLKEAELTK  GTIDLIWNGY  SATDERREKV  AFSNSYMKNE  QVLVTKKSSG  ITTAKDMTGK  120
TLGAQAGSSG  YADFEANPEI  LKNIVANKEA  NQYQTFNEAL  IDLKNDRIDG  LLIDRVYANY  180
YLEAEGVLND  YNVFTVGLET  EAFAVGARKE  DTNLVKKINE  AFSSLYKDGK  FQEISQKWFG  240
EDVATKEVKE  GQ                                                         252
```

| | | |
|---|---|---|
| SEQ ID NO: 8 | moltype = AA  length = 274 | |
| FEATURE | Location/Qualifiers | |
| REGION | 1..274 | |
| | note = Description of Artificial Sequence: Synthetic polypeptide | |
| VARIANT | 1..2 | |
| | note = X can be any amino acid | |
| VARIANT | 9 | |
| | note = X can be any amino acid | |
| VARIANT | 20 | |
| | note = X can be any amino acid | |
| VARIANT | 23 | |
| | note = X can be any amino acid | |
| VARIANT | 32 | |
| | note = X can be any amino acid | |
| VARIANT | 76 | |
| | note = X can be any amino acid | |
| VARIANT | 106 | |
| | note = X can be any amino acid | |
| VARIANT | 116 | |
| | note = X can be any amino acid | |
| VARIANT | 130 | |
| | note = X can be any amino acid | |
| VARIANT | 140 | |
| | note = X can be any amino acid | |
| VARIANT | 143 | |
| | note = X can be any amino acid | |
| VARIANT | 161..162 | |
| | note = X can be any amino acid | |
| VARIANT | 165 | |
| | note = X can be any amino acid | |
| VARIANT | 172 | |
| | note = X can be any amino acid | |
| VARIANT | 177 | |
| | note = X can be any amino acid | |
| VARIANT | 191 | |
| | note = X can be any amino acid | |
| VARIANT | 222 | |
| | note = X can be any amino acid | |
| VARIANT | 229 | |
| | note = X can be any amino acid | |
| VARIANT | 234..235 | |
| | note = X can be any amino acid | |
| VARIANT | 243 | |
| | note = X can be any amino acid | |
| VARIANT | 250 | |
| | note = X can be any amino acid | |
| VARIANT | 264 | |
| | note = X can be any amino acid | |
| VARIANT | 274 | |
| | note = X can be any amino acid | |
| source | 1..274 | |
| | mol_type = protein | |
| | organism = synthetic construct | |

```
SEQUENCE: 8
XXVLVSLMXA  LFLVACGKNX  SEXSGDNWSK  YXSNKSITIG  FDSTFVPMGF  AQKDGSYAGF   60
DIDLATAVFE  KYGITXNWQP  IDWDLKEAEL  TKGTIDLIWN  GYSATXERRE  KVAFSXSYMK  120
NEQVLVTKKX  SGITTAKDMX  GKXLGAQAGS  SGYADFEANP  XXLKXIVANK  EXNQYQXFNE  180
ALIDLKNDRI  XGLLIDRVYA  NYYLEAEGVL  NDYNVFTVGL  EXEAFAVGXR  KEDXXLVKKI  240
NEXFSSLYKX  GKFQEISQKW  FGEXVATKEV  KEGX                                274
```

| | | |
|---|---|---|
| SEQ ID NO: 9 | moltype = DNA  length = 540 | |
| FEATURE | Location/Qualifiers | |
| misc_feature | 1..540 | |
| | note = Description of Unknown: Rhizavidin sequence | |
| source | 1..540 | |
| | mol_type = unassigned DNA | |
| | organism = unidentified | |

```
SEQUENCE: 9
ttgattatta  cgagtttata  tgcaaccttc  ggtacgatcg  ccgacggtcg  gcgcacatca   60
ggaggaaaaa  ccatgatccg  tactaatgca  gttgcagcac  ttgtgttttgc  tgtagcaacc  120
tcagctcttg  ctttcgatgc  aagcaacttc  aaggattttt  caagcatcgc  atcggcttcc  180
agcagttggc  agaaccagtc  cggctcgacg  atgatcattc  aagtcgactc  gttcggaaat  240
```

```
gtctccggcc aatatgtaaa cagagcccag ggcaccggat gccagaactc gccctatccg    300
ctaacaggaa gggtaaacgg gacgttcatc gcattttcgg tcggctggaa caattcgacg    360
gagaactgca attccgcaac cggatggacc ggctacgcac aggtcaacgg caacaacact    420
gagatagtca cgagctggaa cctcgcttac gaaggcggct ccggtccggc cattgagcaa    480
ggacaagaca ctttccagta cgtgccgacg actgagaaca aaagcctctt gaaggattaa    540

SEQ ID NO: 10           moltype = DNA   length = 405
FEATURE                 Location/Qualifiers
misc_feature            1..405
                        note = Description of Unknown: Truncated Rhizavidin sequence
source                  1..405
                        mol_type = unassigned DNA
                        organism = unidentified
SEQUENCE: 10
tttgatgcga gtaactttaa agatttcagc tctattgcga gcgccagtag ctcttggcag     60
aatcagagtg gcagcaccat gattatccag gtggattctt tcgcaacgt tagtggccag    120
tatgttaatc gtgcgcaggg cacggggttgc cagaactctc cgtacccgct gaccggccgc   180
gtgaatggca cgtttatcgc cttcagcgtt ggctggaaca attctaccga aaactgtaat   240
agtgcaaccg gctggacggg ttatgcgcag gtgaacggta acaataccga aattgttacg   300
agctggaatc tggcctatga aggcggttct ggcccggcaa tcgaacaggg tcaggatacc   360
tttcagtacg ttccgaccac ggaaaacaaa agcctgctga agat                    405

SEQ ID NO: 11           moltype = DNA   length = 1197
FEATURE                 Location/Qualifiers
source                  1..1197
                        mol_type = genomic DNA
                        organism = Streptococcus pneumoniae
SEQUENCE: 11
atgaagaaaa agaatggtaa agctaaaaag tggcaactgt atgcagcaat cggtgctgcg     60
agtgtagttg tattgggtgc tgggggggatt ttactcttta gacaaccttc tcagactgct    120
ctaaaagatg agcctactca tcttgttgtt gccaaggaag gaagcgtggc ctcctctgtt    180
ttattgtcag ggacagtaac agcaaaaaat gaacaatatg tttattttga tgctagtaag    240
ggtgatttag atgaaatcct tgtttctgtg gcgataagg tcagcgaagg gcaggcttta    300
gtcaagtaca gtagttcaga agcgcaggcg gcctatgatt cagctagtcg agcagtagct    360
agggcagatc gtcatatcaa tgaactcaat caagcacgaa atgaagccgc ttcagctccg    420
gctccacagt taccagcgcc agtaggagga gaagatgcaa cggtgcaaag cccaactcca    480
gtggctggaa attctgttgc ttctattgac gctcaattgg gtgatgcccg tgatgcgcgt    540
gcagatgctg cggcgcaatt aagcaaggct caaagtcaat tggatgcaac aactgttctc    600
agtaccctag agggaactgt ggtcgaagtc aatagcaatg tttctaaatc tccaacaggg    660
gcgagtcaag ttatggttca tattgtcagc aatgaaaatt tacaagtcaa gggagaattg    720
tctgagtaca atctagccaa ccttttctgta ggtcaagaag taagctttac ttctaaagtg    780
tatcctgata aaaaatggac tgggaaatta agctatattt ctgactatcc taaaaacaat    840
ggtgaagcag ctagtccagc agccgaagaat aatacagatc ctaaataccc ttatactatt    900
gatgtgacag gcgaggttgg tgatttgaaa caaggttttt ctgtcaacat tgaggttaaa    960
agcaaaacta aggctattct tgttcctgtt agcagtctag taatggatga tagtaaaaat   1020
tatgtctgga ttgtggatga acaacaaag gctaaaaaag ttgaggtttc attgggaaat   1080
gctgacgcag aaaatcaaga aatcacttct ggtttaacga acggtgctaa ggtcatcagt   1140
aatccaacat cttccttgga agaaggaaaa gaggtgaagg ctgatgaagc aactaat      1197

SEQ ID NO: 12           moltype = DNA   length = 1101
FEATURE                 Location/Qualifiers
source                  1..1101
                        mol_type = genomic DNA
                        organism = Streptococcus pneumoniae
SEQUENCE: 12
tttagacaac cttctcagac tgctctaaaa gatgagccta ctcatcttgt tgttgccaag     60
gaaggaagcg tggcctcctc tgttttattg tcagggacag taacagcaaa aaatgaacaa    120
tatgtttatt ttgatgctag taagggtgat ttagatgaaa tccttgtttc tgtgggcgat    180
aaggtcagcg aagggcaggc tttagtcaag tacagtagtt cagaagcgca ggcggcccta    240
gattcagcta gtcgagcagt agctagggca gatcgtcata tcaatgaact caatcaagca    300
cgaaatgaag ccgcttcagc tccggctcca cagttaccag cgccagtagg aggagaagat    360
gcaacggtgc aaagcccaac tccagtggct ggaaattctg ttgcttctat tgacgctcaa    420
ttgggtgatg cccgtgatgc gcgtgcagat gctgcggcgc aattaagcaa ggctcaaagt    480
caattggatg caacaactgt tctcagtacc ctagagggaa ctgtggtcga agtcaatgtg    540
aatgttctca atctccaac aggggcgagt caagttatgg ttcatattgt cagcaatgaa    600
aatttacaag tcaagggaga attgtctgag tacaatctag ccaacctttc tgtaggtcaa    660
gaagtaagct tacttctaa agtgtatcct gataaaaaat ggactgggaa attaagctat    720
atttctgact atcctaaaaa caatggtgaa gcagctagtc cagcagccgg gaataataca    780
gatcctaaat accttatac tattgatgtg acaggcgagg ttggtgattt gaaacaaggt    840
tttctgtca acattgaggt taaaagcaaa actaaggcta ttcttgttcc tgttagcagt    900
ctagtaatgg atgatagtaa aattatgtc tggattgtgg atgaacaaca aaaggctaaa    960
aaagttgagg tttcattggg aaatgctgac gcagaaaatc aagaaatcac ttctggttta   1020
acgaacggtg ctaaggtcat cagtaatcca acatcttcct tggaagaagg aaaagaggtg   1080
aaggctgatg aagcaactaa t                                              1101

SEQ ID NO: 13           moltype = DNA   length = 834
FEATURE                 Location/Qualifiers
source                  1..834
                        mol_type = genomic DNA
```

```
                        organism = Streptococcus pneumoniae
SEQUENCE: 13
atgaaaaaat ggatgcttgt attagtcagt ctgatgactg ctttgttctt agtagcttgt     60
gggaaaaatt ctagcgaaac tagtggagat aattggtcaa agtaccagtc taacaagtct    120
attactattg gatttgatag tacttttgtt ccaatgggat tgctcagaa agatggttct     180
tatgcaggat ttgatattga tttagctaca gctgttttg aaaaatacgg aatcacggta     240
aattggcaac cgattgattg ggatttgaaa gaagctgaat tgacaaaagg aacgattgat    300
ctgatttgga tggctattc cgctacagac gaacgccgtg aaaaggtggc tttcagtaac    360
tcatatatga agaatgagca ggtattggtt acgaagaat catctggtat cacgactgga    420
aaggatatga ctggaaagac attaggagct caagctggtt catctggtta tgcggacttt    480
gaagcaaatc cagaaatttt gaagaatatt gtcgctaata aggaagcgaa tcaataccaa    540
acctttaatg aagccttgat tgatttgaaa acgatcgaa ttgatggtct attgattgac     600
cgtgtctatg caaactatta tttagaagca gaaggtgttt aaacgatta taatgtctta     660
acagttggac tagaaacaga agcttttgcg gttggagccc gtaaggaaga tacaaacttg    720
gttaagaaga taaatgaagc ttttttctagt ctttacaagg acggcaagtt ccaagaaatc   780
agccaaaaat ggtttggaga agatgtagca accaaagaag taaagaagg acag           834

SEQ ID NO: 14          moltype = DNA  length = 756
FEATURE                Location/Qualifiers
source                 1..756
                       mol_type = genomic DNA
                       organism = Streptococcus pneumoniae
SEQUENCE: 14
actagtggag ataattggtc aaagtaccag tctaacaagt ctattactat tggatttgat     60
agtacttttg ttccaatggg atttgctcag aaagatggtt cttatgcagg atttgatatt    120
gatttagcta cagctgtttt tgaaaaatac ggaatcacgg taaattggca accgattgat    180
tgggatttga agaagctga attgacaaaa ggaacgattg atctgatttg gaatggctat    240
tccgctacag acgaacgccg tgaaaaggtg gctttcagta actcatatat gaagaatgag    300
caggtattgg ttacgaagaa atcatctggt atcacgactg caaggatat gactggaaag    360
acattaggag ctcaagctgg ttcatctggt tatgcggact ttgaagcaaa tccagaaatt    420
ttgaagaata ttgtcgctaa taaggaagcg aatcaatacc aaacctttaa tgaagccttg    480
attgatttga aaacgatcg aattgatggt ctattgattg accgtgtcta tgcaaactat    540
tatttagaag cagaaggtgt tttaaacgat tataatgtct ttacagttgg actagaaaca    600
gaagcttttg cggttggagc ccgtaaggaa gatacaaact tggttaagaa gataaatgaa    660
gcttttttcta gtctttacaa ggacggcaag ttccaagaaa tcagccaaaa atggtttgga    720
gaagatgtag caaccaaaga agtaaaagaa ggacag                              756

SEQ ID NO: 15          moltype = AA   length = 6
FEATURE                Location/Qualifiers
REGION                 1..6
                       note = Description of Artificial Sequence: Synthetic6xHis
                        tag
source                 1..6
                       mol_type = protein
                       organism = synthetic construct
SEQUENCE: 15
HHHHHH                                                                6

SEQ ID NO: 16          moltype = AA   length = 10
FEATURE                Location/Qualifiers
REGION                 1..10
                       note = Description of Artificial Sequence: Synthetic peptide
source                 1..10
                       mol_type = protein
                       organism = synthetic construct
SEQUENCE: 16
MSYYHHHHHH                                                            10

SEQ ID NO: 17          moltype = AA   length = 620
FEATURE                Location/Qualifiers
REGION                 1..620
                       note = Description of Artificial Sequence: Synthetic
                        polypeptide
source                 1..620
                       mol_type = protein
                       organism = synthetic construct
SEQUENCE: 17
MTSGDNWSKY QSNKSITIGF DSTFVPMGFA QKDGSYAGFD IDLATAVFEK YGITVNWQPI      60
DWDLKEAELT KGTIDLIWNG YSATDERREK VAFSNSYMKN EQVLVTKKSS GITTAKDMTG    120
KTLGAQAGSS GYADFEANPE ILKNIVANKE ANQYQTFNEA LIDLKNDRID GLLIDRVYAN    180
YYLEAEGVLN DYNVFTVGLE TEAFAVGARK EDTNLVKKIN EAFSSLYKDG KFQEISQKWF    240
GEDVATKEVK EGQFRQPSQT ALKDEPTHLV VAKEGSVASS VLLSGTVTAK NEQYVYFDAS    300
KGDLDEILVS VGDKVSEGQA LVKYSSSEAQ AAYDSASRAV ARADRHINEL NQARNEAASA    360
PAPQLPAPVG GEDATVQSPT PVAGNSVASI DAQLGDARDA RADAAAQLSK AQSQLDATTV    420
LSTLEGTVVE VNSNVSKSPT GASQVMVHIV SNENLQVKGE LSEYNLANLS VGQEVSFTSK    480
VYPDKKWTGK LSYISDYPKN NGEAASPAAG NNTGSKYPYT IDVTGEVGDL KQGFSVNIEV    540
KSKTKAILVP VSSLVMDDSK NYVWIVDEQQ KAKKVEVSLG NADAENQEIT SGLTNGAKVI    600
SNPTSSLEEG KEVKADEATN                                                620
```

```
SEQ ID NO: 18            moltype = AA  length = 620
FEATURE                  Location/Qualifiers
REGION                   1..620
                         note = Description of Artificial Sequence: Synthetic
                         polypeptide
source                   1..620
                         mol_type = protein
                         organism = synthetic construct
SEQUENCE: 18
MFRQPSQTAL KDEPTHLVVA KEGSVASSVL LSGTVTAKNE QYVYFDASKG DLDEILVSVG    60
DKVSEGQALV KYSSSEAQAA YDSASRAVAR ADRHINELNQ ARNEAASAPA PQLPAPVGGE   120
DATVQSPTPV AGNSVASIDA QLGDARDARA DAAAQLSKAQ SQLDATTVLS TLEGTVVEVN   180
SNVSKSPTGA SQVMVHIVSN ENLQVKGELS EYNLANLSVG QEVSFTSKVY PDKKWTGKLS   240
YISDYPKNNG EAASPAAGNN TGSKYPYTID VTGEVGDLKQ GFSVNIEVKS KTKAILVPVS   300
SLVMDDSKNY VWIVDEQQKA KKVEVSLGNA DAENQEITSG LTNGAKVISN PTSSLEEGKE   360
VKADEATNTS GDNWSKYQSN KSITIGFDST FVPMGFAQKD GSYAGFDIDL ATAVFEKYGI   420
TVNWQPIDWD LKEAELTKGT IDLIWNGYSA TDERREKVAF SNSYMKNEQV LVTKKSSGIT   480
TAKDMTGKTL GAQAGSSGYA DFEANPEILK NIVANKEANQ YQTFNEALID LKNDRIDGLL   540
IDRVYANYYL EAEGVLNDYN VFTVGLETEA FAVGARKEDT NLVKKINEAF SSLYKDGKFQ   600
EISQKWFGED VATKEVKEGQ                                               620

SEQ ID NO: 19            moltype = AA  length = 755
FEATURE                  Location/Qualifiers
REGION                   1..755
                         note = Description of Artificial Sequence: Synthetic
                         polypeptide
source                   1..755
                         mol_type = protein
                         organism = synthetic construct
SEQUENCE: 19
MFDASNFKDF SSIASASSSW QNQSGSTMII QVDSFGNVSG QYVNRAQGTG CQNSPYPLTG    60
RVNGTFIAFS VGWNNSTENC NSATGWTGYA QVNGNNTEIV TSWNLAYEGG SGPAIEQGQD   120
TFQYVPTTEN KSLLKDTSGD NWSKYQSNKS ITIGFDSTFV PMGFAQKDGS YAGFDIDLAT   180
AVFEKYGITV NWQPIDWDLK EAELTKGTID LIWNGYSATD ERREKVAFSN SYMKNEQVLV   240
TKKSSGITTA KDMTGKTLGA QAGSSGYADF EANPEILKNI VANKEANQYQ TFNEALIDLK   300
NDRIDGLLID RVYANYYLEA EGVLNDYNVF TVGLETEAFA VGARKEDTNL VKKINEAFSS   360
LYKDGKFQEI SQKWFGEDVA TKEVKEGQFR QPSQTALKDE PTHLVVAKEG SVASSVLLSG   420
TVTAKNEQYV YFDASKGDLD EILVSVGDKV SEGQALVKYS SSEAQAAYDS ASRAVARADR   480
HINELNQARN EAASAPAPQL PAPVGGEDAT VQSPTPVAGN SVASIDAQLG DARDARADAA   540
AQLSKAQSQL DATTVLSTLE GTVVEVNSNV SKSPTGASQV MVHIVSNENL QVKGELSEYN   600
LANLSVGQEV SFTSKVYPDK KWTGKLSYIS DYPKNNGEAA SPAAGNNTGS KYPYTIDVTG   660
EVGDLKQGFS VNIEVKSKTK AILVPVSSLV MDDSKNYVWI VDEQQKAKKV EVSLGNADAE   720
NQEITSGLTN GAKVISNPTS SLEEGKEVKA DEATN                              755

SEQ ID NO: 20            moltype = AA  length = 755
FEATURE                  Location/Qualifiers
REGION                   1..755
                         note = Description of Artificial Sequence: Synthetic
                         polypeptide
source                   1..755
                         mol_type = protein
                         organism = synthetic construct
SEQUENCE: 20
MFDASNFKDF SSIASASSSW QNQSGSTMII QVDSFGNVSG QYVNRAQGTG CQNSPYPLTG    60
RVNGTFIAFS VGWNNSTENC NSATGWTGYA QVNGNNTEIV TSWNLAYEGG SGPAIEQGQD   120
TFQYVPTTEN KSLLKDFRQP SQTALKDEPT HLVVAKEGSV ASSVLLSGTV TAKNEQYVYF   180
DASKGDLDEI LVSVGDKVSE GQALVKYSSS EAQAAYDSAS RAVARADRHI NELNQARNEA   240
ASAPAPQLPA PVGGEDATVQ SPTPVAGNSV ASIDAQLGDA RDARADAAAQ LSKAQSQLDA   300
TTVLSTLEGT VVEVNSNVSK SPTGASQVMV HIVSNENLQV KGELSEYNLA NLSVGQEVSF   360
TSKVYPDKKW TGKLSYISDY PKNNGEAASP AAGNNTGSKY PYTIDVTGEV GDLKQGFSVN   420
IEVKSKTKAI LVPVSSLVMD DSKNYVWIVD EQQKAKKVEV SLGNADAENQ EITSGLTNGA   480
KVISNPTSSL EEGKEVKADE ATNTSGDNWS KYQSNKSITI GFDSTFVPMG FAQKDGSYAG   540
FDIDLATAVF EKYGITVNWQ PIDWDLKEAE LTKGTIDLIW NGYSATDERR EKVAFSNSYM   600
KNEQVLVTKK SSGITTAKDM TGKTLGAQAG SSGYADFEAN PEILKNIVAN KEANQYQTFN   660
EALIDLKNDR IDGLLIDRVY ANYYLEAEGV LNDYNVFTVG LETEAFAVGA RKEDTNLVKK   720
INEAFSSLYK DGKFQEISQK WFGEDVATKE VKEGQ                              755

SEQ ID NO: 21            moltype = AA  length = 755
FEATURE                  Location/Qualifiers
REGION                   1..755
                         note = Description of Artificial Sequence: Synthetic
                         polypeptide
source                   1..755
                         mol_type = protein
                         organism = synthetic construct
SEQUENCE: 21
MTSGDNWSKY QSNKSITIGF DSTFVPMGFA QKDGSYAGFD IDLATAVFEK YGITVNWQPI    60
DWDLKEAELT KGTIDLIWNG YSATDERREK VAFSNSYMKN EQVLVTKKSS GITTAKDMTG   120
KTLGAQAGSS GYADFEANPE ILKNIVANKE ANQYQTFNEA LIDLKNDRID GLLIDRVYAN   180
```

```
YYLEAEGVLN DYNVFTVGLE TEAFAVGARK EDTNLVKKIN EAFSSLYKDG KFQEISQKWF  240
GEDVATKEVK EGQFRQPSQT ALKDEPTHLV VAKEGSVASS VLLSGTVTAK NEQYVYFDAS  300
KGDLDEILVS VGDKVSEGQA LVKYSSSEAQ AAYDSASRAV ARADRHINEL NQARNEAASA  360
PAPQLPAPVG GEDATVQSPT PVAGNSVASI DAQLGDARDA RADAAAQLSK AQSQLDATTV  420
LSTLEGTVVE VNSNVSKSPT GASQVMVHIV SNENLQVKGE LSEYNLANLS VGQEVSFTSK  480
VYPDKKWTGK LSYISDYPKN NGEAASPAAG NNTGSKYPYT IDVTGEVGDL KQGFSVNIEV  540
KSKTKAILVP VSSLVMDDSK NYVWIVDEQQ KAKKVEVSLG NADAENQEIT SGLTNGAKVI  600
SNPTSSLEEG KEVKADEATN FDASNFKDFS SIASASSSWQ NQSGSTMIIQ VDSFGNVSGQ  660
YVNRAQGTGC QNSPYPLTGR VNGTFIAFSV GWNNSTENCN SATGWTGYAQ VNGNNTEIVT  720
SWNLAYEGGS GPAIEQGQDT FQYVPTTENK SLLKD                            755

SEQ ID NO: 22          moltype = AA  length = 755
FEATURE                Location/Qualifiers
REGION                 1..755
                       note = Description of Artificial Sequence: Synthetic
                       polypeptide
source                 1..755
                       mol_type = protein
                       organism = synthetic construct
SEQUENCE: 22
MFRQPSQTAL KDEPTHLVVA KEGSVASSVL LSGTVTAKNE QYVYFDASKG DLDEILVSVG  60
DKVSEGQALV KYSSSEAQAA YDSASRAVAR ADRHINELNQ ARNEAASAPA PQLPAPVGGE  120
DATVQSPTPV AGNSVASIDA QLGDARDARA DAAAQLSKAQ SQLDATTVLS TLEGTVVEVN  180
SNVSKSPTGA SQVMVHIVSN ENLQVKGELS EYNLANLSVG QEVSFTSKVY PDKKWTGKLS  240
YISDYPKNNG EAASPAAGNN TGSKYPYTID VTGEVGDLKQ GFSVNIEVKS KTKAILVPVS  300
SLVMDDSKNY VWIVDEQQKA KKVEVSLGNA DAENQEITSG LTNGAKVISN PTSSLEEGKE  360
VKADEATNTS GDNWSKYQSN KSITIGFDST FVPMGFAQKD GSYAGFDIDL ATAVFEKYGI  420
TVNWQPIDWD LKEAELTKGT IDLIWNGYSA TDERREKVAF SNSYMKNEQV LVTKKSSGIT  480
TAKDMTGKTL GAQAGSSGYA DFEANPEILK NIVANKEANQ YQTFNEALID LKNDRIDGLL  540
IDRVYANYYL EAEGVLNDYN VFTVGLETEA FAVGARKEDT NLVKKINEAF SSLYKDGKFQ  600
EISQKWFGED VATKEVKEGQ FDASNFKDFS SIASASSSWQ NQSGSTMIIQ VDSFGNVSGQ  660
YVNRAQGTGC QNSPYPLTGR VNGTFIAFSV GWNNSTENCN SATGWTGYAQ VNGNNTEIVT  720
SWNLAYEGGS GPAIEQGQDT FQYVPTTENK SLLKD                            755

SEQ ID NO: 23          moltype = AA  length = 765
FEATURE                Location/Qualifiers
REGION                 1..765
                       note = Description of Artificial Sequence: Synthetic
                       polypeptide
source                 1..765
                       mol_type = protein
                       organism = synthetic construct
SEQUENCE: 23
MFDASNFKDF SSIASASSSW QNQSGSTMII QVDSFGNVSG QYVNRAQGTG CQNSPYPLTG  60
RVNGTFIAFS VGWNNSTENC NSATGWTGYA QVNGNNTEIV TSWNLAYEGG SGPAIEQGQD  120
TFQYVPTTEN KSLLKDGGGG SSSTSGDNWS KYQSNKSITI GFDSTFVPMG FAQKDGSYAG  180
FDIDLATAVF EKYGITVNWQ PIDWDLKEAE LTKGTIDLIW NGYSATDERR EKVAFSNSYM  240
KNEQVLVTKK SSGITTAKDM TGKTLGAQAG SSGYADFEAN PEILKNIVAN KEANQYQTFN  300
EALIDLKNDR IDGLLIDRVY ANYYLEAEGV LNDYNVFTVG LETEAFAVGA RKEDTNLVKK  360
INEAFSSLYK DGKFQEISQK WFGEDVATKE VKEGQAAAFR QPSQTALKDE PTHLVVAKEG  420
SVASSVLLSG TVTAKNEQYV YFDASKGDLD EILVSVGDKV SEGQALVKYS SSEAQAAYDS  480
ASRAVARADR HINELNQARN EAASAPAPQL PAPVGGEDAT VQSPTPVAGN SVASIDAQLG  540
DARDARADAA AQLSKAQSQL DATTVLSTLE GTVVEVNSNV SKSPTGASQV MVHIVSNENL  600
QVKGELSEYN LANLSVGQEV SFTSKVYPDK KWTGKLSYIS DYPKNNGEAA SPAAGNNTGS  660
KYPYTIDVTG EVGDLKQGFS VNIEVKSKTK AILVPVSSLV MDDSKNYVWI VDEQQKAKKV  720
EVSLGNADAE NQEITSGLTN GAKVISNPTS SLEEGKEVKA DEATN                 765

SEQ ID NO: 24          moltype = AA  length = 765
FEATURE                Location/Qualifiers
REGION                 1..765
                       note = Description of Artificial Sequence: Synthetic
                       polypeptide
source                 1..765
                       mol_type = protein
                       organism = synthetic construct
SEQUENCE: 24
MFDASNFKDF SSIASASSSW QNQSGSTMII QVDSFGNVSG QYVNRAQGTG CQNSPYPLTG  60
RVNGTFIAFS VGWNNSTENC NSATGWTGYA QVNGNNTEIV TSWNLAYEGG SGPAIEQGQD  120
TFQYVPTTEN KSLLKDGGGG SSSFRQPSQT ALKDEPTHLV VAKEGSVASS VLLSGTVTAK  180
NEQYVYFDAS KGDLDEILVS VGDKVSEGQA LVKYSSSEAQ AAYDSASRAV ARADRHINEL  240
NQARNEAASA PAPQLPAPVG GEDATVQSPT PVAGNSVASI DAQLGDARDA RADAAAQLSK  300
AQSQLDATTV LSTLEGTVVE VNSNVSKSPT GASQVMVHIV SNENLQVKGE LSEYNLANLS  360
VGQEVSFTSK VYPDKKWTGK LSYISDYPKN NGEAASPAAG NNTGSKYPYT IDVTGEVGDL  420
KQGFSVNIEV KSKTKAILVP VSSLVMDDSK NYVWIVDEQQ KAKKVEVSLG NADAENQEIT  480
SGLTNGAKVI SNPTSSLEEG KEVKADEATN AAATSGDNWS KYQSNKSITI GFDSTFVPMG  540
FAQKDGSYAG FDIDLATAVF EKYGITVNWQ PIDWDLKEAE LTKGTIDLIW NGYSATDERR  600
EKVAFSNSYM KNEQVLVTKK SSGITTAKDM TGKTLGAQAG SSGYADFEAN PEILKNIVAN  660
KEANQYQTFN EALIDLKNDR IDGLLIDRVY ANYYLEAEGV LNDYNVFTVG LETEAFAVGA  720
RKEDTNLVKK INEAFSSLYK DGKFQEISQK WFGEDVATKE VKEGQ                 765
```

```
SEQ ID NO: 25             moltype = AA  length = 765
FEATURE                   Location/Qualifiers
REGION                    1..765
                          note = Description of Artificial Sequence: Synthetic
                           polypeptide
source                    1..765
                          mol_type = protein
                          organism = synthetic construct
SEQUENCE: 25
MTSGDNWSKY QSNKSITIGF DSTFVPMGFA QKDGSYAGFD IDLATAVFEK YGITVNWQPI   60
DWDLKEAELT KGTIDLIWNG YSATDERREK VAFSNSYMKN EQVLVTKKSS GITTAKDMTG  120
KTLGAQAGSS GYADFEANPE ILKNIVANKE ANQYQTFNEA LIDLKNDRID GLLIDRVYAN  180
YYLEAEGVLN DYNVFTVGLE TEAFAVGARK EDTNLVKKIN EAFSSLYKDG KFQEISQKWF  240
GEDVATKEVK EGQGGGGSSS FRQPSQTALK DEPTHLVVAK EGSVASSVLL SGTVTAKNEQ  300
YVVYFDASKGD LDEILVSVGD KVSEGQALVK YSSSEAQAAY DSASRAVARA DRHINELNQA  360
RNEAASAPAP QLPAPVGGED ATVQSPTPVA GNSVASIDAQ LGDARDARAD AAAQLSKAQS  420
QLDATTVLST LEGTVVEVNS NVSKSPTGAS QVMVHIVSNE NLQVKGELSE YNLANLSVGQ  480
EVSFTSKVYP DKKWTGKLSY ISDYPKNNGE AASPAAGNNT GSKYPYTIDV TGEVGDLKQG  540
FSVNIEVKSK TKAILVPVSS LVMDDSKNYV WIVDEQQKAK KVEVSLGNAD AENQEITSGL  600
TNGAKVISNP TSSLEEGKEV KADEATNAAA FDASNFKDFS SIASASSSWQ NQSGSTMIIQ  660
VDSFGNVSGQ YVNRAQGTGC QNSPYPLTGR VNGTFIAFSV GWNNSTENCN SATGWTGYAQ  720
VNGNNTEIVT SWNLAYEGGS GPAIEQGQDT FQYVPTTENK SLLKD                 765

SEQ ID NO: 26             moltype = AA  length = 764
FEATURE                   Location/Qualifiers
REGION                    1..764
                          note = Description of Artificial Sequence: Synthetic
                           polypeptide
source                    1..764
                          mol_type = protein
                          organism = synthetic construct
SEQUENCE: 26
MFRQPSQTAL KDEPTHLVVA KEGSVASSVL LSGTVTAKNE QYVVFDASKG DLDEILVSVG   60
DKVSEGQALV KYSSSEAQAA YDSASRAVAR ADRHINELNQ ARNEAASAPA PQLPAPVGGE  120
DATVQSPTPV AGNSVASIDA QLGDARDARA DAAAQLSKAQ SQLDATTVLS TLEGTVVEVN  180
SNVSKSPTGA SQVMVHIVSN ENLQVKGELS EYNLANLSVG QEVSFTSKVY PDKKWTGKLS  240
YISDYPKNNG EAASPAAGNN TGSKYPYTID VTGEVGDLKQ GFSVNIEVKS KTKAILVPVS  300
SLVMDDSKNY VWIVDEQQKA KKVEVSLGNA DAENQEITSG LTNGAKVISN PTSSLEEGKE  360
VKADEATNGG GGSSSTSGDN WSKYQSNKSI TIGFDSTFVP MGFAQKDGSY AGFDIDLATA  420
VFEKYGITVN WQPIDWDLKE AELTKGTIDL IWNGYSATDE RREKVAFSNS YMNEQVLVTK  480
KSSGITTAKD MTGKTLGAQA GSSGYADFEA NPEILKNIVA NKEANQYQTF NEALIDLKND  540
RIDGLLIDRV YANYYLEAEG VLNDYNVFTV GLETEAFAVG ARKEDTNLVK KINEAFSSLY  600
KDGKFQEISQ KWFGEDVATK EVKEGQAAAF DASNFKDFSS IASASSSWQN QSGSTMIIQV  660
DSFGNVSGQY VNRAQGTGCQ NSPYPLTGRV NGTFIAFSVG WNNSTENCNS ATGWTGYAQV  720
NGNNTEIVTS WNLAYEGGSG PAIEQGQDTF QYVPTTENKS LLKD                  764

SEQ ID NO: 27             moltype = DNA  length = 1860
FEATURE                   Location/Qualifiers
misc_feature              1..1860
                          note = Description of Artificial Sequence: Synthetic
                           polynucleotide
source                    1..1860
                          mol_type = other DNA
                          organism = synthetic construct
SEQUENCE: 27
atgaccagcg gcgacaattg gtccaaatac cagagcaaca agagcatcac gatcggcttc    60
gacagcactt ttgtgccgat gggtttcgcg caaaaagacg gtagctacgc gggtttcgat   120
attgacctgg cgaccgctgt ctttgagaaa tacggcatta cggttaattg gcagccgatt   180
gattgggacc tgaaagaggc cgaactcacc aaaggcacca tcgacctgat ctggaatggt   240
tactccgcaa ccgatgagcg tcgcgaaaaa gttgccttca gcaacagcta tatgaagaat   300
gaacaagtgt tggtaaccaa gaaatctagc ggcattacga ccgcgaaaga catgaccggt   360
aagacgctgg gtgcgcaggc cggtagctct ggctatgcgg atttcgaggc gaatcctgag   420
attctgaaaa acatcgttgc gaataaagag gcgaaccagt accagaccTt taacgaagca   480
ctgatcgacc tgaaaaacga tcgcattgac ggtctgctga tcgatcgtgt gtacgcgaac   540
tattatctgg aagccgaggg cgttctgaac gattataatg tttttaccgt gggtctggag   600
actgaggcat tcgcggttgg tgcgcgcaag gaagatacca acctggttaa aaagattaat   660
gaggcattta gctcactgta caaggacggc aagttccaaa aattagcca gaagtggact   720
ggtgaagatg ttgcgacgaa agaggttaaa gagggccaat ttcgccaacc gagccagact   780
gcgttgaaag atgagccgac ccatctggtt gttgcgaaaa agggcagcgt ggcatcgagc   840
gtgctgctga gcggtacggt tactgccaaa aacgaacaat acgtgtactt cgatgctagc   900
aagggtgatc tggatgaaat tctggtgagc gtgggtgaca agttagcga aggccaggca   960
ctggtgaagt attcatcctc cgaggcacag gcagcgtacg acagcgcaag ccgcgcagtg  1020
gcgcgtgccg accgtcacat taacgaattg aaccaagcgc gtaacgaagc gaccgcagct  1080
ccagcaccgc agctgccggc tccgGtgggt ggcgaagatg cgacggtgca gagcccgacc  1140
ccggttgcgg gtaattcggt cgccagcatc gatgcgcagc tggtgacgc gcgtgatgcc  1200
cgtgcggatg cggctgctca actgagcaag gctcagagcc aactggacgc gacgacggtg  1260
ctgagcacct tggagggtac cgttgtcgaa gtcaacagca atgtgagcaa gagcccaacg  1320
ggtgcgagcc aggttatggt ccacattgtg agcaatgaaa acttacaggt caagggtgag  1380
```

```
ctgagcgagt ataacctggc gaatctgagc gttggtcaag aggtcagctt taccagcaag  1440
gtctacccgg ataagaaatg gaccggcaag ttgagctaca tcagcgacta cccgaagaac  1500
aatggcgagg cagcctcccc ggcagccggc aacaataccg gctctaagta tccgtacacc  1560
atcgacgtaa ccggtgaggt cggcgacctg aaacagggtt ttagcgtgaa tatcgaagtg  1620
aagtccaaga ccaaggcaat tttggttccg gttagctccc tggtgatgga cgatagcaag  1680
aattatgtgt ggattgtcga cgagcaacag aaagcgaaaa aagttgaagt gagcctgggc  1740
aatgctgatg ccgagaacca agaaatcacg tctggtctga ccaacggtgc gaaagttatt  1800
agcaacccga ccagcagcct ggaagagggt aaagaggtca agccgacgga agctacgaac  1860
```

SEQ ID NO: 28          moltype = DNA   length = 1860
FEATURE                Location/Qualifiers
misc_feature           1..1860
                       note = Description of Artificial Sequence: Synthetic
                       polynucleotide
source                 1..1860
                       mol_type = other DNA
                       organism = synthetic construct
SEQUENCE: 28

```
atgtttcgcc aaccgagcca gactgcgttg aaagatgagc cgacccatct ggttgttgcg   60
aaagagggca gcgtggcatc gagcgtgctg ctgagcggta cggttactgc caaaaacgaa  120
caatacgtgt acttcgatgc tagcaagggt gatctggatg aaattctggt gagcgtgggt  180
gacaaagtta gcgaaggcca ggcactggtg aagtattcat cctccgaggc acaggcagcg  240
tacgacagcg caagccgcgc agtggccgcg tgccgaccgtc acattaacga attgaaccaa  300
gcgcgtaacg aggccgcaag cgcgccagca ccgcagctgc cggctccggt gggtggcgaa  360
gatgcgacgg tgcagagccc gaccccggtt gcgggtaatt cggtcgccag catcgatgcg  420
cagctgggtg acgcgcgtga tgcccgtgcg gatgcggctc tcaactgag caaggctcag  480
agccaactgg acgcgacgac ggtgctgagc accttggagg gtaccgttgt cgaagtcaac  540
agcaatgtga gcaagagccc aacgggtgcg agccaggtta tggtccacat tgtgagcaat  600
gaaaacttac aggtcaaggg tgagctgagc gagtataacc tggcgaatct gagcgttggt  660
caagaggtca gctttaccag caaggtctac ccggataaga aatggaccgg caagttgagc  720
tacatcagcg actacccgaa gaacaatggc gaggcagcct ccccggcagc cggcaacaat  780
accggctcta gtatccgta caccatcgac gtaaccggtg aggtcggcga cctgaaacag  840
ggttttagcg tgaatatcga agtgaagtcc aagaccaagg caattttggt tccggttagc  900
tccctggtga tggacgatag caagaattat gtgtggattg tcgacgagca acagaaaagcg  960
aaaaaagttg aagtgagcct gggcaatgct gatgccgaga accaagaaat cacgtctggt 1020
ctgaccaacg gtgcgaaagt tattagcaac ccgaccagca gcctggaaga gggtaaagag 1080
gtcaaagccg acgaagctac gaacaccagc ggcgacaatt ggtccaaata ccagagcaac 1140
aagagcatca cgatcggctt cgacagcact tttgtgccga tgggtttcgc gcaaaaagac 1200
ggtagctacg cgggtttcga tattgacctg gcgaccgctg tctttgaaga atacggcatt 1260
acggttaatt ggcagccgat tgattgggac ctgaaagagg ccgaactcac caaaggcacc 1320
atcgacctga tctggaatgg ttactccgca accgatgagc gtcgcgaaaa agttgccttc 1380
agcaacagct atatgaagaa tgaacaagtg ttggtaacca agaaatctag cggcattacg 1440
accgcgaaag acatgaccgg taagacgctg ggtgccgaac ccggtagctc tggctatgcg 1500
gatttcgagg cgaatcctga gattctgaaa aacatcgttg caataaaga ggcgaaccag 1560
taccagacct ttaacgaagc actgatcgac ctgaaaaacg atcgcattga cggtctgctg 1620
atcgatcgtg tgtacgcgaa ctattatctg gaagccgagg gcgttctgaa cgattataat 1680
gttttaccgg tgggtctgga gactgaggca ttcgcgctg gtgcgcgcaa ggaagatacc 1740
aacctggtta aaaagattaa tgaggcattt agctcactgt acaaggacgg caagttccaa 1800
gaaattagcc agaagtggtt cggtgaagat gttgcgacga agaggttaa agagggccaa 1860
```

SEQ ID NO: 29          moltype = DNA   length = 2265
FEATURE                Location/Qualifiers
misc_feature           1..2265
                       note = Description of Artificial Sequence: Synthetic
                       polynucleotide
source                 1..2265
                       mol_type = other DNA
                       organism = synthetic construct
SEQUENCE: 29

```
atgttcgacg catccaactt taaagacttt agcagcatcg cgtccgcaag ctctagctgg   60
cagaatcaat ctggtagcac catgattatc caagtggaca gctttggtaa cgtcagcggt  120
caatatgtta tcgtgcaca gggtacgggt tgtcagaatt ctccgtaccc gctgaccggt  180
cgtgttaacg gcacgttcat cgctttcagc gtcggttgga caattctac tgaaaattgc  240
aacagcgcga ccggttggac gggctatgca caagtgacta caataacac gcgaaatgtc  300
acgtcctgga atctggcgta tgagggtggc agcggtccgg ctattgaaca gggccaggat  360
accttccaat acgtccctac gaccgagaat aagtcccttc tgaaagacac cagcggcgac  420
aattggtcca ataccagag caacaagagc atcacgatcg gcttcgacag cactttttgtg  480
ccgatggggt tcgcgcaaaa agacggtagc tacgcgggtt tcgatattga cctggcgacc  540
gctgtctttg agaaatacgg cattacggtt aattggcagc cgattgattg ggacctgaaa  600
gaggccgaac tcaccaaagg caccatcgac ctgatctgga atggttactc cgcaaccgat  660
gagcgtcgcg aaaagttgc cttcagcaac agctatatga gaatgaaca agtgttggta  720
accaagaaat ctagcggcat tacgaccgcg aagacatga ccggtaagac gctgggtgcg  780
caggccggta gctctggcta tgcggattc gaggcgaatc ctgagattct gaaaaacatc  840
gttgcaata aagaggcgaa ccagtaccag accttaacg aagcactgat cgacctgaaa  900
aacgatcgca ttgacggtct gctgatcgat cgtgtgtacg cgaactatta tctggaagcc  960
gagggcgttc tgaacgatta taatgttttt accgtgggtc tggagactga ggcattcgcg 1020
gttggtgcgc gcaaggaaga taccaacctg gttaaaaaga ttaatgaggc atttagctca 1080
ctgtacaagg acggcaagtt ccaagaaatt agccagaagt ggttcggtga agatgttgcg 1140
acgaagagag ttaaagaggg ccaatttcgc caaccgagcc agactgcgtt gaaagatgag 1200
```

```
ccgacccatc tggttgttgc gaaagagggc agcgtggcat cgagcgtgct gctgagcggt 1260
acggttactg ccaaaaacga acaatacgtg tacttcgatg ctagcaaggg tgatctggat 1320
gaaattctgg tgagcgtggg tgacaaagtt agcgaaggcc aggcactggt gaagtattca 1380
tcctccgagg cacaggcagc gtacgacagc gcaagccgcg cagtggcgcg tgccgaccgt 1440
cacattaacg aattgaacca agcgcgtaac gaggccgcag gccgccagc accgcagctg 1500
ccggctccgg tgggtggcga agatgcgacg gtgcagagcc cgaccccggt tgcgggtaat 1560
tcggtcgcca gcatcgatgc gcagctgggt gacgcgcgtg atgcccgtgc ggatgcggct 1620
gctcaactga gcaaggctca gagccaactg gacgcgacga cggtgctgag caccttggag 1680
ggtaccgttg tcgaagtcaa cagcaatgtg agcaagagcc caacgggtgc gagccaggtt 1740
atggtccaca ttgtgagcaa tgaaaactta caggtcaagg gtgagctgga cgagtataac 1800
ctggcgaatc tgagcgttgg tcaagaggtc agctttacca gcaaggtcta cccggataag 1860
aaatggaccg gcaagttgag ctacatcagc gactacccga agaacaatgg cgaggcagcc 1920
tccccggcag ccggcaacaa taccggctct aagtatccgt acaccatcga cgtaaccggt 1980
gaggtcggcg acctgaaaca gggttttagc gtgaatatcg aagtgaagtc caagaccaag 2040
gcaattttgg ttccggttag ctccctggtg atggacgata caagaattaa tgtgtggatt 2100
gtcgacgagc aacagaaagc gaaaaaagtt gaagtgagcc tgggcaatgc tgatgccgag 2160
aaccaagaaa tcacgtctgg tctgaccaac ggtgcgaaag ttattagcaa cccgaccagc 2220
agcctggaag agggtaaaga ggtcaaagcc gacgaagcta cgaac           2265

SEQ ID NO: 30        moltype = DNA  length = 2265
FEATURE              Location/Qualifiers
misc_feature         1..2265
                     note = Description of Artificial Sequence: Synthetic
                     polynucleotide
source               1..2265
                     mol_type = other DNA
                     organism = synthetic construct
SEQUENCE: 30
atgttcgacg catccaactt taaagacttt agcagcatcg cgtccgcaag ctctagctgg 60
cagaatcaat ctggtagcac catgattatc caagtgaca gctttggtaa cgtcagcggt 120
caatatgtta atcgtgcaca gggtacgggt tgtcagaatt ctccgtaccc gctgaccggt 180
cgtgttaacg gcacgttcat cgctttcagc gtcggttgga acaattctac tgaaaattgc 240
aacagcgcga ccgttggac gggctatgca caagtgaatg caataacac gaaatcgtc 300
acgtcctgga atctggcgta tgagggtggc agcggtccgg ctattgaaca gggccaggat 360
accttccaat acgtccctac gaccgagaat aagtccttc tgaaagactt tcgccaaccg 420
agccagactg cgttgaaaga tgagccgacc catctggttg ttgcgaaaga gggcagcgtg 480
gcatcgagcg tgctgctgag cggtacggtt actgccaaaa acgaacaata cgtgtacttc 540
gatgctagca agggtgatct ggatgaaatt ctggtgagcg tgggtgacaa agttagcgaa 600
ggccaggcac tggtgaagta ttcatcctcc gaggcacagg cagcgtacga cagccgcaag 660
cgcgcagtgg cgcgtgccga ccgtcacatt aacgaattga accaagcgcg taacgaggcc 720
gcaagcgcgc cagcaccgca gctgccggct ccggtgggtg gcgaagatgc gacggtgcag 780
agcccgaccc cggttgcggg taattcggtc gccagcatcg atgcgcagct gggtgacgcg 840
cgtgatgccc gtgcggatgc ggctgctcaa ctgagcaagg ctcagagcca actgacgcg 900
acgacggtgc tgagcacctt ggagggtacc gttgtcgaag tcaacagcaa tgtgagcaag 960
agcccaacgg gtgcgagcca ggttatggtc cacattgtga gcaatgaaaa cttacaggtc 1020
aagggtgagc tgagcgagta taacctggcg aatctgagcg ttggtcaaga ggtcagcttt 1080
accagcaagg tctacccgga taagaaatgg accggcaagt tgagctacat cagcgactac 1140
ccgaagaaca atggcgaggc agcctccccg gcagccggca acaataccgg ctctaagtat 1200
ccgtacacca tcgacgtaac cggtgaggtc ggcgacctga acaggggttt tagcgtgaat 1260
atcgaagtga agtccaagac caaggcaatt ttggttccgg ttagctccct ggtgatggac 1320
gatacaagaa ttatgtgtg gattgtcgac gagcaacaga aagcgaaaaa agttgaagtg 1380
agcctgggca atgctgatgc cgagaaccaa gaaatcacgt ctggtctgac caacggtgcg 1440
aaagttatta gcaacccgac cagcagcctg gaagagggta agaggtcaa agccgacgaa 1500
gctacgaaca ccagcggcga caattggtcc aaataccaga gcaacaagag catcacgatc 1560
ggcttcgaca gcacttttgt gccgatgggt tcgcgcaaa aagacggtag ctacgcgggt 1620
ttcgatattg acctggcgac cgctgtcttt gagaaatacg gcattacggt taattgcag 1680
ccgattgatt gggacctgaa agaggccgaa ctcaccaaag gcaccatcga cctgatctgg 1740
aatggttact ccgcaaccga tgagcgtcgc gaaaagttg ccttcagcaa cagctatatg 1800
aagaatgaac aagtgttggt aaccaagaaa tctagcggca ttacgaccgc gaaagacatg 1860
accggtaaga cgctgggtgc gcaggccggt agctctggct atgcggattt cgaggcgaat 1920
cctgagattc tgaaaaacat cgttgcgaat aaagaggcga accagtacca gaccttaac 1980
gaagcactga tcgacctgaa aaacgatcgc attgacggtc tgctgatcga tcgtgtgtac 2040
gcgaactatt atctggaagc cgagggcgtt ctgaacgatt ataatgtttt taccgtgggt 2100
ctggagactg aggcattcgc ggttggtgcg cgcaaagaag ataccaacct ggttaaaaag 2160
attaatgagg catttagctc actgtacaag gacggcaagt tccaagaaat tagccagaag 2220
tggttcggtg aagatgttgc gacgaaagag gttaaagagg gccaa          2265

SEQ ID NO: 31        moltype = DNA  length = 2265
FEATURE              Location/Qualifiers
misc_feature         1..2265
                     note = Description of Artificial Sequence: Synthetic
                     polynucleotide
source               1..2265
                     mol_type = other DNA
                     organism = synthetic construct
SEQUENCE: 31
atgaccagcg gcgacaattg gtccaaatac cagagcaaca agagcatcac gatcggcttc 60
gacagcactt ttgtgccgat gggtttcgcg caaaagacg gtagctacgc gggtttcgat 120
attgacctgc gaccgctgt ctttgagaaa tacggcatta cggttaattg gcagccgatt 180
```

```
gattgggacc tgaaagaggc cgaactcacc aaaggcacca tcgacctgat ctggaatggt    240
tactccgcaa ccgatgagcg tcgcgaaaaa gttgccttca gcaacagcta tatgaagaat    300
gaacaagtgt tggtaaccaa gaaatctagc ggcattacga ccgcgaaaga catgaccggt    360
aagacgctgg gtgcgcaggc cggtagctct ggctatgcgg atttcgaggc gaatcctgag    420
attctgaaaa acatcgttgc gaataaagag gcgaaccagt accagacctt taacgaagca    480
ctgatcgacc tgaaaaacga tcgcattgac ggtctgctga tcgatcgtgt gtacgcgaac    540
tattatctgg aagccagggg cgttctgaac gattataatg ttttaccgt gggtctggag     600
actgaggcat tcgcggttgg tgcgcgcaag gaagatacca acctggttaa aaagattaat    660
gaggcattta gctcactgta caaggacggc aagttccaag aaattagcca gaagtggttc    720
ggtgaagatg ttgcgacgaa agaggttaaa gagggccaat ttcgccaacc gagccagact    780
gcgttgaaag atgagccgac ccatctggtt gttgcgaaaa agggcagcgt ggcatcgagc    840
gtgctgctga gcggtacggt tactgccaaa aacgaacaat acgtgtactt cgatgctagc    900
aagggtgatc tggatgaaat tctggtgagc gtgggtgaca agttagcga aggccaggca    960
ctggtgaagt attcatcctc cgaggcacag gcagcgtacg acagccgcaa ccgcgcagtg   1020
gcgcgtgccg accgtcacat taacgaattg aaccaagcgc gtaacgaggc cgcaagcgcg   1080
ccagcaccgc agctgccggc tccggtgggt ggcgaagatg cgacggtgca gagcccgacc   1140
ccggttgcgg gtaattcggt cgccagcatc gatgcgcagc tgggtgacgc gcgtgatgcc   1200
cgtcgcgatg cggctgctca actgagcaag gctcagagcc aactgagcgg cgacggtg    1260
ctgagcacct tggagggtac cgttgtcgaa gtcaacagca atgtgagcaa gagcccaacg   1320
ggtgcgagcc aggttatggt ccacattgtg agcaatgaaa acttacaggt caagggtgag   1380
ctgagcgagt ataacctggc gaatctgagc gttggtcaag aggtcagctt taccagcaag   1440
gtctacccgg ataagaaatg gaccgccaag ttgagctaca tcagcgacta cccgaagaac   1500
aatggcgagg cagcctcccc ggcagccggc aacaataccg gctctaagta tccgtacacc   1560
atcgacgtaa ccggtgaggt cggcgacctg aaacagggtt ttagcgtgaa tatcgaagtg   1620
aagtccaaga ccaaggcaat tttggttccg gttagctccc tggtgatgga cgatagcaag   1680
aattatgtgt ggattgtcga cgagcaacag aaagcgaaaa aagttgaagt ggcctgggc    1740
aatgctgatg ccgagaacca agaaatcacg tctggtctga ccaacggtgc gaaagttatt   1800
agcaacccga ccagcagcct ggaagagggt aaagaggtca agccgacga agctacgaac    1860
ttcgacgcat ccaactttaa agactttagc agcatcgcgt ccgcaagctc tagctggcag   1920
aatcaatctg gtagcaccat gattatccaa gtggacagct tggtaacgt cagcggtcaa    1980
tatgttaatc gtgcacaggg tacgggttgt cagaattctc cgtacccgct gaccggtcgt   2040
gttaacggca cgttcatcgc tttcagcgtc ggttggaaca attctactga aaattgcaac   2100
agcgcgaccg gttggacggg ctatgcacaa gtgaatggca taacaccga aatcgtcacg    2160
tcctggaatc tggcgtatga gggtggcagc ggtccggcta ttgaacaggg ccaggatacc   2220
ttccaatacg tccctacgac cgagaataag tcccttctga aagac                   2265
```

SEQ ID NO: 32          moltype = DNA   length = 2265
FEATURE                Location/Qualifiers
misc_feature           1..2265
                       note = Description of Artificial Sequence: Synthetic
                       polynucleotide
source                 1..2265
                       mol_type = other DNA
                       organism = synthetic construct
SEQUENCE: 32

```
atgtttcgcc aaccgagcca gactgcgttg aaagatgagc cgacccatct ggttgttgcg     60
aaagagggca gcgtggcatc gagcgtgctg ctgagcggta cggttactgc caaaaacgaa    120
caatacgtgt acttcgatgc tagcaagggt gatctggatg aaattctggt gagcgtgggt    180
gacaaagtta gcgaaggcca ggcactggtg aagtattcat cctccgaggc acaggcagcg   240
tacgacagcc gcaacgcgcg agtggcgcgt gccgaccgtc acattaacga attgaaccaa    300
gcgcgtaacg aggccgcaag cgcgccagca ccgcagctgc cggctccgt gggtggcgaa     360
gatgcgacgg tgcagagccc gaccccggtt gcgggtaatt cggtcgccag catcgatgcg   420
cagctgggtg acgcgcgtga tgcccgtcgc gatgcggctg ctcaactgag caaggctcag    480
agccaactgg acgcgacgac ggtgctgagc accttggagg gtaccgttgt cgaagtcaac   540
agcaatgtga gcaagagccc aacggtgcg agccaggtta tggtccacat tgtgagcaat    600
gaaaacttac aggtcaaggg tgagctgagc gagtataacc tggcgaatct gagcgttggt   660
caagaggtca gctttaccag caaggtctac ccggataaga aatggaccgg caagttgagc    720
tacatcagcg actacccgaa gaacaatggc gaggcagcct ccccggcagc cggcaacaat   780
accggctcta agtatccgta caccatcgac gtaaccggtg aggtcggcga cctgaaacag   840
ggttttagcg tgaatatcga agtgaagtcc aagaccaagg caattttggt tccggttagc    900
tccctggtga tggacgatag caagaattat gtgtggattg tcgacgagca acagaaagcg    960
aaaaaagttg aagtgagcct gggcaatgct gatgccgaga accaagaaat cacgtctggt   1020
ctgaccaacg gtgcgaaagt tattagcaac ccgaccagca gcctgaaaga gggtaaagag   1080
gtcaaagcg acgaagctac gaaccagcag ggcgacaatt ggtccaaata ccagagcaac    1140
aagagcatca cgatcggctt cgacagcact tttgtgccga tgggtttcgc gcaaaaagac   1200
ggtagctacg cgggtttcga tattgacctg cgcaccgctg tctttgagaa atacggcatt   1260
acggttaatt ggcagccgat tgattgggac ctgaaagagg ccgaactcac caaaggcacc   1320
atcgacctga tctggaatgg ttactccgca accgatgagc gtcgcgaaaa agttgccttc    1380
agcaacagct atatgaagaa tgaacaagtg ttggtaacca agaaatctag cggcattacg   1440
accgcgaaag acatgaccgg taagacgctg gtgcgcagg ccggtagctc tggctatgcg    1500
gatttcgagg cgaatcctga gattctgaaa aacatcgttg cgaataaaga ggcgaaccag   1560
taccagacct ttaacgaagc actgatcgac ctgaaaaacg atcgcattga cggtctgctg   1620
atcgatcgtg tgtacgcgaa ctattatctg gaagccgagg gcgttctgaa cgattataat   1680
gttttaccgg tgggtctgga gactgaggca ttcgcggttg gtgcgcgcaa ggaagatacc   1740
aacctggtta aaaagattaa tgaggcattt agctcactgt acaaggacgg caagttccaa   1800
gaaattagcc agaagtggtt cggtgaagat gttgcgacga aagaggttaa agagggccaa   1860
ttcgacgcat ccaactttaa agactttagc agcatcgcgt ccgcaagctc tagctggcag   1920
aatcaatctg gtagcaccat gattatccaa gtggacagct tggtaacgt cagcggtcaa    1980
tatgttaatc gtgcacaggg tacgggttgt cagaattctc cgtacccgct gaccggtcgt   2040
```

```
gttaacggca cgttcatcgc tttcagcgtc ggttggaaca attctactga aaattgcaac  2100
agcgcgaccg gttggacggg ctatgcacaa gtgaatggca ataacaccga aatcgtcacg  2160
tcctggaatc tggcgtatga gggtggcagc ggtccggcta ttgaacaggg ccaggatacc  2220
ttccaatacg tccctacgac cgagaataag tcccttctga aagac                 2265

SEQ ID NO: 33           moltype = DNA  length = 2295
FEATURE                 Location/Qualifiers
misc_feature            1..2295
                        note = Description of Artificial Sequence: Synthetic
                         polynucleotide
source                  1..2295
                        mol_type = other DNA
                        organism = synthetic construct
SEQUENCE: 33
atgttcgacg catccaactt taaagacttt agcagcatcg cgtccgcaag ctctagctgg  60
cagaatcaat ctggtagcac catgattatc caagtggaca gctttggtaa cgtcagcggt  120
caatatgtta atcgtgcaca gggtacgggt tgtcagaatt ctccgtaccc gctgaccggt  180
cgtgttaacg gcacgttcat cgctttcagc gtcggttgga acaattctac tgaaaattgc  240
aacagcgcga ccggttggac gggctatgca caagtgaatg gcaataacac cgaaatcgtc  300
acgtcctgga atctggcgta tgagggtggc agcggtccgg ctattgaaca gggccaggat  360
accttccaat acgtccctac gaccgagaat aagtcccttc tgaaagacgg cggtggcggt  420
tcgagctcga ccagcggcga caattggtcc aaataccaga gcaacaagag catcacgatc  480
ggcttcgaca gcactttgt gccgatgggt ttcgcgcaaa aagacggtag ctacgcgggt  540
ttcgatattg acctggcgac cgctgtcttt gagaaatacg gcattacggt taattggcag  600
ccgattgatt gggacctgaa agaggccgaa ctcaccaaag caccatcga cctgatctgg  660
aatgttact ccgcaaccga tgagcgtcgc gaaaaagttg ccttcagcaa cagctatatg  720
aagaatgaac aagtgttggt aaccaagaaa tctagcggca ttacgaccgc gaaagacatg  780
accggtaaga cgctgggtgc gcaggccggt agctctggct atgcggattt cgaggcgaat  840
cctgagattc tgaaaaacat cgttgcgaat aaagaggcga accagtacca gacctttaac  900
gaagcactga tcgacctgaa aaacgatcgc attgacggtc tgctgatcga tcgtgtgtac  960
gcgaactatt atctggaagc cgagggcgtt ctgaacgatt ataatgtttt taccgtgggt  1020
ctggagactg aggcattcgc ggttggtgcg cgcaaggaag ataccaacct ggttaaaaag  1080
attaatgagg catttagctc actgtacaag gacggcaagt ccaagaaat tagccagaag  1140
tggttcggtg aagatgttgc gacgaaagag gttaaagagg gccaagcggc cgcatttcgc  1200
caaccagccc agactgcgtt gaaagatgag ccgacccatc tggttgttgc gaaagaggc  1260
agcgtggcat cgagcgtgct gctgagcggt acgttactg ccaaaaacga acaatcgtg  1320
tacttcgatg ctagcaaggg tgatctggat gaaattctgg tgagcgtggg tgacaaagtt  1380
agcgaaggcc aggcactggt gaagtattca tcctccgagg cacaggcagc gtacgacagc  1440
gcaagcgcg cagtggcgcg tgccgaccgt cacattaacg aattgaacca agcgcgtaac  1500
gaggccgcaa gcgcgccagc accgcagctg ccggctccgg tgggtggcga agatgcgacg  1560
gtgcagagcc cgaccccggt tgcgggtaat tcggtcgcca gcatcgatgc gcagctgggt  1620
gacgcgcgtg atgcccgtgc ggatgcggct gctcaactga gcaaggctca gagccaactg  1680
gacgcgacga cggtgctgag caccttggag gtaccggttg tcgaagtcaa cagcaatgtg  1740
agcaagagcc aacgggtgc gagccaggtt atggtccaca ttgtgagcaa tgaaaactta  1800
caggtcaagg gtgagctgag cgagtataac ctggcgaatc tgagcgttgg tcaagaggtc  1860
agctttacca gcaaggtcta cccggataag aaatggaccg gcaagttgag ctacatcagc  1920
gactacccga agaacaatgg cgaggcagcc tccccggcaa cacaa taccggctct  1980
aagtatccgt acaccatcga cgtaaccggt gaggtcggcg acctgaaaca gggtttagc  2040
gtgaatatcg aagtgaagtc caagaccaag gcaattttgg ttccggttag ctccctggtg  2100
atggacgata gcaagaatta tgtgtggatt gtcgacgagc aacagaaagc gaaaaaagtt  2160
gaagtgagcc tgggcaatgc tgatgccgag aaccaagaaa tcacgtctgg tctgaccaac  2220
ggtgcgaaag ttattagcaa cccgaccagc agcctggaag agggtaaaga ggtcaaagcc  2280
gacgaagcta cgaac                                                  2295

SEQ ID NO: 34           moltype = DNA  length = 2294
FEATURE                 Location/Qualifiers
misc_feature            1..2294
                        note = Description of Artificial Sequence: Synthetic
                         polynucleotide
source                  1..2294
                        mol_type = other DNA
                        organism = synthetic construct
SEQUENCE: 34
atgttcgacg catccaactt taaagacttt agcagcatcg cgtccgcaag ctctagctgg  60
cagaatcaat ctggtagcac catgattatc caagtggaca gctttggtaa cgtcagcggt  120
caatatgtta atcgtgcaca gggtacgggt tgtcagaatt ctccgtaccc gctgaccggt  180
cgtgttaacg gcacgttcat cgctttcagc gtcggttgga acaattctac tgaaaattgc  240
aacagcgcga ccggttggac gggctatgca caagtgaatg gcaataacac cgaaatcgtc  300
acgtcctgga atctggcgta tgagggtggc agcggtccgg ctattgaaca gggccaggat  360
accttccaat acgtccctac gaccgagaat aagtcccttc tgaaagacgg cggtggcggt  420
tcgagctcgt ttcgccaacc gagccagact gcgttgaaag atgagccgac ccatctggtt  480
gttgcgaaag gggcagcgt ggcatcgagc gtgctgctga gcggtacggt tactgccaaa  540
aacgaacaat cgtgtactt cgatgctagc aagggtgatc tggatgaaat tctggtgagc  600
gtgggtgaca aagttagcga aggccaggca ctggttaagt attcatcctc cgaggcacag  660
gcagcgtacg acagcgcaag ccgcgcagtg gcgcgtgccg accgtcacat taacgaattg  720
aaccaagcgc gtaacgaggc cgcaagcgcg ccagcaccgc agctgccggc tccggtgggt  780
ggcgaagatg cgacggtgca gagcccgacc ccggttgcgg gtaattcggt cgccagcatc  840
gatgcgcagc tgggtgacgc gcgtgatgcc cgtgcggatg cggctgctca actgagcaag  900
gctcagagcc aactggacgc gacgacggtg ctgagcacct tggagggtac cgttgtcgaa  960
```

-continued

```
gtcaacagca atgtgagcaa gagcccaacg ggtgcgagcc aggttatggt ccacattgtg  1020
agcaatgaaa acttacaggt caagggtgag ctgagcgagt ataacctggc gaatctgagc  1080
gttggtcaag aggtcagctt taccagcaag gtctacccgg ataagaaatg gaccggcaag  1140
ttgagctaca tcagcgacta cccgaagaac aatggcgagg cagcctcccc ggcagccggc  1200
aacaataccg gctctaagta tccgtacacc atcgacgtaa ccggtgaggt ccgcgacctg  1260
aaacagggtt ttagcgtgaa tatcgaagtg aagtccaaga ccaaggcaat tttggttccg  1320
gttagctccc tggtgatgga cgatagcaag aattatgtgt ggattgtcga cgagcaacag  1380
aaagcgaaaa aagttgaagt gagcctgggc aatgctgatg ccgagaacca agaaatcacg  1440
tctggtctga ccaacggtgc gaaagttatt agcaacccga ccagcagcct ggaagagggt  1500
aaagaggtca aagccgacga agctacgaac cggccgcaac cagcggcgac aattggtcca  1560
aataccagag caacaagagc atcacgatcg gcttcgacag cacttttgtg ccgatgggtt  1620
tcgcgcaaaa agacggtagc tacgcgggtt tcgatattga cctggcgacc gctgtctttg  1680
agaaatacgg cattacggtt aattggcagc cgattgattg ggacctgaaa gaggccgaac  1740
tcaccaaagg caccatcgac ctgatctgga atggttactc cgcaaccgat gagcgtcgcg  1800
aaaaagttgc cttcagcaac agctatatga agaatgaaca agtgttggta accaagaaat  1860
ctagcggcat tacgaccgcg aaagacatga ccggtaagac gctgggtgcg caggccggta  1920
gctctggcta tgcggatttc gaggcgaatc ctgagattct gaaaaacatc gttgcgaata  1980
aagaggcgaa ccagtaccag acctttaacg aagcactgat cgacctgaaa aacgatcgca  2040
ttgacggtct gctgatcgat cgtgtgtacg cgaactatta tctggaagcc gagggcgttc  2100
tgaacgatta taatgttttt accgtgggtc tggagactga ggcattgcgc gttggtgcgc  2160
gcaaggaaga taccaacctg gttaaaaaga ttaatgaggc atttagctca ctgtacaagg  2220
acggcaagtt ccaagaaatt agccagaagt ggttcggtga agatgttgcg acgaaagagg  2280
ttaaagaggg ccaa                                                   2294
```

SEQ ID NO: 35        moltype = DNA  length = 2294
FEATURE              Location/Qualifiers
misc_feature      1..2294
                     note = Description of Artificial Sequence: Synthetic
                     polynucleotide
source              1..2294
                     mol_type = other DNA
                     organism = synthetic construct
SEQUENCE: 35

```
atgaccagcg gcgacaattg gtccaaatac cagagcaaca agagcatcac gatcggcttc  60
gacagcactt ttgtgccgat gggtttcgcg caaaaagacg gtagctacgc gggtttcgat  120
attgacctgg cgaccgctgt ctttgagaaa tacggcatta cggttaattg gcagccgatt  180
gattgggacc tgaaagaggc cgaactcacc aaaggcacca tcgacctgat ctggaatggt  240
tactccgcaa ccgatgagcg tcgcgaaaaa gttgccttca gcaacagcta tatgaagaat  300
gaacaagtgt tggtaaccaa gaaatctagc ggcattacga ccgcgaaaga catgaccggt  360
aagacgctgg gtgcgcaggc cggtagctct ggctatgcgg atttcgaggc gaatcctgag  420
attctgaaaa acatcgttgc gaataaagag gcgaaccagt accagacctt taacgaagca  480
ctgatcgacc tgaaaaacga tcgcattgac ggtctgctga tcgatcgtgt gtacgcgaac  540
tattatctgg aagccgaggg cgttctgaac gattataatg tttttaccgt gggtctggag  600
actgaggcat tgcgcgttgg tgcgcgcaag gaagatacca acctggttaa aaagattaat  660
gaggcattta gctcactgta caaggacggc aagttccaag aaattagcca gaagtggttc  720
ggtgaagatg ttgcgacgaa agaggttaaa gagggccaag cggtggcgg ttcgagctcg  780
tttcgccaac cgagccagac tgcgttgaaa gatgagccga cccatctggt tgttgcgaaa  840
gagggcagcg tggcatcgag cgtgctgctg agcggtacgc ttactgccaa aaacgaacaa  900
tacgtgtact tcgatgctag caagggtgat ctggatgaaa ttctggtgag cgtgggtgac  960
aaagttagcg aaggccaggc actggtgaag tattcatcct ccgaggcaca ggcagcgtac  1020
gacagcgcaa gccgcgcagt ggcgcgtgcc gaccgtcaca ttaacgaatt gaaccaagcg  1080
cgtaacgagg ccgcaagcgc gccagcaccg cagctgccgg ctccggtggg tgcgaagat  1140
gcgacggtgc agagcccgac cccggttgcg ggtaattcgg tcgccagcat cgatgcgcag  1200
ctgggtgacg cgcgtgatgc ccgtgcggat gcggctgctc aactgagcaa ggctcagagc  1260
caactggacg cgacgcggt gctgagcacc ttggagggta ccgttgtcga agtcaacagc  1320
aatgtgagca agagcccaac gggtgcgagc caggttatgg tccacattgt gagcaatgaa  1380
aacttacagg tcaagggtga gctgagcgag tataacctgg cgaatctgag cgttggtcaa  1440
gaggtcagct ttaccagcaa ggtctacccg gataagaaat ggaccggcaa gttgagctac  1500
atcagcgact acccgaagaa caatggcgag gcagcctccc cggcagccgg caacaatacc  1560
ggctctaagt atccgtacac catcgacgta accggtgagg tccgcgacct gaaacagggt  1620
tttagcgtga atatcgaagt gaagtccaag accaaggcaa ttttggttcc ggttagctcc  1680
ctggtgatgg acgatagcaa gaattatgtg tggattgtcg acgagcaaca gaaagcgaaa  1740
aaagttgaag tgagcctggg caatgctgat gccgagaacc aagaaatcac gtctggtctg  1800
accaacggtg cgaaagttat tagcaacccg accagcagcc tggaagaggg taaagaggtc  1860
aaagccgacg aagctacgaa ccggccgcat tcgacgcatc aactttaaa gactttagca  1920
gcatcgcgtc cgcaagctct agctggcaga atcaatctgg tagcaccatg attatccaag  1980
tggacagctt tggtaacgtc agcggtcaat atgttaatcg tgcacagggt acgggttgtc  2040
agaattctcc gtacccgctg accggtcgtg ttaacggcac gttcatcgct ttcagcgtcg  2100
gttggaacaa ttctactgaa aattgcaaca gcgcagccgg tttggtgcc tatgcaacaag  2160
tgaatgcgcaa taacaccgaa atcgtcacgt cctggaatct ggcgtatgag ggtggcagcg  2220
gtccggctat tgaacagggc caggatacct tccaatacgt ccctacgacc gagaataagt  2280
cccttctgaa agac                                                   2294
```

SEQ ID NO: 36        moltype = DNA  length = 2294
FEATURE              Location/Qualifiers
misc_feature      1..2294
                     note = Description of Artificial Sequence: Synthetic
                     polynucleotide
source              1..2294

```
                        mol_type = other DNA
                        organism = synthetic construct
SEQUENCE: 36
atgtttcgcc aaccgagcca gactgcgttg aaagatgagc cgacccatct ggttgttgcg    60
aaagagggca gcgtggcatc gagcgtgctg ctgagcggta cggttactgc caaaaacgaa   120
caatacgtgt acttcgatgc tagcaagggt gatctggatg aaattctggt gagcgtgggc   180
gacaaagtta gcgaaggcca ggcactggtg aagtattcat cctccgaggc acaggcagcg   240
tacgacagcg caagccgcgc agtggcgcgt gccgaccgtc acattaacga attgaaccaa   300
gcgcgtaacg aggccgcaag cgcgccagca ccgcagctgc cggctccggt gggtggcgaa   360
gatgcgacgg tgcagagccc gaccccggtt gcgggtaatt cggtcgccag catcgatgcg   420
cagctgggtg acgcgcgtga tgcccgtgcg gatcggctg ctcaactgag caaggctcag    480
agccaactgg acgcgacgac ggtgctgagc accttggagg gtaccgttgt cgaagtcaac   540
agcaatgtga gcaagagccc aacgggtgcg agccaggtta tggtccacat tgtgagcaat   600
gaaaacttac aggtcaaggg tgagctgagc gagtataacc tggcgaatct gagcgttggt   660
caagaggtca gctttaccag caaggtctac ccggataaga aatggaccgg caagttgagc   720
tacatcagcg actacccgaa gaacaatggc gaggcagcct ccccggcagc cggcaacaat   780
accggctcta agtatccgta caccatcgac gtaaccggtg aggtcggcga cctgaaacag   840
ggttttagcg tgaatatcga agtgaagtcc aagaccaagg caattttggt tccggttagc   900
tccctggtga tggacgatag caagaattat gtgtggattg tcgacagcga acagaaagcg   960
aaaaaagttg aagtgagcct gggcaatgct gatgccgaga accaagaaat cacgtctggt  1020
ctgaccaacg gtgcgaaagt tattagcaac ccgaccagca gcctgaagaa gggtaaagag  1080
gtcaaagccg acgaagctac gaacgcggt ggcggttcga gctcgaccag ggcgacaat    1140
tggtccaaat accagagcaa caagagcatc acgatcggct tcgacagcac tttttgtgccg  1200
atgggtttcg cgcaaaaaga cggtagctac gcgggtttcg atattgacct ggcgaccgct  1260
gtctttgaga aatacggcat tacggttaat tggcagccga ttgattggga cctgaaagag  1320
gccgaactca ccaaaggcac catcgacctg atctggaatg gttactccga aaccgatgag  1380
cgtcgcgaaa aagttgcctt cagcaacagc tatatgaaga atgaacaagt gttggtaacc  1440
aagaaatcta gcggcattac gaccgcgaaa gacatgaccg gtaagacgct gggtgcgcag  1500
gccggtagct ctggctatgc ggatttcgag gcgaatcctg agattctgaa aaacatcgtt  1560
gcgaataaag aggcgaacca gtaccagacc tttaacgaag cactgatcga cctgaaaaac  1620
gatcgcattg acggtctgct gatcgatcgt gtgtacgcga actattatct ggaagccgaa  1680
ggcgttctga acgattataa tgttttttacc gtgggtctgg agactgaggc attcgcggtt  1740
ggtgcgcgca aggaagatac caacctggtt aaaaagatta tgaggcatt tagctcactg     1800
tacaaggacg gcaagttcca agaaattagc caagaagtggt tcggtgaaga tgttgcgaag  1860
aaagaggtta aagagggcca acggccgcat tcgacgcatc caactttaaa gactttagca  1920
gcatcgcgtc cgcaagctct agctggcaga atcaatctgg tagcaccatg attatccaag  1980
tggacagctt tggtaacgtc agcggtcaat atgttaatcg tgcacagggt acgggttgtc  2040
agaattctcc gtacccgctg accggtcgtg ttaacggcac gttcatcgct ttcagcgtcg  2100
gttggaacaa ttctactgaa aattgcaaca gcgcgaccgg ttggacgggc tatgcacaag  2160
tgaatggcaa taacaccgaa atcgtcacgt cctggaatct ggcgtatgag ggtggcagcg  2220
gtccggctat tgaacagggc caggatacct tccaatacgt ccctacgacc gagaataagt  2280
cccttctgaa agac                                                    2294

SEQ ID NO: 37          moltype = AA  length = 7
FEATURE                Location/Qualifiers
REGION                 1..7
                       note = Description of Artificial Sequence: Synthetic peptide
source                 1..7
                       mol_type = protein
                       organism = synthetic construct
SEQUENCE: 37
GGGGSSS                                                               7

SEQ ID NO: 38          moltype =   length =
SEQUENCE: 38
000

SEQ ID NO: 39          moltype = AA  length = 150
FEATURE                Location/Qualifiers
REGION                 1..150
                       note = Description of Artificial Sequence: Synthetic
                        polypeptide
REGION                 1..150
                       note = MISC_FEATURE-This sequence may encompass 1-20, 25,
                        or 30 "Xaa Pro" repeating units
REGION                 1..150
                       note = See specification as filed for detailed description
                        of substitutions and preferred embodiments
source                 1..150
                       mol_type = protein
                       organism = synthetic construct
SEQUENCE: 39
GGGGSGGGGS GGGGSGGGGS GGGGSGGGGS GGGGSGGGGS GGGGSGGGGS GGGGSGGGGS     60
GGGGSGGGGS GGGGSGGGGS GGGGSGGGGS GGGGSGGGGS GGGGSGGGGS GGGGSGGGGS    120
GGGGSGGGGS GGGGSGGGGS GGGGSGGGGS                                    150

SEQ ID NO: 40          moltype = AA  length = 6
FEATURE                Location/Qualifiers
REGION                 1..6
```

```
                        note = Description of Artificial Sequence: Synthetic peptide
source                  1..6
                        mol_type = protein
                        organism = synthetic construct
SEQUENCE: 40
GGGGGG                                                                          6

SEQ ID NO: 41           moltype = AA  length = 15
FEATURE                 Location/Qualifiers
REGION                  1..15
                        note = Description of Artificial Sequence: Synthetic peptide
source                  1..15
                        mol_type = protein
                        organism = synthetic construct
SEQUENCE: 41
GGGGSGGGGS GGGGS                                                                15

SEQ ID NO: 42           moltype = AA  length = 30
FEATURE                 Location/Qualifiers
REGION                  1..30
                        note = Description of Artificial Sequence: Synthetic
                         polypeptide
source                  1..30
                        mol_type = protein
                        organism = synthetic construct
SEQUENCE: 42
GGGGSGGGGS GGGGSGGGGS GGGGSGGGGS                                                30

SEQ ID NO: 43           moltype = AA  length = 18
FEATURE                 Location/Qualifiers
REGION                  1..18
                        note = Description of Artificial Sequence: Synthetic peptide
source                  1..18
                        mol_type = protein
                        organism = synthetic construct
SEQUENCE: 43
KESGSVSSEQ LAQFRSLD                                                             18

SEQ ID NO: 44           moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 44
EGKSSGSGSE SKST                                                                 14

SEQ ID NO: 45           moltype = AA  length = 30
FEATURE                 Location/Qualifiers
REGION                  1..30
                        note = Description of Artificial Sequence: Synthetic
                         polypeptide
REGION                  1..30
                        note = MISC_FEATURE - This sequence may encompass 1-20, 25
                         or 30 residues
REGION                  1..30
                        note = See specification as filed for detailed description
                         of substitutions and preferred embodiments
source                  1..30
                        mol_type = protein
                        organism = synthetic construct
SEQUENCE: 45
GGGGGGGGGG GGGGGGGGGG GGGGGGGGGG                                                30

SEQ ID NO: 46           moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 46
GGGGGGGG                                                                        8

SEQ ID NO: 47           moltype = AA  length = 12
FEATURE                 Location/Qualifiers
REGION                  1..12
                        note = Description of Artificial Sequence: Synthetic peptide
```

```
                        -continued source                  1..12
                        mol_type = protein
                        organism = synthetic construct
SEQUENCE: 47
GSAGSAAGSG EF                                                             12

SEQ ID NO: 48           moltype = AA  length = 150
FEATURE                 Location/Qualifiers
REGION                  1..150
                        note = Description of Artificial Sequence: Synthetic
                         polypeptide
REGION                  1..150
                        note = MISC_FEATURE - This sequence may encompass 1-20, 25
                         or 30"Glu Ala Ala Ala Lys" repeating units
REGION                  1..150
                        note = See specification as filed for detailed description
                         of substitutions and preferred embodiments
source                  1..150
                        mol_type = protein
                        organism = synthetic construct
SEQUENCE: 48
EAAAKEAAAK EAAAKEAAAK EAAAKEAAAK EAAAKEAAAK EAAAKEAAAK EAAAKEAAAK          60
EAAAKEAAAK EAAAKEAAAK EAAAKEAAAK EAAAKEAAAK EAAAKEAAAK EAAAKEAAAK         120
EAAAKEAAAK EAAAKEAAAK EAAAKEAAAK                                         150

SEQ ID NO: 49           moltype = AA  length = 152
FEATURE                 Location/Qualifiers
REGION                  1..152
                        note = Description of Artificial Sequence: Synthetic
                         polypeptide
REGION                  2..151
                        note = MISC_FEATURE - This region may encompass 1-20, 25 or
                         30"Glu Ala Ala Ala Lys" repeating units
REGION                  1..152
                        note = See specification as filed for detailed description
                         of substitutions and preferred embodiments
source                  1..152
                        mol_type = protein
                        organism = synthetic construct
SEQUENCE: 49
AEAAAKEAAA KEAAAKEAAA KEAAAKEAAA KEAAAKEAAA KEAAAKEAAA KEAAAKEAAA          60
KEAAAKEAAA KEAAAKEAAA KEAAAKEAAA KEAAAKEAAA KEAAAKEAAA KEAAAKEAAA         120
KEAAAKEAAA KEAAAKEAAA KEAAAKEAAA KA                                      152

SEQ ID NO: 50           moltype = AA  length = 46
FEATURE                 Location/Qualifiers
REGION                  1..46
                        note = Description of Artificial Sequence: Synthetic
                         polypeptide
source                  1..46
                        mol_type = protein
                        organism = synthetic construct
SEQUENCE: 50
AEAAAKEAAA KEAAAKEAAA KALEAEAAAK EAAAKEAAAK EAAAKA                        46

SEQ ID NO: 51           moltype = AA  length = 44
FEATURE                 Location/Qualifiers
REGION                  1..44
                        note = Description of Artificial Sequence: Synthetic
                         polypeptide
REGION                  1..44
                        note = MISC_FEATURE - This sequence may encompass 1-2
                         "A(EAAAK)nA"repeating units where n=2-4
REGION                  1..44
                        note = See specification as filed for detailed description
                         of substitutions and preferred embodiments
source                  1..44
                        mol_type = protein
                        organism = synthetic construct
SEQUENCE: 51
AEAAAKEAAA KEAAAKEAAA KAAEAAAKEA AAKEAAAKEA AAKA                          44

SEQ ID NO: 52           moltype = AA  length = 12
FEATURE                 Location/Qualifiers
REGION                  1..12
                        note = Description of Artificial Sequence: Synthetic peptide
source                  1..12
                        mol_type = protein
                        organism = synthetic construct
```

```
SEQUENCE: 52
AEAAAKEAAA KA                                                                   12

SEQ ID NO: 53           moltype = AA  length = 60
FEATURE                 Location/Qualifiers
source                  1..60
                        mol_type = protein
                        organism = synthetic construct
REGION                  1..60
                        note = MISC_FEATURE-This sequence may encompass 1-20, 25,
                        or 30 "Xaa Pro" repeating units
REGION                  1..60
                        note = Description of Artificial Sequence: Synthetic
                        Polypeptide
REGION                  1..60
                        note = See specification as filed for detailed description
                        of substitutions and preferred embodiments
VARIANT                 13
                        note = X is any amino acid
VARIANT                 29
                        note = X is any amino acid
VARIANT                 47
                        note = X is any amino acid
VARIANT                 35
                        note = X is any amino acid
VARIANT                 51
                        note = X is any amino acid
VARIANT                 17
                        note = X is any amino acid
VARIANT                 55
                        note = X is any amino acid
VARIANT                 19
                        note = X is any amino acid
VARIANT                 49
                        note = X is any amino acid
VARIANT                 25
                        note = X is any amino acid
VARIANT                 27
                        note = X is any amino acid
VARIANT                 3
                        note = X is any amino acid
VARIANT                 53
                        note = X is any amino acid
VARIANT                 23
                        note = X is any amino acid
VARIANT                 59
                        note = X is any amino acid
VARIANT                 31
                        note = X is any amino acid
VARIANT                 5
                        note = X is any amino acid
VARIANT                 33
                        note = X is any amino acid
VARIANT                 37
                        note = X is any amino acid
VARIANT                 7
                        note = X is any amino acid
VARIANT                 9
                        note = X is any amino acid
VARIANT                 57
                        note = X is any amino acid
VARIANT                 21
                        note = X is any amino acid
VARIANT                 45
                        note = X is any amino acid
VARIANT                 43
                        note = X is any amino acid
VARIANT                 15
                        note = X is any amino acid
VARIANT                 1
                        note = X is any amino acid
VARIANT                 11
                        note = X is any amino acid
VARIANT                 41
                        note = X is any amino acid
VARIANT                 39
                        note = X is any amino acid
SEQUENCE: 53
XPXPXPXPXP XPXPXPXPXP XPXPXPXPXP XPXPXPXPXP XPXPXPXPXP XPXPXPXPXP   60
```

```
SEQ ID NO: 54            moltype = AA  length = 60
FEATURE                  Location/Qualifiers
REGION                   1..60
                         note = Description of Artificial Sequence: Synthetic
                          polypeptide
REGION                   1..60
                         note = MISC_FEATURE - This sequence may encompass 1-20, 25
                          or 30 "Ala Pro"repeating units
REGION                   1..60
                         note = See specification as filed for detailed description
                          of substitutions and preferred embodiments
source                   1..60
                         mol_type = protein
                         organism = synthetic construct
SEQUENCE: 54
APAPAPAPAP APAPAPAPAP APAPAPAPAP APAPAPAPAP APAPAPAPAP APAPAPAPAP    60

SEQ ID NO: 55            moltype = AA  length = 60
FEATURE                  Location/Qualifiers
REGION                   1..60
                         note = Description of Artificial Sequence: Synthetic
                          polypeptide
REGION                   1..60
                         note = MISC_FEATURE - This sequence may encompass 1-20, 25
                          or 30 "Lys Pro"repeating units
REGION                   1..60
                         note = See specification as filed for detailed description
                          of substitutions and preferred embodiments
source                   1..60
                         mol_type = protein
                         organism = synthetic construct
SEQUENCE: 55
KPKPKPKPKP KPKPKPKPKP KPKPKPKPKP KPKPKPKPKP KPKPKPKPKP KPKPKPKPKP    60

SEQ ID NO: 56            moltype = AA  length = 60
FEATURE                  Location/Qualifiers
REGION                   1..60
                         note = Description of Artificial Sequence: Synthetic
                          polypeptide
REGION                   1..60
                         note = MISC_FEATURE - This sequence may encompass 1-20, 25
                          or 30 "Gln Pro"repeating units
REGION                   1..60
                         note = See specification as filed for detailed description
                          of substitutions and preferred embodiments
source                   1..60
                         mol_type = protein
                         organism = synthetic construct
SEQUENCE: 56
QPQPQPQPQP QPQPQPQPQP QPQPQPQPQP QPQPQPQPQP QPQPQPQPQP QPQPQPQPQP    60

SEQ ID NO: 57            moltype = AA  length = 14
FEATURE                  Location/Qualifiers
REGION                   1..14
                         note = Description of Artificial Sequence: Synthetic peptide
source                   1..14
                         mol_type = protein
                         organism = synthetic construct
SEQUENCE: 57
APAPAPAPAP APAP                                                     14

SEQ ID NO: 58            moltype = AA  length = 21
FEATURE                  Location/Qualifiers
REGION                   1..21
                         note = Description of Artificial Sequence: Synthetic peptide
source                   1..21
                         mol_type = protein
                         organism = synthetic construct
SEQUENCE: 58
GAPGGGGGAA AAAGGGGGGA P                                             21

SEQ ID NO: 59            moltype = AA  length = 39
FEATURE                  Location/Qualifiers
REGION                   1..39
                         note = Description of Artificial Sequence: Synthetic
                          polypeptide
source                   1..39
                         mol_type = protein
```

```
                           organism = synthetic construct
SEQUENCE: 59
GAPGGGGGAA AAAGGGGGA PGGGGGAAAA AGGGGGGAP                    39

SEQ ID NO: 60              moltype = AA   length = 57
FEATURE                    Location/Qualifiers
REGION                     1..57
                           note = Description of Artificial Sequence: Synthetic
                            polypeptide
source                     1..57
                           mol_type = protein
                           organism = synthetic construct
SEQUENCE: 60
GAPGGGGGAA AAAGGGGGA PGGGGGAAAA AGGGGGGAPG GGGGAAAAAG GGGGGAP    57

SEQ ID NO: 61              moltype = AA   length = 4
FEATURE                    Location/Qualifiers
REGION                     1..4
                           note = Description of Artificial Sequence: Synthetic peptide
source                     1..4
                           mol_type = protein
                           organism = synthetic construct
SEQUENCE: 61
GGGG                                                          4

SEQ ID NO: 62              moltype = AA   length = 5
FEATURE                    Location/Qualifiers
REGION                     1..5
                           note = Description of Artificial Sequence: Synthetic peptide
source                     1..5
                           mol_type = protein
                           organism = synthetic construct
SEQUENCE: 62
GGGGS                                                         5

SEQ ID NO: 63              moltype = AA   length = 5
FEATURE                    Location/Qualifiers
REGION                     1..5
                           note = Description of Artificial Sequence: Synthetic peptide
source                     1..5
                           mol_type = protein
                           organism = synthetic construct
SEQUENCE: 63
EAAAK                                                         5

SEQ ID NO: 64              moltype = AA   length = 10
FEATURE                    Location/Qualifiers
REGION                     1..10
                           note = Description of Artificial Sequence: Synthetic peptide
REGION                     1..10
                           note = MISC_FEATURE - This sequence may encompass 2-10
                            residues
source                     1..10
                           mol_type = protein
                           organism = synthetic construct
SEQUENCE: 64
HHHHHHHHHH                                                   10

SEQ ID NO: 65              moltype = AA   length = 5
FEATURE                    Location/Qualifiers
source                     1..5
                           mol_type = protein
                           organism = Streptococcus pneumoniae
SEQUENCE: 65
PAPAP                                                         5

SEQ ID NO: 66              moltype = AA   length = 6
FEATURE                    Location/Qualifiers
source                     1..6
                           mol_type = protein
                           organism = Streptococcus pneumoniae
SEQUENCE: 66
PKEPEQ                                                        6

SEQ ID NO: 67              moltype = AA   length = 4
FEATURE                    Location/Qualifiers
source                     1..4
                           mol_type = protein
                           organism = Streptococcus pneumoniae
```

```
SEQUENCE: 67
PEKP                                                                                      4

SEQ ID NO: 68            moltype = AA  length = 15
FEATURE                  Location/Qualifiers
source                   1..15
                         mol_type = protein
                         organism = Streptococcus pneumoniae
SEQUENCE: 68
SPAAGNNTGS KYPYT                                                                          15

SEQ ID NO: 69            moltype = AA  length = 15
FEATURE                  Location/Qualifiers
source                   1..15
                         mol_type = protein
                         organism = Streptococcus pneumoniae
SEQUENCE: 69
VMDDSKNYVW IVDEQ                                                                          15

SEQ ID NO: 70            moltype = AA  length = 15
FEATURE                  Location/Qualifiers
source                   1..15
                         mol_type = protein
                         organism = Streptococcus pneumoniae
SEQUENCE: 70
ASPAAGNNTG SKYPY                                                                          15

SEQ ID NO: 71            moltype = AA  length = 15
FEATURE                  Location/Qualifiers
source                   1..15
                         mol_type = protein
                         organism = Streptococcus pneumoniae
SEQUENCE: 71
AASPAAGNNT GSKYP                                                                          15

SEQ ID NO: 72            moltype = AA  length = 15
FEATURE                  Location/Qualifiers
source                   1..15
                         mol_type = protein
                         organism = Streptococcus pneumoniae
SEQUENCE: 72
SLGNADAENQ EITSG                                                                          15

SEQ ID NO: 73            moltype = AA  length = 15
FEATURE                  Location/Qualifiers
source                   1..15
                         mol_type = protein
                         organism = Streptococcus pneumoniae
SEQUENCE: 73
FTSKVYPDKK WTGKL                                                                          15

SEQ ID NO: 74            moltype = AA  length = 15
FEATURE                  Location/Qualifiers
source                   1..15
                         mol_type = protein
                         organism = Streptococcus pneumoniae
SEQUENCE: 74
IDVTGEVGDL KQGFS                                                                          15

SEQ ID NO: 75            moltype = AA  length = 15
FEATURE                  Location/Qualifiers
source                   1..15
                         mol_type = protein
                         organism = Streptococcus pneumoniae
SEQUENCE: 75
SSLEEGKEVK ADEAT                                                                          15

SEQ ID NO: 76            moltype = AA  length = 15
FEATURE                  Location/Qualifiers
source                   1..15
                         mol_type = protein
                         organism = Streptococcus pneumoniae
SEQUENCE: 76
SLEEGKEVKA DEATN                                                                          15

SEQ ID NO: 77            moltype = AA  length = 15
FEATURE                  Location/Qualifiers
source                   1..15
                         mol_type = protein
```

```
                        organism = Streptococcus pneumoniae
SEQUENCE: 77
TIDVTGEVGD LKQGF                                                    15

SEQ ID NO: 78          moltype = AA   length = 15
FEATURE                Location/Qualifiers
source                 1..15
                       mol_type = protein
                       organism = Streptococcus pneumoniae
SEQUENCE: 78
AAGNNTGSKY PYTID                                                    15

SEQ ID NO: 79          moltype = AA   length = 15
FEATURE                Location/Qualifiers
source                 1..15
                       mol_type = protein
                       organism = Streptococcus pneumoniae
SEQUENCE: 79
PQLPAPVGGE DATVQ                                                    15

SEQ ID NO: 80          moltype = AA   length = 15
FEATURE                Location/Qualifiers
source                 1..15
                       mol_type = protein
                       organism = Streptococcus pneumoniae
SEQUENCE: 80
QLPAPVGGED ATVQS                                                    15

SEQ ID NO: 81          moltype = AA   length = 15
FEATURE                Location/Qualifiers
source                 1..15
                       mol_type = protein
                       organism = Streptococcus pneumoniae
SEQUENCE: 81
LPAPVGGEDA TVQSP                                                    15

SEQ ID NO: 82          moltype = AA   length = 15
FEATURE                Location/Qualifiers
source                 1..15
                       mol_type = protein
                       organism = Streptococcus pneumoniae
SEQUENCE: 82
PAPVGGEDAT VQSPT                                                    15

SEQ ID NO: 83          moltype = AA   length = 15
FEATURE                Location/Qualifiers
source                 1..15
                       mol_type = protein
                       organism = Streptococcus pneumoniae
SEQUENCE: 83
APVGGEDATV QSPTP                                                    15

SEQ ID NO: 84          moltype = AA   length = 15
FEATURE                Location/Qualifiers
source                 1..15
                       mol_type = protein
                       organism = Streptococcus pneumoniae
SEQUENCE: 84
PAAGNNTGSK YPYTI                                                    15

SEQ ID NO: 85          moltype = AA   length = 15
FEATURE                Location/Qualifiers
source                 1..15
                       mol_type = protein
                       organism = Streptococcus pneumoniae
SEQUENCE: 85
AGNNTGSKYP YTIDV                                                    15

SEQ ID NO: 86          moltype = AA   length = 15
FEATURE                Location/Qualifiers
source                 1..15
                       mol_type = protein
                       organism = Streptococcus pneumoniae
SEQUENCE: 86
TSKVYPDKKW TGKLS                                                    15

SEQ ID NO: 87          moltype = AA   length = 15
FEATURE                Location/Qualifiers
source                 1..15
```

```
                    mol_type = protein
                    organism = Streptococcus pneumoniae
SEQUENCE: 87
SFTSKVYPDK KWTGK                                              15

SEQ ID NO: 88       moltype = AA  length = 15
FEATURE             Location/Qualifiers
source              1..15
                    mol_type = protein
                    organism = Streptococcus pneumoniae
SEQUENCE: 88
AQAGSSGYAD FEANP                                              15

SEQ ID NO: 89       moltype = AA  length = 15
FEATURE             Location/Qualifiers
source              1..15
                    mol_type = protein
                    organism = Streptococcus pneumoniae
SEQUENCE: 89
TVNWQPIDWD LKEAE                                              15

SEQ ID NO: 90       moltype = AA  length = 15
FEATURE             Location/Qualifiers
source              1..15
                    mol_type = protein
                    organism = Streptococcus pneumoniae
SEQUENCE: 90
VANKEANQYQ TFNEA                                              15

SEQ ID NO: 91       moltype = AA  length = 15
FEATURE             Location/Qualifiers
source              1..15
                    mol_type = protein
                    organism = Streptococcus pneumoniae
SEQUENCE: 91
ITVNWQPIDW DLKEA                                              15

SEQ ID NO: 92       moltype = AA  length = 15
FEATURE             Location/Qualifiers
source              1..15
                    mol_type = protein
                    organism = Streptococcus pneumoniae
SEQUENCE: 92
GITVNWQPID WDLKE                                              15

SEQ ID NO: 93       moltype = AA  length = 15
FEATURE             Location/Qualifiers
source              1..15
                    mol_type = protein
                    organism = Streptococcus pneumoniae
SEQUENCE: 93
VNWQPIDWDL KEAEL                                              15

SEQ ID NO: 94       moltype = AA  length = 15
FEATURE             Location/Qualifiers
source              1..15
                    mol_type = protein
                    organism = Streptococcus pneumoniae
SEQUENCE: 94
KDGKFQEISQ KWFGE                                              15

SEQ ID NO: 95       moltype = AA  length = 15
FEATURE             Location/Qualifiers
source              1..15
                    mol_type = protein
                    organism = Streptococcus pneumoniae
SEQUENCE: 95
DGKFQEISQK WFGED                                              15

SEQ ID NO: 96       moltype = AA  length = 15
FEATURE             Location/Qualifiers
source              1..15
                    mol_type = protein
                    organism = Streptococcus pneumoniae
SEQUENCE: 96
GKFQEISQKW FGEDV                                              15

SEQ ID NO: 97       moltype = AA  length = 15
FEATURE             Location/Qualifiers
```

```
source                   1..15
                         mol_type = protein
                         organism = Streptococcus pneumoniae
SEQUENCE: 97
KFQEISQKWF GEDVA                                                    15

SEQ ID NO: 98            moltype = AA  length = 15
FEATURE                  Location/Qualifiers
source                   1..15
                         mol_type = protein
                         organism = Streptococcus pneumoniae
SEQUENCE: 98
WFGEDVATKE VKEGQ                                                    15

SEQ ID NO: 99            moltype = AA  length = 15
FEATURE                  Location/Qualifiers
source                   1..15
                         mol_type = protein
                         organism = Streptococcus pneumoniae
SEQUENCE: 99
GAQAGSSGYA DFEAN                                                    15

SEQ ID NO: 100           moltype = AA  length = 15
FEATURE                  Location/Qualifiers
source                   1..15
                         mol_type = protein
                         organism = Streptococcus pneumoniae
SEQUENCE: 100
YKDGKFQEIS QKWFG                                                    15

SEQ ID NO: 101           moltype = AA  length = 15
FEATURE                  Location/Qualifiers
source                   1..15
                         mol_type = protein
                         organism = Streptococcus pneumoniae
SEQUENCE: 101
NEAFSSLYKD GKFQE                                                    15

SEQ ID NO: 102           moltype = AA  length = 15
FEATURE                  Location/Qualifiers
source                   1..15
                         mol_type = protein
                         organism = Streptococcus pneumoniae
SEQUENCE: 102
YGITVNWQPI DWDLK                                                    15

SEQ ID NO: 103           moltype = AA  length = 15
FEATURE                  Location/Qualifiers
source                   1..15
                         mol_type = protein
                         organism = Streptococcus pneumoniae
SEQUENCE: 103
WNGYSATDER REKVA                                                    15

SEQ ID NO: 104           moltype = AA  length = 15
FEATURE                  Location/Qualifiers
source                   1..15
                         mol_type = protein
                         organism = Streptococcus pneumoniae
SEQUENCE: 104
ARKEDTNLVK KINEA                                                    15

SEQ ID NO: 105           moltype = AA  length = 15
FEATURE                  Location/Qualifiers
source                   1..15
                         mol_type = protein
                         organism = Streptococcus pneumoniae
SEQUENCE: 105
SATDERREKV AFSNS                                                    15

SEQ ID NO: 106           moltype = AA  length = 15
FEATURE                  Location/Qualifiers
source                   1..15
                         mol_type = protein
                         organism = Streptococcus pneumoniae
SEQUENCE: 106
NGYSATDERR EKVAF                                                    15

SEQ ID NO: 107           moltype = AA  length = 15
```

```
FEATURE                 Location/Qualifiers
source                  1..15
                        mol_type = protein
                        organism = Streptococcus pneumoniae
SEQUENCE: 107
GYSATDERRE KVAFS                                                      15

SEQ ID NO: 108          moltype = AA  length = 27
FEATURE                 Location/Qualifiers
REGION                  1..27
                        note = Description of Artificial Sequence: Synthetic peptide
REGION                  2..26
                        note = MISC_FEATURE - This region may encompass 2-5 "Glu
                         Ala Ala Ala Lys"repeating units
REGION                  1..27
                        note = See specification as filed for detailed description
                         of substitutions and preferred embodiments
source                  1..27
                        mol_type = protein
                        organism = synthetic construct
SEQUENCE: 108
AEAAAKEAAA KEAAAKEAAA KEAAAKA                                         27

SEQ ID NO: 109          moltype = AA  length = 34
FEATURE                 Location/Qualifiers
REGION                  1..34
                        note = Description of Artificial Sequence: Synthetic
                         polypeptide
REGION                  1..34
                        note = MISC_FEATURE - This sequence may encompass 5-17 "Ala
                         Pro"repeating units
REGION                  1..34
                        note = See specification as filed for detailed description
                         of substitutions and preferred embodiments
source                  1..34
                        mol_type = protein
                        organism = synthetic construct
SEQUENCE: 109
APAPAPAPAP APAPAPAPAP APAPAPAPAP APAP                                 34

SEQ ID NO: 110          moltype = AA  length = 399
FEATURE                 Location/Qualifiers
source                  1..399
                        mol_type = protein
                        organism = Streptococcus pneumoniae
SEQUENCE: 110
MKKKNGKAKK WQLYAAIGAA SVVVLGAGGI LLFRQPSQTA LKDEPTHLVV AKEGSVASSV     60
LLSGTVTAKN EQYVYFDASK GDLDEILVSV GDKVSEGQAL VKYSSSEAQA AYDSASRAVA    120
RADRHINELN QARNEAASAP APQLPAPVGG EDATVQSPTP VAGNSVASID AQLGDARDAR    180
ADAAAQLSKA QSQLDATTVL STLEGTVVEV NSNVSKSPTG ASQVMVHIVS NENLQVKGEL    240
SEYNLANLSV GQEVSFTSKV YPDKKWTGKL SYISDYPKNN GEAASPAAGN NTGSKYPYTI    300
DVTGEVGDLK QGFSVNIEVK SKTKAILVPV SSLVMDNSKN YVWIVDEQQK AKKVEVSLGN    360
ADAENQEITS GLTNGAKVIS NPTSSLEEGK EVKADEATN                           399

SEQ ID NO: 111          moltype = AA  length = 399
FEATURE                 Location/Qualifiers
source                  1..399
                        mol_type = protein
                        organism = Streptococcus pneumoniae
SEQUENCE: 111
MKKKNGKAKK WQLYAAIGAA SVVVLGAGGI LLFRQPSQTA LKDEPTHLIV AKEGSVASSV     60
LLSGTVTAKN EQYVYFDASK GDLDEILVSV GDKVSEGQAL VKYSSSEAQA AYDSASRAVA    120
RADRHINELN QARNEAASAP APQLPAPVGG EDATVQSPTP VAGNSVASID AQLGDARDAR    180
ADAAAQLSKA QSQLDATTVL STLEGTVVEV NSNVSKSPTG ASQVMVHIVS NENLQVKGEL    240
SEYNLANLSV GQEVSFTSKV YPDKKWTGKL SYISDYPKNN GEAASPAAGN NTGSKYPYTI    300
DVTGEVGDLK QGFSVNIEVK SKTKAILVPV SSLVMDDSKN YVWIVDEQQK AKKVEVSLGN    360
ADAENQEITS GLTNGAKVIS NPTSSLEEGK EVKADEATN                           399

SEQ ID NO: 112          moltype = AA  length = 399
FEATURE                 Location/Qualifiers
source                  1..399
                        mol_type = protein
                        organism = Streptococcus pneumoniae
SEQUENCE: 112
MKKKNGKAKK WQLYAAIGAA SVVVLGAGGI LLFRQPSQTA LKDEPTHLVV AKEGSVASSV     60
LLSGTVTAKN EQYVYFDASK GDLDEILVSV GDKVSEGQAL VKYSSSEAQA AYDSASRAVA    120
RADRHINELN QARNEAASAP APQLPAPVGG EDATVQNPTP VAGNSVASID AQLGDARDAR    180
ADAAAQLSKA QSQLDATTVL STLEGTVVEV NSNVSKSPTG ASQVMVHIVS NENLQVKGEL    240
SEYNLANLSV GQEVSFTSKV YPDKKWTGKL SYISDYPKNN GEAASPAAGN NTGSKYPYTI    300
```

```
DVTGEVGDLK QGFSVNIEVK SKTKAILVPV SSLVMDDSKN YVWIVDEQQK AKKVEVSLGN   360
ADAENQEITS GLTNGAKVIS NPTSSLEEGK EVKADEATN                         399

SEQ ID NO: 113          moltype = AA  length = 399
FEATURE                 Location/Qualifiers
source                  1..399
                        mol_type = protein
                        organism = Streptococcus pneumoniae
SEQUENCE: 113
MKKKNGKAKK WQLYAAIGAA SVVVLGAGGI LLFRQPSQTA LKDEPTHLVV AKEGSVASSV   60
LLSGTVTAKN EQYVYFDASK GDLDEILVSV GDKVSEGQAL VKYSSSEAQA AYDSASRAVA   120
RADRHINELN QARNEAASAP APQLPAPVGG EDATVQSPTP VAGNSVASID AQLGDARDAR   180
ADAAAQLSKA QSQLDATTVL STLEGTVVEV NSNVSKSPTG ASQVMVHIVS NENLQVKGEL   240
SEYNLANLSV GQEVSFTSKV YPDKKWTGKL SYISDYPKNN GEAASPAAGN NTGSKYPYTI   300
DVTGEVGDLK QGFSVNIEVK SKTKAILVPV SSLVMDDSKN YVWIVDEQQK SKKVEVSLGN   360
ADAENQEITS GLTNGAKVIS NPTSSLEEGK EVKADEATN                         399

SEQ ID NO: 114          moltype = AA  length = 399
FEATURE                 Location/Qualifiers
source                  1..399
                        mol_type = protein
                        organism = Streptococcus pneumoniae
SEQUENCE: 114
MKKKNGKAKK WQLYAAIGAA SVVVLGAGGI LLFRQPSQTA LKDEPTHLVV AKEGSVASSV   60
LLSGTVTAKN EQYVYFDASK GDLDEILVSV GDKVSEGQAL VKYSSSEAQA AYDSASRAVA   120
RADRHINELN QARNEAASAP TPQLPAPVGG EDATVQSPTP VAGNSVASID AQLGDARDAR   180
ADAAAQLSKA QSQLDATTVL STLEGTVVEV NSNVSKSPTG ASQVMVHIVS NENLQVKGEL   240
SEYNLANLSV GQEVSFTSKV YPDKKWTGKL SYISDYPKNN GEAASPAAGN NTGSKYPYTI   300
DVTGEVGDLK QGFSVNIEVK SKTKAILVPV SSLVMDDSKN YVWIVDEQQK AKKVEVSLGN   360
ADAENQEITS GLTNGAKVIS NPTSSLEEGK EVKADEATN                         399

SEQ ID NO: 115          moltype = AA  length = 399
FEATURE                 Location/Qualifiers
source                  1..399
                        mol_type = protein
                        organism = Streptococcus pneumoniae
SEQUENCE: 115
MKKKNGKAKK WQLYAAIGAA SVVVLGAGGI LLFRQPSQTA LKDEPTHFVV AKEGSVASSV   60
LLSGTVTAKN EQYVYFDASK GDLDEILVSV GDKVSEGQAL VKYSSSEAQA AYDSASRAVA   120
RADRHINELN QARNEAASAP APQLPAPVGG EDATVQSPTP VAGNSVASID AQLGDARDAR   180
ADAAAQLSKA QSQLDATTVL STLEGTVVEV NSNVSKSPTG ASQVMVHIVS NENLQVKGEL   240
SEYNLANLSV GQEVSFTSKV YPDKKWTGKL SYISDYPKNN GEAASPAAGN NTGSKYPYTI   300
DVTGEVGDLK QGFSVNIEVK SKTKAILVPV SSLVMDDSKN YVWIVDEQQK AKKVEVSLGN   360
ADAENQEITS GLTNGAKVIS NPTSSLEEGK EVKADEATN                         399

SEQ ID NO: 116          moltype = AA  length = 399
FEATURE                 Location/Qualifiers
source                  1..399
                        mol_type = protein
                        organism = Streptococcus pneumoniae
SEQUENCE: 116
MKKKNGKAKK WQLYAAIGAA SVVVLGAGGI LLFRQPSQTA LKDEPTHLVV AKEGSVASSV   60
LLSGTVTAKN EQYVYFDASK GDLDEILVSV GDKVSEGQAL VKYSSSEAQA AYDSASRAVA   120
RADRHINELN QARNEAASAP APQLPAPVGG EDATVQSPTP VAGNSVASID AQLGDARDAR   180
ADAAAQLSKA QSQLDATTVL STLEGTVVEV NSNVSKSPTG ASQVMVHIVS NENLQVKGEL   240
SEYNLANLSV GQEVSFTSKV YPDKKWTGKL SYISDYPKNN GEAASPAAGN NTGSKYPYTI   300
DVTGEVGDLK QGFSVNIEVK SKTKAILVPV SSLVMDDSKN YVWIVDEQQK AKKVEVSLGN   360
ADAENQEITS GLTNGAKVIS NPTFSLEEGK EVKADEATN                         399

SEQ ID NO: 117          moltype = AA  length = 399
FEATURE                 Location/Qualifiers
source                  1..399
                        mol_type = protein
                        organism = Streptococcus pneumoniae
SEQUENCE: 117
MKKKNGKAKK WQLYAAIGAA SVVVLGAGGI LLFRQPSQTA LKDEPTHLVV AKEGSVASSV   60
LLSGTVTAKN EQYVYFDASK GDLDEILVSV GDKVSEGQAL VKYSSSEAQA AYDSASRAVA   120
RADRHINELN QARNEAASAP APQLPAPVGG EDATVQSPTP VAGNSVASID AQLGDARDAR   180
ADAAAQLSKA QSQLDATTVL STLEGTVVEV NSNVSKSPTG ASQVMVHIVS NENLQVKGEL   240
SEYNLANLSV GQEVSFTSKV YPDKKWTGKL SYISDYPKNN GAAASPAAGN NTGSKYPYTI   300
DVTGEVGDLK QGFSVNIEVK SKTKAILVPV SSLVMDDSKN YVWIVDEQQK AKKVEVSLGN   360
ADAENQEITS GLTNGAKVIS NPTSSLEEGK EVKADEATN                         399

SEQ ID NO: 118          moltype = AA  length = 399
FEATURE                 Location/Qualifiers
source                  1..399
                        mol_type = protein
                        organism = Streptococcus pneumoniae
SEQUENCE: 118
```

```
MKKKNGKAKK WQLYAAIGAA SVVVLGAGGI LLFRQPSQTA LKDEPIHLVV AKEGSVASSV    60
LLSGTVTAKN EQYVYFDASK GDLDEILVSV GDKVSEGQAL VKYSSSEAQA AYDSASRAVA   120
RADRHINELN QARNEAASAP APQLPAPVGG EDATVQSPTP VAGNSVASID AQLGDARDAR   180
ADAAAQLSKA QSQLDATTVL STLEGTVVEV NSNVSKSPTG ASQVMVHIVS NENLQVKGEL   240
SEYNLANLSV GQEVSFTSKV YPDKKWTGKL SYISDYPKNN GEAASPAAGN NTGSKYPYTI   300
DVTGEVGDLK QGFSVNIEVK SKTKAILVPV SSLVMDDSKN YVWIVDEQQK AKKVEVSLGN   360
ADAENQEITS GLTNGAKVIS NPTSSLEEGK EVKADEATN                          399

SEQ ID NO: 119              moltype = AA   length = 399
FEATURE                     Location/Qualifiers
source                      1..399
                            mol_type = protein
                            organism = Streptococcus pneumoniae
SEQUENCE: 119
MKKKNGKAKK WQLYAAIGAA SVVVLGAGGI LLFRQPSQTA LKDEPTHLVV AKEGSVASSV    60
LLSGTVTAKN EQYVYFDASK GDLDEILVSV GDKVSEGQAL VKYSSSEAQA AYDSASRAVA   120
RADRHINELN QARNEAASAP APQLPAPVGG EDATVQSPTP VAGNSVASID AQLGDARDAR   180
ADAAAQLSKA QSQLDATTVL STLEGTVVEV NSNVSKSPTG ASQVMVHIVS NENLQVKGEL   240
SEYNLANLSV GQEVSFTSKV YPDKKWTGKL SYISDYPKNN GEAASPAAGN NTGSKYPYTI   300
DVTGEGGDLK QGFSVNIEVK SKTKAILVPV SSLVMDDSKN YVWIVDEQQK AKKVEVSLGN   360
ADAENQEITS GLTNGAKVIS NPTSSLEEGK EVKADEATN                          399

SEQ ID NO: 120              moltype = AA   length = 399
FEATURE                     Location/Qualifiers
source                      1..399
                            mol_type = protein
                            organism = Streptococcus pneumoniae
SEQUENCE: 120
MKKKNGKAKK WQLYAAIGAA SVVVLGAGGI LLFRQPSQTA LKDEPTHLVV AKEGSVASSV    60
LLSGTVTAKN EQYVYFDASK GDLDEILVSV GDKVSEGQAL VKYSSSEAQA AYDSASRAVA   120
RADRHINELN QARNEAASAL APQLPAPVGG EDATVQSPTP VAGNSVASID AQLGDARDAR   180
ADAAAQLSKA QSQLDATTVL STLEGTVVEV NSNVSKSPTG ASQVMVHIVS NENLQVKGEL   240
SEYNLANLSV GQEVSFTSKV YPDKKWTGKL SYISDYPKNN GEAASPAAGN NTGSKYPYTI   300
DVTGEVGDLK QGFSVNIEVK SKTKAILVPV SSLVMDDSKN YVWIVDEQQK AKKVEVSLGN   360
ADAENQEITS GLTNGAKVIS NPTSSLEEGK EVKADEATN                          399

SEQ ID NO: 121              moltype = AA   length = 399
FEATURE                     Location/Qualifiers
source                      1..399
                            mol_type = protein
                            organism = Streptococcus pneumoniae
SEQUENCE: 121
MKKKNGKAKK WQLYAAIGAA SVVVLGAGGI LLFRQPSQTA LKDEPTHLVV AKEGSVASSV    60
LLSGTVTAKN EQYVYFDASK GDLDEILVSV GDKVSEGQAL VKYSSSEAQA AYDSASRAVA   120
RADRHINELN QARNEAASAP APQLPAPVGG EDATVPSPTP VAGNSVASID AQLGDARDAR   180
ADAAAQLSKA QSQLDATTVL STLEGTVVEV NSNVSKSPTG ASQVMVHIVS NENLQVKGEL   240
SEYNLANLSV GQEVSFTSKV YPDKKWTGKL SYISDYPKNN GEAASPAAGN NTGSKYPYTI   300
DVTGEVGDLK QGFSVNIEVK SKTKAILVPV SSLVMDDSKN YVWIVDEQQK AKKVEVSLGN   360
ADAENQEITS GLTNGAKVIS NPTSSLEEGK EVKADEATN                          399

SEQ ID NO: 122              moltype = AA   length = 399
FEATURE                     Location/Qualifiers
source                      1..399
                            mol_type = protein
                            organism = Streptococcus pneumoniae
SEQUENCE: 122
MKKKNGKAKK WQLYAAIGAA SVVILGAGGI LLFRQPSQTA LKDEPIHLVV AKEGSVASSV    60
LLSGTVTAKN EQYVYFDASK GDLDEILVSV GDKVSEGQAL VKYSSSEAQA AYDSASRAVA   120
RADRHINELN QARNEAASAP APQLPAPVGG EDATVQSPTP VAGNSVASID AQLGDARDAR   180
ADAAAQLSKA QSQLDATTVL STLEGTVVEV NSNVSKSPTG ASQVMVHIVS NENLQVKGEL   240
SEYNLANLSV GQEVSFTSKV YPDKKWTGKL SYISDYPKNN GEAASPAAGN NTGSKYPYTI   300
DVTGEVGDLK QGFSVNIEVK SKTKAILVPV SSLVMDDSKN YVWIVDEQQK AKKVEVSLGN   360
ADAENQEITS GLTNGAKVIS NPTSSLEEGK EVKADEATN                          399

SEQ ID NO: 123              moltype = AA   length = 399
FEATURE                     Location/Qualifiers
source                      1..399
                            mol_type = protein
                            organism = Streptococcus pneumoniae
SEQUENCE: 123
MKKKNGKAKK WQLYAAIGAA SVVVLGAGGI LLFRQPSQTA LKDELTHLVV AKEGSVASSV    60
LLSGTVTAKN EQYVYFDASK GDLDEILVSV GDKVSEGQAL VKYSSSEAQA AYDSASRAVA   120
RADRHINELN QARNEAASAP APQLPAPVGG EDATVQSPTP VAGNSVASID AQLGDARDAR   180
ADAAAQLSKA QSQLDATTVL STLEGTVVEV NSNVSKSPTG ASQVMVHIVS NENLQVKGEL   240
SEYNLANLSV GQEVSFTSKV YPDKKWTGKL SYISDYPKNN GEAASPAAGN NTGSKYPYTI   300
DVTGEVGDLK QGFSVNIEVK SKTKAILVPV SSLVMDDSKN YVWIVDEQQK AKKVEVSLGN   360
ADAENQEITS GLTNGAKVIS NPTSSLEEGK EVKADEATN                          399

SEQ ID NO: 124              moltype = AA   length = 399
```

```
FEATURE              Location/Qualifiers
source               1..399
                     mol_type = protein
                     organism = Streptococcus pneumoniae
SEQUENCE: 124
MKKKNGKAKK WQLYAAIGAA SVVVLGAGGI LLFRQPSQTA LKDEPTHLVV AKEGSVASSV    60
LLSGTVTAKN EQYVYFDASK GDLDEILVSV GDKVSEGQAL VKYSSSEAQA AYDSASRAVA   120
RADRHINELN QARNEAASAP APQLPAPVGG EDATVQSPTP VAGNSVASID AQLGDARDAR   180
ADAAAQLSKA QSQLDATTVL STLEGTVVEV NSNVSKSPTG ASQVMVHIVS NENLQVKGEL   240
SEYNLANLSV GQEVSFTSKV YPDKKWTGKL SYISDYPKNN GEAASPASGN NTGSKYPYTI   300
DVTGEIGDLK QGFSVNIEVK SKTKAILVPV SSLVMDDSKN YVWIVDEQQK AKKVEVSLGN   360
ADAENQEITS GLTNGAKVIS NPTSSLEEGK EVKADEATN                         399

SEQ ID NO: 125       moltype = AA  length = 399
FEATURE              Location/Qualifiers
source               1..399
                     mol_type = protein
                     organism = Streptococcus pneumoniae
SEQUENCE: 125
MKKKNGKAKK WQLYAAIGAA SVVVLGAGGI LLFRQPSQTA LKDEPTHLVV AKEGSVASSV    60
LLSGTVTAKN EQYVYFDASK GDLDEILVSV GDKVSEGQAL VKYSSSEAQA AYDSASRAVA   120
KADRHINELN QARNEAASAP APQLPAPVGG EDATVQSPTP VAGNSVASID AQLGDARDAR   180
ADAAAQLSKA QSQLDATTVL STLEGTVVEV NSNVSKSPTG ASQVMVHIVS NENLQVKGEL   240
SEYNLANLSV GQEVSFTSKV YPDKKWTGRL SYISDYPKNN GEAASPAAGN NTGSKYPYTI   300
DVTGEVGDLK QGFSVNIEVK SKTKAILVPV SSLVMDDSKN YVWIVDEQQK AKKVEVSLGN   360
ADAENQEITS GLTNGAKVIS NPTSSLEEGK EVKADEATN                         399

SEQ ID NO: 126       moltype = AA  length = 399
FEATURE              Location/Qualifiers
source               1..399
                     mol_type = protein
                     organism = Streptococcus pneumoniae
SEQUENCE: 126
MKKKNGKAKK WQLYAAIGAA SVVVLGAGGI LLFRQPSQTA LKDEPIHLVV AKEGSVASSV    60
LLSGTVTAKN EQYVYFDASK GDLDEILVSV GDKVSEGQAL VKYSSSEAQA AYDSASRAVA   120
RADRHINELN QARNEAASAP APQLPAPVGG EDATVQSPTP VAGNSVASID AQLGDARDAR   180
ADAAAQLSKA QSQLDATTVL STLEGTVVEV NSNVSKSPTG ASQVMVHIVS NENLQVKGEL   240
SEYNLANLSV GQEVSFTSKV YPDKKWTGKL SYISDYPKNN GEAASPASGN NTGSKYPYTI   300
DVTGEIGDLK QGFSVNIEVK SKTKAILVPV SSLVMDDSKN YVWIVDEQQK AKKVEVSLGN   360
ADAENQEITS GLTNGAKVIS NPTSSLEEGK EVKADEATN                         399

SEQ ID NO: 127       moltype = AA  length = 399
FEATURE              Location/Qualifiers
source               1..399
                     mol_type = protein
                     organism = Streptococcus pneumoniae
SEQUENCE: 127
MKKKNGKAKK WQLYAAIGAA SVVVLGAGGI LLFRQPSQTA LKDEPTHLVV AKEGSVASSV    60
LLSGTVTAKN EQYVYFDASK GDLDEILVSV GDKVSEGQAL VKYSSSEAQA AYDSASRAVA   120
KADRHINELN QARNEAASAQ APQLPAPVGG EDATVQSPTP VAGNSVASID AQLGDARDAR   180
ADAAAQLSKA QSQLDATTVL STLEGTVVEV NSNVSKSPTG ASQVMVHIVS NENLQVKGEL   240
SEYNLANLSV GQEVSFTSKV YPDKKWTGKL SYISDYPKNN GEAASPAAGN NTGSKYPYTI   300
DVTGEVGDLK QGFSVNIEVK SKTKAILVPV SSLVMDDSKN YVWIVDEQQK AKKVEVSLGN   360
ADAENQEITS GLTNGAKVIS NPTSSLEEGK EVKADEATN                         399

SEQ ID NO: 128       moltype = AA  length = 399
FEATURE              Location/Qualifiers
source               1..399
                     mol_type = protein
                     organism = Streptococcus pneumoniae
SEQUENCE: 128
MKKKNGKAKK WQLYAAIGAA SVVVLGAGGI LLFRQPSQTA LKDEPTHLVV AKEGSVASSV    60
LLSGTVTAKN EQYVYFDASK GDLDEILVSV GDKVSEGQAL VKYSSSEAQA AYDSASRAVA   120
RVDCHINELN QARNEAASAP APQLPAPVGG EDATVQSPTP VAGNSVASID AQLGDARDAR   180
ADAAAQLSKA QSQLDATTVL STLEGTVVEV NSNVSKSPTG ASQVMVHIVS NENLQVKGEL   240
SEYNLANLSV GQEVSFTSKV YPDKKWTGKL SYISDYPKNN GEAASPAAGN NTGSKYPYTI   300
DVTGEVGDLK QGFSVNIEVK SKTKAILVPV SSLVMDDSKN YVWIVDEQQK AKKVEVSLGN   360
ADAENQEITS GLTNGAKVIS NPTSSLEEGK EVKADEATN                         399

SEQ ID NO: 129       moltype = AA  length = 399
FEATURE              Location/Qualifiers
source               1..399
                     mol_type = protein
                     organism = Streptococcus pneumoniae
SEQUENCE: 129
MKKKNGKAKK WQLYAAIGAA SVVVLGAGGI LLFRQPYQTA LKDEPTHLVV VKEGSVASSV    60
LLSGTVTAKN EQYVYFDASK GDLDEILVSV GDKVSEGQAL VKYSSSEAQA AYDSASRAVA   120
RADRHINELN QARNEAASAP APQLPAPVGG EDATVQSPTP VAGNSVASID AQLGDARDAR   180
ADAAAQLSKA QSQLDATTVL STLEGTVVEV NSNVSKSPTG ASQVMVHIVS NENLQVKGEL   240
```

```
SEYNLANLSV GQEVSFTSKV YPDKKWTGKL SYISDYPKNN GEAASPAAGN NTGSKYPYTI   300
DVTGEVGDLK QGFSVNIEVK SKTKAILVPV SSLVMDDSKN YVWIVDEQQK AKKVEVSLGN   360
ADAENQEITS GLTNGAKVIS NPTSSLEEGK EVKADEATN                         399

SEQ ID NO: 130           moltype = AA   length = 399
FEATURE                  Location/Qualifiers
source                   1..399
                         mol_type = protein
                         organism = Streptococcus pneumoniae
SEQUENCE: 130
MKKKNGKAKK WQLYAAIGAA SVVVLGAGGI LLFRQPSQTA VKDEPTHLVV AKEGSVASSV    60
LLSGTVTAKN EQYVYFDASK GDLDEILVSV GDKVSEGQAL VKYSSSEAQA AYDSASRAVA   120
KADRHINELN QARNEAASAP APQLPAPVGG EDATVQSPTP VAGNSVASID AQLGDARDAR   180
ADAAAQLSKA QSQLDATTVL STLEGTVVEV NSNVSKSPTG ASQVMVHIVS NENLQVKGEL   240
SEYNLANLSV GQEVSFTSKV YPDKKWTGKL SYISDYPKNN GEAASPAAGN NTGSKYPYTI   300
DVTGEVGNLK QGFSVNIEVK SKTKAILVPV SSLVMDDSKN YVWIVDEQQK AKKVEVSLGN   360
ADAENQEITS GLTNGAKVIS NPTSSLEEGK EVKADEATN                         399

SEQ ID NO: 131           moltype = AA   length = 399
FEATURE                  Location/Qualifiers
source                   1..399
                         mol_type = protein
                         organism = Streptococcus pneumoniae
SEQUENCE: 131
MKKKNGKAKK WQLYAAIGAA SVVILGAGGI LLFRQPSQTA LKDEPIHLVV AKEGSVASSV    60
LLSGTVTAKN EQYVYFDASK GDLDEILVSV GDKVSEGQAL VKYSSSEAQA AYDSASRAVA   120
KADRHINELN QARNEAASAP APQLPAPVGG EDATVQSPTP VAGNSVASID AQLGDARDAR   180
ADAAAQLSKA QSQLDATTVL STLEGTVVEV NSNVSKSPTG ASQVMVHIVS NENLQVKGEL   240
SEYNLANLSV GQEVSFTSKV YPDKKWTGKL SYISDYPKNN GEAASPAAGN NTGSKYPYTI   300
DVTGEVGDLK QGFSVNIEVK SKTKAILVPV SSLVMDDSKN YVWIVDEQQK AKKVEVSLGN   360
ADAENQEITS GLTNGAKVIS NPTSSLEEGK EVKADEATN                         399

SEQ ID NO: 132           moltype = AA   length = 399
FEATURE                  Location/Qualifiers
source                   1..399
                         mol_type = protein
                         organism = Streptococcus pneumoniae
SEQUENCE: 132
MKKKNGKAKK WQLYAAIGAA SVVVLGAGGI LLFRQPSQTA LKDEPTHLVV AKEGSVASSV    60
LLSGTVTAKN EQYVYFDASK GDLDEILVSV GDKVSEGQAL VKYSSSEAQA VYDSASRAVA   120
KADRHINELN QARNEAASAP APQLPAPVGG EDATVQSPTP VAGNSVASID AQLGDARDAR   180
ADAAAQLSKA QSQLDATTVL STLEGTVVEV NSNVSKSPTG ASQVMVHIVS NENLQVKGEL   240
SEYNLANLSV GQEVSFTSKV YPDKKWTGKL SYISDYPKNN GEAASPAAGN NTGSKYPYTI   300
DVTGEVGDLK QGFSVNIEVK SKTKAILVPV SSLVMDDSKN YVWIVDEQQK AKKVEVSLGN   360
ADAENQEITS GLTNGAKVIS NPTSSLEEGK EVKTDEATN                         399

SEQ ID NO: 133           moltype = AA   length = 399
FEATURE                  Location/Qualifiers
source                   1..399
                         mol_type = protein
                         organism = Streptococcus pneumoniae
SEQUENCE: 133
MKKKNGKAKK WQLYAAIGAA SVVVLGAGGI LLFRQPSQTA LKDEPTHLVV AKEGSVASSI    60
LLSGTVTAKN EQYVYFDASK GDLDEILVSV GDKVSEGQAL VKYSSSEAQA AYDSASRAVA   120
KADRHINELN QVRNEAASAP APQLPAPVGG EDATVQSPTP VAGNSVASID AQLGDARDAR   180
ADAAAQLSKA QSQLDATTVL STLEGTVVEV NSNVSKSPTG ASQVMVHIVS NENLQVKGEL   240
SEYNLANLSV GQEVSFTSKV YPDKKWTGKL SYISDYPKNN GEAASPAAGN NTGSKYPYTI   300
DVTGEVGDLK QGFSVNIEVK SKTKAILVPV SSLVMDDSKN YVWIVDEQQK AKKVEVSLGN   360
ADAENQEITS GLTNGAKVIS NPTSSLEEGK EVKADEATN                         399

SEQ ID NO: 134           moltype = AA   length = 399
FEATURE                  Location/Qualifiers
source                   1..399
                         mol_type = protein
                         organism = Streptococcus pneumoniae
SEQUENCE: 134
MKKKNGKAKK WQLYAAIGAA SVVVLGAGGI LLFRQPSQTA LKDEPTHLVV ANEGSVASSV    60
LLSGTVTAKN EQYVYFDASK GDLDEILVSV GDKVSEGQAL VKYSSSEAQA AYDSASRAVA   120
KADRHINELN QARNEAASAQ APQLPAPVGG EDATVQSPTP VAGNSVASID AQLGDARDAR   180
ADAAAQLSKA QSQLDATTVL STLEGTVVEV NSNVSKSPTG ASQVMVHIVS NENLQVKGEL   240
SEYNLANLSV GQEVSFTSKV YPDKKWTGKL SYISDYPKNN GEAASPAAGN NTGSKYPYTI   300
DVTGEVGDLK QGFSVNIEVK SKTKAILVPV SSLVMDDSKN YVWIVDEQQK AKKVEVSLGN   360
ADAENQEITS GLTNGAKVIS NPTSSLEEGK EVKADEATN                         399

SEQ ID NO: 135           moltype = AA   length = 278
FEATURE                  Location/Qualifiers
source                   1..278
                         mol_type = protein
                         organism = Streptococcus pneumoniae
```

```
SEQUENCE: 135
MKKWMLVLVS LMTALFLVAC GKNSSETSGD NWSKYQSNKS ITIGFDSTFV PMGFAQKDGS    60
YAGFDIDLAT AVFEKYGITV NWQPIDWDLK EAELTKGTID LIWNGYSATD ERREKVAFSN   120
SYMKNEQVLV TKKSSGITTA KDMTGKTLGA QAGSSGYADF EANPELLKNI VANEKEVNQYQ  180
TFNEALIDLK NDRIDGLLID RVYANYYLEA EGVLNDYNVF TVGLETEAFA VGARKEDTTL   240
VKKINEAFSS LYKDGKFQEI SQKWFGEDVA TKEVKEGQ                          278

SEQ ID NO: 136          moltype = AA  length = 278
FEATURE                 Location/Qualifiers
source                  1..278
                        mol_type = protein
                        organism = Streptococcus pneumoniae
SEQUENCE: 136
MKKWMLVLVS LMTALFLVAC GKNSSETSGD NWSKYQSNKS ITIGFDSTFV PMGFAQKDGS    60
YAGFDIDLAT AVFEKYGITV NWQPIDWDLK EAELTKGTID LIWNGYSATD ERREKVAFSN   120
SYMKNEQVLV TKKSSGITTA KDMTGKTLGA QAGSSGYADF EANPELLKNI VANKEANQYQ   180
TFNEALIDLK NDRIDGLLID RVYANYYLEA EGVLNDYNVF TVGLETEAFA VGARKEDTTL   240
VKKINEDFSS LYKNGKFQEI SQKWFGEDVA TKEVKEGQ                          278

SEQ ID NO: 137          moltype = AA  length = 278
FEATURE                 Location/Qualifiers
source                  1..278
                        mol_type = protein
                        organism = Streptococcus pneumoniae
SEQUENCE: 137
MKKWMHVLVS LMTALFLVAC GKNSSETSGD NWSKYQSNKS ITIGFDSTFV PMGFAQKDGS    60
YAGFDIDLAT AVFEKYGITV NWQPIDWDLK EAELTKGTID LIWNGYSATD ERREKVAFSN   120
SYMKNEQVLV TKKLSGITTA KDMTGKTLGA QAGSSGYADF EANPELLKNI VANKEANQYQ   180
TFNEALIDLK NDRIDGLLID RVYANYYLEA EGVLNDYNVF TVGLETEAFA VGARKEDTNL   240
VKKINEAFSS LYKDGKFQEI SQKWFGEDVA TKEVKEGQ                          278

SEQ ID NO: 138          moltype = AA  length = 278
FEATURE                 Location/Qualifiers
source                  1..278
                        mol_type = protein
                        organism = Streptococcus pneumoniae
SEQUENCE: 138
MKKWMLVLVS LMTALFLVAC GKNSSETSGD NWSKYQSNKS ITIGFDSTFV PMGFAQKDGS    60
YAGFDIDLAT AVFEKYGITV NWQPIDWDLK EAELTKGTID LIWNGYSATD ERREKVAFSN   120
SYMKNEQVLV TKKLSGITTA KDMTGKTLGA QAGSSGYADF EANPELLKNI VANKEANQYQ   180
TFNEALIDLK NDRIDGLLID RVYANYYLEA EGVLNDYNVF TVGLETEAFA VGARKEDTTL   240
VKKINEAFSS LYKDGKFQEI SQKWFGEDVA TKEVKEGQ                          278

SEQ ID NO: 139          moltype = AA  length = 278
FEATURE                 Location/Qualifiers
source                  1..278
                        mol_type = protein
                        organism = Streptococcus pneumoniae
SEQUENCE: 139
MKKWMLVLVS LMTALFLVAC GKNTSETSGD NWSKYESNKS ITIGFDSTFV PMGFAQKDGS    60
YAGFDIDLAT AVFEKYGITV NWQPIDWDLK EAELTKGTID LIWNGYSATD ERREKVAFSN   120
SYMKNEQVLV TKKSSGITTA KDMAGKTLGA QAGSSGYADF EANPELLKNI VANKEANQYQ   180
TFNEALIDLK NDRIDGLLID RVYANYYLEA EGVLNDYNVF TVGLETEAFA VGARKEDTTL   240
VKKINEAFSS LYKDGKFQEI SQKWFGEDVA TKEVKEGQ                          278

SEQ ID NO: 140          moltype = AA  length = 278
FEATURE                 Location/Qualifiers
source                  1..278
                        mol_type = protein
                        organism = Streptococcus pneumoniae
SEQUENCE: 140
MKKWMLVLVS LMTALFLVAC GKNSSETSGD NWSKYESNKS ITIGFDSTFV PMGFAQKDGS    60
YAGFDIDLAT AVFEKYGITV NWQPIDWDLK EAELTKGTID LIWNGYSATD ERREKVAFSN   120
SYMKNEQVLV TKKSSGITTA KDMAGKTLGA QAGSSGYADF EANPAILKDI VANKEANQYQ   180
TFNEALIDLK NDRIDGLLID RVYANYYLEA EGVLNDYNVF TVGLETEAFA VGARKEDTTL   240
VKKINEAFSS LYKDGKFQEI SQKWFGEDVA TKEVKEGQ                          278

SEQ ID NO: 141          moltype = AA  length = 282
FEATURE                 Location/Qualifiers
source                  1..282
                        mol_type = protein
                        organism = Streptococcus pneumoniae
SEQUENCE: 141
MKKWMKKWML VLVSLMTALF LVACGKNTSE TSGDNWSKYE SNKSITIGFD STFVPMGFAQ    60
KDGSYAGFDI DLATAVFEKY GITVNWQPID WDLKEAELTK GTIDLIWNGY SATDERREKV   120
AFSNSYMKNE QVLVTKKSSG ITTAKDMAGK TLGAQAGSSG YADFEANPEL LKNIVANKEA   180
NQYQTFNEAL IDLKNDRIDG LLIDRVYANY YLEAEGVLND YNVFTVGLET EAFAVGARKE   240
DTTLVKKINE AFSSLYKDGK FQEISQKWFG EDVATKEVKE GQ                     282
```

```
SEQ ID NO: 142            moltype = AA   length = 278
FEATURE                   Location/Qualifiers
source                    1..278
                          mol_type = protein
                          organism = Streptococcus pneumoniae
SEQUENCE: 142
MKKWMLVLVS LMTALFLVAC GKNSSETSGD NWSKYQSNKS ITIGFDSTFV PMGFAQKDGS   60
YAGFDIDLAT AVFEKYGITV NWQPIDWDLK EAELTKGTID LIWNGYSATD ERREKVAFSN  120
SYMKNEQVLV TKKLSGITTA KDMTGKTLGA QAGSSGYADF EANPELLKNI VANKEANQYQ  180
TFNEALIDLK NDRIDGLLID RVYANYYLEA EGVLNDYNVF TVGLETEAFA VGARKEDTTL  240
VKKINEAFSS LYKDGKFQEI SQKWFGEGVA TKEVKEGQ                          278

SEQ ID NO: 143            moltype = AA   length = 278
FEATURE                   Location/Qualifiers
source                    1..278
                          mol_type = protein
                          organism = Streptococcus pneumoniae
SEQUENCE: 143
MKKWMLVLVS LMTALFLVAC GKNSSETSGD NWSKYESNKS ITIGFDSTFV PMGFAQKDGS   60
YAGFDIDLAT AVFEKYGITV NWQPIDWDLK EAELTKGTID LIWNGYSATD ERREKVAFSN  120
SYMKNEQVLV TKKSSGITTA KDMAGKTLGA QAGSSGYADF EANPAILKDI VANKEANQYQ  180
TFNEALIDLK NDRIEGLLID RVYANYYLEA EGVLNDYNVF TVGLETEAFA VGARKEDTTL  240
VKKINEAFSS LYKDGKFQEI SQKWFGEDVA TKEVKEGQ                          278

SEQ ID NO: 144            moltype = AA   length = 282
FEATURE                   Location/Qualifiers
source                    1..282
                          mol_type = protein
                          organism = Streptococcus pneumoniae
SEQUENCE: 144
MKKWMKKWML VLVSLMTALF LVACGKNSSE TSGDNWSKYQ SNKSITIGFD STFVPMGFAQ   60
KDGSYAGFDI DLATAVFEKY GITVNWQPID WDLKEAELTK GTIDLIWNGY SATDERREKV  120
AFSNSYMKNE QVLVTKKLSG ITTAKDMNGK TLGAQAGSSG YADFEANPEL LKNIVANKEA  180
NQYQTFNEAL IDLKNDRIDG LLIDRVYANY YLEAEGVLND YNVFTVGLET EAFAVGARKE  240
DTTLVKKINE AFSSLYKDGK FQEISQKWFG EDVATKEVKE GQ                     282

SEQ ID NO: 145            moltype = AA   length = 274
FEATURE                   Location/Qualifiers
source                    1..274
                          mol_type = protein
                          organism = Streptococcus pneumoniae
SEQUENCE: 145
MLVLVSLMTA LFLVACGKNS SETSGDNWSK YQSNKSITIG FDSTFVPMGF AQKDGSYAGF   60
DIDLATAVFE KYGITVNWQP IDWDLKEAEL TKGTIDLIWN GYSATDERRE KVAFSNSYMK  120
NEQVLVTKKS SGITTAKDMT GKTLGAQAGS SGYADFEANP EILKNIVANK EANQYQTFNE  180
ALIDLKNDRI DGLLIDRVYA NYYLEAEGVL NDYNVFTVGL ETEAFAVGAR KEDTTLVKKI  240
NEAFSSLYKD GKFQEISQKW FGEDVATKEV KEGQ                              274

SEQ ID NO: 146            moltype = AA   length = 278
FEATURE                   Location/Qualifiers
source                    1..278
                          mol_type = protein
                          organism = Streptococcus pneumoniae
SEQUENCE: 146
MKKWILVLVS LMTALFLVAC GKNSSETSGD NWSKYESNKS ITIGFDSTFV PMGFAQKDGS   60
YAGFDIDLAT AVFEKYGITV NWQPIDWDLK EAELTKGTID LIWNGYSATD ERREKVAFSN  120
SYMKNEQVLV TKKSSGITTA KDMAGKTLGA QAGSSGYADF EANPAILKDI VANKEANQYQ  180
TFNEALIDLK NDRIDGLLID RVYANYYLEA EGVLNDYNVF TVGLETEAFA VGARKEDTTL  240
VKKINEAFSS LYKDGKFQEI SQKWFGEDVA TKEVKEGQ                          278

SEQ ID NO: 147            moltype = AA   length = 278
FEATURE                   Location/Qualifiers
source                    1..278
                          mol_type = protein
                          organism = Streptococcus pneumoniae
SEQUENCE: 147
MKKWMLVLVS LMTALFLVAC GKNSSETSGD NWSKYESNKS ITIGFDSTFV PMGFAQKDGS   60
YAGFDIDLAT AVFEKYGITV NWQPIDWDLK EAELTKGTID LIWNGYSATY ERREKVAFSN  120
SYMKNEQVLV TKKLSGITTA KDMTGKTLGA QAGSSGYADF EANPEILKNI VANKEANQYQ  180
TFNEALIDLK NDRIDGLLID RVYANYYLEA EGVLNDYNVF TVGLETEAFA VGARKEDTTL  240
VKKINEAFSS LYKDGKFQEI SQKWFGEDVA TKEVKEGQ                          278

SEQ ID NO: 148            moltype = AA   length = 278
FEATURE                   Location/Qualifiers
source                    1..278
                          mol_type = protein
                          organism = Streptococcus pneumoniae
SEQUENCE: 148
MKKWILVLVS LMTALFLVAC GKNSSETSGD NWSKYESNKS ITIGFDSTFV PMGFAQKDGS   60
```

```
YAGFDIDLAT AVFEKYGITV NWQPIDWDLK EAELTKGTID LIWNGYSATD ERREKVAFSH    120
SYMKNEQVLV TKKSSGITTA KDMAGKTLGA QAGSSGYADF EANPAILKDI VANKEANQYQ    180
TFNEALIDLK NDRIDGLLID RVYANYYLEA EGVLNDYNVF TVGLETEAFA VGARKEDTTL    240
VKKINEAFSS LYKDGKFQEI SQKWFGEDVA TKEVKEGQ                           278

SEQ ID NO: 149           moltype = AA   length = 278
FEATURE                  Location/Qualifiers
source                   1..278
                         mol_type = protein
                         organism = Streptococcus pneumoniae
SEQUENCE: 149
MKKWMLVLVS LMTALFLVAC GKNASEISGD NWSKYQSNKS ITIGFDSTFV PMGFAQKDGS    60
YAGFDIDLAT AVFEKYGITV NWQPIDWDLK EAELTKGTID LIWNGYSATD ERREKVAFSH    120
SYMKNEQVLV TKKSSGITTA KDMAGKTLGA QAGSSGYADF EANPAILKDI VANKEANQYQ    180
TFNEALIDLK NDRIDGLLID RVYANYYLEA EGVLNDYNVF TVGLETEAFA VGTRKEDTTL    240
VKKINEAFSS LYKDGKFQEI SQKWFGEDVA TKEVKEGQ                           278

SEQ ID NO: 150           moltype = AA   length = 278
FEATURE                  Location/Qualifiers
source                   1..278
                         mol_type = protein
                         organism = Streptococcus pneumoniae
SEQUENCE: 150
MKKWMFVLVS LMTALFLVAC GKNASETSGD NWSKYESNKS ITIGFDSTFV PMGFAQKDGS    60
YAGFDIDLAT AVFEKYGITV NWQPIDWDLK EAELTKGTID LIWNGYSATD ERREKVAFSN    120
SYMKNEQVLV TKKSSGITTA KDMAGKTLGA QAGSSGYADF EANPAILKDI VANKEANQYQ    180
TFNEALIDLK NDRIDGLLID RVYANYYLEA EGVLNDYNVF TVGLETEAFA VGARKEDTTL    240
VKKINEAFSS LYKDGKFQEI SQKWFGEDVA TKEVKEGQ                           278

SEQ ID NO: 151           moltype = AA   length = 274
FEATURE                  Location/Qualifiers
source                   1..274
                         mol_type = protein
                         organism = Streptococcus pneumoniae
SEQUENCE: 151
MLVLVSLMTA LFLVACGKNS SETSGDNWSK YQSNKSITIG FDSTFVPMGF AQKDGSYAGF    60
DIDLATAVFE KYGITVNWQP IDWDLKEAEL TKGTIDLIWN GYSATDERRE KVAFSNSYMK    120
NEQVLVTKKS SGITTAKDMT GKTLGAQAGS SGYADFEANP EILKNIVANK EANQYQTFNE    180
ALIDLKNDRI DGLLIDRVYA NYYLEAEGVL NDYNVFTVGL ETEAFAVGSR KEDTTLVKKI    240
NEAFSSLYKD GKFQEISQKW FGEDVATKEV KEGQ                               274

SEQ ID NO: 152           moltype = AA   length = 274
FEATURE                  Location/Qualifiers
source                   1..274
                         mol_type = protein
                         organism = Streptococcus pneumoniae
SEQUENCE: 152
MLVLVSLMTA LFLVACGKNS SETSGDNWSK YQSNKSITIG FDSTFVPMGF AQKDGSYAGF    60
DIDLATAVFE KYGITVNWQP IDWDLKEAEL TKGTIDLIWN GYSATDERRE KVAFSNSYMK    120
NEQVLVTKKS SGITTAKDMT GKTLGAQAGS SGYADFEANP ELLKNIVANK EANQYQTFNE    180
ALIDLKNDRI DGLLIDRVYA NYYLEAEGVL NDYNVFTVGL ETEAFAVGAR KEDTTLVKKI    240
NEAFSSLYKD GKFQEISQKW FGEDVATKEV KEGQ                               274

SEQ ID NO: 153           moltype = AA   length = 277
FEATURE                  Location/Qualifiers
source                   1..277
                         mol_type = protein
                         organism = Streptococcus pneumoniae
SEQUENCE: 153
MKKWMLVLVS LMTALFLVAC GKNSSETSGD NWSKYESNKS ITIGFDSTFV PMGFAQKDGS    60
YAGFDIDLAT AVFEKYGITV NWQPIDWDLK EAELTKGTID LIWNGYSATY ERREKVAFSN    120
SYMKNEQVLV TKKLSGITTA KDMTGKTLGA QAGSSGYADF EANPEILKNI VANKEANQYQ    180
TFNEALIDLK NDRIDGLLID RVYANYYLEA EGVLNDYNVF TVGLETEAFA VGARKEDTTL    240
VKKINEAFSS LYKDGKFQEI SQKWFGEDVA TKEVKEG                            277

SEQ ID NO: 154           moltype = AA   length = 282
FEATURE                  Location/Qualifiers
source                   1..282
                         mol_type = protein
                         organism = Streptococcus pneumoniae
SEQUENCE: 154
MKKWMKKWML VLVSLMTALF LVACGKNASE TSGDNWSKYE SNKSITIGFD STFVPMGFAQ    60
KDGSYAGFDI DLATAVFEKY GITVNWQPID WDLKEAELTK GTIDLIWNGY SATDERREKV    120
AFSNSYMKNE QVLVTKKLSG ITTAKDMTGK ILGAQAGSSG YADFEANPEI LKNIVANKEA    180
NQYQTFNEAL IDLKNDRIDG LLIDRVYANY YLEAEGVLND YNVFTVGLEI EAFAVGARKE    240
DTTLVKKINE AFSSLYKDGK FQEISQKWFG EDVATKEVKE GQ                      282

SEQ ID NO: 155           moltype = AA   length = 278
FEATURE                  Location/Qualifiers
```

```
source                  1..278
                        mol_type = protein
                        organism = Streptococcus pneumoniae
SEQUENCE: 155
MKKWMLVLVS LMTALFLVAC GKNASETSGD NWSKYESNKS ITIGFDSTFV PMGFAQKDGS    60
YAGFDIDLAT AVFEKYGITV NWQPIDWDLK EAELTKGTID LIWNGYSATD ERREKVAFSN   120
SYMKNEQVLV TKKSSGITTA KDMAGKTLGA QAGSSGYADF EANPAILKDI VANKEANQYQ   180
IFNEALIDLK NDRIDGLLID RVYANYYLEA EGVLNDYNVF TVGLETEAFA VGARKEDITL   240
VKKINEAFSS LYKDGKFQEI SQKWFGEDVA TKEVKEGQ                          278

SEQ ID NO: 156          moltype = AA  length = 278
FEATURE                 Location/Qualifiers
source                  1..278
                        mol_type = protein
                        organism = Streptococcus pneumoniae
SEQUENCE: 156
MKKWMLVLVS LMIALFLVAC GKNTSETSGD NWSKYESNKS ITIGFDSTFV PMGFAQKDGS    60
YAGFDIDLAT AVFEKYGITI NWQPIDWDLK EAELTKGTID LIWNGYSATD ERREKVAFSH   120
SYMKNEQVLV TKKSSGITTA KDMAGKTLGA QAGSSGYADF EANPAILKDI VANKEANQYQ   180
TFNEALIDLK NDRIDGLLID RVYANYYLEA EGVLNDYNVF TVGLETEAFA VGARKEDTTL   240
VKKINEAFSS LYKDGKFQEI SQKWFGEDVA TKEVKEGQ                          278

SEQ ID NO: 157          moltype = AA  length = 286
FEATURE                 Location/Qualifiers
source                  1..286
                        mol_type = protein
                        organism = Streptococcus pneumoniae
SEQUENCE: 157
MKKWMKKWMK KWMLVLVSLM TALFLVACGK NASETSGDNW SKYESNKSIT IGFDSTFVPM    60
GFAQKDGSYA GFDIDLATAV FEKYGITVNW QPIDWDLKEA ELTKGTIDLI WNGYSATDER   120
REKVAFSNSY MKNEQVLVTK KLSGITTAKD MTGKILGAQA GSSGYADFEA NPEILKNIVA   180
NKEANQYQTF NEALIDLKND RIDGLLIDRV YANYYLEAEG VLNDYNVFTV GLEIEAFAVG   240
ARKEDTTLVK KINEAFSSLY KDGKFQEISQ KWFGEDVATK EVKEGQ                 286
```